US011780897B2

(12) United States Patent
Schreiber et al.

(10) Patent No.: US 11,780,897 B2
(45) Date of Patent: *Oct. 10, 2023

(54) HETERODIMERIC PROTEINS AND USES THEREOF

(71) Applicant: Shattuck Labs, Inc., Austin, TX (US)

(72) Inventors: Taylor Schreiber, Austin, TX (US); George Fromm, Austin, TX (US); Suresh De Silva, Austin, TX (US)

(73) Assignee: Shattuck Labs, Inc., Austin, TX (US)

( * ) Notice: Subject to any disclaimer, the term of this patent is extended or adjusted under 35 U.S.C. 154(b) by 210 days.

This patent is subject to a terminal disclaimer.

(21) Appl. No.: 17/211,180

(22) Filed: Mar. 24, 2021

(65) Prior Publication Data

US 2021/0214409 A1    Jul. 15, 2021

Related U.S. Application Data

(63) Continuation of application No. 16/571,853, filed on Sep. 16, 2019, now Pat. No. 10,995,127, which is a continuation of application No. PCT/US2019/038451, filed on Jun. 21, 2019.

(60) Provisional application No. 62/703,248, filed on Jul. 25, 2018, provisional application No. 62/688,167, filed on Jun. 21, 2018.

(51) Int. Cl.
   *C07K 14/54* (2006.01)
   *C07K 14/715* (2006.01)
   *A61K 47/60* (2017.01)
   *A61K 38/00* (2006.01)

(52) U.S. Cl.
   CPC .............. *C07K 14/54* (2013.01); *A61K 47/60* (2017.08); *C07K 14/7155* (2013.01); *C07K 14/7156* (2013.01); *A61K 38/00* (2013.01); *C07K 2319/30* (2013.01)

(58) Field of Classification Search
   CPC . C07K 14/54; C07K 14/7155; C07K 14/7156
   See application file for complete search history.

(56) References Cited

U.S. PATENT DOCUMENTS

| 10,188,701 | B2 | 1/2019 | Schreiber et al. |
| 10,995,127 | B2 * | 5/2021 | Schreiber ............ C07K 14/7156 |

| 2002/0193570 | A1 | 12/2002 | Gillies et al. |
| 2013/0330335 | A1 | 12/2013 | Bremel et al. |
| 2014/0356415 | A1 | 12/2014 | DeShong et al. |
| 2017/0095531 | A1 | 4/2017 | Schreiber et al. |
| 2020/0216505 | A1 | 7/2020 | Schreiber et al. |

FOREIGN PATENT DOCUMENTS

| WO | WO 95/31480 A1 | 11/1995 |
| WO | WO 01/10912 A1 | 2/2001 |
| WO | WO 2017/059168 A1 | 4/2017 |
| WO | WO 2018/064190 A1 | 4/2018 |
| WO | WO 2021/041958 A1 | 3/2021 |

OTHER PUBLICATIONS

Xue, et al., "Interleukin-35 as an Emerging Player in Tumor Microenvironment," Journal of Cancer, vol. 10, No. 9, pp. 2074-2082, 2019.
Acres, et al., "Fusokine Interleukin-2/Interleukin-18, a Novel Potent Innate and Adaptive Immune Stimulator with Decreased Toxicity," Cancer Res; 65: (20) Oct. 15, 2005, 12 pages.
Ancey, et al., "A Fusion Protein of the gp130 and Interleukin-6Rα Ligand-binding Domains Acts as a Potent Interleukin-6 Inhibitor," The Journal of Biological Chemistry, vol. 278, No. 19, May 9, 2003, pp. 16968-16972.
Fromm, et al., "Agonist redirected checkpoint, PD1-Fc-OX40L, for cancer immunotherapy," Journal for ImmunoTherapy of Cancer, (2018) 6:149, 16 pages.
Ng, et al., "Concise Review: Engineering the Fusion of Cytokines for the Modulation of Immune Cellular Responses in Cancer and Autoimmune Disorders," Stem Cells Translational Medicine, 2015, 4:66-73.
Niedbala, et al., "IL-35 is a novel cytokine with therapeutic effects against collagen-induced arthritis through the expansion of regulatory T cells and suppression of Th17 cells," Eur. J. Immunol., (2007), 37: 3021-3029.
Tanaka, et al., "IL-6 in Inflammation, Immunity, and Disease," Cold Spring Harb Perspect Biol 2014; 6:a016295.
International Search Report & Written Opinion, PCT Application No. PCT/US19/38451, dated Oct. 1, 2019, 11 pages.

* cited by examiner

*Primary Examiner* — Prema M Mertz
(74) *Attorney, Agent, or Firm* — Morgan, Lewis & Bockius LLP

(57) ABSTRACT

The present invention relates, inter alia, to compositions and methods, including heterodimeric proteins that find use in the treatment of disease, such as immunotherapies for cancer and autoimmunity.

20 Claims, 21 Drawing Sheets

Specification includes a Sequence Listing.

SEQUENCE LISTING

```
<160> NUMBER OF SEQ ID NOS: 39

<210> SEQ ID NO 1
<211> LENGTH: 5
<212> TYPE: PRT
<213> ORGANISM: Artificial Sequence
<220> FEATURE:
<223> OTHER INFORMATION: Synthetic sequence
<220> FEATURE:
<221> NAME/KEY: REPEAT
<222> LOCATION: (1)..(1)
<223> OTHER INFORMATION: A spacer amino acid such as serine or glycine
<220> FEATURE:
<221> NAME/KEY: REPEAT
<222> LOCATION: (2)..(2)
<223> OTHER INFORMATION: A positively charged amino acid such as
      arginine, histidine or lysine
<220> FEATURE:
<221> NAME/KEY: REPEAT
<222> LOCATION: (3)..(3)
<223> OTHER INFORMATION: A spacer amino acid such as serine or glycine
<220> FEATURE:
<221> NAME/KEY: REPEAT
<222> LOCATION: (4)..(4)
<223> OTHER INFORMATION: A positively charged amino acid such as
      arginine, histidine or lysine
<220> FEATURE:
<221> NAME/KEY: REPEAT
<222> LOCATION: (5)..(5)
<223> OTHER INFORMATION: A spacer amino acid such as serine or glycine

<400> SEQUENCE: 1

Xaa Xaa Xaa Xaa Xaa
1               5

<210> SEQ ID NO 2
<211> LENGTH: 5
<212> TYPE: PRT
<213> ORGANISM: Artificial sequence
```

```
<220> FEATURE:
<223> OTHER INFORMATION: Synthetic sequence
<220> FEATURE:
<221> NAME/KEY: REPEAT
<222> LOCATION: (1)..(1)
<223> OTHER INFORMATION: A spacer amino acid such as serine or glycine
<220> FEATURE:
<221> NAME/KEY: REPEAT
<222> LOCATION: (2)..(2)
<223> OTHER INFORMATION: A negatively charged amino acid such as
      aspartic acid or glutamic acid
<220> FEATURE:
<221> NAME/KEY: REPEAT
<222> LOCATION: (3)..(3)
<223> OTHER INFORMATION: A spacer amino acid such as serine or glycine
<220> FEATURE:
<221> NAME/KEY: REPEAT
<222> LOCATION: (4)..(4)
<223> OTHER INFORMATION: A negatively charged amino acid such as
      aspartic acid or glutamic acid
<220> FEATURE:
<221> NAME/KEY: REPEAT
<222> LOCATION: (5)..(5)
<223> OTHER INFORMATION: A spacer amino acid such as serine or glycine

<400> SEQUENCE: 2

Xaa Xaa Xaa Xaa Xaa
1               5

<210> SEQ ID NO 3
<211> LENGTH: 10
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (1)..(1)
<223> OTHER INFORMATION: A spacer amino acid such as serine or glycine
<220> FEATURE:
<221> NAME/KEY: REPEAT
<222> LOCATION: (2)..(2)
<223> OTHER INFORMATION: A spacer amino acid such as serine or glycine
<220> FEATURE:
<221> NAME/KEY: MISC_FEATURE
<222> LOCATION: (3)..(3)
<223> OTHER INFORMATION: A positively charged amino acid such as
      arginine, histidine or lysine
<220> FEATURE:
<221> NAME/KEY: REPEAT
<222> LOCATION: (4)..(4)
<223> OTHER INFORMATION: A positively charged amino acid such as
      arginine, histidine or lysine
<220> FEATURE:
<221> NAME/KEY: MISC_FEATURE
<222> LOCATION: (5)..(5)
<223> OTHER INFORMATION: A spacer amino acid such as serine or glycine
<220> FEATURE:
<221> NAME/KEY: REPEAT
<222> LOCATION: (6)..(6)
<223> OTHER INFORMATION: A spacer amino acid such as serine or glycine
<220> FEATURE:
<221> NAME/KEY: MISC_FEATURE
<222> LOCATION: (7)..(7)
<223> OTHER INFORMATION: A positively charged amino acid such as
      arginine, histidine or lysine
<220> FEATURE:
<221> NAME/KEY: REPEAT
<222> LOCATION: (8)..(8)
<223> OTHER INFORMATION: A positively charged amino acid such as
      arginine, histidine or lysine
<220> FEATURE:
<221> NAME/KEY: MISC_FEATURE
<222> LOCATION: (9)..(9)
<223> OTHER INFORMATION: A spacer amino acid such as serine or glycine
<220> FEATURE:
<221> NAME/KEY: REPEAT
```

```
<222> LOCATION: (10)..(10)
<223> OTHER INFORMATION: A spacer amino acid such as serine or glycine

<400> SEQUENCE: 3

Xaa Xaa Xaa Xaa Xaa Xaa Xaa Xaa Xaa Xaa
1               5                   10

<210> SEQ ID NO 4
<211> LENGTH: 10
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (1)..(1)
<223> OTHER INFORMATION: A spacer amino acid such as serine or glycine
<220> FEATURE:
<221> NAME/KEY: REPEAT
<222> LOCATION: (2)..(2)
<223> OTHER INFORMATION: A spacer amino acid such as serine or glycine
<220> FEATURE:
<221> NAME/KEY: MISC_FEATURE
<222> LOCATION: (3)..(3)
<223> OTHER INFORMATION: A negatively charged amino acid such as
      aspartic acid or glutamic acid
<220> FEATURE:
<221> NAME/KEY: REPEAT
<222> LOCATION: (4)..(4)
<223> OTHER INFORMATION: A negatively charged amino acid such as
      aspartic acid or glutamic acid
<220> FEATURE:
<221> NAME/KEY: MISC_FEATURE
<222> LOCATION: (5)..(5)
<223> OTHER INFORMATION: A spacer amino acid such as serine or glycine
<220> FEATURE:
<221> NAME/KEY: REPEAT
<222> LOCATION: (6)..(6)
<223> OTHER INFORMATION: A spacer amino acid such as serine or glycine
<220> FEATURE:
<221> NAME/KEY: MISC_FEATURE
<222> LOCATION: (7)..(7)
<223> OTHER INFORMATION: A negatively charged amino acid such as
      aspartic acid or glutamic acid
<220> FEATURE:
<221> NAME/KEY: REPEAT
<222> LOCATION: (8)..(8)
<223> OTHER INFORMATION: A negatively charged amino acid such as
      aspartic acid or glutamic acid
<220> FEATURE:
<221> NAME/KEY: MISC_FEATURE
<222> LOCATION: (9)..(9)
<223> OTHER INFORMATION: A spacer amino acid such as serine or glycine
<220> FEATURE:
<221> NAME/KEY: REPEAT
<222> LOCATION: (10)..(10)
<223> OTHER INFORMATION: A spacer amino acid such as serine or glycine

<400> SEQUENCE: 4

Xaa Xaa Xaa Xaa Xaa Xaa Xaa Xaa Xaa Xaa
1               5                   10

<210> SEQ ID NO 5
<211> LENGTH: 6
<212> TYPE: PRT
<213> ORGANISM: Artificial sequence
<220> FEATURE:
<223> OTHER INFORMATION: Synthetic sequence
<220> FEATURE:
<221> NAME/KEY: REPEAT
<222> LOCATION: (1)..(1)
<223> OTHER INFORMATION: A spacer amino acid such as serine or glycine
<220> FEATURE:
<221> NAME/KEY: REPEAT
<222> LOCATION: (2)..(2)
```

```
<223> OTHER INFORMATION: A positively charged amino acid such as
      arginine, histidine or lysine
<220> FEATURE:
<221> NAME/KEY: REPEAT
<222> LOCATION: (4)..(4)
<223> OTHER INFORMATION: A spacer amino acid such as serine or glycine
<220> FEATURE:
<221> NAME/KEY: REPEAT
<222> LOCATION: (5)..(5)
<223> OTHER INFORMATION: A positively charged amino acid such as
      arginine, histidine or lysine
<220> FEATURE:
<221> NAME/KEY: REPEAT
<222> LOCATION: (6)..(6)
<223> OTHER INFORMATION: A spacer amino acid such as serine or glycine

<400> SEQUENCE: 5

Xaa Xaa Cys Xaa Xaa Xaa
1               5

<210> SEQ ID NO 6
<211> LENGTH: 6
<212> TYPE: PRT
<213> ORGANISM: Artificial sequence
<220> FEATURE:
<223> OTHER INFORMATION: Synthetic sequence
<220> FEATURE:
<221> NAME/KEY: REPEAT
<222> LOCATION: (1)..(1)
<223> OTHER INFORMATION: A spacer amino acid such as serine or glycine
<220> FEATURE:
<221> NAME/KEY: REPEAT
<222> LOCATION: (2)..(2)
<223> OTHER INFORMATION: A negatively charged amino acid such as
      aspartic acid or glutamic acid
<220> FEATURE:
<221> NAME/KEY: REPEAT
<222> LOCATION: (4)..(4)
<223> OTHER INFORMATION: A spacer amino acid such as serine or glycine
<220> FEATURE:
<221> NAME/KEY: REPEAT
<222> LOCATION: (5)..(5)
<223> OTHER INFORMATION: A negatively charged amino acid such as
      aspartic acid or glutamic acid
<220> FEATURE:
<221> NAME/KEY: REPEAT
<222> LOCATION: (6)..(6)
<223> OTHER INFORMATION: A spacer amino acid such as serine or glycine

<400> SEQUENCE: 6

Xaa Xaa Cys Xaa Xaa Xaa
1               5

<210> SEQ ID NO 7
<211> LENGTH: 12
<212> TYPE: PRT
<213> ORGANISM: Artificial sequence
<220> FEATURE:
<223> OTHER INFORMATION: Synthetic sequence

<400> SEQUENCE: 7

Gly Ser Gly Ser Arg Lys Gly Gly Lys Arg Gly Ser
1               5                   10

<210> SEQ ID NO 8
<211> LENGTH: 12
<212> TYPE: PRT
<213> ORGANISM: Artificial sequence
<220> FEATURE:
<223> OTHER INFORMATION: Synthetic sequence

<400> SEQUENCE: 8
```

```
Gly Ser Gly Ser Arg Lys Cys Gly Lys Arg Gly Ser
1               5                   10
```

<210> SEQ ID NO 9
<211> LENGTH: 12
<212> TYPE: PRT
<213> ORGANISM: Artificial sequence
<220> FEATURE:
<223> OTHER INFORMATION: Synthetic sequence

<400> SEQUENCE: 9

```
Gly Ser Gly Ser Asp Glu Gly Gly Glu Asp Gly Ser
1               5                   10
```

<210> SEQ ID NO 10
<211> LENGTH: 12
<212> TYPE: PRT
<213> ORGANISM: Artificial sequence
<220> FEATURE:
<223> OTHER INFORMATION: Synthetic sequence

<400> SEQUENCE: 10

```
Gly Ser Gly Ser Asp Glu Cys Gly Glu Asp Gly Ser
1               5                   10
```

<210> SEQ ID NO 11
<211> LENGTH: 6
<212> TYPE: PRT
<213> ORGANISM: Artificial sequence
<220> FEATURE:
<223> OTHER INFORMATION: Synthetic sequence

<400> SEQUENCE: 11

```
Arg Lys Gly Gly Lys Arg
1               5
```

<210> SEQ ID NO 12
<211> LENGTH: 12
<212> TYPE: PRT
<213> ORGANISM: Artificial sequence
<220> FEATURE:
<223> OTHER INFORMATION: Synthetic sequence

<400> SEQUENCE: 12

```
Gly Ser Gly Ser Arg Lys Gly Gly Lys Arg Gly Ser
1               5                   10
```

<210> SEQ ID NO 13
<211> LENGTH: 6
<212> TYPE: PRT
<213> ORGANISM: Artificial sequence
<220> FEATURE:
<223> OTHER INFORMATION: Synthetic sequence

<400> SEQUENCE: 13

```
Asp Glu Gly Gly Glu Asp
1               5
```

<210> SEQ ID NO 14
<211> LENGTH: 12
<212> TYPE: PRT
<213> ORGANISM: Artificial sequence
<220> FEATURE:
<223> OTHER INFORMATION: Synthetic sequence

<400> SEQUENCE: 14

Gly Ser Gly Ser Asp Glu Gly Gly Glu Asp Gly Ser

<210> SEQ ID NO 15
<211> LENGTH: 234
<212> TYPE: PRT
<213> ORGANISM: Artificial sequence
<220> FEATURE:
<223> OTHER INFORMATION: Synthetic sequence

<400> SEQUENCE: 15

```
Ser Lys Tyr Gly Pro Pro Cys Pro Pro Cys Pro Ala Pro Glu Phe Leu
1               5                   10                  15

Gly Gly Pro Ser Val Phe Leu Phe Pro Pro Lys Pro Lys Asp Gln Leu
            20                  25                  30

Met Ile Ser Arg Thr Pro Glu Val Thr Cys Val Val Val Asp Val Ser
        35                  40                  45

Gln Glu Asp Pro Glu Val Gln Phe Asn Trp Tyr Val Asp Gly Val Glu
    50                  55                  60

Val His Asn Ala Lys Thr Lys Pro Arg Glu Glu Gln Phe Asn Ser Thr
65                  70                  75                  80

Tyr Arg Val Val Ser Val Leu Thr Val Leu His Gln Asp Trp Leu Ser
                85                  90                  95

Gly Lys Glu Tyr Lys Cys Lys Val Ser Ser Lys Gly Leu Pro Ser Ser
            100                 105                 110

Ile Glu Lys Thr Ile Ser Asn Ala Thr Gly Gln Pro Arg Glu Pro Gln
        115                 120                 125

Val Tyr Thr Leu Pro Pro Ser Gln Glu Glu Met Thr Lys Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Arg Leu Thr
            180                 185                 190

Val Asp Lys Ser Arg Trp Gln Glu Gly Asn Val Phe Ser Cys Ser Val
        195                 200                 205

Leu His Glu Ala Leu His Asn His Tyr Thr Gln Lys Ser Leu Ser Leu
    210                 215                 220

Ser Leu Gly Lys Ile Glu Gly Arg Met Asp
225                 230
```

<210> SEQ ID NO 16
<211> LENGTH: 249
<212> TYPE: PRT
<213> ORGANISM: Artificial sequence
<220> FEATURE:
<223> OTHER INFORMATION: Synthetic sequence

<400> SEQUENCE: 16

```
Gly Ser Gly Ser Arg Lys Gly Gly Lys Arg Gly Ser Lys Tyr Gly Pro
1               5                   10                  15

Pro Cys Pro Pro Cys Pro Ala Pro Glu Phe Leu Gly Gly Pro Ser Val
            20                  25                  30

Phe Leu Phe Pro Pro Lys Pro Lys Asp Gln Leu Met Ile Ser Arg Thr
        35                  40                  45

Pro Glu Val Thr Cys Val Val Val Asp Val Ser Gln Glu Asp Pro Glu
    50                  55                  60
```

```
Val Gln Phe Asn Trp Tyr Val Asp Gly Val Glu Val His Asn Ala Lys
 65                  70                  75                  80

Thr Lys Pro Arg Glu Glu Gln Phe Asn Ser Thr Tyr Arg Val Val Ser
                 85                  90                  95

Val Leu Thr Val Leu His Gln Asp Trp Leu Ser Gly Lys Glu Tyr Lys
            100                 105                 110

Cys Lys Val Ser Ser Lys Gly Leu Pro Ser Ser Ile Glu Lys Thr Ile
        115                 120                 125

Ser Asn Ala Thr Gly Gln Pro Arg Glu Pro Gln Val Tyr Thr Leu Pro
    130                 135                 140

Pro Ser Gln Glu Glu Met Thr Lys Asn Gln Val Ser Leu Thr Cys Leu
145                 150                 155                 160

Val Lys Gly Phe Tyr Pro Ser Asp Ile Ala Val Glu Trp Glu Ser Asn
                165                 170                 175

Gly Gln Pro Glu Asn Asn Tyr Lys Thr Thr Pro Pro Val Leu Asp Ser
            180                 185                 190

Asp Gly Ser Phe Phe Leu Tyr Ser Arg Leu Thr Val Asp Lys Ser Arg
        195                 200                 205

Trp Gln Glu Gly Asn Val Phe Ser Cys Ser Val Leu His Glu Ala Leu
    210                 215                 220

His Asn His Tyr Thr Gln Lys Ser Leu Ser Leu Ser Leu Gly Lys Asp
225                 230                 235                 240

Glu Gly Gly Glu Asp Gly Ser Gly Ser
                245

<210> SEQ ID NO 17
<211> LENGTH: 249
<212> TYPE: PRT
<213> ORGANISM: Artificial sequence
<220> FEATURE:
<223> OTHER INFORMATION: Synthetic sequence

<400> SEQUENCE: 17

Gly Ser Gly Ser Asp Glu Gly Glu Asp Gly Ser Lys Tyr Gly Pro
1               5                   10                  15

Pro Cys Pro Pro Cys Pro Ala Pro Glu Phe Leu Gly Gly Pro Ser Val
                 20                  25                  30

Phe Leu Phe Pro Pro Lys Pro Lys Asp Gln Leu Met Ile Ser Arg Thr
             35                  40                  45

Pro Glu Val Thr Cys Val Val Asp Val Ser Gln Glu Asp Pro Glu
 50                  55                  60

Val Gln Phe Asn Trp Tyr Val Asp Gly Val Glu Val His Asn Ala Lys
 65                  70                  75                  80

Thr Lys Pro Arg Glu Glu Gln Phe Asn Ser Thr Tyr Arg Val Val Ser
                 85                  90                  95

Val Leu Thr Val Leu His Gln Asp Trp Leu Ser Gly Lys Glu Tyr Lys
            100                 105                 110

Cys Lys Val Ser Ser Lys Gly Leu Pro Ser Ser Ile Glu Lys Thr Ile
        115                 120                 125

Ser Asn Ala Thr Gly Gln Pro Arg Glu Pro Gln Val Tyr Thr Leu Pro
    130                 135                 140

Pro Ser Gln Glu Glu Met Thr Lys Asn Gln Val Ser Leu Thr Cys Leu
145                 150                 155                 160

Val Lys Gly Phe Tyr Pro Ser Asp Ile Ala Val Glu Trp Glu Ser Asn
                165                 170                 175
```

```
Gly Gln Pro Glu Asn Asn Tyr Lys Thr Thr Pro Val Leu Asp Ser
                180                 185                 190

Asp Gly Ser Phe Phe Leu Tyr Ser Arg Leu Thr Val Asp Lys Ser Arg
            195                 200                 205

Trp Gln Glu Gly Asn Val Phe Ser Cys Ser Val Leu His Glu Ala Leu
210                 215                 220

His Asn His Tyr Thr Gln Lys Ser Leu Ser Leu Ser Leu Gly Lys Arg
225                 230                 235                 240

Lys Gly Gly Lys Arg Gly Ser Gly Ser
                245
```

<210> SEQ ID NO 18
<211> LENGTH: 597
<212> TYPE: PRT
<213> ORGANISM: Artificial sequence
<220> FEATURE:
<223> OTHER INFORMATION: Synthetic sequence

<400> SEQUENCE: 18

```
Glu Leu Leu Asp Pro Cys Gly Tyr Ile Ser Pro Glu Ser Pro Val Val
1               5                   10                  15

Gln Leu His Ser Asn Phe Thr Ala Val Cys Val Leu Lys Glu Lys Cys
                20                  25                  30

Met Asp Tyr Phe His Val Asn Ala Asn Tyr Ile Val Trp Lys Thr Asn
            35                  40                  45

His Phe Thr Ile Pro Lys Glu Gln Tyr Thr Ile Ile Asn Arg Thr Ala
        50                  55                  60

Ser Ser Val Thr Phe Thr Asp Ile Ala Ser Leu Asn Ile Gln Leu Thr
65                  70                  75                  80

Cys Asn Ile Leu Thr Phe Gly Gln Leu Glu Gln Asn Val Tyr Gly Ile
                85                  90                  95

Thr Ile Ile Ser Gly Leu Pro Pro Glu Lys Pro Lys Asn Leu Ser Cys
            100                 105                 110

Ile Val Asn Glu Gly Lys Lys Met Arg Cys Glu Trp Asp Gly Gly Arg
        115                 120                 125

Glu Thr His Leu Glu Thr Asn Phe Thr Leu Lys Ser Glu Trp Ala Thr
    130                 135                 140

His Lys Phe Ala Asp Cys Lys Ala Lys Arg Asp Thr Pro Thr Ser Cys
145                 150                 155                 160

Thr Val Asp Tyr Ser Thr Val Tyr Phe Val Asn Ile Glu Val Trp Val
                165                 170                 175

Glu Ala Glu Asn Ala Leu Gly Lys Val Thr Ser Asp His Ile Asn Phe
            180                 185                 190

Asp Pro Val Tyr Lys Val Lys Pro Asn Pro Pro His Asn Leu Ser Val
        195                 200                 205

Ile Asn Ser Glu Glu Leu Ser Ser Ile Leu Lys Leu Thr Trp Thr Asn
    210                 215                 220

Pro Ser Ile Lys Ser Val Ile Ile Leu Lys Tyr Asn Ile Gln Tyr Arg
225                 230                 235                 240

Thr Lys Asp Ala Ser Thr Trp Ser Gln Ile Pro Pro Glu Asp Thr Ala
                245                 250                 255

Ser Thr Arg Ser Ser Phe Thr Val Gln Asp Leu Lys Pro Phe Thr Glu
            260                 265                 270

Tyr Val Phe Arg Ile Arg Cys Met Lys Glu Asp Gly Lys Gly Tyr Trp
        275                 280                 285
```

Ser Asp Trp Ser Glu Glu Ala Ser Gly Ile Thr Tyr Glu Asp Arg Pro
    290                 295                 300

Ser Lys Ala Pro Ser Phe Trp Tyr Lys Ile Asp Pro Ser His Thr Gln
305                 310                 315                 320

Gly Tyr Arg Thr Val Gln Leu Val Trp Lys Thr Leu Pro Pro Phe Glu
                325                 330                 335

Ala Asn Gly Lys Ile Leu Asp Tyr Glu Val Thr Leu Thr Arg Trp Lys
                340                 345                 350

Ser His Leu Gln Asn Tyr Thr Val Asn Ala Thr Lys Leu Thr Val Asn
                355                 360                 365

Leu Thr Asn Asp Arg Tyr Leu Ala Thr Leu Thr Val Arg Asn Leu Val
370                 375                 380

Gly Lys Ser Asp Ala Ala Val Leu Thr Ile Pro Ala Cys Asp Phe Gln
385                 390                 395                 400

Ala Thr His Pro Val Met Asp Leu Lys Ala Phe Pro Lys Asp Asn Met
                405                 410                 415

Leu Trp Val Glu Trp Thr Thr Pro Arg Glu Ser Val Lys Lys Tyr Ile
                420                 425                 430

Leu Glu Trp Cys Val Leu Ser Asp Lys Ala Pro Cys Ile Thr Asp Trp
                435                 440                 445

Gln Gln Glu Asp Gly Thr Val His Arg Thr Tyr Leu Arg Gly Asn Leu
450                 455                 460

Ala Glu Ser Lys Cys Tyr Leu Ile Thr Val Thr Pro Val Tyr Ala Asp
465                 470                 475                 480

Gly Pro Gly Ser Pro Glu Ser Ile Lys Ala Tyr Leu Lys Gln Ala Pro
                485                 490                 495

Pro Ser Lys Gly Pro Thr Val Arg Thr Lys Lys Val Gly Lys Asn Glu
                500                 505                 510

Ala Val Leu Glu Trp Asp Gln Leu Pro Val Asp Val Gln Asn Gly Phe
                515                 520                 525

Ile Arg Asn Tyr Thr Ile Phe Tyr Arg Thr Ile Ile Gly Asn Glu Thr
530                 535                 540

Ala Val Asn Val Asp Ser Ser His Thr Glu Tyr Thr Leu Ser Ser Leu
545                 550                 555                 560

Thr Ser Asp Thr Leu Tyr Met Val Arg Met Ala Ala Tyr Thr Asp Glu
                565                 570                 575

Gly Gly Lys Asp Gly Pro Glu Phe Thr Phe Thr Thr Pro Lys Phe Ala
                580                 585                 590

Gln Gly Glu Ile Glu
        595

<210> SEQ ID NO 19
<211> LENGTH: 346
<212> TYPE: PRT
<213> ORGANISM: Artificial sequence
<220> FEATURE:
<223> OTHER INFORMATION: Synthetic sequence

<400> SEQUENCE: 19

Leu Ala Pro Arg Arg Cys Pro Ala Gln Glu Val Ala Arg Gly Val Leu
1               5                   10                  15

Thr Ser Leu Pro Gly Asp Ser Val Thr Leu Thr Cys Pro Gly Val Glu
                20                  25                  30

Pro Glu Asp Asn Ala Thr Val His Trp Val Leu Arg Lys Pro Ala Ala
                35                  40                  45

Gly Ser His Pro Ser Arg Trp Ala Gly Met Gly Arg Leu Leu Leu
        50                  55                  60

Arg Ser Val Gln Leu His Asp Ser Gly Asn Tyr Ser Cys Tyr Arg Ala
 65                  70                  75                  80

Gly Arg Pro Ala Gly Thr Val His Leu Leu Val Asp Val Pro Pro Glu
                85                  90                  95

Glu Pro Gln Leu Ser Cys Phe Arg Lys Ser Pro Leu Ser Asn Val Val
               100                 105                 110

Cys Glu Trp Gly Pro Arg Ser Thr Pro Ser Leu Thr Thr Lys Ala Val
               115                 120                 125

Leu Leu Val Arg Lys Phe Gln Asn Ser Pro Ala Glu Asp Phe Gln Glu
           130                 135                 140

Pro Cys Gln Tyr Ser Gln Glu Ser Gln Lys Phe Ser Cys Gln Leu Ala
145                 150                 155                 160

Val Pro Glu Gly Asp Ser Ser Phe Tyr Ile Val Ser Met Cys Val Ala
                165                 170                 175

Ser Ser Val Gly Ser Lys Phe Ser Lys Thr Gln Thr Phe Gln Gly Cys
            180                 185                 190

Gly Ile Leu Gln Pro Asp Pro Pro Ala Asn Ile Thr Val Thr Ala Val
            195                 200                 205

Ala Arg Asn Pro Arg Trp Leu Ser Val Thr Trp Gln Asp Pro His Ser
    210                 215                 220

Trp Asn Ser Ser Phe Tyr Arg Leu Arg Phe Glu Leu Arg Tyr Arg Ala
225                 230                 235                 240

Glu Arg Ser Lys Thr Phe Thr Thr Trp Met Val Lys Asp Leu Gln His
                245                 250                 255

His Cys Val Ile His Asp Ala Trp Ser Gly Leu Arg His Val Val Gln
                260                 265                 270

Leu Arg Ala Gln Glu Glu Phe Gly Gln Gly Glu Trp Ser Glu Trp Ser
            275                 280                 285

Pro Glu Ala Met Gly Thr Pro Trp Thr Glu Ser Arg Ser Pro Pro Ala
            290                 295                 300

Glu Asn Glu Val Ser Thr Pro Met Gln Ala Leu Thr Thr Asn Lys Asp
305                 310                 315                 320

Asp Asp Asn Ile Leu Phe Arg Asp Ser Ala Asn Ala Thr Ser Leu Pro
                325                 330                 335

Val Gln Asp Ser Ser Val Pro Leu Pro
            340                 345

<210> SEQ ID NO 20
<211> LENGTH: 197
<212> TYPE: PRT
<213> ORGANISM: Artificial Sequence
<220> FEATURE:
<223> OTHER INFORMATION: Synthetic Sequence

<400> SEQUENCE: 20

Arg Asn Leu Pro Val Ala Thr Pro Asp Pro Gly Met Phe Pro Cys Leu
1               5                   10                  15

His His Ser Gln Asn Leu Leu Arg Ala Val Ser Asn Met Leu Gln Lys
            20                  25                  30

Ala Arg Gln Thr Leu Glu Phe Tyr Pro Cys Thr Ser Glu Glu Ile Asp
        35                  40                  45

His Glu Asp Ile Thr Lys Asp Lys Thr Ser Thr Val Glu Ala Cys Leu
    50                  55                  60

```
Pro Leu Glu Leu Thr Lys Asn Glu Ser Cys Leu Asn Ser Arg Glu Thr
 65                  70                  75                  80

Ser Phe Ile Thr Asn Gly Ser Cys Leu Ala Ser Arg Lys Thr Ser Phe
                 85                  90                  95

Met Met Ala Leu Cys Leu Ser Ser Ile Tyr Glu Asp Leu Lys Met Tyr
            100                 105                 110

Gln Val Glu Phe Lys Thr Met Asn Ala Lys Leu Leu Met Asp Pro Lys
        115                 120                 125

Arg Gln Ile Phe Leu Asp Gln Asn Met Leu Ala Val Ile Asp Glu Leu
130                 135                 140

Met Gln Ala Leu Asn Phe Asn Ser Glu Thr Val Pro Gln Lys Ser Ser
145                 150                 155                 160

Leu Glu Glu Pro Asp Phe Tyr Lys Thr Lys Ile Lys Leu Cys Ile Leu
                165                 170                 175

Leu His Ala Phe Arg Ile Arg Ala Val Thr Ile Asp Arg Val Met Ser
            180                 185                 190

Tyr Leu Asn Ala Ser
        195
```

<210> SEQ ID NO 21
<211> LENGTH: 209
<212> TYPE: PRT
<213> ORGANISM: Artificial Sequence
<220> FEATURE:
<223> OTHER INFORMATION: Synthetic Sequence

<400> SEQUENCE: 21

```
Arg Lys Gly Pro Pro Ala Ala Leu Thr Leu Pro Arg Val Gln Cys Arg
  1               5                  10                  15

Ala Ser Arg Tyr Pro Ile Ala Val Asp Cys Ser Trp Thr Leu Pro Pro
             20                  25                  30

Ala Pro Asn Ser Thr Ser Pro Val Ser Phe Ile Ala Thr Tyr Arg Leu
             35                  40                  45

Gly Met Ala Ala Arg Gly His Ser Trp Pro Cys Leu Gln Gln Thr Pro
 50                  55                  60

Thr Ser Thr Ser Cys Thr Ile Thr Asp Val Gln Leu Phe Ser Met Ala
 65                  70                  75                  80

Pro Tyr Val Leu Asn Val Thr Ala Val His Pro Trp Gly Ser Ser Ser
                 85                  90                  95

Ser Phe Val Pro Phe Ile Thr Glu His Ile Ile Lys Pro Asp Pro Pro
            100                 105                 110

Glu Gly Val Arg Leu Ser Pro Leu Ala Glu Arg Gln Leu Gln Val Gln
        115                 120                 125

Trp Glu Pro Pro Gly Ser Trp Pro Phe Pro Glu Ile Phe Ser Leu Lys
130                 135                 140

Tyr Trp Ile Arg Tyr Lys Arg Gln Gly Ala Ala Arg Phe His Arg Val
145                 150                 155                 160

Gly Pro Ile Glu Ala Thr Ser Phe Ile Leu Arg Ala Val Arg Pro Arg
                165                 170                 175

Ala Arg Tyr Tyr Val Gln Val Ala Ala Gln Asp Leu Thr Asp Tyr Gly
            180                 185                 190

Glu Leu Ser Asp Trp Ser Leu Pro Ala Thr Ala Thr Met Ser Leu Gly
        195                 200                 205

Lys
```

-continued

<210> SEQ ID NO 22
<211> LENGTH: 1043
<212> TYPE: PRT
<213> ORGANISM: Artificial Sequence
<220> FEATURE:
<223> OTHER INFORMATION: Synthetic Sequence

<400> SEQUENCE: 22

```
Glu Leu Leu Asp Pro Cys Gly Tyr Ile Ser Pro Glu Ser Pro Val Val
1               5                   10                  15

Gln Leu His Ser Asn Phe Thr Ala Val Cys Val Leu Lys Glu Lys Cys
            20                  25                  30

Met Asp Tyr Phe His Val Asn Ala Asn Tyr Ile Val Trp Lys Thr Asn
        35                  40                  45

His Phe Thr Ile Pro Lys Glu Gln Tyr Thr Ile Ile Asn Arg Thr Ala
    50                  55                  60

Ser Ser Val Thr Phe Thr Asp Ile Ala Ser Leu Asn Ile Gln Leu Thr
65                  70                  75                  80

Cys Asn Ile Leu Thr Phe Gly Gln Leu Glu Gln Asn Val Tyr Gly Ile
                85                  90                  95

Thr Ile Ile Ser Gly Leu Pro Pro Glu Lys Pro Lys Asn Leu Ser Cys
            100                 105                 110

Ile Val Asn Glu Gly Lys Lys Met Arg Cys Glu Trp Asp Gly Gly Arg
        115                 120                 125

Glu Thr His Leu Glu Thr Asn Phe Thr Leu Lys Ser Glu Trp Ala Thr
    130                 135                 140

His Lys Phe Ala Asp Cys Lys Ala Lys Arg Asp Thr Pro Thr Ser Cys
145                 150                 155                 160

Thr Val Asp Tyr Ser Thr Val Tyr Phe Val Asn Ile Glu Val Trp Val
                165                 170                 175

Glu Ala Glu Asn Ala Leu Gly Lys Val Thr Ser Asp His Ile Asn Phe
            180                 185                 190

Asp Pro Val Tyr Lys Val Lys Pro Asn Pro Pro His Asn Leu Ser Val
        195                 200                 205

Ile Asn Ser Glu Glu Leu Ser Ser Ile Leu Lys Leu Thr Trp Thr Asn
    210                 215                 220

Pro Ser Ile Lys Ser Val Ile Ile Leu Lys Tyr Asn Ile Gln Tyr Arg
225                 230                 235                 240

Thr Lys Asp Ala Ser Thr Trp Ser Gln Ile Pro Pro Glu Asp Thr Ala
                245                 250                 255

Ser Thr Arg Ser Ser Phe Thr Val Gln Asp Leu Lys Pro Phe Thr Glu
            260                 265                 270

Tyr Val Phe Arg Ile Arg Cys Met Lys Glu Asp Gly Lys Gly Tyr Trp
        275                 280                 285

Ser Asp Trp Ser Glu Glu Ala Ser Gly Ile Thr Tyr Glu Asp Arg Pro
    290                 295                 300

Ser Lys Ala Pro Ser Phe Trp Tyr Lys Ile Asp Pro Ser His Thr Gln
305                 310                 315                 320

Gly Tyr Arg Thr Val Gln Leu Val Trp Lys Thr Leu Pro Pro Phe Glu
                325                 330                 335

Ala Asn Gly Lys Ile Leu Asp Tyr Glu Val Thr Leu Thr Arg Trp Lys
            340                 345                 350

Ser His Leu Gln Asn Tyr Thr Val Asn Ala Thr Lys Leu Thr Val Asn
        355                 360                 365

Leu Thr Asn Asp Arg Tyr Leu Ala Thr Leu Thr Val Arg Asn Leu Val
```

```
                370             375             380
Gly Lys Ser Asp Ala Ala Val Leu Thr Ile Pro Ala Cys Asp Phe Gln
385             390             395             400

Ala Thr His Pro Val Met Asp Leu Lys Ala Phe Pro Lys Asp Asn Met
                405             410             415

Leu Trp Val Glu Trp Thr Thr Pro Arg Glu Ser Val Lys Lys Tyr Ile
                420             425             430

Leu Glu Trp Cys Val Leu Ser Asp Lys Ala Pro Cys Ile Thr Asp Trp
                435             440             445

Gln Gln Glu Asp Gly Thr Val His Arg Thr Tyr Leu Arg Gly Asn Leu
                450             455             460

Ala Glu Ser Lys Cys Tyr Leu Ile Thr Val Thr Pro Val Tyr Ala Asp
465             470             475             480

Gly Pro Gly Ser Pro Glu Ser Ile Lys Ala Tyr Leu Lys Gln Ala Pro
                485             490             495

Pro Ser Lys Gly Pro Thr Val Arg Thr Lys Lys Val Gly Lys Asn Glu
                500             505             510

Ala Val Leu Glu Trp Asp Gln Leu Pro Val Asp Val Gln Asn Gly Phe
                515             520             525

Ile Arg Asn Tyr Thr Ile Phe Tyr Arg Thr Ile Ile Gly Asn Glu Thr
                530             535             540

Ala Val Asn Val Asp Ser Ser His Thr Glu Tyr Thr Leu Ser Ser Leu
545             550             555             560

Thr Ser Asp Thr Leu Tyr Met Val Arg Met Ala Ala Tyr Thr Asp Glu
                565             570             575

Gly Gly Lys Asp Gly Pro Glu Phe Thr Phe Thr Thr Pro Lys Phe Ala
                580             585             590

Gln Gly Glu Ile Glu Gly Ser Gly Ser Arg Lys Gly Gly Lys Arg Gly
                595             600             605

Ser Lys Tyr Gly Pro Pro Cys Pro Pro Cys Pro Ala Pro Glu Phe Leu
                610             615             620

Gly Gly Pro Ser Val Phe Leu Phe Pro Pro Lys Pro Lys Asp Gln Leu
625             630             635             640

Met Ile Ser Arg Thr Pro Glu Val Thr Cys Val Val Val Asp Val Ser
                645             650             655

Gln Glu Asp Pro Glu Val Gln Phe Asn Trp Tyr Val Asp Gly Val Glu
                660             665             670

Val His Asn Ala Lys Thr Lys Pro Arg Glu Glu Gln Phe Asn Ser Thr
                675             680             685

Tyr Arg Val Val Ser Val Leu Thr Val Leu His Gln Asp Trp Leu Ser
                690             695             700

Gly Lys Glu Tyr Lys Cys Lys Val Ser Ser Lys Gly Leu Pro Ser Ser
705             710             715             720

Ile Glu Lys Thr Ile Ser Asn Ala Thr Gly Gln Pro Arg Glu Pro Gln
                725             730             735

Val Tyr Thr Leu Pro Pro Ser Gln Glu Glu Met Thr Lys Asn Gln Val
                740             745             750

Ser Leu Thr Cys Leu Val Lys Gly Phe Tyr Pro Ser Asp Ile Ala Val
                755             760             765

Glu Trp Glu Ser Asn Gly Gln Pro Glu Asn Asn Tyr Lys Thr Thr Pro
                770             775             780

Pro Val Leu Asp Ser Asp Gly Ser Phe Phe Leu Tyr Ser Arg Leu Thr
785             790             795             800
```

-continued

Val Asp Lys Ser Arg Trp Gln Glu Gly Asn Val Phe Ser Cys Ser Val
            805                 810                 815

Leu His Glu Ala Leu His Asn His Tyr Thr Gln Lys Ser Leu Ser Leu
        820                 825                 830

Ser Leu Gly Lys Asp Glu Gly Glu Asp Gly Ser Gly Ser Arg Asn
        835                 840                 845

Leu Pro Val Ala Thr Pro Asp Pro Gly Met Phe Pro Cys Leu His His
        850                 855                 860

Ser Gln Asn Leu Leu Arg Ala Val Ser Asn Met Leu Gln Lys Ala Arg
865                 870                 875                 880

Gln Thr Leu Glu Phe Tyr Pro Cys Thr Ser Glu Glu Ile Asp His Glu
                885                 890                 895

Asp Ile Thr Lys Asp Lys Thr Ser Thr Val Glu Ala Cys Leu Pro Leu
            900                 905                 910

Glu Leu Thr Lys Asn Glu Ser Cys Leu Asn Ser Arg Glu Thr Ser Phe
        915                 920                 925

Ile Thr Asn Gly Ser Cys Leu Ala Ser Arg Lys Thr Ser Phe Met Met
    930                 935                 940

Ala Leu Cys Leu Ser Ser Ile Tyr Glu Asp Leu Lys Met Tyr Gln Val
945                 950                 955                 960

Glu Phe Lys Thr Met Asn Ala Lys Leu Leu Met Asp Pro Lys Arg Gln
                965                 970                 975

Ile Phe Leu Asp Gln Asn Met Leu Ala Val Ile Asp Glu Leu Met Gln
            980                 985                 990

Ala Leu Asn Phe Asn Ser Glu Thr Val Pro Gln Lys Ser Ser Leu Glu
        995                 1000                1005

Glu Pro Asp Phe Tyr Lys Thr Lys Ile Lys Leu Cys Ile Leu Leu
    1010                1015                1020

His Ala Phe Arg Ile Arg Ala Val Thr Ile Asp Arg Val Met Ser
    1025                1030                1035

Tyr Leu Asn Ala Ser
    1040

<210> SEQ ID NO 23
<211> LENGTH: 804
<212> TYPE: PRT
<213> ORGANISM: Artificial Sequence
<220> FEATURE:
<223> OTHER INFORMATION: Synthetic Sequence

<400> SEQUENCE: 23

Leu Ala Pro Arg Arg Cys Pro Ala Gln Glu Val Ala Arg Gly Val Leu
1               5                   10                  15

Thr Ser Leu Pro Gly Asp Ser Val Thr Leu Thr Cys Pro Gly Val Glu
            20                  25                  30

Pro Glu Asp Asn Ala Thr Val His Trp Val Leu Arg Lys Pro Ala Ala
        35                  40                  45

Gly Ser His Pro Ser Arg Trp Ala Gly Met Gly Arg Arg Leu Leu Leu
    50                  55                  60

Arg Ser Val Gln Leu His Asp Ser Gly Asn Tyr Ser Cys Tyr Arg Ala
65                  70                  75                  80

Gly Arg Pro Ala Gly Thr Val His Leu Leu Val Asp Val Pro Pro Glu
                85                  90                  95

Glu Pro Gln Leu Ser Cys Phe Arg Lys Ser Pro Leu Ser Asn Val Val
            100                 105                 110

```
Cys Glu Trp Gly Pro Arg Ser Thr Pro Ser Leu Thr Thr Lys Ala Val
    115                 120                 125

Leu Leu Val Arg Lys Phe Gln Asn Ser Pro Ala Glu Asp Phe Gln Glu
130                 135                 140

Pro Cys Gln Tyr Ser Gln Glu Ser Gln Lys Phe Ser Cys Gln Leu Ala
145                 150                 155                 160

Val Pro Glu Gly Asp Ser Ser Phe Tyr Ile Val Ser Met Cys Val Ala
                165                 170                 175

Ser Ser Val Gly Ser Lys Phe Ser Lys Thr Gln Thr Phe Gln Gly Cys
                180                 185                 190

Gly Ile Leu Gln Pro Asp Pro Ala Asn Ile Thr Val Thr Ala Val
    195                 200                 205

Ala Arg Asn Pro Arg Trp Leu Ser Val Thr Trp Gln Asp Pro His Ser
    210                 215                 220

Trp Asn Ser Ser Phe Tyr Arg Leu Arg Phe Glu Leu Arg Tyr Arg Ala
225                 230                 235                 240

Glu Arg Ser Lys Thr Phe Thr Thr Trp Met Val Lys Asp Leu Gln His
                245                 250                 255

His Cys Val Ile His Asp Ala Trp Ser Gly Leu Arg His Val Val Gln
                260                 265                 270

Leu Arg Ala Gln Glu Glu Phe Gly Gln Gly Glu Trp Ser Glu Trp Ser
    275                 280                 285

Pro Glu Ala Met Gly Thr Pro Trp Thr Glu Ser Arg Ser Pro Pro Ala
    290                 295                 300

Glu Asn Glu Val Ser Thr Pro Met Gln Ala Leu Thr Thr Asn Lys Asp
305                 310                 315                 320

Asp Asp Asn Ile Leu Phe Arg Asp Ser Ala Asn Ala Thr Ser Leu Pro
                325                 330                 335

Val Gln Asp Ser Ser Ser Val Pro Leu Pro Gly Ser Gly Ser Asp Glu
                340                 345                 350

Gly Gly Glu Asp Gly Ser Lys Tyr Gly Pro Pro Cys Pro Cys Pro
    355                 360                 365

Ala Pro Glu Phe Leu Gly Gly Pro Ser Val Phe Leu Phe Pro Pro Lys
    370                 375                 380

Pro Lys Asp Gln Leu Met Ile Ser Arg Thr Pro Glu Val Thr Cys Val
385                 390                 395                 400

Val Val Asp Val Ser Gln Glu Asp Pro Glu Val Gln Phe Asn Trp Tyr
                405                 410                 415

Val Asp Gly Val Glu Val His Asn Ala Lys Thr Lys Pro Arg Glu Glu
                420                 425                 430

Gln Phe Asn Ser Thr Tyr Arg Val Val Ser Val Leu Thr Val Leu His
    435                 440                 445

Gln Asp Trp Leu Ser Gly Lys Glu Tyr Lys Cys Lys Val Ser Ser Lys
450                 455                 460

Gly Leu Pro Ser Ser Ile Glu Lys Thr Ile Ser Asn Ala Thr Gly Gln
465                 470                 475                 480

Pro Arg Glu Pro Gln Val Tyr Thr Leu Pro Pro Ser Gln Glu Met
                485                 490                 495

Thr Lys Asn Gln Val Ser Leu Thr Cys Leu Val Lys Gly Phe Tyr Pro
                500                 505                 510

Ser Asp Ile Ala Val Glu Trp Glu Ser Asn Gly Gln Pro Glu Asn Asn
                515                 520                 525
```

-continued

```
Tyr Lys Thr Thr Pro Pro Val Leu Asp Ser Asp Gly Ser Phe Phe Leu
    530                 535                 540

Tyr Ser Arg Leu Thr Val Asp Lys Ser Arg Trp Gln Glu Gly Asn Val
545                 550                 555                 560

Phe Ser Cys Ser Val Leu His Glu Ala Leu His Asn His Tyr Thr Gln
                565                 570                 575

Lys Ser Leu Ser Leu Ser Leu Gly Lys Arg Lys Gly Lys Arg Gly
            580                 585                 590

Ser Gly Ser Arg Lys Gly Pro Pro Ala Ala Leu Thr Leu Pro Arg Val
            595                 600                 605

Gln Cys Arg Ala Ser Arg Tyr Pro Ile Ala Val Asp Cys Ser Trp Thr
610                 615                 620

Leu Pro Pro Ala Pro Asn Ser Thr Ser Pro Val Ser Phe Ile Ala Thr
625                 630                 635                 640

Tyr Arg Leu Gly Met Ala Ala Arg Gly His Ser Trp Pro Cys Leu Gln
                645                 650                 655

Gln Thr Pro Thr Ser Thr Ser Cys Thr Ile Thr Asp Val Gln Leu Phe
            660                 665                 670

Ser Met Ala Pro Tyr Val Leu Asn Val Thr Ala Val His Pro Trp Gly
            675                 680                 685

Ser Ser Ser Ser Phe Val Pro Phe Ile Thr Glu His Ile Ile Lys Pro
690                 695                 700

Asp Pro Pro Glu Gly Val Arg Leu Ser Pro Leu Ala Glu Arg Gln Leu
705                 710                 715                 720

Gln Val Gln Trp Glu Pro Pro Gly Ser Trp Pro Phe Pro Glu Ile Phe
                725                 730                 735

Ser Leu Lys Tyr Trp Ile Arg Tyr Lys Arg Gln Gly Ala Ala Arg Phe
            740                 745                 750

His Arg Val Gly Pro Ile Glu Ala Thr Ser Phe Ile Leu Arg Ala Val
            755                 760                 765

Arg Pro Arg Ala Arg Tyr Tyr Val Gln Val Ala Ala Gln Asp Leu Thr
770                 775                 780

Asp Tyr Gly Glu Leu Ser Asp Trp Ser Leu Pro Ala Thr Ala Thr Met
785                 790                 795                 800

Ser Leu Gly Lys
```

```
<210> SEQ ID NO 24
<211> LENGTH: 232
<212> TYPE: PRT
<213> ORGANISM: Artificial Sequence
<220> FEATURE:
<223> OTHER INFORMATION: Synthetic Polypeptide
<220> FEATURE:
<221> NAME/KEY: LALA
<222> LOCATION: (19)..(20)
<223> OTHER INFORMATION: L234A and L235A
<220> FEATURE:
<221> NAME/KEY: M252Y
<222> LOCATION: (37)..(37)
<220> FEATURE:
<221> NAME/KEY: S254T
<222> LOCATION: (39)..(39)
<220> FEATURE:
<221> NAME/KEY: T256E
<222> LOCATION: (41)..(41)
<220> FEATURE:
<221> NAME/KEY: T-Y
<222> LOCATION: (151)..(151)
<223> OTHER INFORMATION: Knob mutation
<220> FEATURE:
<221> NAME/KEY: T-Y
```

<222> LOCATION: (192)..(192)
<223> OTHER INFORMATION: Knob mutation

<400> SEQUENCE: 24

```
Glu Pro Lys Ser Cys Asp Lys Thr His Thr Cys Pro Pro Cys Pro Ala
1               5                   10                  15

Pro Glu Ala Ala Gly Gly Pro Ser Val Phe Leu Phe Pro Pro Lys Pro
            20                  25                  30

Lys Asp Thr Leu Tyr Ile Thr Arg Glu Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
130                 135                 140

Lys Asn Gln Val Ser Leu Tyr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
210                 215                 220

Ser Leu Ser Leu Ser Pro Gly Lys
225                 230
```

<210> SEQ ID NO 25
<211> LENGTH: 232
<212> TYPE: PRT
<213> ORGANISM: Artificial Sequence
<220> FEATURE:
<223> OTHER INFORMATION: Synthetic Polypeptide
<220> FEATURE:
<221> NAME/KEY: LALA
<222> LOCATION: (19)..(20)
<223> OTHER INFORMATION: L234A and L235A
<220> FEATURE:
<221> NAME/KEY: M252Y
<222> LOCATION: (37)..(37)
<220> FEATURE:
<221> NAME/KEY: S254T
<222> LOCATION: (39)..(39)
<220> FEATURE:
<221> NAME/KEY: T256E
<222> LOCATION: (41)..(41)
<220> FEATURE:
<221> NAME/KEY: Y-T
<222> LOCATION: (151)..(151)
<223> OTHER INFORMATION: Hole Mutation
<220> FEATURE:
<221> NAME/KEY: Y-T
<222> LOCATION: (192)..(192)
<223> OTHER INFORMATION: Hole Mutation -continued

<400> SEQUENCE: 25

Glu Pro Lys Ser Cys Asp Lys Thr His Thr Cys Pro Pro Cys Pro Ala
1               5                   10                  15

Pro Glu Ala Ala Gly Gly Pro Ser Val Phe Leu Phe Pro Pro Lys Pro
            20                  25                  30

Lys Asp Thr Leu Tyr Ile Thr Arg Glu Pro Glu Val Thr Cys Val Val
        35                  40                  45

Val Asp Val Ser His Glu Asp Pro Glu Val Lys Phe Asn Trp Tyr Val
50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Thr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 26
<211> LENGTH: 213
<212> TYPE: PRT
<213> ORGANISM: Artificial Sequence
<220> FEATURE:
<223> OTHER INFORMATION: Synthetic Polypeptide

<400> SEQUENCE: 26

Cys Pro Asp Leu Val Cys Tyr Thr Asp Tyr Leu Gln Thr Val Ile Cys
1               5                   10                  15

Ile Leu Glu Met Trp Asn Leu His Pro Ser Thr Leu Thr Leu Thr Trp
            20                  25                  30

Gln Asp Gln Tyr Glu Glu Leu Lys Asp Glu Ala Thr Ser Cys Ser Leu
        35                  40                  45

His Arg Ser Ala His Asn Ala Thr His Ala Thr Tyr Thr Cys His Met
50                  55                  60

Asp Val Phe His Phe Met Ala Asp Ile Phe Ser Val Asn Ile Thr
65                  70                  75                  80

Asp Gln Ser Gly Asn Tyr Ser Gln Glu Cys Gly Ser Phe Leu Leu Ala
                85                  90                  95

Glu Ser Ile Lys Pro Ala Pro Pro Phe Asn Val Thr Val Thr Phe Ser
            100                 105                 110

Gly Gln Tyr Asn Ile Ser Trp Arg Ser Asp Tyr Glu Asp Pro Ala Phe

```
              115                 120                 125
Tyr Met Leu Lys Gly Lys Leu Gln Tyr Glu Leu Gln Tyr Arg Asn Arg
    130                 135                 140

Gly Asp Pro Trp Ala Val Ser Pro Arg Arg Lys Leu Ile Ser Val Asp
145                 150                 155                 160

Ser Arg Ser Val Ser Leu Leu Pro Leu Glu Phe Arg Lys Asp Ser Ser
                165                 170                 175

Tyr Glu Leu Gln Val Arg Ala Gly Pro Met Pro Gly Ser Ser Tyr Gln
            180                 185                 190

Gly Thr Trp Ser Glu Trp Ser Asp Pro Val Ile Phe Gln Thr Gln Ser
                195                 200                 205

Glu Glu Leu Lys Glu
    210

<210> SEQ ID NO 27
<211> LENGTH: 240
<212> TYPE: PRT
<213> ORGANISM: Artificial Sequence
<220> FEATURE:
<223> OTHER INFORMATION: Synthetic Polypeptide

<400> SEQUENCE: 27

Leu Asn Thr Thr Ile Leu Thr Pro Asn Gly Asn Glu Asp Thr Thr Ala
1               5                   10                  15

Asp Phe Phe Leu Thr Thr Met Pro Thr Asp Ser Leu Ser Val Ser Thr
                20                  25                  30

Leu Pro Leu Pro Glu Val Gln Cys Phe Val Phe Asn Val Glu Tyr Met
                35                  40                  45

Asn Cys Thr Trp Asn Ser Ser Ser Glu Pro Gln Pro Thr Asn Leu Thr
 50                  55                  60

Leu His Tyr Trp Tyr Lys Asn Ser Asp Asn Asp Lys Val Gln Lys Cys
 65                  70                  75                  80

Ser His Tyr Leu Phe Ser Glu Glu Ile Thr Ser Gly Cys Gln Leu Gln
                 85                  90                  95

Lys Lys Glu Ile His Leu Tyr Gln Thr Phe Val Val Gln Leu Gln Asp
                100                 105                 110

Pro Arg Glu Pro Arg Arg Gln Ala Thr Gln Met Leu Lys Leu Gln Asn
            115                 120                 125

Leu Val Ile Pro Trp Ala Pro Glu Asn Leu Thr Leu His Lys Leu Ser
    130                 135                 140

Glu Ser Gln Leu Glu Leu Asn Trp Asn Asn Arg Phe Leu Asn His Cys
145                 150                 155                 160

Leu Glu His Leu Val Gln Tyr Arg Thr Asp Trp Asp His Ser Trp Thr
                165                 170                 175

Glu Gln Ser Val Asp Tyr Arg His Lys Phe Ser Leu Pro Ser Val Asp
            180                 185                 190

Gly Gln Lys Arg Tyr Thr Phe Arg Val Arg Ser Arg Phe Asn Pro Leu
        195                 200                 205

Cys Gly Ser Ala Gln His Trp Ser Glu Trp Ser His Pro Ile His Trp
    210                 215                 220

Gly Ser Asn Thr Ser Lys Glu Asn Pro Phe Leu Phe Ala Leu Glu Ala
225                 230                 235                 240

<210> SEQ ID NO 28
<211> LENGTH: 659
<212> TYPE: PRT
```

<213> ORGANISM: Artificial Sequence
<220> FEATURE:
<223> OTHER INFORMATION: Synthetic Polypeptide

<400> SEQUENCE: 28

```
Cys Pro Asp Leu Val Cys Tyr Thr Asp Tyr Leu Gln Thr Val Ile Cys
1               5                   10                  15

Ile Leu Glu Met Trp Asn Leu His Pro Ser Thr Leu Thr Leu Thr Trp
            20                  25                  30

Gln Asp Gln Tyr Glu Glu Leu Lys Asp Glu Ala Thr Ser Cys Ser Leu
        35                  40                  45

His Arg Ser Ala His Asn Ala Thr His Ala Thr Tyr Thr Cys His Met
    50                  55                  60

Asp Val Phe His Phe Met Ala Asp Asp Ile Phe Ser Val Asn Ile Thr
65              70                  75                  80

Asp Gln Ser Gly Asn Tyr Ser Gln Glu Cys Gly Ser Phe Leu Leu Ala
                85                  90                  95

Glu Ser Ile Lys Pro Ala Pro Pro Phe Asn Val Thr Val Thr Phe Ser
            100                 105                 110

Gly Gln Tyr Asn Ile Ser Trp Arg Ser Asp Tyr Glu Asp Pro Ala Phe
        115                 120                 125

Tyr Met Leu Lys Gly Lys Leu Gln Tyr Glu Leu Gln Tyr Arg Asn Arg
    130                 135                 140

Gly Asp Pro Trp Ala Val Ser Pro Arg Arg Lys Leu Ile Ser Val Asp
145                 150                 155                 160

Ser Arg Ser Val Ser Leu Leu Pro Leu Glu Phe Arg Lys Asp Ser Ser
                165                 170                 175

Tyr Glu Leu Gln Val Arg Ala Gly Pro Met Pro Gly Ser Ser Tyr Gln
            180                 185                 190

Gly Thr Trp Ser Glu Trp Ser Asp Pro Val Ile Phe Gln Thr Gln Ser
        195                 200                 205

Glu Glu Leu Lys Glu Gly Ser Gly Ser Arg Lys Gly Gly Lys Arg Gly
    210                 215                 220

Ser Lys Tyr Gly Pro Pro Cys Pro Pro Cys Pro Ala Pro Glu Phe Leu
225                 230                 235                 240

Gly Gly Pro Ser Val Phe Leu Phe Pro Pro Lys Pro Lys Asp Gln Leu
                245                 250                 255

Met Ile Ser Arg Thr Pro Glu Val Thr Cys Val Val Val Asp Val Ser
            260                 265                 270

Gln Glu Asp Pro Glu Val Gln Phe Asn Trp Tyr Val Asp Gly Val Glu
        275                 280                 285

Val His Asn Ala Lys Thr Lys Pro Arg Glu Glu Gln Phe Asn Ser Thr
    290                 295                 300

Tyr Arg Val Val Ser Val Leu Thr Val Leu His Gln Asp Trp Leu Ser
305                 310                 315                 320

Gly Lys Glu Tyr Lys Cys Lys Val Ser Ser Lys Gly Leu Pro Ser Ser
                325                 330                 335

Ile Glu Lys Thr Ile Ser Asn Ala Thr Gly Gln Pro Arg Glu Pro Gln
            340                 345                 350

Val Tyr Thr Leu Pro Pro Ser Gln Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
```

```
                385                 390                 395                 400
Pro Val Leu Asp Ser Asp Gly Ser Phe Phe Leu Tyr Ser Arg Leu Thr
                    405                 410                 415

Val Asp Lys Ser Arg Trp Gln Glu Gly Asn Val Phe Ser Cys Ser Val
                    420                 425                 430

Leu His Glu Ala Leu His Asn His Tyr Thr Gln Lys Ser Leu Ser Leu
                    435                 440                 445

Ser Leu Gly Lys Asp Glu Gly Glu Asp Gly Ser Gly Ser Arg Asn
                    450                 455                 460

Leu Pro Val Ala Thr Pro Asp Pro Gly Met Phe Pro Cys Leu His His
465                 470                 475                 480

Ser Gln Asn Leu Leu Arg Ala Val Ser Asn Met Leu Gln Lys Ala Arg
                    485                 490                 495

Gln Thr Leu Glu Phe Tyr Pro Cys Thr Ser Glu Glu Ile Asp His Glu
                    500                 505                 510

Asp Ile Thr Lys Asp Lys Thr Ser Thr Val Glu Ala Cys Leu Pro Leu
                    515                 520                 525

Glu Leu Thr Lys Asn Glu Ser Cys Leu Asn Ser Arg Glu Thr Ser Phe
                    530                 535                 540

Ile Thr Asn Gly Ser Cys Leu Ala Ser Arg Lys Thr Ser Phe Met Met
545                 550                 555                 560

Ala Leu Cys Leu Ser Ser Ile Tyr Glu Asp Leu Lys Met Tyr Gln Val
                    565                 570                 575

Glu Phe Lys Thr Met Asn Ala Lys Leu Leu Met Asp Pro Lys Arg Gln
                    580                 585                 590

Ile Phe Leu Asp Gln Asn Met Leu Ala Val Ile Asp Glu Leu Met Gln
                    595                 600                 605

Ala Leu Asn Phe Asn Ser Glu Thr Val Pro Gln Lys Ser Ser Leu Glu
                    610                 615                 620

Glu Pro Asp Phe Tyr Lys Thr Lys Ile Lys Leu Cys Ile Leu Leu His
625                 630                 635                 640

Ala Phe Arg Ile Arg Ala Val Thr Ile Asp Arg Val Met Ser Tyr Leu
                    645                 650                 655

Asn Ala Ser

<210> SEQ ID NO 29
<211> LENGTH: 698
<212> TYPE: PRT
<213> ORGANISM: Artificial Sequence
<220> FEATURE:
<223> OTHER INFORMATION: Synthetic Polypeptide

<400> SEQUENCE: 29

Leu Asn Thr Thr Ile Leu Thr Pro Asn Gly Asn Glu Asp Thr Thr Ala
1               5                   10                  15

Asp Phe Phe Leu Thr Thr Met Pro Thr Asp Ser Leu Ser Val Ser Thr
                20                  25                  30

Leu Pro Leu Pro Glu Val Gln Cys Phe Val Phe Asn Val Glu Tyr Met
                35                  40                  45

Asn Cys Thr Trp Asn Ser Ser Glu Pro Gln Pro Thr Asn Leu Thr
                50                  55                  60

Leu His Tyr Trp Tyr Lys Asn Ser Asp Asn Asp Lys Val Gln Lys Cys
65                  70                  75                  80

Ser His Tyr Leu Phe Ser Glu Glu Ile Thr Ser Gly Cys Gln Leu Gln
                85                  90                  95
```

-continued

```
Lys Lys Glu Ile His Leu Tyr Gln Thr Phe Val Val Gln Leu Gln Asp
            100                 105                 110

Pro Arg Glu Pro Arg Gln Ala Thr Gln Met Leu Lys Leu Gln Asn
        115                 120                 125

Leu Val Ile Pro Trp Ala Pro Glu Asn Leu Thr Leu His Lys Leu Ser
130                 135                 140

Glu Ser Gln Leu Glu Leu Asn Trp Asn Asn Arg Phe Leu Asn His Cys
145                 150                 155                 160

Leu Glu His Leu Val Gln Tyr Arg Thr Asp Trp Asp His Ser Trp Thr
                165                 170                 175

Glu Gln Ser Val Asp Tyr Arg His Lys Phe Ser Leu Pro Ser Val Asp
            180                 185                 190

Gly Gln Lys Arg Tyr Thr Phe Arg Val Arg Ser Arg Phe Asn Pro Leu
        195                 200                 205

Cys Gly Ser Ala Gln His Trp Ser Glu Trp Ser His Pro Ile His Trp
    210                 215                 220

Gly Ser Asn Thr Ser Lys Glu Asn Pro Phe Leu Phe Ala Leu Glu Ala
225                 230                 235                 240

Gly Ser Gly Ser Asp Glu Gly Glu Asp Gly Ser Lys Tyr Gly Pro
                245                 250                 255

Pro Cys Pro Pro Cys Pro Ala Pro Glu Phe Leu Gly Gly Pro Ser Val
            260                 265                 270

Phe Leu Phe Pro Pro Lys Pro Lys Asp Gln Leu Met Ile Ser Arg Thr
        275                 280                 285

Pro Glu Val Thr Cys Val Val Val Asp Val Ser Gln Glu Asp Pro Glu
    290                 295                 300

Val Gln Phe Asn Trp Tyr Val Asp Gly Val Glu Val His Asn Ala Lys
305                 310                 315                 320

Thr Lys Pro Arg Glu Glu Gln Phe Asn Ser Thr Tyr Arg Val Val Ser
                325                 330                 335

Val Leu Thr Val Leu His Gln Asp Trp Leu Ser Gly Lys Glu Tyr Lys
            340                 345                 350

Cys Lys Val Ser Ser Lys Gly Leu Pro Ser Ser Ile Glu Lys Thr Ile
        355                 360                 365

Ser Asn Ala Thr Gly Gln Pro Arg Glu Pro Gln Val Tyr Thr Leu Pro
    370                 375                 380

Pro Ser Gln Glu Glu Met Thr Lys Asn Gln Val Ser Leu Thr Cys Leu
385                 390                 395                 400

Val Lys Gly Phe Tyr Pro Ser Asp Ile Ala Val Glu Trp Glu Ser Asn
                405                 410                 415

Gly Gln Pro Glu Asn Asn Tyr Lys Thr Thr Pro Pro Val Leu Asp Ser
            420                 425                 430

Asp Gly Ser Phe Phe Leu Tyr Ser Arg Leu Thr Val Asp Lys Ser Arg
        435                 440                 445

Trp Gln Glu Gly Asn Val Phe Ser Cys Ser Val Leu His Glu Ala Leu
    450                 455                 460

His Asn His Tyr Thr Gln Lys Ser Leu Ser Leu Ser Leu Gly Lys Arg
465                 470                 475                 480

Lys Gly Gly Lys Arg Gly Ser Gly Ser Arg Lys Gly Pro Ala Ala
                485                 490                 495

Leu Thr Leu Pro Arg Val Gln Cys Arg Ala Ser Arg Tyr Pro Ile Ala
            500                 505                 510
```

```
Val Asp Cys Ser Trp Thr Leu Pro Pro Ala Pro Asn Ser Thr Ser Pro
        515                 520                 525

Val Ser Phe Ile Ala Thr Tyr Arg Leu Gly Met Ala Ala Arg Gly His
    530                 535                 540

Ser Trp Pro Cys Leu Gln Gln Thr Pro Thr Ser Thr Ser Cys Thr Ile
545                 550                 555                 560

Thr Asp Val Gln Leu Phe Ser Met Ala Pro Tyr Val Leu Asn Val Thr
                565                 570                 575

Ala Val His Pro Trp Gly Ser Ser Ser Phe Val Pro Phe Ile Thr
            580                 585                 590

Glu His Ile Ile Lys Pro Asp Pro Glu Gly Val Arg Leu Ser Pro
        595                 600                 605

Leu Ala Glu Arg Gln Leu Gln Val Gln Trp Glu Pro Pro Gly Ser Trp
    610                 615                 620

Pro Phe Pro Glu Ile Phe Ser Leu Lys Tyr Trp Ile Arg Tyr Lys Arg
625                 630                 635                 640

Gln Gly Ala Ala Arg Phe His Arg Val Gly Pro Ile Glu Ala Thr Ser
                645                 650                 655

Phe Ile Leu Arg Ala Val Arg Pro Arg Ala Arg Tyr Tyr Val Gln Val
            660                 665                 670

Ala Ala Gln Asp Leu Thr Asp Tyr Gly Glu Leu Ser Asp Trp Ser Leu
        675                 680                 685

Pro Ala Thr Ala Thr Met Ser Leu Gly Lys
    690                 695

<210> SEQ ID NO 30
<211> LENGTH: 228
<212> TYPE: PRT
<213> ORGANISM: Artificial Sequence
<220> FEATURE:
<223> OTHER INFORMATION: Synthetic Polypeptide

<400> SEQUENCE: 30

Glu Met Gly Thr Ala Asp Leu Gly Pro Ser Ser Val Pro Thr Pro Thr
1               5                   10                  15

Asn Val Thr Ile Glu Ser Tyr Asn Met Asn Pro Ile Val Tyr Trp Glu
            20                  25                  30

Tyr Gln Ile Met Pro Gln Val Pro Val Phe Thr Val Glu Val Lys Asn
        35                  40                  45

Tyr Gly Val Lys Asn Ser Glu Trp Ile Asp Ala Cys Ile Asn Ile Ser
    50                  55                  60

His His Tyr Cys Asn Ile Ser Asp His Val Gly Asp Pro Ser Asn Ser
65                  70                  75                  80

Leu Trp Val Arg Val Lys Ala Arg Val Gly Gln Lys Glu Ser Ala Tyr
                85                  90                  95

Ala Lys Ser Glu Glu Phe Ala Val Cys Arg Asp Gly Lys Ile Gly Pro
            100                 105                 110

Pro Lys Leu Asp Ile Arg Lys Glu Glu Lys Gln Ile Met Ile Asp Ile
        115                 120                 125

Phe His Pro Ser Val Phe Val Asn Gly Asp Glu Gln Glu Val Asp Tyr
    130                 135                 140

Asp Pro Glu Thr Thr Cys Tyr Ile Arg Val Tyr Asn Val Tyr Val Arg
145                 150                 155                 160

Met Asn Gly Ser Glu Ile Gln Tyr Lys Ile Leu Thr Gln Lys Glu Asp
                165                 170                 175
```

Asp Cys Asp Glu Ile Gln Cys Gln Leu Ala Ile Pro Val Ser Ser Leu
            180                 185                 190

Asn Ser Gln Tyr Cys Val Ser Ala Glu Gly Val Leu His Val Trp Gly
        195                 200                 205

Val Thr Thr Glu Lys Ser Lys Glu Val Cys Ile Thr Ile Phe Asn Ser
    210                 215                 220

Ser Ile Lys Gly
225

<210> SEQ ID NO 31
<211> LENGTH: 220
<212> TYPE: PRT
<213> ORGANISM: Artificial Sequence
<220> FEATURE:
<223> OTHER INFORMATION: Synthetic Polypeptide

<400> SEQUENCE: 31

Ser Gln Leu Pro Ala Pro Gln His Pro Lys Ile Arg Leu Tyr Asn Ala
1               5                   10                  15

Glu Gln Val Leu Ser Trp Glu Pro Val Ala Leu Ser Asn Ser Thr Arg
            20                  25                  30

Pro Val Val Tyr Gln Val Gln Phe Lys Tyr Thr Asp Ser Lys Trp Phe
        35                  40                  45

Thr Ala Asp Ile Met Ser Ile Gly Val Asn Cys Thr Gln Ile Thr Ala
    50                  55                  60

Thr Glu Cys Asp Phe Thr Ala Ala Ser Pro Ser Ala Gly Phe Pro Met
65                  70                  75                  80

Asp Phe Asn Val Thr Leu Arg Leu Arg Ala Glu Leu Gly Ala Leu His
                85                  90                  95

Ser Ala Trp Val Thr Met Pro Trp Phe Gln His Tyr Arg Asn Val Thr
            100                 105                 110

Val Gly Pro Pro Glu Asn Ile Glu Val Thr Pro Gly Glu Gly Ser Leu
        115                 120                 125

Ile Ile Arg Phe Ser Ser Pro Phe Asp Ile Ala Asp Thr Ser Thr Ala
    130                 135                 140

Phe Phe Cys Tyr Tyr Val His Tyr Trp Glu Lys Gly Gly Ile Gln Gln
145                 150                 155                 160

Val Lys Gly Pro Phe Arg Ser Asn Ser Ile Ser Leu Asp Asn Leu Lys
                165                 170                 175

Pro Ser Arg Val Tyr Cys Leu Gln Val Gln Ala Gln Leu Leu Trp Asn
            180                 185                 190

Lys Ser Asn Ile Phe Arg Val Gly His Leu Ser Asn Ile Ser Cys Tyr
        195                 200                 205

Glu Thr Met Ala Asp Ala Ser Thr Glu Leu Gln Gln
    210                 215                 220

<210> SEQ ID NO 32
<211> LENGTH: 674
<212> TYPE: PRT
<213> ORGANISM: Artificial Sequence
<220> FEATURE:
<223> OTHER INFORMATION: Synthetic Polypeptide

<400> SEQUENCE: 32

Glu Met Gly Thr Ala Asp Leu Gly Pro Ser Ser Val Pro Thr Pro Thr
1               5                   10                  15

Asn Val Thr Ile Glu Ser Tyr Asn Met Asn Pro Ile Val Tyr Trp Glu
            20                  25                  30

```
Tyr Gln Ile Met Pro Gln Val Pro Val Phe Thr Val Glu Val Lys Asn
            35                  40                  45

Tyr Gly Val Lys Asn Ser Glu Trp Ile Asp Ala Cys Ile Asn Ile Ser
        50                  55                  60

His His Tyr Cys Asn Ile Ser Asp His Val Gly Asp Pro Ser Asn Ser
65                  70                  75                  80

Leu Trp Val Arg Val Lys Ala Arg Val Gly Gln Lys Glu Ser Ala Tyr
                85                  90                  95

Ala Lys Ser Glu Glu Phe Ala Val Cys Arg Asp Gly Lys Ile Gly Pro
               100                 105                 110

Pro Lys Leu Asp Ile Arg Lys Glu Lys Gln Ile Met Ile Asp Ile
               115                 120                 125

Phe His Pro Ser Val Phe Val Asn Gly Asp Glu Gln Glu Val Asp Tyr
               130                 135                 140

Asp Pro Glu Thr Thr Cys Tyr Ile Arg Val Tyr Asn Val Tyr Val Arg
145                 150                 155                 160

Met Asn Gly Ser Glu Ile Gln Tyr Lys Ile Leu Thr Gln Lys Glu Asp
                165                 170                 175

Asp Cys Asp Glu Ile Gln Cys Gln Leu Ala Ile Pro Val Ser Ser Leu
                180                 185                 190

Asn Ser Gln Tyr Cys Val Ser Ala Glu Gly Val Leu His Val Trp Gly
                195                 200                 205

Val Thr Thr Glu Lys Ser Lys Glu Val Cys Ile Thr Ile Phe Asn Ser
                210                 215                 220

Ser Ile Lys Gly Gly Ser Gly Arg Lys Gly Gly Lys Arg Gly Ser
225                 230                 235                 240

Lys Tyr Gly Pro Pro Cys Pro Pro Cys Pro Ala Pro Glu Phe Leu Gly
                245                 250                 255

Gly Pro Ser Val Phe Leu Phe Pro Pro Lys Pro Lys Asp Gln Leu Met
                260                 265                 270

Ile Ser Arg Thr Pro Glu Val Thr Cys Val Val Val Asp Val Ser Gln
                275                 280                 285

Glu Asp Pro Glu Val Gln Phe Asn Trp Tyr Val Asp Gly Val Glu Val
                290                 295                 300

His Asn Ala Lys Thr Lys Pro Arg Glu Glu Gln Phe Asn Ser Thr Tyr
305                 310                 315                 320

Arg Val Val Ser Val Leu Thr Val Leu His Gln Asp Trp Leu Ser Gly
                325                 330                 335

Lys Glu Tyr Lys Cys Lys Val Ser Ser Lys Gly Leu Pro Ser Ser Ile
                340                 345                 350

Glu Lys Thr Ile Ser Asn Ala Thr Gly Gln Pro Arg Glu Pro Gln Val
                355                 360                 365

Tyr Thr Leu Pro Pro Ser Gln Glu Glu Met Thr Lys Asn Gln Val Ser
                370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Arg Leu Thr Val
                420                 425                 430

Asp Lys Ser Arg Trp Gln Glu Gly Asn Val Phe Ser Cys Ser Val Leu
                435                 440                 445
```

```
His Glu Ala Leu His Asn His Tyr Thr Gln Lys Ser Leu Ser Leu Ser
    450                 455                 460

Leu Gly Lys Asp Glu Gly Glu Asp Gly Ser Gly Ser Arg Asn Leu
465                 470                 475                 480

Pro Val Ala Thr Pro Asp Pro Gly Met Phe Pro Cys Leu His His Ser
                485                 490                 495

Gln Asn Leu Leu Arg Ala Val Ser Asn Met Leu Gln Lys Ala Arg Gln
            500                 505                 510

Thr Leu Glu Phe Tyr Pro Cys Thr Ser Glu Ile Asp His Glu Asp
        515                 520                 525

Ile Thr Lys Asp Lys Thr Ser Thr Val Glu Ala Cys Leu Pro Leu Glu
    530                 535                 540

Leu Thr Lys Asn Glu Ser Cys Leu Asn Ser Arg Glu Thr Ser Phe Ile
545                 550                 555                 560

Thr Asn Gly Ser Cys Leu Ala Ser Arg Lys Thr Ser Phe Met Met Ala
                565                 570                 575

Leu Cys Leu Ser Ser Ile Tyr Glu Asp Leu Lys Met Tyr Gln Val Glu
            580                 585                 590

Phe Lys Thr Met Asn Ala Lys Leu Leu Met Asp Pro Lys Arg Gln Ile
        595                 600                 605

Phe Leu Asp Gln Asn Met Leu Ala Val Ile Asp Glu Leu Met Gln Ala
    610                 615                 620

Leu Asn Phe Asn Ser Glu Thr Val Pro Gln Lys Ser Ser Leu Glu Glu
625                 630                 635                 640

Pro Asp Phe Tyr Lys Thr Lys Ile Lys Leu Cys Ile Leu Leu His Ala
                645                 650                 655

Phe Arg Ile Arg Ala Val Thr Ile Asp Arg Val Met Ser Tyr Leu Asn
            660                 665                 670

Ala Ser

<210> SEQ ID NO 33
<211> LENGTH: 678
<212> TYPE: PRT
<213> ORGANISM: Artificial Sequence
<220> FEATURE:
<223> OTHER INFORMATION: Synthetic Polypeptide

<400> SEQUENCE: 33

Ser Gln Leu Pro Ala Pro Gln His Pro Lys Ile Arg Leu Tyr Asn Ala
1               5                   10                  15

Glu Gln Val Leu Ser Trp Glu Pro Val Ala Leu Ser Asn Ser Thr Arg
                20                  25                  30

Pro Val Val Tyr Gln Val Gln Phe Lys Tyr Thr Asp Ser Lys Trp Phe
            35                  40                  45

Thr Ala Asp Ile Met Ser Ile Gly Val Asn Cys Thr Gln Ile Thr Ala
    50                  55                  60

Thr Glu Cys Asp Phe Thr Ala Ala Ser Pro Ser Ala Gly Phe Pro Met
65                  70                  75                  80

Asp Phe Asn Val Thr Leu Arg Leu Arg Ala Glu Leu Gly Ala Leu His
                85                  90                  95

Ser Ala Trp Val Thr Met Pro Trp Phe Gln His Tyr Arg Asn Val Thr
            100                 105                 110

Val Gly Pro Pro Glu Asn Ile Glu Val Thr Pro Gly Glu Gly Ser Leu
        115                 120                 125

Ile Ile Arg Phe Ser Ser Pro Phe Asp Ile Ala Asp Thr Ser Thr Ala
```

-continued

```
                130                 135                 140
Phe Phe Cys Tyr Tyr Val His Tyr Trp Glu Lys Gly Ile Gln Gln
145                 150                 155                 160

Val Lys Gly Pro Phe Arg Ser Asn Ser Ile Ser Leu Asp Asn Leu Lys
                165                 170                 175

Pro Ser Arg Val Tyr Cys Leu Gln Val Gln Ala Gln Leu Leu Trp Asn
                180                 185                 190

Lys Ser Asn Ile Phe Arg Val Gly His Leu Ser Asn Ile Ser Cys Tyr
                195                 200                 205

Glu Thr Met Ala Asp Ala Ser Thr Glu Leu Gln Gln Gly Ser Gly Ser
210                 215                 220

Asp Glu Gly Gly Glu Asp Gly Ser Lys Tyr Gly Pro Pro Cys Pro Pro
225                 230                 235                 240

Cys Pro Ala Pro Glu Phe Leu Gly Gly Pro Ser Val Phe Leu Phe Pro
                245                 250                 255

Pro Lys Pro Lys Asp Gln Leu Met Ile Ser Arg Thr Pro Glu Val Thr
                260                 265                 270

Cys Val Val Val Asp Val Ser Gln Glu Asp Pro Glu Val Gln Phe Asn
                275                 280                 285

Trp Tyr Val Asp Gly Val Glu Val His Asn Ala Lys Thr Lys Pro Arg
                290                 295                 300

Glu Glu Gln Phe Asn Ser Thr Tyr Arg Val Val Ser Val Leu Thr Val
305                 310                 315                 320

Leu His Gln Asp Trp Leu Ser Gly Lys Glu Tyr Lys Cys Lys Val Ser
                325                 330                 335

Ser Lys Gly Leu Pro Ser Ser Ile Glu Lys Thr Ile Ser Asn Ala Thr
                340                 345                 350

Gly Gln Pro Arg Glu Pro Gln Val Tyr Thr Leu Pro Pro Ser Gln Glu
                355                 360                 365

Glu Met Thr Lys Asn Gln Val Ser Leu Thr Cys Leu Val Lys Gly Phe
                370                 375                 380

Tyr Pro Ser Asp Ile Ala Val Glu Trp Glu Ser Asn Gly Gln Pro Glu
385                 390                 395                 400

Asn Asn Tyr Lys Thr Thr Pro Pro Val Leu Asp Ser Asp Gly Ser Phe
                405                 410                 415

Phe Leu Tyr Ser Arg Leu Thr Val Asp Lys Ser Arg Trp Gln Glu Gly
                420                 425                 430

Asn Val Phe Ser Cys Ser Val Leu His Glu Ala Leu His Asn His Tyr
                435                 440                 445

Thr Gln Lys Ser Leu Ser Leu Ser Leu Gly Lys Arg Lys Gly Gly Lys
                450                 455                 460

Arg Gly Ser Gly Ser Arg Lys Gly Pro Pro Ala Leu Thr Leu Pro
465                 470                 475                 480

Arg Val Gln Cys Arg Ala Ser Arg Tyr Pro Ile Ala Val Asp Cys Ser
                485                 490                 495

Trp Thr Leu Pro Pro Ala Pro Asn Ser Thr Ser Pro Val Ser Phe Ile
                500                 505                 510

Ala Thr Tyr Arg Leu Gly Met Ala Ala Arg Gly His Ser Trp Pro Cys
                515                 520                 525

Leu Gln Gln Thr Pro Thr Ser Thr Ser Cys Thr Ile Thr Asp Val Gln
                530                 535                 540

Leu Phe Ser Met Ala Pro Tyr Val Leu Asn Val Thr Ala Val His Pro
545                 550                 555                 560
```

```
Trp Gly Ser Ser Ser Ser Phe Val Pro Phe Ile Thr Glu His Ile Ile
                565                 570                 575

Lys Pro Asp Pro Pro Glu Gly Val Arg Leu Ser Pro Leu Ala Glu Arg
            580                 585                 590

Gln Leu Gln Val Gln Trp Glu Pro Pro Gly Ser Trp Pro Phe Pro Glu
        595                 600                 605

Ile Phe Ser Leu Lys Tyr Trp Ile Arg Tyr Lys Arg Gln Gly Ala Ala
    610                 615                 620

Arg Phe His Arg Val Gly Pro Ile Glu Ala Thr Ser Phe Ile Leu Arg
625                 630                 635                 640

Ala Val Arg Pro Arg Ala Arg Tyr Tyr Val Gln Val Ala Ala Gln Asp
                645                 650                 655

Leu Thr Asp Tyr Gly Glu Leu Ser Asp Trp Ser Leu Pro Ala Thr Ala
            660                 665                 670

Thr Met Ser Leu Gly Lys
            675

<210> SEQ ID NO 34
<211> LENGTH: 792
<212> TYPE: PRT
<213> ORGANISM: Artificial Sequence
<220> FEATURE:
<223> OTHER INFORMATION: Synthetic Polypeptide

<400> SEQUENCE: 34

Leu Ala Pro Arg Arg Cys Pro Ala Gln Glu Val Ala Arg Gly Val Leu
1               5                   10                  15

Thr Ser Leu Pro Gly Asp Ser Val Thr Leu Thr Cys Pro Gly Val Glu
            20                  25                  30

Pro Glu Asp Asn Ala Thr Val His Trp Val Leu Arg Lys Pro Ala Ala
        35                  40                  45

Gly Ser His Pro Ser Arg Trp Ala Gly Met Gly Arg Arg Leu Leu Leu
    50                  55                  60

Arg Ser Val Gln Leu His Asp Ser Gly Asn Tyr Ser Cys Tyr Arg Ala
65                  70                  75                  80

Gly Arg Pro Ala Gly Thr Val His Leu Leu Val Asp Val Pro Pro Glu
                85                  90                  95

Glu Pro Gln Leu Ser Cys Phe Arg Lys Ser Pro Leu Ser Asn Val Val
            100                 105                 110

Cys Glu Trp Gly Pro Arg Ser Thr Pro Ser Leu Thr Thr Lys Ala Val
        115                 120                 125

Leu Leu Val Arg Lys Phe Gln Asn Ser Pro Ala Glu Asp Phe Gln Glu
    130                 135                 140

Pro Cys Gln Tyr Ser Gln Glu Ser Gln Lys Phe Ser Cys Gln Leu Ala
145                 150                 155                 160

Val Pro Glu Gly Asp Ser Ser Phe Tyr Ile Val Ser Met Cys Val Ala
                165                 170                 175

Ser Ser Val Gly Ser Lys Phe Ser Lys Thr Gln Thr Phe Gln Gly Cys
            180                 185                 190

Gly Ile Leu Gln Pro Asp Pro Ala Asn Ile Thr Val Thr Ala Val
    195                 200                 205

Ala Arg Asn Pro Arg Trp Leu Ser Val Thr Trp Gln Asp Pro His Ser
    210                 215                 220

Trp Asn Ser Ser Phe Tyr Arg Leu Arg Phe Glu Leu Arg Tyr Arg Ala
225                 230                 235                 240
```

-continued

```
Glu Arg Ser Lys Thr Phe Thr Thr Trp Met Val Lys Asp Leu Gln His
            245                 250                 255

His Cys Val Ile His Asp Ala Trp Ser Gly Leu Arg His Val Val Gln
            260                 265                 270

Leu Arg Ala Gln Glu Glu Phe Gly Gln Gly Glu Trp Ser Glu Trp Ser
        275                 280                 285

Pro Glu Ala Met Gly Thr Pro Trp Thr Glu Ser Arg Ser Pro Pro Ala
    290                 295                 300

Glu Asn Glu Val Ser Thr Pro Met Gln Ala Leu Thr Thr Asn Lys Asp
305                 310                 315                 320

Asp Asp Asn Ile Leu Phe Arg Asp Ser Ala Asn Ala Thr Ser Leu Pro
                325                 330                 335

Val Gln Asp Ser Ser Ser Val Pro Leu Pro Gly Ser Gly Ser Arg Lys
            340                 345                 350

Gly Gly Lys Arg Gly Ser Lys Tyr Gly Pro Pro Cys Pro Pro Cys Pro
        355                 360                 365

Ala Pro Glu Phe Leu Gly Gly Pro Ser Val Phe Leu Phe Pro Pro Lys
    370                 375                 380

Pro Lys Asp Gln Leu Met Ile Ser Arg Thr Pro Glu Val Thr Cys Val
385                 390                 395                 400

Val Val Asp Val Ser Gln Glu Asp Pro Glu Val Gln Phe Asn Trp Tyr
                405                 410                 415

Val Asp Gly Val Glu Val His Asn Ala Lys Thr Lys Pro Arg Glu Glu
            420                 425                 430

Gln Phe Asn Ser Thr Tyr Arg Val Val Ser Val Leu Thr Val Leu His
        435                 440                 445

Gln Asp Trp Leu Ser Gly Lys Glu Tyr Lys Cys Lys Val Ser Ser Lys
    450                 455                 460

Gly Leu Pro Ser Ser Ile Glu Lys Thr Ile Ser Asn Ala Thr Gly Gln
465                 470                 475                 480

Pro Arg Glu Pro Gln Val Tyr Thr Leu Pro Pro Ser Gln Glu Glu Met
                485                 490                 495

Thr Lys Asn Gln Val Ser Leu Thr Cys Leu Val Lys Gly Phe Tyr Pro
            500                 505                 510

Ser Asp Ile Ala Val Glu Trp Glu Ser Asn Gly Gln Pro Glu Asn Asn
        515                 520                 525

Tyr Lys Thr Thr Pro Pro Val Leu Asp Ser Asp Gly Ser Phe Phe Leu
    530                 535                 540

Tyr Ser Arg Leu Thr Val Asp Lys Ser Arg Trp Gln Glu Gly Asn Val
545                 550                 555                 560

Phe Ser Cys Ser Val Leu His Glu Ala Leu His Asn His Tyr Thr Gln
                565                 570                 575

Lys Ser Leu Ser Leu Ser Leu Gly Lys Asp Glu Gly Gly Glu Asp Gly
            580                 585                 590

Ser Gly Ser Arg Asn Leu Pro Val Ala Thr Pro Asp Pro Gly Met Phe
        595                 600                 605

Pro Cys Leu His His Ser Gln Asn Leu Leu Arg Ala Val Ser Asn Met
    610                 615                 620

Leu Gln Lys Ala Arg Gln Thr Leu Glu Phe Tyr Pro Cys Thr Ser Glu
625                 630                 635                 640

Glu Ile Asp His Glu Asp Ile Thr Lys Asp Lys Thr Ser Thr Val Glu
                645                 650                 655
```

```
Ala Cys Leu Pro Leu Glu Leu Thr Lys Asn Glu Ser Cys Leu Asn Ser
            660                 665                 670

Arg Glu Thr Ser Phe Ile Thr Asn Gly Ser Cys Leu Ala Ser Arg Lys
        675                 680                 685

Thr Ser Phe Met Met Ala Leu Cys Leu Ser Ser Ile Tyr Glu Asp Leu
    690                 695                 700

Lys Met Tyr Gln Val Glu Phe Lys Thr Met Asn Ala Lys Leu Leu Met
705                 710                 715                 720

Asp Pro Lys Arg Gln Ile Phe Leu Asp Gln Asn Met Leu Ala Val Ile
            725                 730                 735

Asp Glu Leu Met Gln Ala Leu Asn Phe Asn Ser Glu Thr Val Pro Gln
        740                 745                 750

Lys Ser Ser Leu Glu Glu Pro Asp Phe Tyr Lys Thr Lys Ile Lys Leu
    755                 760                 765

Cys Ile Leu Leu His Ala Phe Arg Ile Arg Ala Val Thr Ile Asp Arg
770                 775                 780

Val Met Ser Tyr Leu Asn Ala Ser
785                 790

<210> SEQ ID NO 35
<211> LENGTH: 597
<212> TYPE: PRT
<213> ORGANISM: Artificial Sequence
<220> FEATURE:
<223> OTHER INFORMATION: Synthetic Polypeptide

<400> SEQUENCE: 35

Glu Leu Leu Asp Pro Cys Gly Tyr Ile Ser Pro Glu Ser Pro Val Val
1               5                   10                  15

Gln Leu His Ser Asn Phe Thr Ala Val Cys Val Leu Lys Glu Lys Cys
            20                  25                  30

Met Asp Tyr Phe His Val Asn Ala Asn Tyr Ile Val Trp Lys Thr Asn
        35                  40                  45

His Phe Thr Ile Pro Lys Glu Gln Tyr Thr Ile Ile Asn Arg Thr Ala
    50                  55                  60

Ser Ser Val Thr Phe Thr Asp Ile Ala Ser Leu Asn Ile Gln Leu Thr
65                  70                  75                  80

Cys Asn Ile Leu Thr Phe Gly Gln Leu Glu Gln Asn Val Tyr Gly Ile
                85                  90                  95

Thr Ile Ile Ser Gly Leu Pro Pro Glu Lys Pro Lys Asn Leu Ser Cys
            100                 105                 110

Ile Val Asn Glu Gly Lys Lys Met Arg Cys Glu Trp Asp Gly Gly Arg
        115                 120                 125

Glu Thr His Leu Glu Thr Asn Phe Thr Leu Lys Ser Glu Trp Ala Thr
    130                 135                 140

His Lys Phe Ala Asp Cys Lys Ala Lys Arg Asp Thr Pro Thr Ser Cys
145                 150                 155                 160

Thr Val Asp Tyr Ser Thr Val Tyr Phe Val Asn Ile Glu Val Trp Val
                165                 170                 175

Glu Ala Glu Asn Ala Leu Gly Lys Val Thr Ser Asp His Ile Asn Phe
            180                 185                 190

Asp Pro Val Tyr Lys Val Lys Pro Asn Pro Pro His Asn Leu Ser Val
        195                 200                 205

Ile Asn Ser Glu Glu Leu Ser Ser Ile Leu Lys Leu Thr Trp Thr Asn
    210                 215                 220
```

Pro Ser Ile Lys Ser Val Ile Ile Leu Lys Tyr Asn Ile Gln Tyr Arg
225                 230                 235                 240

Thr Lys Asp Ala Ser Thr Trp Ser Gln Ile Pro Pro Glu Asp Thr Ala
            245                 250                 255

Ser Thr Arg Ser Ser Phe Thr Val Gln Asp Leu Lys Pro Phe Thr Glu
        260                 265                 270

Tyr Val Phe Arg Ile Arg Cys Met Lys Glu Asp Gly Lys Gly Tyr Trp
    275                 280                 285

Ser Asp Trp Ser Glu Glu Ala Ser Gly Ile Thr Tyr Glu Asp Arg Pro
290                 295                 300

Ser Lys Ala Pro Ser Phe Trp Tyr Lys Ile Asp Pro Ser His Thr Gln
305                 310                 315                 320

Gly Tyr Arg Thr Val Gln Leu Val Trp Lys Thr Leu Pro Pro Phe Glu
            325                 330                 335

Ala Asn Gly Lys Ile Leu Asp Tyr Glu Val Thr Leu Thr Arg Trp Lys
        340                 345                 350

Ser His Leu Gln Asn Tyr Thr Val Asn Ala Thr Lys Leu Thr Val Asn
    355                 360                 365

Leu Thr Asn Asp Arg Tyr Leu Ala Thr Leu Thr Val Arg Asn Leu Val
370                 375                 380

Gly Lys Ser Asp Ala Ala Val Leu Thr Ile Pro Ala Cys Asp Phe Gln
385                 390                 395                 400

Ala Thr His Pro Val Met Asp Leu Lys Ala Phe Pro Lys Asp Asn Met
            405                 410                 415

Leu Trp Val Glu Trp Thr Thr Pro Arg Glu Ser Val Lys Lys Tyr Ile
        420                 425                 430

Leu Glu Trp Cys Val Leu Ser Asp Lys Ala Pro Cys Ile Thr Asp Trp
    435                 440                 445

Gln Gln Glu Asp Gly Thr Val His Arg Thr Tyr Leu Arg Gly Asn Leu
450                 455                 460

Ala Glu Ser Lys Cys Tyr Leu Ile Thr Val Thr Pro Val Tyr Ala Asp
465                 470                 475                 480

Gly Pro Gly Ser Pro Glu Ser Ile Lys Ala Tyr Leu Lys Gln Ala Pro
            485                 490                 495

Pro Ser Lys Gly Pro Thr Val Arg Thr Lys Lys Val Gly Lys Asn Glu
        500                 505                 510

Ala Val Leu Glu Trp Asp Gln Leu Pro Val Asp Val Gln Asn Gly Phe
    515                 520                 525

Ile Arg Asn Tyr Thr Ile Phe Tyr Arg Thr Ile Ile Gly Asn Glu Thr
530                 535                 540

Ala Val Asn Val Asp Ser Ser His Thr Glu Tyr Thr Leu Ser Ser Leu
545                 550                 555                 560

Thr Ser Asp Thr Leu Tyr Met Val Arg Met Ala Ala Tyr Thr Asp Glu
            565                 570                 575

Gly Gly Lys Asp Gly Pro Glu Phe Thr Phe Thr Pro Lys Phe Ala
        580                 585                 590

Gln Gly Glu Ile Glu
        595

<210> SEQ ID NO 36
<211> LENGTH: 698
<212> TYPE: PRT
<213> ORGANISM: Artificial Sequence
<220> FEATURE:
<223> OTHER INFORMATION: Synthetic Polypeptide

<400> SEQUENCE: 36

```
Leu Asn Thr Thr Ile Leu Thr Pro Asn Gly Asn Glu Asp Thr Thr Ala
1               5                   10                  15

Asp Phe Phe Leu Thr Thr Met Pro Thr Asp Ser Leu Ser Val Ser Thr
            20                  25                  30

Leu Pro Leu Pro Glu Val Gln Cys Phe Val Phe Asn Val Glu Tyr Met
        35                  40                  45

Asn Cys Thr Trp Asn Ser Ser Glu Pro Gln Pro Thr Asn Leu Thr
    50                  55                  60

Leu His Tyr Trp Tyr Lys Asn Ser Asp Asn Asp Lys Val Gln Lys Cys
65                  70                  75                  80

Ser His Tyr Leu Phe Ser Glu Glu Ile Thr Ser Gly Cys Gln Leu Gln
                85                  90                  95

Lys Lys Glu Ile His Leu Tyr Gln Thr Phe Val Val Gln Leu Gln Asp
            100                 105                 110

Pro Arg Glu Pro Arg Arg Gln Ala Thr Gln Met Leu Lys Leu Gln Asn
        115                 120                 125

Leu Val Ile Pro Trp Ala Pro Glu Asn Leu Thr Leu His Lys Leu Ser
    130                 135                 140

Glu Ser Gln Leu Glu Leu Asn Trp Asn Asn Arg Phe Leu Asn His Cys
145                 150                 155                 160

Leu Glu His Leu Val Gln Tyr Arg Thr Asp Trp Asp His Ser Trp Thr
                165                 170                 175

Glu Gln Ser Val Asp Tyr Arg His Lys Phe Ser Leu Pro Ser Val Asp
            180                 185                 190

Gly Gln Lys Arg Tyr Thr Phe Arg Val Arg Ser Arg Phe Asn Pro Leu
        195                 200                 205

Cys Gly Ser Ala Gln His Trp Ser Glu Trp Ser His Pro Ile His Trp
    210                 215                 220

Gly Ser Asn Thr Ser Lys Glu Asn Pro Phe Leu Phe Ala Leu Glu Ala
225                 230                 235                 240

Gly Ser Gly Ser Arg Lys Gly Lys Arg Gly Ser Lys Tyr Gly Pro
                245                 250                 255

Pro Cys Pro Pro Cys Pro Ala Pro Glu Phe Leu Gly Gly Pro Ser Val
            260                 265                 270

Phe Leu Phe Pro Pro Lys Pro Lys Asp Gln Leu Met Ile Ser Arg Thr
        275                 280                 285

Pro Glu Val Thr Cys Val Val Asp Val Ser Gln Glu Asp Pro Glu
    290                 295                 300

Val Gln Phe Asn Trp Tyr Val Asp Gly Val Glu Val His Asn Ala Lys
305                 310                 315                 320

Thr Lys Pro Arg Glu Glu Gln Phe Asn Ser Thr Tyr Arg Val Val Ser
                325                 330                 335

Val Leu Thr Val Leu His Gln Asp Trp Leu Ser Gly Lys Glu Tyr Lys
            340                 345                 350

Cys Lys Val Ser Ser Lys Gly Leu Pro Ser Ser Ile Glu Lys Thr Ile
        355                 360                 365

Ser Asn Ala Thr Gly Gln Pro Arg Glu Pro Gln Val Tyr Thr Leu Pro
    370                 375                 380

Pro Ser Gln Glu Glu Met Thr Lys Asn Gln Val Ser Leu Thr Cys Leu
385                 390                 395                 400

Val Lys Gly Phe Tyr Pro Ser Asp Ile Ala Val Glu Trp Glu Ser Asn
```

```
                405                 410                 415
Gly Gln Pro Glu Asn Asn Tyr Lys Thr Thr Pro Pro Val Leu Asp Ser
        420                 425                 430

Asp Gly Ser Phe Phe Leu Tyr Ser Arg Leu Thr Val Asp Lys Ser Arg
    435                 440                 445

Trp Gln Glu Gly Asn Val Phe Ser Cys Ser Val Leu His Glu Ala Leu
450                 455                 460

His Asn His Tyr Thr Gln Lys Ser Leu Ser Leu Ser Leu Gly Lys Asp
465                 470                 475                 480

Glu Gly Gly Glu Asp Gly Ser Gly Ser Arg Lys Gly Pro Pro Ala Ala
                485                 490                 495

Leu Thr Leu Pro Arg Val Gln Cys Arg Ala Ser Arg Tyr Pro Ile Ala
                500                 505                 510

Val Asp Cys Ser Trp Thr Leu Pro Pro Ala Pro Asn Ser Thr Ser Pro
            515                 520                 525

Val Ser Phe Ile Ala Thr Tyr Arg Leu Gly Met Ala Ala Arg Gly His
        530                 535                 540

Ser Trp Pro Cys Leu Gln Gln Thr Pro Thr Ser Thr Ser Cys Thr Ile
545                 550                 555                 560

Thr Asp Val Gln Leu Phe Ser Met Ala Pro Tyr Val Leu Asn Val Thr
                565                 570                 575

Ala Val His Pro Trp Gly Ser Ser Ser Phe Val Pro Phe Ile Thr
            580                 585                 590

Glu His Ile Ile Lys Pro Asp Pro Pro Glu Gly Val Arg Leu Ser Pro
        595                 600                 605

Leu Ala Glu Arg Gln Leu Gln Val Gln Trp Glu Pro Pro Gly Ser Trp
    610                 615                 620

Pro Phe Pro Glu Ile Phe Ser Leu Lys Tyr Trp Ile Arg Tyr Lys Arg
625                 630                 635                 640

Gln Gly Ala Ala Arg Phe His Arg Val Gly Pro Ile Glu Ala Thr Ser
                645                 650                 655

Phe Ile Leu Arg Ala Val Arg Pro Arg Ala Arg Tyr Tyr Val Gln Val
                660                 665                 670

Ala Ala Gln Asp Leu Thr Asp Tyr Gly Glu Leu Ser Asp Trp Ser Leu
            675                 680                 685

Pro Ala Thr Ala Thr Met Ser Leu Gly Lys
        690                 695

<210> SEQ ID NO 37
<211> LENGTH: 659
<212> TYPE: PRT
<213> ORGANISM: Artificial Sequence
<220> FEATURE:
<223> OTHER INFORMATION: Synthetic Polypeptide

<400> SEQUENCE: 37

Cys Pro Asp Leu Val Cys Tyr Thr Asp Tyr Leu Gln Thr Val Ile Cys
1               5                   10                  15

Ile Leu Glu Met Trp Asn Leu His Pro Ser Thr Leu Thr Leu Thr Trp
                20                  25                  30

Gln Asp Gln Tyr Glu Glu Leu Lys Asp Glu Ala Thr Ser Cys Ser Leu
            35                  40                  45

His Arg Ser Ala His Asn Ala Thr His Ala Tyr Thr Cys His Met
        50                  55                  60

Asp Val Phe His Phe Met Ala Asp Asp Ile Phe Ser Val Asn Ile Thr
```

-continued

```
              65                  70                  75                  80
         Asp Gln Ser Gly Asn Tyr Ser Gln Glu Cys Gly Ser Phe Leu Leu Ala
                         85                  90                  95

Glu Ser Ile Lys Pro Ala Pro Pro Phe Asn Val Thr Val Thr Phe Ser
                        100                 105                 110

Gly Gln Tyr Asn Ile Ser Trp Arg Ser Asp Tyr Glu Asp Pro Ala Phe
                        115                 120                 125

Tyr Met Leu Lys Gly Lys Leu Gln Tyr Glu Leu Gln Tyr Arg Asn Arg
                        130                 135                 140

Gly Asp Pro Trp Ala Val Ser Pro Arg Arg Lys Leu Ile Ser Val Asp
         145                 150                 155                 160

Ser Arg Ser Val Ser Leu Leu Pro Leu Glu Phe Arg Lys Asp Ser Ser
                             165                 170                 175

Tyr Glu Leu Gln Val Arg Ala Gly Pro Met Pro Gly Ser Ser Tyr Gln
                        180                 185                 190

Gly Thr Trp Ser Glu Trp Ser Asp Pro Val Ile Phe Gln Thr Gln Ser
                        195                 200                 205

Glu Glu Leu Lys Glu Gly Ser Gly Ser Asp Glu Gly Gly Glu Asp Gly
                        210                 215                 220

Ser Lys Tyr Gly Pro Pro Cys Pro Pro Cys Pro Ala Pro Glu Phe Leu
         225                 230                 235                 240

Gly Gly Pro Ser Val Phe Leu Phe Pro Pro Lys Pro Lys Asp Gln Leu
                             245                 250                 255

Met Ile Ser Arg Thr Pro Glu Val Thr Cys Val Val Val Asp Val Ser
                        260                 265                 270

Gln Glu Asp Pro Glu Val Gln Phe Asn Trp Tyr Val Asp Gly Val Glu
                        275                 280                 285

Val His Asn Ala Lys Thr Lys Pro Arg Glu Glu Gln Phe Asn Ser Thr
                        290                 295                 300

Tyr Arg Val Val Ser Val Leu Thr Val Leu His Gln Asp Trp Leu Ser
         305                 310                 315                 320

Gly Lys Glu Tyr Lys Cys Lys Val Ser Ser Lys Gly Leu Pro Ser Ser
                             325                 330                 335

Ile Glu Lys Thr Ile Ser Asn Ala Thr Gly Gln Pro Arg Glu Pro Gln
                        340                 345                 350

Val Tyr Thr Leu Pro Pro Ser Gln Glu Glu Met Thr Lys Asn Gln Val
                        355                 360                 365

Ser Leu Thr Cys Leu Val Lys Gly Phe Tyr Pro Ser Asp Ile Ala Val
                        370                 375                 380

Glu Trp Glu Ser Asn Gly Gln Pro Glu Asn Asn Tyr Lys Thr Thr Pro
         385                 390                 395                 400

Pro Val Leu Asp Ser Asp Gly Ser Phe Phe Leu Tyr Ser Arg Leu Thr
                             405                 410                 415

Val Asp Lys Ser Arg Trp Gln Glu Gly Asn Val Phe Ser Cys Ser Val
                        420                 425                 430

Leu His Glu Ala Leu His Asn His Tyr Thr Gln Lys Ser Leu Ser Leu
                        435                 440                 445

Ser Leu Gly Lys Arg Lys Gly Gly Lys Arg Gly Ser Gly Ser Arg Asn
         450                 455                 460

Leu Pro Val Ala Thr Pro Asp Pro Gly Met Phe Pro Cys Leu His His
         465                 470                 475                 480

Ser Gln Asn Leu Leu Arg Ala Val Ser Asn Met Leu Gln Lys Ala Arg
                             485                 490                 495
```

```
Gln Thr Leu Glu Phe Tyr Pro Cys Thr Ser Glu Glu Ile Asp His Glu
            500                 505                 510

Asp Ile Thr Lys Asp Lys Thr Ser Thr Val Glu Ala Cys Leu Pro Leu
            515                 520                 525

Glu Leu Thr Lys Asn Glu Ser Cys Leu Asn Ser Arg Glu Thr Ser Phe
            530                 535                 540

Ile Thr Asn Gly Ser Cys Leu Ala Ser Arg Lys Thr Ser Phe Met Met
545                 550                 555                 560

Ala Leu Cys Leu Ser Ser Ile Tyr Glu Asp Leu Lys Met Tyr Gln Val
            565                 570                 575

Glu Phe Lys Thr Met Asn Ala Lys Leu Leu Met Asp Pro Lys Arg Gln
            580                 585                 590

Ile Phe Leu Asp Gln Asn Met Leu Ala Val Ile Asp Glu Leu Met Gln
            595                 600                 605

Ala Leu Asn Phe Asn Ser Glu Thr Val Pro Gln Lys Ser Ser Leu Glu
            610                 615                 620

Glu Pro Asp Phe Tyr Lys Thr Lys Ile Lys Leu Cys Ile Leu Leu His
625                 630                 635                 640

Ala Phe Arg Ile Arg Ala Val Thr Ile Asp Arg Val Met Ser Tyr Leu
            645                 650                 655

Asn Ala Ser

<210> SEQ ID NO 38
<211> LENGTH: 674
<212> TYPE: PRT
<213> ORGANISM: Artificial Sequence
<220> FEATURE:
<223> OTHER INFORMATION: Synthetic Polypeptide

<400> SEQUENCE: 38

Glu Met Gly Thr Ala Asp Leu Gly Pro Ser Ser Val Pro Thr Pro Thr
1               5                   10                  15

Asn Val Thr Ile Glu Ser Tyr Asn Met Asn Pro Ile Val Tyr Trp Glu
            20                  25                  30

Tyr Gln Ile Met Pro Gln Val Pro Val Phe Thr Val Glu Val Lys Asn
            35                  40                  45

Tyr Gly Val Lys Asn Ser Glu Trp Ile Asp Ala Cys Ile Asn Ile Ser
        50                  55                  60

His His Tyr Cys Asn Ile Ser Asp His Val Gly Asp Pro Ser Asn Ser
65                  70                  75                  80

Leu Trp Val Arg Val Lys Ala Arg Val Gly Gln Lys Glu Ser Ala Tyr
            85                  90                  95

Ala Lys Ser Glu Glu Phe Ala Val Cys Arg Asp Gly Lys Ile Gly Pro
            100                 105                 110

Pro Lys Leu Asp Ile Arg Lys Glu Lys Gln Ile Met Ile Asp Ile
            115                 120                 125

Phe His Pro Ser Val Phe Val Asn Gly Asp Glu Gln Glu Val Asp Tyr
            130                 135                 140

Asp Pro Glu Thr Thr Cys Tyr Ile Arg Val Tyr Asn Val Tyr Val Arg
145                 150                 155                 160

Met Asn Gly Ser Glu Ile Gln Tyr Lys Ile Leu Thr Gln Lys Glu Asp
            165                 170                 175

Asp Cys Asp Glu Ile Gln Cys Gln Leu Ala Ile Pro Val Ser Ser Leu
            180                 185                 190
```

-continued

```
Asn Ser Gln Tyr Cys Val Ser Ala Glu Gly Val Leu His Val Trp Gly
        195                 200                 205
Val Thr Thr Glu Lys Ser Lys Glu Val Cys Ile Thr Ile Phe Asn Ser
210                 215                 220
Ser Ile Lys Gly Gly Ser Gly Ser Asp Glu Gly Gly Glu Asp Gly Ser
225                 230                 235                 240
Lys Tyr Gly Pro Pro Cys Pro Pro Cys Pro Ala Pro Glu Phe Leu Gly
                245                 250                 255
Gly Pro Ser Val Phe Leu Phe Pro Pro Lys Pro Lys Asp Gln Leu Met
            260                 265                 270
Ile Ser Arg Thr Pro Glu Val Thr Cys Val Val Val Asp Val Ser Gln
        275                 280                 285
Glu Asp Pro Glu Val Gln Phe Asn Trp Tyr Val Asp Gly Val Glu Val
290                 295                 300
His Asn Ala Lys Thr Lys Pro Arg Glu Glu Gln Phe Asn Ser Thr Tyr
305                 310                 315                 320
Arg Val Val Ser Val Leu Thr Val Leu His Gln Asp Trp Leu Ser Gly
                325                 330                 335
Lys Glu Tyr Lys Cys Lys Val Ser Ser Lys Gly Leu Pro Ser Ser Ile
            340                 345                 350
Glu Lys Thr Ile Ser Asn Ala Thr Gly Gln Pro Arg Glu Pro Gln Val
        355                 360                 365
Tyr Thr Leu Pro Pro Ser Gln Glu Glu Met Thr Lys Asn Gln Val Ser
370                 375                 380
Leu Thr Cys Leu Val Lys Gly Phe Tyr Pro Ser Asp Ile Ala Val Glu
385                 390                 395                 400
Trp Glu Ser Asn Gly Gln Pro Glu Asn Asn Tyr Lys Thr Thr Pro Pro
                405                 410                 415
Val Leu Asp Ser Asp Gly Ser Phe Phe Leu Tyr Ser Arg Leu Thr Val
            420                 425                 430
Asp Lys Ser Arg Trp Gln Glu Gly Asn Val Phe Ser Cys Ser Val Leu
        435                 440                 445
His Glu Ala Leu His Asn His Tyr Thr Gln Lys Ser Leu Ser Leu Ser
450                 455                 460
Leu Gly Lys Arg Lys Gly Gly Lys Arg Gly Ser Gly Ser Arg Asn Leu
465                 470                 475                 480
Pro Val Ala Thr Pro Asp Pro Gly Met Phe Pro Cys Leu His His Ser
                485                 490                 495
Gln Asn Leu Leu Arg Ala Val Ser Asn Met Leu Gln Lys Ala Arg Gln
            500                 505                 510
Thr Leu Glu Phe Tyr Pro Cys Thr Ser Glu Glu Ile Asp His Glu Asp
        515                 520                 525
Ile Thr Lys Asp Lys Thr Ser Thr Val Glu Ala Cys Leu Pro Leu Glu
530                 535                 540
Leu Thr Lys Asn Glu Ser Cys Leu Asn Ser Arg Glu Thr Ser Phe Ile
545                 550                 555                 560
Thr Asn Gly Ser Cys Leu Ala Ser Arg Lys Thr Ser Phe Met Met Ala
                565                 570                 575
Leu Cys Leu Ser Ser Ile Tyr Glu Asp Leu Lys Met Tyr Gln Val Glu
            580                 585                 590
Phe Lys Thr Met Asn Ala Lys Leu Leu Met Asp Pro Lys Arg Gln Ile
        595                 600                 605
Phe Leu Asp Gln Asn Met Leu Ala Val Ile Asp Glu Leu Met Gln Ala
```

```
                    610                 615                 620
Leu Asn Phe Asn Ser Glu Thr Val Pro Gln Lys Ser Ser Leu Glu Glu
625                 630                 635                 640

Pro Asp Phe Tyr Lys Thr Lys Ile Lys Leu Cys Ile Leu Leu His Ala
                    645                 650                 655

Phe Arg Ile Arg Ala Val Thr Ile Asp Arg Val Met Ser Tyr Leu Asn
                660                 665                 670

Ala Ser

<210> SEQ ID NO 39
<211> LENGTH: 678
<212> TYPE: PRT
<213> ORGANISM: Artificial Sequence
<220> FEATURE:
<223> OTHER INFORMATION: Synthetic Polypeptide

<400> SEQUENCE: 39

Ser Gln Leu Pro Ala Pro Gln His Pro Lys Ile Arg Leu Tyr Asn Ala
1               5                   10                  15

Glu Gln Val Leu Ser Trp Glu Pro Val Ala Leu Ser Asn Ser Thr Arg
                20                  25                  30

Pro Val Val Tyr Gln Val Gln Phe Lys Tyr Thr Asp Ser Lys Trp Phe
            35                  40                  45

Thr Ala Asp Ile Met Ser Ile Gly Val Asn Cys Thr Gln Ile Thr Ala
    50                  55                  60

Thr Glu Cys Asp Phe Thr Ala Ala Ser Pro Ser Ala Gly Phe Pro Met
65                  70                  75                  80

Asp Phe Asn Val Thr Leu Arg Leu Arg Ala Glu Leu Gly Ala Leu His
                85                  90                  95

Ser Ala Trp Val Thr Met Pro Trp Phe Gln His Tyr Arg Asn Val Thr
            100                 105                 110

Val Gly Pro Pro Glu Asn Ile Glu Val Thr Pro Gly Glu Gly Ser Leu
        115                 120                 125

Ile Ile Arg Phe Ser Ser Pro Phe Asp Ile Ala Asp Thr Ser Thr Ala
    130                 135                 140

Phe Phe Cys Tyr Tyr Val His Tyr Trp Glu Lys Gly Gly Ile Gln Gln
145                 150                 155                 160

Val Lys Gly Pro Phe Arg Ser Asn Ser Ile Ser Leu Asp Asn Leu Lys
                165                 170                 175

Pro Ser Arg Val Tyr Cys Leu Gln Val Gln Ala Gln Leu Leu Trp Asn
            180                 185                 190

Lys Ser Asn Ile Phe Arg Val Gly His Leu Ser Asn Ile Ser Cys Tyr
        195                 200                 205

Glu Thr Met Ala Asp Ala Ser Thr Glu Leu Gln Gln Gly Ser Gly Ser
    210                 215                 220

Arg Lys Gly Gly Lys Arg Gly Ser Lys Tyr Gly Pro Pro Cys Pro Pro
225                 230                 235                 240

Cys Pro Ala Pro Glu Phe Leu Gly Gly Pro Ser Val Phe Leu Phe Pro
                245                 250                 255

Pro Lys Pro Lys Asp Gln Leu Met Ile Ser Arg Thr Pro Glu Val Thr
            260                 265                 270

Cys Val Val Val Asp Val Ser Gln Glu Asp Pro Glu Val Gln Phe Asn
        275                 280                 285

Trp Tyr Val Asp Gly Val Glu Val His Asn Ala Lys Thr Lys Pro Arg
    290                 295                 300
```

```
Glu Glu Gln Phe Asn Ser Thr Tyr Arg Val Val Ser Val Leu Thr Val
305                 310                 315                 320

Leu His Gln Asp Trp Leu Ser Gly Lys Glu Tyr Lys Cys Lys Val Ser
            325                 330                 335

Ser Lys Gly Leu Pro Ser Ser Ile Glu Lys Thr Ile Ser Asn Ala Thr
        340                 345                 350

Gly Gln Pro Arg Glu Pro Gln Val Tyr Thr Leu Pro Pro Ser Gln Glu
        355                 360                 365

Glu Met Thr Lys Asn Gln Val Ser Leu Thr Cys Leu Val Lys Gly Phe
    370                 375                 380

Tyr Pro Ser Asp Ile Ala Val Glu Trp Glu Ser Asn Gly Gln Pro Glu
385                 390                 395                 400

Asn Asn Tyr Lys Thr Thr Pro Pro Val Leu Asp Ser Asp Gly Ser Phe
            405                 410                 415

Phe Leu Tyr Ser Arg Leu Thr Val Asp Lys Ser Arg Trp Gln Glu Gly
            420                 425                 430

Asn Val Phe Ser Cys Ser Val Leu His Glu Ala Leu His Asn His Tyr
        435                 440                 445

Thr Gln Lys Ser Leu Ser Leu Ser Leu Gly Lys Asp Glu Gly Gly Glu
    450                 455                 460

Asp Gly Ser Gly Ser Arg Lys Gly Pro Pro Ala Ala Leu Thr Leu Pro
465                 470                 475                 480

Arg Val Gln Cys Arg Ala Ser Arg Tyr Pro Ile Ala Val Asp Cys Ser
            485                 490                 495

Trp Thr Leu Pro Pro Ala Pro Asn Ser Thr Ser Pro Val Ser Phe Ile
            500                 505                 510

Ala Thr Tyr Arg Leu Gly Met Ala Ala Arg Gly His Ser Trp Pro Cys
            515                 520                 525

Leu Gln Gln Thr Pro Thr Ser Thr Ser Cys Thr Ile Thr Asp Val Gln
    530                 535                 540

Leu Phe Ser Met Ala Pro Tyr Val Leu Asn Val Thr Ala Val His Pro
545                 550                 555                 560

Trp Gly Ser Ser Ser Ser Phe Val Pro Phe Ile Thr Glu His Ile Ile
            565                 570                 575

Lys Pro Asp Pro Pro Glu Gly Val Arg Leu Ser Pro Leu Ala Glu Arg
            580                 585                 590

Gln Leu Gln Val Gln Trp Glu Pro Pro Gly Ser Trp Pro Phe Pro Glu
    595                 600                 605

Ile Phe Ser Leu Lys Tyr Trp Ile Arg Tyr Lys Arg Gln Gly Ala Ala
            610                 615                 620

Arg Phe His Arg Val Gly Pro Ile Glu Ala Thr Ser Phe Ile Leu Arg
625                 630                 635                 640

Ala Val Arg Pro Arg Ala Arg Tyr Tyr Val Gln Val Ala Ala Gln Asp
            645                 650                 655

Leu Thr Asp Tyr Gly Glu Leu Ser Asp Trp Ser Leu Pro Ala Thr Ala
            660                 665                 670

Thr Met Ser Leu Gly Lys
            675
```

HETERODIMERIC PROTEINS AND USES THEREOF

PRIORITY

This application is a continuation of U.S. application Ser. No. 16/571,853, filed Sep. 16, 2019, now U.S. Pat. No. 10,995,127, which is a continuation of International Application No. PCT/US19/38451, filed Jun. 21, 2019, which claims the benefit of U.S. Provisional Application No. 62/688,167, filed Jun. 21, 2018 and U.S. Provisional Application No. 62/703,248, filed Jul. 25, 2018, the contents of each of which are incorporated herein by reference in their entirety.

TECHNICAL FIELD

The present invention relates to heterodimeric proteins that find use in the treatment of diseases, such as immunotherapies for cancer and autoimmunity.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: SHK-00402_116981-5004_ST25; date created on: Mar. 24, 2021; file size: 114,059 bytes).

BACKGROUND

Protein-protein interactions are critical for the normal physiological functions of cells and multicellular organisms. For example, cytokines act as ligands which bind to their cognate receptors so as to regulate essential biological processes such as inflammation and immunity. In this regard, many natural cytokines, cytokine receptors, integrins, and other proteins exist or function as multimeric protein complexes. Some multimers, such as those within the tumor necrosis factor superfamily function as homotrimers, other ligands including the IL-12 family of cytokines (e.g., IL12, IL23, IL27, or IL-35) form heterodimers. Similarly, cytokine receptors may also function as heterodimeric complexes. For example, many interleukin receptors form heterodimers for signal transduction.

The modulation of protein-protein interactions is a useful mechanism for therapeutic intervention in various diseases and pathologies. Soluble binding proteins which interact with ligands can potentially sequester the ligand away from the receptor, thereby reducing the activation of that particular receptor pathway. Alternatively, sequestration of the ligand may delay its elimination or degradation, thereby increasing its duration of effect and biological activity. Additionally, soluble ligands may be utilized to either activate or inhibit specific receptors. Nevertheless, the synthesis and manufacturing of soluble proteins may be hampered where it is desirable to produce heterodimeric proteins. Particularly, the efficiency of synthesis may be greatly compromised by the formation of mixtures of homodimers and heterodimers.

Accordingly, there remains a need for novel methods for the efficient synthesis and manufacturing of heterodimeric proteins for therapeutic use.

SUMMARY

In various embodiments, the present invention provides a heterodimeric protein comprising a first polypeptide chain and a second polypeptide chain, wherein the first polypeptide chain comprises a first subunit of a first protein at the amino terminus linked by a first charge polarized core domain to a first subunit of a second protein at the carboxy terminus; and the second polypeptide chain comprises a second subunit of the first protein at the amino terminus linked by a second charge polarized core domain to a second subunit of the second protein at the carboxy terminus.

In various embodiments, the first polypeptide chain and the second polypeptide chain heterodimers through electrostatic interactions between positively charged amino acid residues and negatively charged amino acid residues on the first and second charge polarized core domains. In some embodiments, the positively charged amino acid residues may include one or more of amino acids selected from His, Lys, and Arg. In some embodiments, the negatively charged amino acid residues may include one or more amino acids selected from Asp and Glu.

Accordingly, in various embodiments, each of the first and/or second charge polarized core domains comprises peptides having positively or negatively charged amino acid residues at the amino and carboxy terminus of the core domain. In an exemplary embodiment, the first charge polarized core domain may comprise a peptide having positively charged amino acids at the amino terminus which are adjoined by a linker (e.g., a stabilizing domain) to a peptide having negatively charged amino acid residues at the carboxy terminus. In such an embodiment, the second charge polarized core domain may comprise a peptide having negatively charged amino acids at the amino terminus which are adjoined by a linker (e.g., a stabilizing domain) to a peptide having positively charged amino acid residues at the carboxy terminus. In another exemplary embodiment, the first charge polarized core domain may comprise a peptide having negatively charged amino acids at the amino terminus which are adjoined by a linker (e.g., a stabilizing domain) to a peptide having positively charged amino acid residues at the carboxy terminus. In such an embodiment, the second charge polarized core domain may comprise peptides having positively charged amino acids at the amino terminus which are adjoined by a linker (e.g., a stabilizing domain) to a peptide having negatively charged amino acid residues at the carboxy terminus.

In various embodiments, each of the first and/or second charge polarized core domains further comprise a linker (e.g., a stabilizing domain) which adjoins the peptides having positively or negatively charged amino acids. In some embodiments, the linker (e.g., a stabilizing domain) is optionally selected from a flexible amino acid sequence, IgG hinge region, or antibody sequence. In an embodiment, the linker (e.g., a stabilizing domain) comprises the hinge-CH2-CH3 Fc domain derived from IgG1, optionally human IgG1. In another embodiment, the linker (e.g., a stabilizing domain) comprises the hinge-CH2-CH3 Fc domain derived from IgG4, optionally human IgG4.

In some embodiments, the first and/or second protein is selected from a cytokine, a growth factor, and/or a hormone. In some embodiments, the first and/or second protein is selected from a receptor for a cytokine, a growth factor, and/or a hormone.

In embodiments, in a heterodimeric protein, the first protein is selected from Table 1 and/or the second protein is selected from Table 1.

In embodiments, the first and/or second protein is an interleukin. In embodiments, the first and/or second protein is IL-35 comprising the IL12α and IL27β subunits.

In embodiments, the first and/or second protein is selected from a receptor for a cytokine, a growth factor, and/or a hormone. In embodiments, the first and/or second protein is a receptor for an interleukin.

In embodiments, the first and/or second protein is IL6 receptor comprising the IL6Rα and gp130 subunits.

In embodiments, the first and/or second protein is IL21 receptor comprising the IL21r and IL2rg subunits.

In embodiments, the first and/or second protein is IL21 receptor comprising the IFNgR and IFNGR2 subunits.

In embodiments, the protein on the amino- or carboxyterminus is natively heterodimeric, and wherein the protein on the opposite terminus is not natively heterodimeric.

Also in various aspects, the present heterodimeric protein is used in a method for treating autoimmune diseases comprising administering an effective amount of a pharmaceutical composition comprising the heterodimeric protein to a patient in need thereof. In further aspects, the present heterodimeric protein is used in a method for treating infections, including without limitation, viral infections or other intracellular pathogens. In still further aspects, the present heterodimeric protein is used in a method for treating cancers.

Any aspect or embodiment disclosed herein can be combined with any other aspect or embodiment as disclosed herein.

BRIEF DESCRIPTION OF THE DRAWINGS

In FIG. 16A, the absorbance wavelength was 210 nm and in FIG. 16B, the absorbance wavelength was 280 nm.

DETAILED DESCRIPTION

Figure 1:
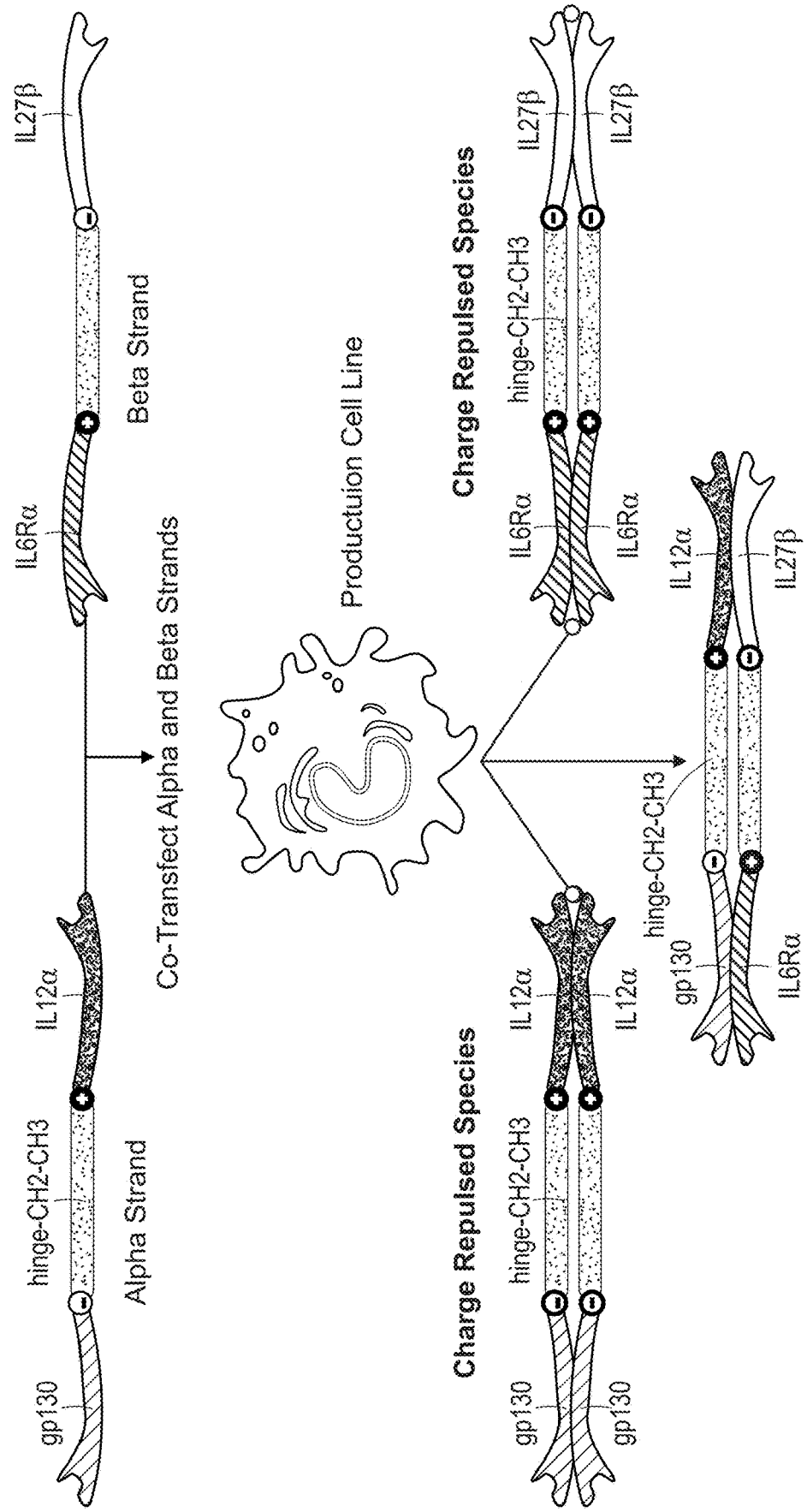
FIG. 1 provides illustrations protein engineering embodiments of the invention, showing an exemplary heterodimeric protein of the invention comprising the IL6 receptor (which includes the IL6Rα and gp130 subunits) and the IL-35 cytokine (which includes the IL12α and IL27β subunits). The heterodimeric protein is preferentially formed through electrostatic interactions between the charge polarized core domains.

The present invention is directed to a protein engineering platform for synthesizing and manufacturing heterodimeric proteins. The method of the invention allows for the efficient production of heterodimeric proteins for use in modulating immune signals for the treatment of various diseases, including, without limitation, autoimmune diseases.

Charge Polarized Core Domains

In one aspect, the present invention relates to heterodimeric proteins. In various embodiments, the heterodimeric protein of the invention comprises two polypeptide chains. The first polypeptide chain comprises a first subunit of a first protein at the amino terminus linked by a first charge polarized core domain to a first subunit of a second protein at the carboxy terminus. The second polypeptide chain comprises a second subunit of the first protein at the amino terminus linked by a second charge polarized core domain to a second subunit of the second protein at the carboxy terminus. In various embodiments, the first polypeptide chain and the second polypeptide chain forms a heterodimer through electrostatic interactions between positively charged amino acid residues and negatively charged amino acid residues on the first and second polarized core domains.

In various embodiments, each of the first and second charge polarized core domains comprises peptides having positively or negatively charged amino acid residues at the amino and carboxy terminus of the core domain. In an exemplary embodiment, the first charge polarized core domain may comprise a peptide having positively charged amino acids at the amino terminus which are adjoined by a linker (e.g., a stabilizing domain) to a peptide having negatively charged amino acid residues at the carboxy terminus. The second charge polarized core domain may comprise a peptide having negatively charged amino acids at the amino terminus which are adjoined by a linker (e.g., a stabilizing domain) to a peptide having positively charged amino acid residues at the carboxy terminus.

In another exemplary embodiment, the first charge polarized core domain may comprise a peptide having negatively charged amino acids at the amino terminus which are adjoined by a linker (e.g., a stabilizing domain) to a peptide having positively charged amino acid residues at the carboxy terminus. The second charge polarized core domain may comprise peptides having positively charged amino acids at the amino terminus which are adjoined by a linker (e.g., a stabilizing domain) to a peptide having negatively charged amino acid residues at the carboxy terminus.

In various embodiments, formation of heterodimeric proteins is driven by electrostatic interactions between the positively charged and negatively charged amino acid residues located at the amino and carboxy termini of the first and second charge polarized core domains. Further, formation of homodimeric proteins is prevented by the repulsion between the positively charged amino acid residues or negatively charged amino acid residues located at the amino and carboxy termini of the first and second charge polarized core domains.

In various embodiments, the peptide comprising positively and/or negatively charged amino acid residues at the amino or carboxy terminus of the charge polarized core domains is about 2 to about 50 amino acids long. For example, the peptide comprising positively and/or negatively charged amino acid residues at either terminus of the charge polarized core domain may be about 50, about 45, about 40, about 35, about 30, about 25, about 20, about 19, about 18, about 17, about 16, about 15, about 14, about 13, about 12, about 11, about 10, about 9, about 8, about 7, about 6, about 5, about 4, about 3, or about 2 amino acids long.

In various embodiments, the peptide comprising positively charged amino acid residues may include one or more of amino acids selected from His, Lys, and Arg. In various embodiments, the peptide comprising negatively charged amino acid residues may include one or more amino acids selected from Asp and Glu.

In various embodiments, each of the first and/or second charge polarized core domains may comprise a peptide comprising an amino acid sequence as provided in the Table below or an amino acid sequence having at least 90%, or 93%, or 95%, or 97%, or 98%, or 99% identity thereto.

| SEQ ID NO. | Sequence |
|---|---|
| 1 | $Y_nX_nY_nX_nY_n$ (where X is a positively charged amino acid such as arginine, histidine or lysine and Y is a spacer amino acid such as serine or glycine) |
| 2 | $Y_nZ_nY_nZ_nY_n$ (where Z is a negatively charged amino acid such as aspartic acid or glutamic acid and Y is a spacer amino acid such as serine or glycine) |
| 3 | $YY_nXX_nYY_nXX_nYY_n$ (where X is a positively charged amino acid such as arginine, histidine or lysine and Y is a spacer amino acid such as serine or glycine) |

| SEQ ID NO. | Sequence |
|---|---|
| 4 | YY$_n$ZZ$_n$YY$_n$ZZ$_n$YY$_n$ (where Z is a negatively charged amino acid such as aspartic acid or glutamic acid and Y is a spacer amino acid such as serine or glycine) |
| 5 | Y$_n$X$_n$CY$_n$X$_n$Y$_n$ (where X is a positively charged amino acid such as arginine, histidine or lysine and Y is a spacer amino acid such as serine or glycine) |
| 6 | Y$_n$Z$_n$CY$_n$Z$_n$Y$_n$ (where Z is a negatively charged amino acid such as aspartic acid or glutamic acid and Y is a spacer amino acid such as serine or glycine) |
| 7 | GSGSRKGGKRGS |
| 8 | GSGSRKCGKRGS |
| 9 | GSGSDEGGEDGS |
| 10 | GSGSDECGEDGS |

For example, in an embodiment, each of the first and second charge polarized core domains may comprise a peptide comprising the sequence YY$_n$XX$_n$YY$_n$XX$_n$YY$_n$ (where X is a positively charged amino acid such as arginine, histidine or lysine and Y is a spacer amino acid such as serine or glycine; SEQ ID NO: 3). Exemplary peptide sequences include, but are not limited to, RKGGKR (SEQ ID NO: 11) or GSGSRKGGKRGS (SEQ ID NO: 12).

In another exemplary embodiment, each of the first and second charge polarized core domains may comprise a peptide comprising the sequence YY$_n$ZZ$_n$YY$_n$ZZ$_n$YY$_n$ (where Z is a negatively charged amino acid such as aspartic acid or glutamic acid and Y is a spacer amino acid such as serine or glycine). Exemplary peptide sequences include, but are not limited to, DEGGED (SEQ ID NO: 13) or GSGSDEGGEDGS (SEQ ID NO: 14).

In embodiments, a charge polarized core domain (negative-positive, also referred herein as an "alpha core domain") is provided below:

(SEQ ID NO: 16)
GSGSRKGGKRGSKYGPPCPPCPAPEFLGGPSVFLFPPKPKDQLMISRTPE

VTCVVVDVSQEDPEVQFNWYVDGVEVHNAKTKPREEQFNSTYRVVSVLTV

LHQDWLSGKEYKCKVSSKGLPSSIEKTISNATGQPREPQVYTLPPSQEEM

TKNQVSLTCLVKGFYPSDIAVEWESNGQPENNYKTTPPVLDSDGSFFLYS

RLTVDKSRWQEGNVFSCSVLHEALHNHYTQKSLSLSLGKDEGGEDGSGS

In embodiments, a heterodimeric protein comprises a variant alpha core domain. As examples, the variant may have at least about 60%, or at least about 61%, or at least about 62%, or at least about 63%, or at least about 64%, or at least about 65%, or at least about 66%, or at least about 67%, or at least about 68%, or at least about 69%, or at least about 70%, or at least about 71%, or at least about 72%, or at least about 73%, or at least about 74%, or at least about 75%, or at least about 76%, or at least about 77%, or at least about 78%, or at least about 79%, or at least about 80%, or at least about 81%, or at least about 82%, or at least about 83%, or at least about 84%, or at least about 85%, or at least about 86%, or at least about 87%, or at least about 88%, or at least about 89%, or at least about 90%, or at least about 91%, or at least about 92%, or at least about 93%, or at least about 94%, or at least about 95%, or at least about 96%, or at least about 97%, or at least about 98%, or at least about 99% sequence identity with SEQ ID NO: 16.

In embodiments, a charge polarized core domain (positive-negative, also referred herein as a "beta core domain") is provided below:

(SEQ ID NO: 17)
GSGSDEGGEDGSKYGPPCPPCPAPEFLGGPSVFLFPPKPKDQLMISRTPE

VTCVVVDVSQEDPEVQFNWYVDGVEVHNAKTKPREEQFNSTYRVVSVLTV

LHQDWLSGKEYKCKVSSKGLPSSIEKTISNATGQPREPQVYTLPPSQEEM

TKNQVSLTCLVKGFYPSDIAVEWESNGQPENNYKTTPPVLDSDGSFFLYS

RLTVDKSRWQEGNVFSCSVLHEALHNHYTQKSLSLSLGKRKGGKRGSGS

In embodiments, a heterodimeric protein comprises a variant beta core domain. As examples, the variant may have at least about 60%, or at least about 61%, or at least about 62%, or at least about 63%, or at least about 64%, or at least about 65%, or at least about 66%, or at least about 67%, or at least about 68%, or at least about 69%, or at least about 70%, or at least about 71%, or at least about 72%, or at least about 73%, or at least about 74%, or at least about 75%, or at least about 76%, or at least about 77%, or at least about 78%, or at least about 79%, or at least about 80%, or at least about 81%, or at least about 82%, or at least about 83%, or at least about 84%, or at least about 85%, or at least about 86%, or at least about 87%, or at least about 88%, or at least about 89%, or at least about 90%, or at least about 91%, or at least about 92%, or at least about 93%, or at least about 94%, or at least about 95%, or at least about 96%, or at least about 97%, or at least about 98%, or at least about 99% sequence identity with SEQ ID NO: 17.

In various embodiments, the peptide comprising the charged amino acid residues may further comprise one or more cysteine residues to facilitate disulfide bonding between the electrostatically charged core domains as an additional method to stabilize the heterodimer.

In various embodiments, each of the first and second charge polarized core domains comprises a linker sequence which may optionally function as a stabilizing domain. In various embodiments, the linker may be derived from naturally-occurring multi-domain proteins or are empirical linkers as described, for example, in Chichili et al., (2013), Protein Sci. 22(2):153-167, Chen et al., (2013), Adv Drug Deliv Rev. 65(10):1357-1369, the entire contents of which are hereby incorporated by reference. In some embodiments, the linker may be designed using linker designing databases and computer programs such as those described in Chen et al., (2013), Adv Drug Deliv Rev. 65(10):1357-1369 and Crasto et. al., (2000), Protein Eng. 13(5):309-312, the entire contents of which are hereby incorporated by reference.

In some embodiments, the linker (e.g., a stabilizing domain) is a synthetic linker such as PEG.

In other embodiments, the linker (e.g., a stabilizing domain) is a polypeptide. In some embodiments, the linker (e.g., a stabilizing domain) is less than about 500 amino acids long, about 450 amino acids long, about 400 amino acids long, about 350 amino acids long, about 300 amino acids long, about 250 amino acids long, about 200 amino acids long, about 150 amino acids long, or about 100 amino acids long. For example, the linker (e.g., a stabilizing domain) may be less than about 100, about 95, about 90, about 85, about 80, about 75, about 70, about 65, about 60, about 55, about 50, about 45, about 40, about 35, about 30, about 25, about 20, about 19, about 18, about 17, about 16, about 15, about 14, about 13, about 12, about 11, about 10, about 9, about 8, about 7, about 6, about 5, about 4, about 3, or about 2 amino acids long.

In various embodiments, the linker (e.g., a stabilizing domain) is substantially comprised of glycine and serine residues (e.g., about 30%, or about 40%, or about 50%, or about 60%, or about 70%, or about 80%, or about 90%, or about 95%, or about 97% glycines and serines).

In various embodiments, the linker (e.g., a stabilizing domain) is a hinge region of an antibody (e.g., of IgG, IgA, IgD, and IgE, inclusive of subclasses (e.g., IgG1, IgG2, IgG3, and IgG4, and IgA1 and IgA2)). The hinge region, found in IgG, IgA, IgD, and IgE class antibodies, acts as a flexible spacer, allowing the Fab portion to move freely in space. In contrast to the constant regions, the hinge domains are structurally diverse, varying in both sequence and length among immunoglobulin classes and subclasses. For example, the length and flexibility of the hinge region varies among the IgG subclasses. The hinge region of IgG1 encompasses amino acids 216-231 and, because it is freely flexible, the Fab fragments can rotate about their axes of symmetry and move within a sphere centered at the first of two inter-heavy chain disulfide bridges. IgG2 has a shorter hinge than IgG1, with 12 amino acid residues and four disulfide bridges. The hinge region of IgG2 lacks a glycine residue, is relatively short, and contains a rigid poly-proline double helix, stabilized by extra inter-heavy chain disulfide bridges. These properties restrict the flexibility of the IgG2 molecule. IgG3 differs from the other subclasses by its unique extended hinge region (about four times as long as the IgG1 hinge), containing 62 amino acids (including 21 prolines and 11 cysteines), forming an inflexible poly-proline double helix. In IgG3, the Fab fragments are relatively far away from the Fc fragment, giving the molecule a greater flexibility. The elongated hinge in IgG3 is also responsible for its higher molecular weight compared to the other subclasses. The hinge region of IgG4 is shorter than that of IgG1 and its flexibility is intermediate between that of IgG1 and IgG2. The flexibility of the hinge regions reportedly decreases in the order IgG3>IgG1>IgG4>IgG2. In other embodiments, the linker may be derived from human IgG4 and contain one or more mutations to enhance dimerization (including S228P) or FcRn binding.

According to crystallographic studies, the immunoglobulin hinge region can be further subdivided functionally into three regions: the upper hinge region, the core region, and the lower hinge region. See Shin et al., 1992 Immunological Reviews 130:87. The upper hinge region includes amino acids from the carboxyl end of CH1 to the first residue in the hinge that restricts motion, generally the first cysteine residue that forms an interchain disulfide bond between the two heavy chains. The length of the upper hinge region correlates with the segmental flexibility of the antibody. The core hinge region contains the inter-heavy chain disulfide bridges, and the lower hinge region joins the amino terminal end of the CH2 domain and includes residues in $C_{H2}$. Id. The core hinge region of wild-type human IgG1 contains the sequence Cys-Pro-Pro-Cys which, when dimerized by disulfide bond formation, results in a cyclic octapeptide believed to act as a pivot, thus conferring flexibility. In various embodiments, the present linker (e.g., a stabilizing domain) comprises, one, or two, or three of the upper hinge region, the core region, and the lower hinge region of any antibody (e.g., of IgG, IgA, IgD, and IgE, inclusive of subclasses (e.g., IgG1, IgG2, IgG3, and IgG4, and IgA1 and IgA2)). The hinge region may also contain one or more glycosylation sites, which include a number of structurally distinct types of sites for carbohydrate attachment. For example, IgA1 contains five glycosylation sites within a 17-amino-acid segment of the hinge region, conferring resistance of the hinge region polypeptide to intestinal proteases, considered an advantageous property for a secretory immunoglobulin. In various embodiments, the linker (e.g., a stabilizing domain) of the present invention comprises one or more glycosylation sites.

In various embodiments, the linker (e.g., a stabilizing domain) comprises an Fc domain of an antibody (e.g., of IgG, IgA, IgD, and IgE, inclusive of subclasses (e.g., IgG1, IgG2, IgG3, and IgG4, and IgA1 and IgA2)). In various embodiments, the linker (e.g., a stabilizing domain) comprises a hinge-CH2-CH3 Fc domain derived from a human IgG4 antibody. In various embodiments, the linker (e.g., a stabilizing domain) comprises a hinge-CH2-CH3 Fc domain derived from a human IgG1 antibody. In some embodiments, the Fc domain exhibits increased affinity for and enhanced binding to the neonatal Fc receptor (FcRn). In some embodiments, the Fc domain includes one or more mutations that increases the affinity and enhances binding to FcRn. Without wishing to be bound by theory, it is believed that increased affinity and enhanced binding to FcRn increases the in vivo half-life of the present heterodimeric proteins.

In some embodiments, the Fc domain contains one or more amino acid substitutions at amino acid residue 250, 252, 254, 256, 308, 309, 311, 428, 433 or 434 (in accordance with Kabat numbering), or equivalents thereof. In an embodiment, the amino acid substitution at amino acid residue 250 is a substitution with glutamine. In an embodiment, the amino acid substitution at amino acid residue 252 is a substitution with tyrosine, phenylalanine, tryptophan or threonine. In an embodiment, the amino acid substitution at amino acid residue 254 is a substitution with threonine. In an embodiment, the amino acid substitution at amino acid residue 256 is a substitution with serine, arginine, glutamine, glutamic acid, aspartic acid, or threonine. In an embodiment, the amino acid substitution at amino acid residue 308 is a substitution with threonine. In an embodiment, the amino acid substitution at amino acid residue 309 is a substitution with proline. In an embodiment, the amino acid substitution at amino acid residue 311 is a substitution with serine. In an embodiment, the amino acid substitution at amino acid residue 385 is a substitution with arginine, aspartic acid, serine, threonine, histidine, lysine, alanine or glycine. In an embodiment, the amino acid substitution at amino acid residue 386 is a substitution with threonine, proline, aspartic acid, serine, lysine, arginine, isoleucine, or methionine. In an embodiment, the amino acid substitution at amino acid residue 387 is a substitution with arginine, proline, histidine, serine, threonine, or alanine. In an embodiment, the amino acid substitution at amino acid residue 389 is a substitution with proline, serine or asparagine. In an embodiment, the amino acid substitution at amino acid residue 428 is a substitution with leucine. In an embodiment, the amino acid substitution at amino acid residue 433 is a substitution with arginine, serine, isoleucine, proline, or glutamine. In an embodiment, the amino acid substitution at amino acid residue 434 is a substitution with histidine, phenylalanine, or tyrosine.

In some embodiments, the Fc domain (e.g., comprising an IgG constant region) comprises one or more mutations such as substitutions at amino acid residue 252, 254, 256, 433, 434, or 436 (in accordance with Kabat numbering). In an embodiment, the IgG constant region includes a triple M252Y/S254T/T256E mutation or YTE mutation. In another embodiment, the IgG constant region includes a triple H433K/N434F/Y436H mutation or KFH mutation. In a further embodiment, the IgG constant region includes an YTE and KFH mutation in combination.

In some embodiments, the modified humanized antibodies of the invention comprise an IgG constant region that contains one or more mutations at amino acid residues 250, 253, 307, 310, 380, 428, 433, 434, and 435. Illustrative mutations include T250Q, M428, T307A, E380A, I253A, H310A, M428L, H433K, N434A, N434F, N434S, and H435A. In an embodiment, the IgG constant region comprises a M428L/N434S mutation or LS mutation. In another embodiment, the IgG constant region comprises a T250Q/M428L mutation or QL mutation. In another embodiment, the IgG constant region comprises an N434A mutation. In another embodiment, the IgG constant region comprises a T307A/E380A/N434A mutation or MA mutation. In another embodiment, the IgG constant region comprises an I253A/H310A/H435A mutation or IHH mutation. In another embodiment, the IgG constant region comprises a H433K/N434F mutation. In another embodiment, the IgG constant region comprises a M252Y/S254T/T256E and a H433K/N434F mutation in combination.

In various embodiments, mutations are introduced to increase stability and/or half-life of the Fc domain. An illustrative Fc stabilizing mutant is S228P. Additional illustrative Fc half-life extending mutants are T250Q, M428L, V308T, L309P, and Q311S and the present linkers (e.g., stabilizing domains) may comprise 1, or 2, or 3, or 4, or 5 of these mutants.

In embodiments, a core domain, which lacks charge polarization, has the following sequence:

```
                                        (SEQ ID NO: 15)
SKYGPPCPPCPAPEFLGGPSVFLFPPKPKDQLMISRTPEVTCVVVDVSQE

DPEVQFNWYVDGVEVHNAKTKPREEQFNSTYRVVSVLTVLHQDWLSGKEY

KCKVSSKGLPSSIEKTISNATGQPREPQVYTLPPSQEEMTKNQVSLTCLV

KGFYPSDIAVEWESNGQPENNYKTTPPVLDSDGSFFLYSRLTVDKSRWQE

GNVFSCSVLHEALHNHYTQKSLSLSLGKIEGRMD
```

Additional exemplary mutations in the IgG constant region are described, for example, in Robbie, et al., Antimicrobial Agents and Chemotherapy (2013), 57(12):6147-6153, Dall'Acqua et al., JBC (2006), 281(33):23514-24, Dall'Acqua et al., Journal of Immunology (2002), 169:5171-80, Ko et al. Nature (2014) 514:642-645, Grevys et al. Journal of Immunology. (2015), 194(11):5497-508, and U.S. Pat. No. 7,083,784, the entire contents of which are hereby incorporated by reference.

In various embodiments, the linker may be flexible, including without limitation highly flexible. In various embodiments, the linker may be rigid, including without limitation a rigid alpha helix.

In various embodiments, the linker may be functional. For example, without limitation, the linker may function to improve the folding and/or stability, improve the expression, improve the pharmacokinetics, and/or improve the bioactivity of the present heterodimeric protein. In another example, the linker may function to target the heterodimeric protein to a particular cell type or location.

In embodiments, a core domain comprises one or more "Knobs-into-holes" amino acid changes. A "Knobs-into-holes" amino acid change is a rational design strategy previously used in antibody engineering for the heterodimerization of their heavy chains. See, e.g., Ridgway, J. B. et al. "Knobs-into-holes" engineering of antibody CH3 domains for heavy chain heterodimerization," *Protein Eng.* 9(7):617-2 (1996) and Carter, "Bispecific human IgG by design." *Immunol. Methods,* 248(1-2):7-15 (2001), the contents of each of which is incorporated herein by reference in its entirety. Here, amino acid changes are engineered in order to create a "knob" in the CH3 domain of an "alpha" heavy chain and a "hole" in the CH3 of the "beta" heavy chain; alternately, Here, amino acid changes are engineered in order to create a "knob" in the CH3 domain of an "beta" heavy chain and a "hole" in the CH3 of the "alpha" heavy chain. In one example, the "knob" is represented by a tyrosine (Y) that belongs to the "very large" IMGT volume class of amino acids, whereas the "hole" is represented by a threonine (T) that belongs to the "small" IMGT volume class. Characterizations of the IMGT classes of amino acids is described at Pommié, C. et al., "IMGT standardized criteria for statistical analysis of immunoglobulin V-REGION amino acid properties." *J. Mol. Recognit.,* 17, 17-32 (2004), the contents of which is incorporated herein by reference in its entirety. In the interface between two CH3 domains on separate heavy chains, the threonine (T) T22 in the beta heavy chain is within hydrogen-bonding distance of tyrosine (Y) Y86 in the alpha heavy chain. The Y86 is the principal interdomain contact of T22 and these amino acids are involved in a hydrogen bond. However, Y86 also makes numerous van der Waals contacts with Y86 and with Lysine (K) K88 on its opposite heavy chain.

Below are illustrative hinge-CH2-CH3 comprising "knobs-into-holes" amino acid changes and useful in the present invention. The below illustrative sequences are based on IgG1 and further comprise additional effector and complement silencing substitutions: L234A and L235A (LALA) and optionally, P329G; and half-life extension mutations: M252Y, S254T, T256E.

An illustrative human IGHG1 Knob In Hole "alpha core domain" (T22Y) is shown below:

```
                                        (SEQ ID NO: 24)
EPKSCDKTHTCPPCPAPEAAGGPSVFLFPPKPKDTLYITREPEVTCVVVD

VSHEDPEVKFNWYVDGVEVHNAKTKPREEQYNSTYRVVSVLTVLHQDWLN

GKEYKCKVSNKALPAPIEKTISKAKGQPREPQVYTLPPSRDELTKNQVSL

YCLVKGFYPSDIAVEWESNGQPENNYKTTPPVLDSDGSFFLYSKLTVDKS

RWQQGNVFSCSVMHEALHNHYTQKSLSLSPGK
```

An illustrative human IGHG1 Knob In Hole "beta core domain" (Y86T)

(SEQ ID NO: 25)
EPKSCDKTHTCPPCPAPEAAGGPSVFLFPPKPKDTLYITREPEVTCVVVD

VSHEDPEVKFNWYVDGVEVHNAKTKPREEQYNSTYRVVSVLTVLHQDWLN

GKEYKCKVSNKALPAPIEKTISKAKGQPREPQVYTLPPSRDELTKNQVSL

TCLVKGFYPSDIAVEWESNGQPENNYKTTPPVLDSDGSFFLTSKLTVDKS

RWQQGNVFSCSVMHEALHNHYTQKSLSLSPGK

Any core domain useful in the present invention may comprise one or more "knob in holes" mutation.

Protein Subunits

In various embodiments, the heterodimeric protein of the invention comprises two polypeptide chains. In various embodiments, each polypeptide chain comprises a subunit of a first protein linked by a charge polarized core domain to a subunit of a second protein. Upon electrostatic interactions between the charge polarized core domains, the subunits are heterodimerized to form a functional dimeric first protein and a functional dimeric second protein. In some embodiments, the polypeptide chains form a functional two-sided heterodimeric protein linked via the charge polarized core domains, which optionally include a linker (e.g., a stabilizing domain) such as an Fc region.

In various embodiments, the first and second proteins may be any multimeric protein having two or more subunits. In some embodiments, the first protein and second protein are selected from cytokines, growth factors, and/or hormones. Illustrative examples of such cytokines, growth factors, and hormones include, but are not limited to, lymphokines, monokines, traditional polypeptide hormones, including, but not limited to, colony stimulating factors (CSFs) such as macrophage-CSF (M-CSF); granulocyte-macrophage-CSF (GM-CSF); and granulocyte-CSF (G-CSF); interleukins (ILs) such as, without limitation, IL-18, IL-27, and IL-35; interleukin receptors such as, without limitation, IL-2R, IL-3R, IL-4R, IL-5R, IL-6R, IL-7R, IL-9R, IL-10R, IL-11R, IL-12R, IL-13R, IL-15R, IL-17R, IL-18R, IL-20R, IL-21R, IL-22R, IL-23R, IL-27R, IL-35R; and other polypeptide factors including, without limitation, EGFR, integrins, neuropilins, and somatostatin receptors. As used herein, cytokines, growth factors, and hormones include proteins obtained from natural sources or produced from recombinant bacterial, eukaryotic or mammalian cell culture systems and biologically active equivalents of the native sequence cytokines.

In some embodiments, the first and/or second protein is an immune-modulating agent, e.g., one or more of an interleukin and interferon.

In some embodiments, the first and/or second protein is an interleukin, including for example IL-18, IL-27, and IL-35, or a fragment, variant, analogue, or family-member thereof. Interleukins are a group of multi-functional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. Interleukin activity can be determined using assays known in the art: Matthews et al., in *Lymphokines and Interferons: A Practical Approach*, Clemens et al., eds, IRL Press, Washington, D.C. 1987, pp. 221-225; and Orencole & Dinarello (1989) Cytokine 1, 14-20.

In some embodiments, the first and/or second protein is a hormone such as somatostatin.

In various embodiments, the first and/or second protein is a receptor for a cytokine, growth factor, and/or hormone. In some embodiments, the first and/or second protein is a type I cytokine receptor, a type II cytokine receptor, a chemokine receptor, TGF-beta Receptors, a receptor in the immunoglobulin (Ig) superfamily, and/or a receptor in the tyrosine kinase superfamily.

In some embodiments, the first and/or second protein is a Type I cytokine receptor. Type I cytokine receptors are known in the art and include, but are not limited to receptors for IL2 (beta-subunit), IL3, IL4, IL5, IL6, IL7, IL9, 11_11, IL12, GM-CSF, G-CSF, LIF, CNTF, and also the receptors for Thrombopoietin (TPO), Prolactin, and Growth hormone. Illustrative type I cytokine receptors include, but are not limited to, GM-CSF receptor, G-CSF receptor, LIF receptor, CNTF receptor, TPO receptor, and type I IL receptors.

In some embodiments, the first and/or second protein is a Type II cytokine receptor. Type II cytokine receptors are multimeric receptors composed of heterologous subunits, and are receptors mainly for interferons. This family of receptors includes, but is not limited to, receptors for interferon-α, interferon-β and interferon-γ, IL10, IL22, and tissue factor. Illustrative type II cytokine receptors include, but are not limited to, IFN-α receptor (e.g., IFNAR1 and IFNAR2), IFN-β receptor, IFN-γ receptor (e.g., IFNGR1 and IFNGR2), and type II IL receptors.

In some embodiments, the first and/or second protein is a G protein-coupled receptor. Chemokine receptors are G protein-coupled receptors with seven transmembrane structure and coupled to G-protein for signal transduction. Chemokine receptors include, but are not limited to, CC chemokine receptors, CXC chemokine receptors, CX3C chemokine receptors, and XC chemokine receptor (XCR1). Exemplary chemokine receptors include, but are not limited to, CCR1, CCR2, CCR3, CCR4, CCR5, CCR6, CCR7, CCR8, CCR9, CCR10, CXCR1, CXCR2, CXCR3, CXCR3B, CXCR4, CXCR5, CSCR6, CXCR7, XCR1, and CX3CR1.

In some embodiments, the first and/or second protein is a TGF-beta receptor. TGF-beta receptors are single pass serine/threonine kinase receptors. TGF-beta receptors include, but are not limited to, TGFBR1, TGFBR2, and TGFBR3.

In some embodiments, the first and/or second protein is an Ig superfamily receptor. Receptors in the immunoglobulin (Ig) superfamily share structural homology with immunoglobulins. Receptors in the Ig superfamily include, but are not limited to, interleukin-1 receptors, CSF-1R, PDGFR (e.g., PDGFRA and PDGFRB), and SCFR.

In some embodiments, the first and/or second protein is a B7 superfamily member. Members of the B7 superfamily share structural homology with one another. Members of this family include, but are not limited to, CD28, CD80, CD86, ICOS, ICOSL, B7-H3, B7-H4, PD-1, PD-L1, PD-L2, etc.

In some embodiments, the first and/or second protein is a tyrosine kinase superfamily receptor. Receptors in the tyrosine kinase superfamily are well known in the art. There are about 58 known receptor tyrosine kinases (RTKs), grouped into 20 subfamilies. Receptors in the tyrosine kinase superfamily include, but are not limited to, FGF receptors and their various isoforms such as FGFR1, FGFR2, FGFR3, FGFR4, and FGFR5.

In an exemplary embodiment, the first and/or second protein is an IFN-α/β receptor (IFNAR) comprising IFNAR1 and/or IFNAR2 subunits.

In an exemplary embodiment, the first and/or second protein is an interferon-gamma receptor (IFNGR) comprising IFNGR1 (also known as IFNgR) and IFNGR2 subunits.

In an exemplary embodiment, the first and/or second protein is a VEGF receptor including VEGFR-1, VEGFR-2, and VEGFR-3.

In any heterodimeric protein disclosed herein, the amino- or carboxy-terminus is natively heterodimeric, and wherein the protein on the opposite terminus is not natively heterodimeric.

In an exemplary embodiment, the first and/or second protein is a receptor for IL-1 such as IL-1R1 and/or IL-1RAcP.

In an exemplary embodiment, the first and/or second protein is a receptor for IL-2 such as IL-2Rα or IL-2Rβ or IL-2Rγ.

In an exemplary embodiment, the first and/or second protein is an IL-3 receptor, which is a heterodimer with a unique alpha chain paired with the common beta (beta c or CD131) subunit.

In an exemplary embodiment, the first and/or second protein is a receptor for IL-4 such as a type 1 or type 2 IL-4 receptor.

In an exemplary embodiment, the first and/or second protein is a receptor for IL-6, which is a cell-surface type I cytokine receptor complex including the ligand-binding IL-6R chain (CD126 or IL-6Rα) and the signal-transducing component gp130.

In an exemplary embodiment, the first and/or second protein is a receptor for IL-10, such as IL-10 receptor-1 and IL-10 receptor-2.

In an exemplary embodiment, the first and/or second protein is a receptor for IL-11, such as IL-11Rα or IL-11Rβ or gp130.

In an exemplary embodiment, the first and/or second protein is a receptor for IL-12, such as IL-12Rβ1 and/or IL-12Rβ2.

In an exemplary embodiment, the first and/or second protein is a receptor for IL-13, such as the IL-4 receptor (IL-4Rα) or IL-13Rα1.

In an exemplary embodiment, the first and/or second protein is IL-18. In another exemplary embodiment, the first and/or second protein is a receptor for IL-18, such as IL-18Rα and/or IL-18Rβ.

In an exemplary embodiment, the first and/or second protein is a receptor for IL-21, which is a cell-surface type I cytokine receptor complex including the ligand-binding IL-21R chain comprising IL-21r and IL-2rg.

In an exemplary embodiment, the first and/or second protein is a receptor for IL-33, such as the ST-2 receptor or IL-1RAcP.

In an exemplary embodiment, the first and/or second protein is IL-35 (e.g., comprising the IL12α and IL27β subunits). In another exemplary embodiment, the first and/or second protein is a receptor for IL-35, such as an IL-35 receptor comprising IL6Rα and gp130 subunits.

In an exemplary embodiment, the first and/or second protein is a receptor for EGP such as EGFR (ErbB1), ErbB2, ErbB3 and ErbB4.

In an exemplary embodiment, the first and/or second protein is a receptor for insulin or an insulin analog such as the insulin receptor and/or IGF1 or IGF2 receptor.

In an exemplary embodiment, the first and/or second protein is a receptor for EPO such as the EPO receptor (EPOR) receptor and/or the ephrin receptor (EphR).

In various embodiments, the first and second proteins may comprise a domain of a soluble (e.g., non-membrane associated) protein. In various embodiments, the first and second proteins may comprise a fragment of the soluble protein which is involved in signaling (e.g., a portion of the soluble protein which interacts with a receptor).

In various embodiments, the first and second proteins may comprise the extracellular domain of a transmembrane protein. In various embodiments, one of the extracellular domains transduces an immune inhibitory signal and one of the extracellular domains transduces an immune stimulatory signal.

In some embodiments, an extracellular domain refers to a portion of a transmembrane protein which is capable of interacting with the extracellular environment. In various embodiments, an extracellular domain refers to a portion of a transmembrane protein which is sufficient to bind to a ligand or receptor and effective transmit a signal to a cell. In various embodiments, an extracellular domain is the entire amino acid sequence of a transmembrane protein which is external of a cell or the cell membrane. In various embodiments, an extracellular domain is the that portion of an amino acid sequence of a transmembrane protein which is external of a cell or the cell membrane and is needed for signal transduction and/or ligand binding as may be assayed using methods know in the art (e.g., in vitro ligand binding and/or cellular activation assays).

In some embodiments, an immune inhibitory signal refers to a signal that diminishes or eliminates an immune response. For example, in the context of oncology, such signals may diminish or eliminate antitumor immunity. Under normal physiological conditions, inhibitory signal are useful in the maintenance of self-tolerance (e.g., prevention of autoimmunity) and also to protect tissues from damage when the immune system is responding to pathogenic infection. For instance, without limitation, immune inhibitory signal may be identified by detecting an increase in cellular proliferation, cytokine production, cell killing activity or phagocytic activity when such an inhibitory signal is blocked.

In some embodiments, an immune stimulatory signal refers to a signal that enhances an immune response. For example, in the context of oncology, such signals may enhance antitumor immunity. For instance, without limitation, immune stimulatory signal may be identified by directly stimulating proliferation, cytokine production, killing activity or phagocytic activity of leukocytes. Specific examples include direct stimulation of cytokine receptors such as IL-2R, IL-7R, IL-15R, IL-17R or IL-21R using fusion proteins encoding the ligands for such receptors (IL-2, IL-7, IL-15, IL-17 or IL-21, respectively). Stimulation from any one of these receptors may directly stimulate the proliferation and cytokine production of individual T cell subsets.

In some embodiments, the extracellular domain may be used to produce a soluble protein to competitively inhibit signaling by that receptor's ligand. For instance, without limitation, competitive inhibition of PD-L1 or PD-L2 could be achieved using PD-1, or competitive inhibition of PVR could be achieved using TIGIT. In some embodiments, the extracellular domain may be used to provide artificial signaling.

In some embodiments, the present heterodimeric proteins deliver or mask an immune inhibitory signal. In some embodiments, the present heterodimeric proteins deliver or mask an immune stimulatory signal.

In various embodiments, the present heterodimeric proteins comprise two independent binding domains, each from one subunit of a heterodimeric human protein. Exemplary proteins that may be formed as part of the heterodimeric protein of the invention are provided in Table 1. In various embodiments, the present heterodimeric proteins have one of the exemplary proteins provided in Table 1. In various embodiments, the present heterodimeric proteins have two of the exemplary proteins provided in Table 1.

TABLE 1

Illustrative proteins which may be incorporated into the present compositions and methods include the following (as used herein, "Entry" refers to the protein entry in the Uniprot database and "Entry name" refers to the protein entry in the Uniprot database):

| Entry | Entry name | Protein names | Gene names |
|---|---|---|---|
| P00533 | EGFR_HUMAN | Epidermal growth factor receptor (EC 2.7.10.1) (Proto-oncogene c-ErbB-1) (Receptor tyrosine-protein kinase erbB-1) | EGFR ERBB ERBB1 HER1 |
| P49768 | PSN1_HUMAN | Presenilin-1 (PS-1) (EC 3.4.23.-) (Protein S182) [Cleaved into: Presenilin-1 NTF subunit; Presenilin-1 CTF subunit; Presenilin-1 CTF12 (PS1-CTF12)] | PSEN1 AD3 PS1 PSNL1 |
| P13569 | CFTR_HUMAN | Cystic fibrosis transmembrane conductance regulator (CFTR) (ATP-binding cassette sub-family C member 7) (Channel conductance-controlling ATPase) (EC 3.6.3.49) (cAMP-dependent chloride channel) | CFTR ABCC7 |
| P04626 | ERBB2_HUMAN | Receptor tyrosine-protein kinase erbB-2 (EC 2.7.10.1) (Metastatic lymph node gene 19 protein) (MLN 19) (Proto-oncogene Neu) (Proto-oncogene c-ErbB-2) (Tyrosine kinase-type cell surface receptor HER2) (p185erbB2) (CD antigen CD340) | ERBB2 HER2 MLN19 NEU NGL |
| P08581 | MET_HUMAN | Hepatocyte growth factor receptor (HGF receptor) (EC 2.7.10.1) (HGF/SF receptor) (Proto-oncogene c-Met) (Scatter factor receptor) (SF receptor) (Tyrosine-protein kinase Met) | MET |
| P17861 | XBP1_HUMAN | X-box-binding protein 1 (XBP-1) (Tax-responsive element-binding protein 5) (TREB-5) [Cleaved into: X-box-binding protein 1, cytoplasmic form; X-box-binding protein 1, luminal form] | XBP1 TREB5 XBP2 |
| P05106 | ITB3_HUMAN | Integrin beta-3 (Platelet membrane glycoprotein IIIa) (GPIIIa) (CD antigen CD61) | ITGB3 GP3A |
| P05556 | ITB1_HUMAN | Integrin beta-1 (Fibronectin receptor subunit beta) (Glycoprotein IIa) (GPIIA) (VLA-4 subunit beta) (CD antigen CD29) | ITGB1 FNRB MDF2 MSK12 |
| P46531 | NOTC1_HUMAN | Neurogenic locus notch homolog protein 1 (Notch 1) (hN1) (Translocation-associated notch protein TAN-1) [Cleaved into: Notch 1 extracellular truncation (NEXT); Notch 1 intracellular domain (NICD)] | NOTCH1 TAN1 |
| P16671 | CD36_HUMAN | Platelet glycoprotein 4 (Fatty acid translocase) (FAT) (Glycoprotein IIIb) (GPIIIB) (Leukocyte differentiation antigen CD36) (PAS IV) (PAS-4) (Platelet collagen receptor) (Platelet glycoprotein IV) (GPIV) (Thrombospondin receptor) (CD antigen CD36) | CD36 GP3B GP4 |
| Q15303 | ERBB4_HUMAN | Receptor tyrosine-protein kinase erbB-4 (EC 2.7.10.1) (Proto-oncogene-like protein c-ErbB-4) (Tyrosine kinase-type cell surface receptor HER4) (p180erbB4) [Cleaved into: ERBB4 intracellular domain (4ICD) (E4ICD) (s80HER4)] | ERBB4 HER4 |
| Q02763 | TIE2_HUMAN | Angiopoietin-1 receptor (EC 2.7.10.1) (Endothelial tyrosine kinase) (Tunica interna endothelial cell kinase) (Tyrosine kinase with Ig and EGF homology domains-2) (Tyrosine-protein kinase receptor TEK) (Tyrosine-protein kinase receptor TIE-2) (hTIE2) (p140 TEK) (CD antigen CD202b) | TEK TIE2 VMCM VMCM1 |
| O00206 | TLR4_HUMAN | Toll-like receptor 4 (hToll) (CD antigen CD284) | TLR4 |
| Q14118 | DAG1_HUMAN | Dystroglycan (Dystrophin-associated glycoprotein 1) [Cleaved into: Alpha-dystroglycan (Alpha-DG); Beta-dystroglycan (Beta-DG)] | DAG1 |
| P16473 | TSHR_HUMAN | Thyrotropin receptor (Thyroid-stimulating hormone receptor) (TSH-R) | TSHR LGR3 |
| Q99527 | GPER1_HUMAN | G-protein coupled estrogen receptor 1 (Chemoattractant receptor-like 2) (Flow-induced endothelial G-protein coupled receptor 1) (FEG-1) (G protein-coupled estrogen receptor 1) (G-protein coupled receptor 30) (GPCR-Br) (IL8-related receptor DRY12) (Lymphocyte-derived G-protein coupled receptor) (LYGPR) (Membrane estrogen receptor) (mER) | GPER1 CEPR CMKRL2 DRY12 GPER GPR30 |
| P17948 | VGFR1_HUMAN | Vascular endothelial growth factor receptor 1 (VEGFR-1) (EC 2.7.10.1) (Fms-like tyrosine kinase 1) (FLT-1) (Tyrosine-protein kinase FRT) (Tyrosine-protein kinase receptor FLT) (FLT) (Vascular permeability factor receptor) | FLT1 FLT FRT VEGFR1 |
| Q9UM47 | NOTC3_HUMAN | Neurogenic locus notch homolog protein 3 (Notch 3) [Cleaved into: Notch 3 extracellular truncation; Notch 3 intracellular domain] | NOTCH3 |
| P21860 | ERBB3_HUMAN | Receptor tyrosine-protein kinase erbB-3 (EC 2.7.10.1) (Proto-oncogene-like protein c-ErbB-3) (Tyrosine kinase-type cell surface receptor HER3) | ERBB3 HER3 |
| P01920 | DQB1_HUMAN | HLA class II histocompatibility antigen, DQ beta 1 chain (MHC class II antigen DQB1) | HLA-DQB1 HLA-DQB |
| P06756 | ITAV_HUMAN | Integrin alpha-V (Vitronectin receptor) (Vitronectin receptor subunit alpha) (CD antigen CD51) [Cleaved into: Integrin alpha-V heavy chain; Integrin alpha-V light chain] | ITGAV MSK8 VNRA VTNR |
| Q9H251 | CAD23_HUMAN | Cadherin-23 (Otocadherin) | CDH23 KIAA1774 KIAA1812 |

TABLE 1-continued

Illustrative proteins which may be incorporated into the present compositions and methods include the following (as used herein, "Entry" refers to the protein entry in the Uniprot database and "Entry name" refers to the protein entry in the Uniprot database):

| Entry | Entry name | Protein names | Gene names |
|---|---|---|---|
| Q07954 | LRP1_HUMAN | Prolow-density lipoprotein receptor-related protein 1 (LRP-1) (Alpha-2-macroglobulin receptor) (A2MR) (Apolipoprotein E receptor) (APOER) (CD antigen CD91) [Cleaved into: Low-density lipoprotein receptor-related protein 1 85 kDa subunit (LRP-85); Low-density lipoprotein receptor-related protein 1 515 kDa subunit (LRP-515); Low-density lipoprotein receptor-related protein 1 intracellular domain (LRPICD)] | UNQ1894/ PRO4340 LRP1 A2MR APR |
| O60603 | TLR2_HUMAN | Toll-like receptor 2 (Toll/interleukin-1 receptor-like protein 4) (CD antigen CD282) | TLR2 TIL4 |
| P04839 | CY24B_HUMAN | Cytochrome b-245 heavy chain (EC 1.-.-.-) (CGD91-phox) (Cytochrome b(558) subunit beta) (Cytochrome b558 subunit beta) (Heme-binding membrane glycoprotein gp91phox) (NADPH oxidase 2) (Neutrophil cytochrome b 91 kDa polypeptide) (Superoxide-generating NADPH oxidase heavy chain subunit) (gp91-1) (gp91-phox) (p22 phagocyte B-cytochrome) | CYBB NOX2 |
| P04233 | HG2A_HUMAN | HLA class II histocompatibility antigen gamma chain (HLA-DR antigens-associated invariant chain) (Ia antigen-associated invariant chain) (Ii) (p33) (CD antigen CD74) | CD74 DHLAG |
| P13746 | 1A11_HUMAN | HLA class I histocompatibility antigen, A-11 alpha chain (MHC class I antigen A*11) | HLA-A HLAA |
| P18462 | 1A25_HUMAN | HLA class I histocompatibility antigen, A-25 alpha chain (HLA class I histocompatibility antigen, A-10 alpha chain) (MHC class I antigen A*25) | HLA-A HLAA |
| P16188 | 1A30_HUMAN | HLA class I histocompatibility antigen, A-30 alpha chain (MHC class I antigen A*30) | HLA-A HLAA |
| P30457 | 1A66_HUMAN | HLA class I histocompatibility antigen, A-66 alpha chain (Aw-66) (HLA class I histocompatibility antigen, A-10 alpha chain) (MHC class I antigen A*66) | HLA-A HLAA |
| P10316 | 1A69_HUMAN | HLA class I histocompatibility antigen, A-69 alpha chain (Aw-69) (HLA class I histocompatibility antigen, A-28 alpha chain) (MHC class I antigen A*69) | HLA-A HLAA |
| Q09160 | 1A80_HUMAN | HLA class I histocompatibility antigen, A-80 alpha chain (Aw-80) (HLA class I histocompatibility antigen, A-1 alpha chain) (MHC class I antigen A*80) | HLA-A HLAA |
| P30460 | 1B08_HUMAN | HLA class I histocompatibility antigen, B-8 alpha chain (MHC class I antigen B*8) | HLA-B HLAB |
| P30685 | 1B35_HUMAN | HLA class I histocompatibility antigen, B-35 alpha chain (MHC class I antigen B*35) | HLA-B HLAB |
| P08195 | 4F2_HUMAN | 4F2 cell-surface antigen heavy chain (4F2hc) (4F2 heavy chain antigen) (Lymphocyte activation antigen 4F2 large subunit) (Solute carrier family 3 member 2) (CD antigen CD98) | SLC3A2 MDU1 |
| P28222 | 5HT1B_HUMAN | 5-hydroxytryptamine receptor 1B (5-HT-1B) (5-HT1B) (S12) (Serotonin 1D beta receptor) (5-HT-1D-beta) (Serotonin receptor 1B) | HTR1B HTR1DB |
| P28221 | 5HT1D_HUMAN | 5-hydroxytryptamine receptor 1D (5-HT-1D) (5-HT1D) (Serotonin 1D alpha receptor) (5-HT-1D-alpha) (Serotonin receptor 1D) | HTR1D HTR1DA HTRL |
| O14678 | ABCD4_HUMAN | ATP-binding cassette sub-family D member 4 (PMP70-related protein) (P70R) (Peroxisomal membrane protein 1-like) (PXMP1-L) (Peroxisomal membrane protein 69) (PMP69) | ABCD4 PXMP1L |
| P30462 | 1B14_HUMAN | HLA class I histocompatibility antigen, B-14 alpha chain (MHC class I antigen B*14) | HLA-B HLAB |
| P30466 | 1B18_HUMAN | HLA class I histocompatibility antigen, B-18 alpha chain (MHC class I antigen B*18) | HLA-B HLAB |
| Q04826 | 1B40_HUMAN | HLA class I histocompatibility antigen, B-40 alpha chain (Bw-60) (MHC class I antigen B*40) | HLA-B HLAB |
| P30480 | 1B42_HUMAN | HLA class I histocompatibility antigen, B-42 alpha chain (MHC class I antigen B*42) | HLA-B HLAB |
| P30484 | 1B46_HUMAN | HLA class I histocompatibility antigen, B-46 alpha chain (Bw-46) (MHC class I antigen B*46) | HLA-B HLAB |
| P30487 | 1B49_HUMAN | HLA class I histocompatibility antigen, B-49 alpha chain (HLA class I histocompatibility antigen, B-21 alpha chain) (MHC class I antigen B*49) | HLA-B HLAB |
| P18464 | 1B51_HUMAN | HLA class I histocompatibility antigen, B-51 alpha chain (MHC class I antigen B*51) | HLA-B HLAB |
| P30495 | 1B56_HUMAN | HLA class I histocompatibility antigen, B-56 alpha chain (Bw-22) (Bw-56) (MHC class I antigen B*56) | HLA-B HLAB |
| P30498 | 1B78_HUMAN | HLA class I histocompatibility antigen, B-78 alpha chain (MHC class I antigen B*78) | HLA-B HLAB |
| Q29718 | 1B82_HUMAN | HLA class I histocompatibility antigen, B-82 alpha chain (MHC class I antigen B*82) | HLA-B HLAB |
| P30501 | 1C02_HUMAN | HLA class I histocompatibility antigen, Cw-2 alpha chain (MHC class I antigen Cw*2) | HLA-C HLAC |
| P30504 | 1C04_HUMAN | HLA class I histocompatibility antigen, Cw-4 alpha chain (MHC class I antigen Cw*4) | HLA-C HLAC |
| P01912 | 2B13_HUMAN | HLA class II histocompatibility antigen, DRB1-3 chain (Clone P2-beta-3) (MHC class II antigen DRB1*3) | HLA-DRB1 |
| P13760 | 2B14_HUMAN | HLA class II histocompatibility antigen, DRB1-4 beta chain (MHC class II antigen DRB1*4) (DR-4) (DR4) | HLA-DRB1 |
| P01911 | 2B1F_HUMAN | HLA class II histocompatibility antigen, DRB1-15 beta chain (DW2.2/DR2.2) (MHC class II antigen DRB1*15) | HLA-DRB1 HLA-DRB2 |

TABLE 1-continued

Illustrative proteins which may be incorporated into the present compositions and methods include the following (as used herein, "Entry" refers to the protein entry in the Uniprot database and "Entry name" refers to the protein entry in the Uniprot database):

| Entry | Entry name | Protein names | Gene names |
|---|---|---|---|
| P01892 | 1A02_HUMAN | HLA class I histocompatibility antigen, A-2 alpha chain (MHC class I antigen A*2) | HLA-A HLAA |
| P03989 | 1B27_HUMAN | HLA class I histocompatibility antigen, B-27 alpha chain (MHC class I antigen B*27) | HLA-B HLAB |
| P13761 | 2B17_HUMAN | HLA class II histocompatibility antigen, DRB1-7 beta chain (MHC class II antigen DRB1*7) (DR-7) (DR7) | HLA-DRB1 |
| Q9TQE0 | 2B19_HUMAN | HLA class II histocompatibility antigen, DRB1-9 beta chain (MHC class II antigen DRB1*9) (DR-9) (DR9) | HLA-DRB1 |
| P20039 | 2B1B_HUMAN | HLA class II histocompatibility antigen, DRB1-11 beta chain (DR-5) (DR5) (DRw11) (MHC class II antigen DRB1*11) | HLA-DRB1 |
| O75027 | ABCB7_HUMAN | ATP-binding cassette sub-family B member 7, mitochondrial (ATP-binding cassette transporter 7) (ABC transporter 7 protein) | ABCB7 ABC7 |
| P16189 | 1A31_HUMAN | HLA class I histocompatibility antigen, A-31 alpha chain (MHC class I antigen A*31) | HLA-A HLAA |
| P30456 | 1A43_HUMAN | HLA class I histocompatibility antigen, A-43 alpha chain (Aw-43) (MHC class I antigen A*43) | HLA-A HLAA |
| P30459 | 1A74_HUMAN | HLA class I histocompatibility antigen, A-74 alpha chain (Aw-19) (Aw-74) (MHC class I antigen A*74) | HLA-A HLAA |
| P18463 | 1B37_HUMAN | HLA class I histocompatibility antigen, B-37 alpha chain (MHC class I antigen B*37) | HLA-B HLAB |
| P30483 | 1B45_HUMAN | HLA class I histocompatibility antigen, B-45 alpha chain (Bw-45) (MHC class I antigen B*45) | HLA-B HLAB |
| P30485 | 1B47_HUMAN | HLA class I histocompatibility antigen, B-47 alpha chain (Bw-47) (MHC class I antigen B*47) | HLA-B HLAB |
| P30486 | 1B48_HUMAN | HLA class I histocompatibility antigen, B-48 alpha chain (Bw-48) (MHC class I antigen B*48) | HLA-B HLAB |
| P30491 | 1B53_HUMAN | HLA class I histocompatibility antigen, B-53 alpha chain (Bw-53) (MHC class I antigen B*53) | HLA-B HLAB |
| Q29940 | 1B59_HUMAN | HLA class I histocompatibility antigen, B-59 alpha chain (MHC class I antigen B*59) | HLA-B HLAB |
| Q31612 | 1B73_HUMAN | HLA class I histocompatibility antigen, B-73 alpha chain (MHC class I antigen B*73) | HLA-B HLAB |
| Q31610 | 1B81_HUMAN | HLA class I histocompatibility antigen, B-81 alpha chain (B'DT) (MHC class I antigen B*81) | HLA-B HLAB |
| P30499 | 1C01_HUMAN | HLA class I histocompatibility antigen, Cw-1 alpha chain (MHC class I antigen Cw*1) | HLA-C HLAC |
| Q9TNN7 | 1C05_HUMAN | HLA class I histocompatibility antigen, Cw-5 alpha chain (MHC class I antigen Cw*5) | HLA-C HLAC |
| P30508 | 1C12_HUMAN | HLA class I histocompatibility antigen, Cw-12 alpha chain (MHC class I antigen Cw*12) | HLA-C HLAC |
| Q29865 | 1C18_HUMAN | HLA class I histocompatibility antigen, Cw-18 alpha chain (MHC class I antigen Cw*18) | HLA-C HLAC |
| Q5Y7A7 | 2B1D_HUMAN | HLA class II histocompatibility antigen, DRB1-13 beta chain (MHC class II antigen DRB1*13) (DR-13) (DR13) | HLA-DRB1 |
| Q29974 | 2B1G_HUMAN | HLA class II histocompatibility antigen, DRB1-16 beta chain (MHC class II antigen DRB1*16) (DR-16) (DR16) | HLA-DRB1 |
| Q9NS82 | AAA1_HUMAN | Asc-type amino acid transporter 1 (Asc-1) (Solute carrier family 7 member 10) | SLC7A10 ASC1 |
| P30447 | 1A23_HUMAN | HLA class I histocompatibility antigen, A-23 alpha chain (HLA class I histocompatibility antigen, A-9 alpha chain) (MHC class I antigen A*23) | HLA-A HLAA |
| P30450 | 1A26_HUMAN | HLA class I histocompatibility antigen, A-26 alpha chain (MHC class I antigen A*26) | HLA-A HLAA |
| P10314 | 1A32_HUMAN | HLA class I histocompatibility antigen, A-32 alpha chain (MHC class I antigen A*32) | HLA-A HLAA |
| P30455 | 1A36_HUMAN | HLA class I histocompatibility antigen, A-36 alpha chain (Aw-36) (MHC class I antigen A*36) | HLA-A HLAA |
| P30461 | 1B13_HUMAN | HLA class I histocompatibility antigen, B-13 alpha chain (MHC class I antigen B*13) | HLA-B HLAB |
| P30464 | 1B15_HUMAN | HLA class I histocompatibility antigen, B-15 alpha chain (MHC class I antigen B*15) | HLA-B HLAB |
| P30475 | 1B39_HUMAN | HLA class I histocompatibility antigen, B-39 alpha chain (MHC class I antigen B*39) | HLA-B HLAB |
| P30479 | 1B41_HUMAN | HLA class I histocompatibility antigen, B-41 alpha chain (Bw-41) (MHC class I antigen B*41) | HLA-B HLAB |
| P30481 | 1B44_HUMAN | HLA class I histocompatibility antigen, B-44 alpha chain (Bw-44) (MHC class I antigen B*44) | HLA-B HLAB |
| P30488 | 1B50_HUMAN | HLA class I histocompatibility antigen, B-50 alpha chain (Bw-50) (HLA class I histocompatibility antigen, B-21 alpha chain) (MHC class I antigen B*50) | HLA-B HLAB |
| P30490 | 1B52_HUMAN | HLA class I histocompatibility antigen, B-52 alpha chain (Bw-52) (HLA class I histocompatibility antigen, B-5 alpha chain) (MHC class I antigen B*52) | HLA-B HLAB |
| P30493 | 1B55_HUMAN | HLA class I histocompatibility antigen, B-55 alpha chain (Bw-55) (HLA class I histocompatibility antigen, B-12 alpha chain) (MHC class I antigen B*55) | HLA-B HLAB CDABP0067 |
| P18465 | 1B57_HUMAN | HLA class I histocompatibility antigen, B-57 alpha chain (Bw-57) (MHC class I antigen B*57) | HLA-B HLAB |

TABLE 1-continued

Illustrative proteins which may be incorporated into the present compositions and methods include the following (as used herein, "Entry" refers to the protein entry in the Uniprot database and "Entry name" refers to the protein entry in the Uniprot database):

| Entry | Entry name | Protein names | Gene names |
| --- | --- | --- | --- |
| Q29836 | 1B67_HUMAN | HLA class I histocompatibility antigen, B-67 alpha chain (MHC class I antigen B*67) | HLA-B<br>HLAB |
| P10319 | 1B58_HUMAN | HLA class I histocompatibility antigen, B-58 alpha chain (Bw-58) (MHC class I antigen B*58) | HLA-B<br>HLAB |
| P04222 | 1C03_HUMAN | HLA class I histocompatibility antigen, Cw-3 alpha chain (MHC class I antigen Cw*3) | HLA-C<br>HLAC |
| Q29963 | 1C06_HUMAN | HLA class I histocompatibility antigen, Cw-6 alpha chain (MHC class I antigen Cw*6) | HLA-C<br>HLAC |
| P30505 | 1C08_HUMAN | HLA class I histocompatibility antigen, Cw-8 alpha chain (MHC class I antigen Cw*8) | HLA-C<br>HLAC |
| Q07000 | 1C15_HUMAN | HLA class I histocompatibility antigen, Cw-15 alpha chain (MHC class I antigen Cw*15) | HLA-C<br>HLAC |
| Q95604 | 1C17_HUMAN | HLA class I histocompatibility antigen, Cw-17 alpha chain (MHC class I antigen Cw*17) | HLA-C<br>D6S204<br>HLA-JY3<br>HLAC |
| Q95365 | 1B38_HUMAN | HLA class I histocompatibility antigen, B-38 alpha chain (Bw-4) (MHC class I antigen B*38) | HLA-B<br>HLAB |
| P30492 | 1B54_HUMAN | HLA class I histocompatibility antigen, B-54 alpha chain (Bw-22) (Bw-54) (MHC class I antigen B*54) | HLA-B<br>HLAB |
| P10321 | 1C07_HUMAN | HLA class I histocompatibility antigen, Cw-7 alpha chain (MHC class I antigen Cw*7) | HLA-C<br>HLAC |
| P30510 | 1C14_HUMAN | HLA class I histocompatibility antigen, Cw-14 alpha chain (MHC class I antigen Cw*14) | HLA-C<br>HLAC |
| Q29960 | 1C16_HUMAN | HLA class I histocompatibility antigen, Cw-16 alpha chain (MHC class I antigen Cw*16) | HLA-C<br>HLAC |
| P04229 | 2B11_HUMAN | HLA class II histocompatibility antigen, DRB1-1 beta chain (MHC class II antigen DRB1*1) (DR-1) (DR1) | HLA-DRB1 |
| Q30167 | 2B1A_HUMAN | HLA class II histocompatibility antigen, DRB1-10 beta chain (DRw10) (MHC class II antigen DRB1*10) | HLA-DRB1 |
| Q9GIY3 | 2B1E_HUMAN | HLA class II histocompatibility antigen, DRB1-14 beta chain (MHC class II antigen DRB1*14) (DR-14) (DR14) | HLA-DRB1 |
| P08908 | 5HT1A_HUMAN | 5-hydroxytryptamine receptor 1A (5-HT-1A) (5-HT1A) (G-21) (Serotonin receptor 1A) | HTR1A<br>ADRB2RL1<br>ADRBRL1 |
| Q96PE1 | AGRA2_HUMAN | Adhesion G protein-coupled receptor A2 (G-protein coupled receptor 124) (Tumor endothelial marker 5) | ADGRA2<br>GPR124<br>KIAA1531<br>TEM5 |
| P05534 | 1A24_HUMAN | HLA class I histocompatibility antigen, A-24 alpha chain (Aw-24) (HLA class I histocompatibility antigen, A-9 alpha chain) (MHC class I antigen A*24) | HLA-A<br>HLAA |
| P30512 | 1A29_HUMAN | HLA class I histocompatibility antigen, A-29 alpha chain (Aw-19) (MHC class I antigen A*29) | HLA-A<br>HLAA |
| P16190 | 1A33_HUMAN | HLA class I histocompatibility antigen, A-33 alpha chain (Aw-19) (Aw-33) (MHC class I antigen A*33) | HLA-A<br>HLAA |
| P30453 | 1A34_HUMAN | HLA class I histocompatibility antigen, A-34 alpha chain (Aw-34) (HLA class I histocompatibility antigen, A-10 alpha chain) (MHC class I antigen A*34) | HLA-A<br>HLAA |
| P01891 | 1A68_HUMAN | HLA class I histocompatibility antigen, A-68 alpha chain (Aw-68) (HLA class I histocompatibility antigen, A-28 alpha chain) (MHC class I antigen A*68) | HLA-A<br>HLAA |
| P01889 | 1B07_HUMAN | HLA class I histocompatibility antigen, B-7 alpha chain (MHC class I antigen B*7) | HLA-B<br>HLAB |
| Q95IE3 | 2B1C_HUMAN | HLA class II histocompatibility antigen, DRB1-12 beta chain (MHC class II antigen DRB1*12) (DR-12) (DR12) | HLA-DRB1 |
| Q99965 | ADAM2_HUMAN | Disintegrin and metalloproteinase domain-containing protein 2 (ADAM 2) (Cancer/testis antigen 15) (CT15) (Fertilin subunit beta) (PH-30) (PH30) (PH30-beta) | ADAM2<br>FTNB |
| Q30134 | 2B18_HUMAN | HLA class II histocompatibility antigen, DRB1-8 beta chain (MHC class II antigen DRB1*8) (DR-8) (DR8) (DRw8) | HLA-DRB1 |
| Q9UHX3 | AGRE2_HUMAN | Adhesion G protein-coupled receptor E2 (EGF-like module receptor 2) (EGF-like module-containing mucin-like hormone receptor-like 2) (CD antigen CD312) | ADGRE2<br>EMR2 |
| O60242 | AGRB3_HUMAN | Adhesion G protein-coupled receptor B3 (Brain-specific angiogenesis inhibitor 3) | ADGRB3<br>BAI3<br>KIAA0550 |
| Q96F25 | ALG14_HUMAN | UDP-N-acetylglucosamine transferase subunit ALG14 homolog | ALG14 |
| Q9Y653 | AGRG1_HUMAN | Adhesion G-protein coupled receptor G1 (G-protein coupled receptor 56) (Protein TM7XN1) [Cleaved into: ADGRG1 N-terminal fragment (ADGRG1 NT) (GPR56 N-terminal fragment) (GPR56 NT) (GPR56(N)) (GPR56 extracellular subunit) (GPR56 subunit alpha); ADGRG1 C-terminal fragment (ADGRG1 CT) (GPR56 C-terminal fragment) (GPR56 CT) (GPR56(C)) (GPR56 seven-transmembrane subunit) (GPR56 7TM) (GPR56 subunit beta)] | ADGRG1<br>GPR56<br>TM7LN4<br>TM7XN1<br>UNQ540/<br>PRO1083 |
| Q8IZF2 | AGRF5_HUMAN | Adhesion G protein-coupled receptor F5 (G-protein coupled receptor 116) | ADGRF5<br>GPR116<br>KIAA0758 |
| O60241 | AGRB2_HUMAN | Adhesion G protein-coupled receptor B2 (Brain-specific angiogenesis inhibitor 2) | ADGRB2<br>BAI2 |

TABLE 1-continued

Illustrative proteins which may be incorporated into the present compositions and methods include the following (as used herein, "Entry" refers to the protein entry in the Uniprot database and "Entry name" refers to the protein entry in the Uniprot database):

| Entry | Entry name | Protein names | Gene names |
|---|---|---|---|
| Q86SQ3 | AGRE4_HUMAN | Putative adhesion G protein-coupled receptor E4P (EGF-like module receptor 4) (EGF-like module-containing mucin-like hormone receptor-like 4) (G-protein coupled receptor 127) (G-protein coupled receptor PGR16) | ADGRE4P EMR4 EMR4P GPR127 PGR16 |
| Q8IZP9 | AGRG2_HUMAN | Adhesion G-protein coupled receptor G2 (G-protein coupled receptor 64) (Human epididymis-specific protein 6) (He6) | ADGRG2 GPR64 HE6 TM7LN2 |
| Q9HBW9 | AGRL4_HUMAN | Adhesion G protein-coupled receptor L4 (EGF, latrophilin and seven transmembrane domain-containing protein 1) (EGF-TM7-latrophilin-related protein) (ETL protein) | ADGRL4 ELTD1 ETL UNQ202/ PRO228 |
| Q16853 | AOC3_HUMAN | Membrane primary amine oxidase (EC 1.4.3.21) (Copper amine oxidase) (HPAO) (Semicarbazide-sensitive amine oxidase) (SSAO) (Vascular adhesion protein 1) (VAP-1) | AOC3 VAP1 |
| Q9BY15 | AGRE3_HUMAN | Adhesion G protein-coupled receptor E3 (EGF-like module receptor 3) (EGF-like module-containing mucin-like hormone receptor-like 3) | ADGRE3 EMR3 UNQ683/ PRO1562 |
| O94910 | AGRL1_HUMAN | Adhesion G protein-coupled receptor L1 (Calcium-independent alpha-latrotoxin receptor 1) (CIRL-1) (Latrophilin-1) (Lectomedin-2) | ADGRL1 KIAA0821 LEC2 LPHN1 |
| O95490 | AGRL2_HUMAN | Adhesion G protein-coupled receptor L2 (Calcium-independent alpha-latrotoxin receptor 2) (CIRL-2) (Latrophilin homolog 1) (Latrophilin-2) (Lectomedin-1) | ADGRL2 KIAA0786 LEC1 LPHH1 LPHN2 |
| Q86WK6 | AMGO1_HUMAN | Amphoterin-induced protein 1 (AMIGO-1) (Alivin-2) | AMIGO1 ALI2 AMIGO KIAA1163 |
| P21397 | AOFA_HUMAN | Amine oxidase [flavin-containing] A (EC 1.4.3.4) (Monoamine oxidase type A) (MAO-A) | MAOA |
| P27338 | AOFB_HUMAN | Amine oxidase [flavin-containing] B (EC 1.4.3.4) (Monoamine oxidase type B) (MAO-B) | MAOB |
| Q99941 | ATF6B_HUMAN | Cyclic AMP-dependent transcription factor ATF-6 beta (cAMP-dependent transcription factor ATF-6 beta) (Activating transcription factor 6 beta) (ATF6-beta) (Protein G13) (cAMP response element-binding protein-related protein) (Creb-rp) (cAMP-responsive element-binding protein-like 1) [Cleaved into: Processed cyclic AMP-dependent transcription factor ATF-6 beta] | ATF6B CREBL1 G13 |
| Q15041 | AR6P1_HUMAN | ADP-ribosylation factor-like protein 6-interacting protein 1 (ARL-6-interacting protein 1) (Aip-1) (Apoptotic regulator in the membrane of the endoplasmic reticulum) | ARL6IP1 ARL6IP ARMER KIAA0069 |
| P18850 | ATF6A_HUMAN | Cyclic AMP-dependent transcription factor ATF-6 alpha (cAMP-dependent transcription factor ATF-6 alpha) (Activating transcription factor 6 alpha) (ATF6-alpha) [Cleaved into: Processed cyclic AMP-dependent transcription factor ATF-6 alpha] | ATF6 |
| Q9UHQ4 | BAP29_HUMAN | B-cell receptor-associated protein 29 (BCR-associated protein 29) (Bap29) | BCAP29 BAP29 |
| P82251 | BAT1_HUMAN | b(0, +)-type amino acid transporter 1 (b(0, +)AT1) (Glycoprotein-associated amino acid transporter b0, +AT1) (Solute carrier family 7 member 9) | SLC7A9 BAT1 |
| P51572 | BAP31_HUMAN | B-cell receptor-associated protein 31 (BCR-associated protein 31) (Bap31) (6C6-AG tumor-associated antigen) (Protein CDM) (p28) | BCAP31 BAP31 DXS1357E |
| O60238 | BNI3L_HUMAN | BCL2/adenovirus E1B 19 kDa protein-interacting protein 3-like (Adenovirus E1B19K-binding protein B5) (BCL2/adenovirus E1B 19 kDa protein-interacting protein 3A) (NIP3-like protein X) (NIP3L) | BNIP3L BNIP3A BNIP3H NIX |
| Q9UMX3 | BOK_HUMAN | Bcl-2-related ovarian killer protein (hBOK) (Bcl-2-like protein 9) (Bcl2-L-9) | BOK BCL2L9 |
| P15291 | B4GT1_HUMAN | Beta-1,4-galactosyltransferase 1 (Beta-1,4-GalTase 1) (Beta4Gal-T1) (b4Gal-T1) (EC 2.4.1.-) (UDP-Gal: beta-GlcNAc beta-1,4-galactosyltransferase 1) (UDP-galactose: beta-N-acetylglucosamine beta-1,4-galactosyltransferase 1) [Cleaved into: Processed beta-1,4-galactosyltransferase 1] [Includes: Lactose synthase A protein (EC 2.4.1.22); N-acetyllactosamine synthase (EC 2.4.1.90) (Nal synthase); Beta-N-acetylglucosaminylglycopeptide beta-1,4-galactosyltransferase (EC 2.4.1.38); Beta-N-acetylglucosaminyl-glycolipid beta-1,4-galactosyltransferase (EC 2.4.1.-)] | B4GALT1 GGTB2 |
| Q12983 | BNIP3_HUMAN | BCL2/adenovirus E1B 19 kDa protein-interacting protein 3 | BNIP3 NIP3 |

TABLE 1-continued

Illustrative proteins which may be incorporated into the present compositions and methods include the following (as used herein, "Entry" refers to the protein entry in the Uniprot database and "Entry name" refers to the protein entry in the Uniprot database):

| Entry | Entry name | Protein names | Gene names |
|---|---|---|---|
| Q16602 | CALRL_HUMAN | Calcitonin gene-related peptide type 1 receptor (CGRP type 1 receptor) (Calcitonin receptor-like receptor) | CALCRL CGRPR |
| P10966 | CD8B_HUMAN | T-cell surface glycoprotein CD8 beta chain (CD antigen CD8b) | CD8B CD8B1 |
| P09693 | CD3G_HUMAN | T-cell surface glycoprotein CD3 gamma chain (T-cell receptor T3 gamma chain) (CD antigen CD3g) | CD3G T3G |
| P60033 | CD81_HUMAN | CD81 antigen (26 kDa cell surface protein TAPA-1) (Target of the antiproliferative antibody 1) (Tetraspanin-28) (Tspan-28) (CD antigen CD81) | CD81 TAPA1 TSPAN28 |
| P01732 | CD8A_HUMAN | T-cell surface glycoprotein CD8 alpha chain (T-lymphocyte differentiation antigen T8/Leu-2) (CD antigen CD8a) | CD8A MAL |
| P06126 | CD1A_HUMAN | T-cell surface glycoprotein CD1a (T-cell surface antigen T6/Leu-6) (hTa1 thymocyte antigen) (CD antigen CD1a) | CD1A |
| P40259 | CD79B_HUMAN | B-cell antigen receptor complex-associated protein beta chain (B-cell-specific glycoprotein B29) (Ig-beta) (Immunoglobulin-associated B29 protein) (CD antigen CD79b) | CD79B B29 IGB |
| P11912 | CD79A_HUMAN | B-cell antigen receptor complex-associated protein alpha chain (Ig-alpha) (MB-1 membrane glycoprotein) (Membrane-bound immunoglobulin-associated protein) (Surface IgM-associated protein) (CD antigen CD79a) | CD79A IGA MB1 |
| P15812 | CD1E_HUMAN | T-cell surface glycoprotein CD1e, membrane-associated (hCD1e) (R2G1) (CD antigen CD1e) [Cleaved into: T-cell surface glycoprotein CD1e, soluble (sCD1e)] | CD1E |
| P20963 | CD3Z_HUMAN | T-cell surface glycoprotein CD3 zeta chain (T-cell receptor T3 zeta chain) (CD antigen CD247) | CD247 CD3Z T3Z TCRZ |
| A6NJW9 | CD8B2_HUMAN | Putative T-cell surface glycoprotein CD8 beta-2 chain (CD8b pseudogene) | CD8B2 CD8BP |
| P29017 | CD1C_HUMAN | T-cell surface glycoprotein CD1c (CD antigen CD1c) | CD1C |
| P13688 | CEAM1_HUMAN | Carcinoembryonic antigen-related cell adhesion molecule 1 (Biliary glycoprotein 1) (BGP-1) (CD antigen CD66a) | CEACAM1 BGP BGP1 |
| P29016 | CD1B_HUMAN | T-cell surface glycoprotein CD1b (CD antigen CD1b) | CD1B |
| P15813 | CD1D_HUMAN | Antigen-presenting glycoprotein CD1d (R3G1) (CD antigen CD1d) | CD1D |
| P20273 | CD22_HUMAN | B-cell receptor CD22 (B-lymphocyte cell adhesion molecule) (BL-CAM) (Sialic acid-binding Ig-like lectin 2) (Siglec-2) (T-cell surface antigen Leu-14) (CD antigen CD22) | CD22 SIGLEC2 |
| P04234 | CD3D_HUMAN | T-cell surface glycoprotein CD3 delta chain (T-cell receptor T3 delta chain) (CD antigen CD3d) | CD3D T3D |
| P07766 | CD3E_HUMAN | T-cell surface glycoprotein CD3 epsilon chain (T-cell surface antigen T3/Leu-4 epsilon chain) | CD3E T3E |
| P48960 | CD97_HUMAN | CD97 antigen (Leukocyte antigen CD97) (CD antigen CD97) [Cleaved into: CD97 antigen subunit alpha; CD97 antigen subunit beta] | CD97 |
| Q9UHP7 | CLC2D_HUMAN | C-type lectin domain family 2 member D (Lectin-like NK cell receptor) (Lectin-like transcript 1) (LLT-1) (Osteoclast inhibitory lectin) | CLEC2D CLAX LLT1 OCIL |
| P51790 | CLCN3_HUMAN | H(+)/Cl(−) exchange transporter 3 (Chloride channel protein 3) (ClC-3) (Chloride transporter ClC-3) | CLCN3 |
| Q68CJ9 | CR3L3_HUMAN | Cyclic AMP-responsive element-binding protein 3-like protein 3 (cAMP-responsive element-binding protein 3-like protein 3) (Transcription factor CREB-H) [Cleaved into: Processed cyclic AMP-responsive element-binding protein 3-like protein 3] | CREB3L3 CREBH HYST1481 |
| P34998 | CRFR1_HUMAN | Corticotropin-releasing factor receptor 1 (CRF-R-1) (CRF-R1) (CRFR-1) (Corticotropin-releasing hormone receptor 1) (CRH-R-1) (CRH-R1) | CRHR1 CRFR CRFR1 CRHR |
| Q9HC73 | CRLF2_HUMAN | Cytokine receptor-like factor 2 (Cytokine receptor-like 2) (IL-XR) (Thymic stromal lymphopoietin protein receptor) (TSLP receptor) | CRLF2 CRL2 ILXR TSLPR |
| P09603 | CSF1_HUMAN | Macrophage colony-stimulating factor 1 (CSF-1) (M-CSF) (MCSF) (Lanimostim) [Cleaved into: Processed macrophage colony-stimulating factor 1] | CSF1 |
| P15509 | CSF2R_HUMAN | Granulocyte-macrophage colony-stimulating factor receptor subunit alpha (GM-CSF-R-alpha) (GMCSFR-alpha) (GMR-alpha) (CDw116) (CD antigen CD116) | CSF2RA CSF2R CSF2RY |
| P06340 | DOA_HUMAN | HLA class II histocompatibility antigen, DO alpha chain (MHC DN-alpha) (MHC DZ alpha) (MHC class II antigen DOA) | HLA-DOA HLA-DNA HLA-DZA |
| P01906 | DQA2_HUMAN | HLA class II histocompatibility antigen, DQ alpha 2 chain (DX alpha chain) (HLA class II histocompatibility antigen, DQ(6) alpha chain) (HLA-DQA1) (MHC class II DQA2) | HLA-DQA2 HLA-DXA |
| P13762 | DRB4_HUMAN | HLA class II histocompatibility antigen, DR beta 4 chain (MHC class II antigen DRB4) | HLA-DRB4 |

TABLE 1-continued

Illustrative proteins which may be incorporated into the present compositions and methods include the following (as used herein, "Entry" refers to the protein entry in the Uniprot database and "Entry name" refers to the protein entry in the Uniprot database):

| Entry | Entry name | Protein names | Gene names |
|---|---|---|---|
| P13765 | DOB_HUMAN | HLA class II histocompatibility antigen, DO beta chain (MHC class II antigen DOB) | HLA-DOB |
| P04440 | DPB1_HUMAN | HLA class II histocompatibility antigen, DP beta 1 chain (HLA class II histocompatibility antigen, DP(W4) beta chain) (MHC class II antigen DPB1) | HLA-DPB1 HLA-DP1B |
| P01909 | DQA1_HUMAN | HLA class II histocompatibility antigen, DQ alpha 1 chain (DC-1 alpha chain) (DC-alpha) (HLA-DCA) (MHC class II DQA1) | HLA-DQA1 |
| P28067 | DMA_HUMAN | HLA class II histocompatibility antigen, DM alpha chain (MHC class II antigen DMA) (Really interesting new gene 6 protein) | HLA-DMA DMA RING6 |
| P79483 | DRB3_HUMAN | HLA class II histocompatibility antigen, DR beta 3 chain (MHC class II antigen DRB3) | HLA-DRB3 |
| P28068 | DMB_HUMAN | HLA class II histocompatibility antigen, DM beta chain (MHC class II antigen DMB) (Really interesting new gene 7 protein) | HLA-DMB DMB RING7 |
| P01903 | DRA_HUMAN | HLA class II histocompatibility antigen, DR alpha chain (MHC class II antigen DRA) | HLA-DRA HLA-DRA1 |
| P20036 | DPA1_HUMAN | HLA class II histocompatibility antigen, DP alpha 1 chain (DP(W3)) (DP(W4)) (HLA-SB alpha chain) (MHC class II DP3-alpha) (MHC class II DPA1) | HLA-DPA1 HLA-DP1A HLASB |
| P05538 | DQB2_HUMAN | HLA class II histocompatibility antigen, DQ beta 2 chain (HLA class II histocompatibility antigen, DX beta chain) (MHC class II antigen DQB2) | HLA-DQB2 HLA-DXB |
| P27487 | DPP4_HUMAN | Dipeptidyl peptidase 4 (EC 3.4.14.5) (ADABP) (Adenosine deaminase complexing protein 2) (ADCP-2) (Dipeptidyl peptidase IV) (DPP IV) (T-cell activation antigen CD26) (TP103) (CD antigen CD26) [Cleaved into: Dipeptidyl peptidase 4 membrane form (Dipeptidyl peptidase IV membrane form); Dipeptidyl peptidase 4 soluble form (Dipeptidyl peptidase IV soluble form)] | DPP4 ADCP2 CD26 |
| Q30154 | DRB5_HUMAN | HLA class II histocompatibility antigen, DR beta 5 chain (DR beta-5) (DR2-beta-2) (Dw2) (MHC class II antigen DRB5) | HLA-DRB5 |
| P61565 | ENK21_HUMAN | Endogenous retrovirus group K member 21 Env polyprotein (EnvK1 protein) (Envelope polyprotein) (HERV-K_12q14.1 provirus ancestral Env polyprotein) [Cleaved into: Surface protein (SU); Transmembrane protein (TM)] | ERVK-21 |
| Q902F9 | EN113_HUMAN | Endogenous retrovirus group K member 113 Env polyprotein (EnvK5 protein) (Envelope polyprotein) (HERV-K113 envelope protein) (HERV-K_19p13.11 provirus ancestral Env polyprotein) [Cleaved into: Surface protein (SU); Transmembrane protein (TM)] | HERVK_113 |
| P60507 | EFC1_HUMAN | Endogenous retrovirus group FC1 Env polyprotein (Envelope polyprotein) (Fc1env) [HERV-F(c)1_Xq21.33 provirus ancestral Env polyprotein) (HERV-Fc1env) [Cleaved into: Surface protein (SU); Transmembrane protein (TM)] | ERVFC1 |
| P13224 | GP1BB_HUMAN | Platelet glycoprotein Ib beta chain (GP-Ib beta) (GPIb-beta) (GPIbB) (Antigen CD42b-beta) (CD antigen CD42c) | GP1BB |
| Q9HB15 | KCNKC_HUMAN | Potassium channel subfamily K member 12 (Tandem pore domain halothane-inhibited potassium channel 2) (THIK-2) | KCNK12 |
| P23276 | KELL_HUMAN | Kell blood group glycoprotein (EC 3.4.24.-) (CD antigen CD238) | KEL |
| Q13241 | KLRD1_HUMAN | Natural killer cells antigen CD94 (KP43) (Killer cell lectin-like receptor subfamily D member 1) (NK cell receptor) (CD antigen CD94) | KLRD1 CD94 |
| O14649 | KCNK3_HUMAN | Potassium channel subfamily K member 3 (Acid-sensitive potassium channel protein TASK-1) (TWIK-related acid-sensitive K(+) channel 1) (Two pore potassium channel KT3.1) (Two pore K(+) channel KT3.1) | KCNK3 TASK TASK1 |
| Q09470 | KCNA1_HUMAN | Potassium voltage-gated channel subfamily A member 1 (Voltage-gated K(+) channel HuKI) (Voltage-gated potassium channel HBK1) (Voltage-gated potassium channel subunit Kv1.1) | KCNA1 |
| O00180 | KCNK1_HUMAN | Potassium channel subfamily K member 1 (Inward rectifying potassium channel protein TWIK-1) (Potassium channel K2P1) (Potassium channel KCNO1) | KCNK1 HOHO1 KCNO1 TWIK1 |
| Q9NPC2 | KCNK9_HUMAN | Potassium channel subfamily K member 9 (Acid-sensitive potassium channel protein TASK-3) (TWIK-related acid-sensitive K(+) channel 3) (Two pore potassium channel KT3.2) (Two pore K(+) channel KT3.2) | KCNK9 TASK3 |
| P54851 | EMP2_HUMAN | Epithelial membrane protein 2 (EMP-2) (Protein XMP) | EMP2 XMP |
| O71037 | ENK19_HUMAN | Endogenous retrovirus group K member 19 Env polyprotein (EnvK3 protein) (Envelope polyprotein) (HERV-K(C19) envelope protein) (HERV-K_19q11 provirus ancestral Env polyprotein) [Cleaved into: Surface protein (SU); Transmembrane protein (TM)] | ERVK-19 |
| P61567 | ENK7_HUMAN | Endogenous retrovirus group K member 7 Env polyprotein (Envelope polyprotein) (HERV-K(III) envelope protein) (HERV-K102 envelope protein) (HERV-K_1q22 provirus ancestral Env polyprotein) [Cleaved into: Surface protein (SU); Transmembrane protein (TM)] | ERVK-7 |
| Q9UKH3 | ENK9_HUMAN | Endogenous retrovirus group K member 9 Env polyprotein (EnvK4 protein) (Envelope polyprotein) (HERV-K(C6) envelope protein) (HERV-K109 envelope protein) (HERV-K_6q14.1 provirus ancestral Env polyprotein) [Cleaved into: Surface protein (SU); Transmembrane protein (TM)] | ERVK-9 |
| Q9NZ08 | ERAP1_HUMAN | Endoplasmic reticulum aminopeptidase 1 (EC 3.4.11.-) (ARTS-1) (Adipocyte-derived leucine aminopeptidase) (A-LAP) (Aminopeptidase PILS) (Puromycin-insensitive leucyl-specific aminopeptidase) (PILS-AP) (Type 1 tumor necrosis factor receptor shedding aminopeptidase regulator) | ERAP1 APPILS ARTS1 KIAA0525 |

TABLE 1-continued

Illustrative proteins which may be incorporated into the present compositions and methods include the following (as used herein, "Entry" refers to the protein entry in the Uniprot database and "Entry name" refers to the protein entry in the Uniprot database):

| Entry | Entry name | Protein names | Gene names |
|---|---|---|---|
| | | | UNQ584/ PRO1154 |
| Q9N2K0 | ENH1_HUMAN | HERV-H_2q24.3 provirus ancestral Env polyprotein (Env protein HERV-H/p62) (Env protein HERV-H19) (Env protein HERV-Hcl.3) (Envelope polyprotein) (HERV-H/env62) [Cleaved into: Surface protein (SU); Transmembrane protein (TM)] | |
| Q9NX77 | ENK13_HUMAN | Endogenous retrovirus group K member 13-1 Env polyprotein (Envelope polyprotein) (HERV-K_16p13.3 provirus ancestral Env polyprotein) [Cleaved into: Surface protein (SU); Transmembrane protein (TM)] | ERVK13-1 |
| P61566 | ENK24_HUMAN | Endogenous retrovirus group K member 24 Env polyprotein (Envelope polyprotein) (HERV-K101 envelope protein) (HERV-K_22q11.21 provirus ancestral Env polyprotein) [Cleaved into: Surface protein (SU); Transmembrane protein (TM)] | ERVK-24 |
| Q69384 | ENK6_HUMAN | Endogenous retrovirus group K member 6 Env polyprotein (EnvK2 protein) (Envelope polyprotein) (HERV-K(C7) envelope protein) (HERV-K(HML-2.HOM) envelope protein) (HERV-K108 envelope protein) (HERV-K_7p22.1 provirus ancestral Env polyprotein) [Cleaved into: Surface protein (SU); Transmembrane protein (TM)] | ERVK-6 ERVK6 |
| Q9N2J8 | ENH3_HUMAN | HERV-H_2q24.1 provirus ancestral Env polyprotein (Env protein HERV-H/p59) (Envelope polyprotein) (HERV-H/env59) [Cleaved into: Surface protein (SU); Transmembrane protein (TM)] | |
| O42043 | ENK18_HUMAN | Endogenous retrovirus group K member 18 Env polyprotein (Envelope polyprotein) (HERV-K(C1a) envelope protein) (HERV-K110 envelope protein) (HERV-K18 envelope protein) (HERV-K18 superantigen) (HERV-K_1q23.3 provirus ancestral Env polyprotein) (IDDMK1,2 22 envelope protein) (IDDMK1,2 22 superantigen) [Cleaved into: Surface protein (SU); Transmembrane protein (TM)] | ERVK-18 |
| Q902F8 | ENK8_HUMAN | Endogenous retrovirus group K member 8 Env polyprotein (EnvK6 protein) (Envelope polyprotein) (HERV-K115 envelope protein) (HERV-K_8p23.1 provirus ancestral Env polyprotein) [Cleaved into: Surface protein (SU); Transmembrane protein (TM)] | ERVK-8 |
| P29317 | EPHA2_HUMAN | Ephrin type-A receptor 2 (EC 2.7.10.1) (Epithelial cell kinase) (Tyrosine-protein kinase receptor ECK) | EPHA2 ECK |
| P61570 | ENK25_HUMAN | Endogenous retrovirus group K member 25 Env polyprotein (Envelope polyprotein) (HERV-K_11q22.1 provirus ancestral Env polyprotein) [Cleaved into: Surface protein (SU); Transmembrane protein (TM)] | ERVK-25 |
| P98073 | ENTK_HUMAN | Enteropeptidase (EC 3.4.21.9) (Enterokinase) (Serine protease 7) (Transmembrane protease serine 15) [Cleaved into: Enteropeptidase non-catalytic heavy chain; Enteropeptidase catalytic light chain] | TMPRSS15 ENTK PRSS7 |
| Q6P179 | ERAP2_HUMAN | Endoplasmic reticulum aminopeptidase 2 (EC 3.4.11.-) (Leukocyte-derived arginine aminopeptidase) (L-RAP) | ERAP2 LRAP |
| P55899 | FCGRN_HUMAN | IgG receptor FcRn large subunit p51 (FcRn) (IgG Fc fragment receptor transporter alpha chain) (Neonatal Fc receptor) | FCGRT FCRN |
| O75899 | GABR2_HUMAN | Gamma-aminobutyric acid type B receptor subunit 2 (GABA-B receptor 2) (GABA-B-R2) (GABA-BR2) (GABABR2) (Gb2) (G-protein coupled receptor 51) (HG20) | GABBR2 GPR51 GPRC3B |
| Q14318 | FKBP8_HUMAN | Peptidyl-prolyl cis-trans isomerase FKBP8 (PPIase FKBP8) (EC 5.2.1.8) (38 kDa FK506-binding protein) (38 kDa FKBP) (FKBP-38) (hFKBP38) (FK506-binding protein 8) (FKBP-8) (FKBPR38) (Rotamase) | FKBP8 FKBP38 |
| Q9UBS5 | GABR1_HUMAN | Gamma-aminobutyric acid type B receptor subunit 1 (GABA-B receptor 1) (GABA-B-R1) (GABA-BR1) (GABABR1) (Gb1) | GABBR1 GPRC3A |
| Q9UG22 | GIMA2_HUMAN | GTPase IMAP family member 2 (Immunity-associated protein 2) (hIMAP2) | GIMAP2 IMAP2 |
| Q6P531 | GGT6_HUMAN | Gamma-glutamyltransferase 6 (GGT 6) (EC 2.3.2.2) (Gamma-glutamyltranspeptidase 6) (Glutathione hydrolase 6) (EC 3.4.19.13) [Cleaved into: Gamma-glutamyltransferase 6 heavy chain; Gamma-glutamyltransferase 6 light chain] | GGT6 |
| Q9UJ14 | GGT7_HUMAN | Gamma-glutamyltransferase 7 (GGT 7) (EC 2.3.2.2) (Gamma-glutamyltransferase-like 3) (Gamma-glutamyltransferase-like 5) (Gamma-glutamyltranspeptidase 7) (Glutathione hydrolase 7) (EC 3.4.19.13) [Cleaved into: Gamma-glutamyltransferase 7 heavy chain; Gamma-glutamyltransferase 7 light chain] | GGT7 GGTL3 GGTL5 |
| P14770 | GPIX_HUMAN | Platelet glycoprotein IX (GP-IX) (GPIX) (Glycoprotein 9) (CD antigen CD42a) | GP9 |
| P19440 | GGT1_HUMAN | Gamma-glutamyltranspeptidase 1 (GGT 1) (EC 2.3.2.2) (Gamma-glutamyltransferase 1) (Glutathione hydrolase 1) (EC 3.4.19.13) (Leukotriene-C4 hydrolase) (EC 3.4.19.14) (CD antigen CD224) [Cleaved into: Gamma-glutamyltranspeptidase 1 heavy chain; Gamma-glutamyltranspeptidase 1 light chain] | GGT1 GGT |
| P36269 | GGT5_HUMAN | Gamma-glutamyltransferase 5 (GGT 5) (EC 2.3.2.2) (Gamma-glutamyl transpeptidase-related enzyme) (GGT-rel) (Gamma-glutamyltransferase-like activity 1) (Gamma-glutamyltranspeptidase 5) (Glutathione hydrolase 5) (EC 3.4.19.13) (Leukotriene-C4 hydrolase) (EC 3.4.19.14) [Cleaved into: Gamma-glutamyltransferase 5 heavy chain; Gamma-glutamyltransferase 5 light chain] | GGT5 GGTLA1 |

TABLE 1-continued

Illustrative proteins which may be incorporated into the present compositions and methods include the following (as used herein, "Entry" refers to the protein entry in the Uniprot database and "Entry name" refers to the protein entry in the Uniprot database):

| Entry | Entry name | Protein names | Gene names |
|---|---|---|---|
| P07359 | GP1BA_HUMAN | Platelet glycoprotein Ib alpha chain (GP-Ib alpha) (GPIb-alpha) (GPIbA) (Glycoprotein Ibalpha) (Antigen CD42b-alpha) (CD antigen CD42b) [Cleaved into: Glycocalicin] | GP1BA |
| P32249 | GP183_HUMAN | G-protein coupled receptor 183 (Epstein-Barr virus-induced G-protein coupled receptor 2) (EBI2) (EBV-induced G-protein coupled receptor 2) (hEBI2) | GPR183 EBI2 |
| P17693 | HLAG_HUMAN | HLA class I histocompatibility antigen, alpha chain G (HLA G antigen) (MHC class I antigen G) | HLA-G HLA-6.0 HLAG |
| P01893 | HLAH_HUMAN | Putative HLA class I histocompatibility antigen, alpha chain H (HLA-12.4) (HLA-AR) (MHC class I antigen H) | HLA-H HLAH |
| P13747 | HLAE_HUMAN | HLA class I histocompatibility antigen, alpha chain E (MHC class I antigen E) | HLA-E HLA-6.2 HLAE |
| Q99665 | I12R2_HUMAN | Interleukin-12 receptor subunit beta-2 (IL-12 receptor subunit beta-2) (IL-12R subunit beta-2) (IL-12R-beta-2) (IL-12RB2) | IL12RB2 |
| P30511 | HLAF_HUMAN | HLA class I histocompatibility antigen, alpha chain F (CDA12) (HLA F antigen) (Leukocyte antigen F) (MHC class I antigen F) | HLA-F HLA-5.4 HLAF |
| P42701 | I12R1_HUMAN | Interleukin-12 receptor subunit beta-1 (IL-12 receptor subunit beta-1) (IL-12R subunit beta-1) (IL-12R-beta-1) (IL-12RB1) (IL-12 receptor beta component) (CD antigen CD212) | IL12RB1 IL12R IL12RB |
| Q96F46 | I17RA_HUMAN | Interleukin-17 receptor A (IL-17 receptor A) (IL-17RA) (CDw217) (CD antigen CD217) | IL17RA IL17R |
| Q9NPH3 | IL1AP_HUMAN | Interleukin-1 receptor accessory protein (IL-1 receptor accessory protein) (IL-1RAcP) (Interleukin-1 receptor 3) (IL-1R-3) (IL-1R3) | IL1RAP C3orf13 IL1R3 |
| P32927 | IL3RB_HUMAN | Cytokine receptor common subunit beta (CDw131) (GM-CSF/IL-3/IL-5 receptor common beta subunit) (CD antigen CD131) | CSF2RB IL3RB IL5RB |
| Q08334 | I10R2_HUMAN | Interleukin-10 receptor subunit beta (IL-10 receptor subunit beta) (IL-10R subunit beta) (IL-10RB) (Cytokine receptor class-II member 4) (Cytokine receptor family 2 member 4) (CRF2-4) (Interleukin-10 receptor subunit 2) (IL-10R subunit 2) (IL-10R2) (CD antigen CDw210b) | IL10RB CRFB4 D21S58 D21S66 |
| Q8NAC3 | I17RC_HUMAN | Interleukin-17 receptor C (IL-17 receptor C) (IL-17RC) (Interleukin-17 receptor homolog) (IL17Rhom) (Interleukin-17 receptor-like protein) (IL-17RL) (ZcytoR14) | IL17RC UNQ6118/ PRO20040/ PRO38901 |
| Q8NFR9 | I17RE_HUMAN | Interleukin-17 receptor E (IL-17 receptor E) (IL-17RE) | IL17RE UNQ3056/ PRO9877 |
| O95256 | I18RA_HUMAN | Interleukin-18 receptor accessory protein (IL-18 receptor accessory protein) (IL-18RAcP) (Accessory protein-like) (AcPL) (CD218 antigen-like family member B) (CDw218b) (IL-1R accessory protein-like) (IL-1RAcPL) (Interleukin-1 receptor 7) (IL-1R-7) (IL-1R7) (Interleukin-18 receptor accessory protein-like) (Interleukin-18 receptor beta) (IL-18R-beta) (IL-18Rbeta) (CD antigen CD218b) | IL18RAP IL1R7 |
| Q6UXL0 | I20RB_HUMAN | Interleukin-20 receptor subunit beta (IL-20 receptor subunit beta) (IL-20R-beta) (IL-20RB) (Fibronectin type III domain containing 6) (FNDC6) (IL-20R2) | IL20RB DIRS1 UNQ557/P RO1114 |
| Q9HBE5 | IL21R_HUMAN | Interleukin-21 receptor (IL-21 receptor) (IL-21R) (Novel interleukin receptor) (CD antigen CD360) | IL21R NILR UNQ3121/ PRO10273 |
| Q9UHF4 | I20RA_HUMAN | Interleukin-20 receptor subunit alpha (IL-20 receptor subunit alpha) (IL-20R-alpha) (IL-20RA) (Cytokine receptor class-II member 8) (Cytokine receptor family 2 member 8) (CRF2-8) (IL-20R1) (ZcytoR7) | IL20RA UNQ681/ PRO1315 |
| P14778 | IL1R1_HUMAN | Interleukin-1 receptor type 1 (IL-1R-1) (IL-1RT-1) (IL-1RT1) (CD121 antigen-like family member A) (Interleukin-1 receptor alpha) (IL-1R-alpha) (Interleukin-1 receptor type I) (p80) (CD antigen CD121a) [Cleaved into: Interleukin-1 receptor type 1, membrane form (mIL-1R1) (mIL-1RI); Interleukin-1 receptor type 1, soluble form (sIL-1RI) (sIL-1RI)] | IL1R1 IL1R IL1RA IL1RT1 |
| Q8N6P7 | I22R1_HUMAN | Interleukin-22 receptor subunit alpha-1 (IL-22 receptor subunit alpha-1) (IL-22R-alpha-1) (IL-22RA1) (Cytokine receptor class-II member 9) (Cytokine receptor family 2 member 9) (CRF2-9) (ZcytoR11) | IL22RA1 IL22R |
| Q13478 | IL18R_HUMAN | Interleukin-18 receptor 1 (IL-18R-1) (IL-18R1) (CD218 antigen-like family member A) (CDw218a) (IL1 receptor-related protein) (IL-1Rrp) (IL1R-rp) (CD antigen CD218a) | IL18R1 IL1RRP |
| P26951 | IL3RA_HUMAN | Interleukin-3 receptor subunit alpha (IL-3 receptor subunit alpha) (IL-3R subunit alpha) (IL-3R-alpha) (IL-3RA) (CD antigen CD123) | IL3RA IL3R |
| Q01344 | IL5RA_HUMAN | Interleukin-5 receptor subunit alpha (IL-5 receptor subunit alpha) (IL-5R subunit alpha) (IL-5R-alpha) (IL-5RA) (CDw125) (CD antigen CD125) | IL5RA IL5R |
| Q8NI17 | IL31R_HUMAN | Interleukin-31 receptor subunit alpha (IL-31 receptor subunit alpha) (IL-31R subunit alpha) (IL-31R-alpha) (IL-31RA) (Cytokine receptor-like 3) (GLM-R) (hGLM-R) (Gp130-like monocyte receptor) (Gp130-like receptor) (ZcytoR17) | IL31RA CRL3 GPL |

TABLE 1-continued

Illustrative proteins which may be incorporated into the present compositions and methods include the following (as used herein, "Entry" refers to the protein entry in the Uniprot database and "Entry name" refers to the protein entry in the Uniprot database):

| Entry | Entry name | Protein names | Gene names |
|---|---|---|---|
| | | | UNQ6368/ PRO21073/ PRO21384 |
| Q9UKX5 | ITA11_HUMAN | Integrin alpha-11 | ITGA11 MSTP018 |
| P17301 | ITA2_HUMAN | Integrin alpha-2 (CD49 antigen-like family member B) (Collagen receptor) (Platelet membrane glycoprotein Ia) (GPIa) (VLA-2 subunit alpha) (CD antigen CD49b) | ITGA2 CD49B |
| Q13683 | ITA7_HUMAN | Integrin alpha-7 [Cleaved into: Integrin alpha-7 heavy chain; Integrin alpha-7 light chain; Integrin alpha-7 70 kDa form] | ITGA7 UNQ406/ PRO768 |
| P53708 | ITA8_HUMAN | Integrin alpha-8 [Cleaved into: Integrin alpha-8 heavy chain; Integrin alpha-8 light chain] | ITGA8 |
| P38570 | ITAE_HUMAN | Integrin alpha-E (HML-1 antigen) (Integrin alpha-IEL) (Mucosal lymphocyte 1 antigen) (CD antigen CD103) [Cleaved into: Integrin alpha-E light chain; Integrin alpha-E heavy chain] | ITGAE |
| P05107 | ITB2_HUMAN | Integrin beta-2 (Cell surface adhesion glycoproteins LFA-1/CR3/p150, 95 subunit beta) (Complement receptor C3 subunit beta) (CD antigen CD18) | ITGB2 CD18 MFI7 |
| P18564 | ITB6_HUMAN | Integrin beta-6 | ITGB6 |
| Q8IU57 | INLR1_HUMAN | Interferon lambda receptor 1 (IFN-lambda receptor 1) (IFN-lambda-R1) (Cytokine receptor class-II member 12) (Cytokine receptor family 2 member 12) (CRF2-12) (Interleukin-28 receptor subunit alpha) (IL-28 receptor subunit alpha) (IL-28R-alpha) (Likely interleukin or cytokine receptor 2) (LICR2) | IFNLR1 IL28RA LICR2 |
| Q5VWK5 | IL23R_HUMAN | Interleukin-23 receptor (IL-23 receptor) (IL-23R) | IL23R |
| P17181 | INAR1_HUMAN | Interferon alpha/beta receptor 1 (IFN-R-1) (IFN-alpha/beta receptor 1) (Cytokine receptor class-II member 1) (Cytokine receptor family 2 member 1) (CRF2-1) (Type I interferon receptor 1) | IFNAR1 IFNAR |
| P16871 | IL7RA_HUMAN | Interleukin-7 receptor subunit alpha (IL-7 receptor subunit alpha) (IL-7R subunit alpha) (IL-7R-alpha) (IL-7RA) (CDw127) (CD antigen CD127) | IL7R |
| Q96T52 | IMP2L_HUMAN | Mitochondrial inner membrane protease subunit 2 (EC 3.4.21.-) (IMP2-like protein) | IMMP2L |
| P13612 | ITA4_HUMAN | Integrin alpha-4 (CD49 antigen-like family member D) (Integrin alpha-IV) (VLA-4 subunit alpha) (CD antigen CD49d) | ITGA4 CD49D |
| Q13349 | ITAD_HUMAN | Integrin alpha-D (ADB2) (CD11 antigen-like family member D) (Leukointegrin alpha D) (CD antigen CD11d) | ITGAD |
| P78508 | KCJ10_HUMAN | ATP-sensitive inward rectifier potassium channel 10 (ATP-dependent inwardly rectifying potassium channel Kir4.1) (Inward rectifier K(+) channel Kir1.2) (Potassium channel, inwardly rectifying subfamily J member 10) | KCNJ10 |
| P11215 | ITAM_HUMAN | Integrin alpha-M (CD11 antigen-like family member B) (CR-3 alpha chain) (Cell surface glycoprotein MAC-1 subunit alpha) (Leukocyte adhesion receptor MO1) (Neutrophil adherence receptor) (CD antigen CD11b) | ITGAM CD11B CR3A |
| P16144 | ITB4_HUMAN | Integrin beta-4 (GP150) (CD antigen CD104) | ITGB4 |
| P26012 | ITB8_HUMAN | Integrin beta-8 | ITGB8 |
| Q9NPI9 | KCJ16_HUMAN | Inward rectifier potassium channel 16 (Inward rectifier K(+) channel Kir5.1) (Potassium channel, inwardly rectifying subfamily J member 16) | KCNJ16 |
| P38484 | INGR2_HUMAN | Interferon gamma receptor 2 (IFN-gamma receptor 2) (IFN-gamma-R2) (Interferon gamma receptor accessory factor 1) (AF-1) (Interferon gamma receptor beta-chain) (IFN-gamma-R-beta) (Interferon gamma transducer 1) | IFNGR2 IFNGT1 |
| P56199 | ITA1_HUMAN | Integrin alpha-1 (CD49 antigen-like family member A) (Laminin and collagen receptor) (VLA-1) (CD antigen CD49a) | ITGA1 |
| P26006 | ITA3_HUMAN | Integrin alpha-3 (CD49 antigen-like family member C) (FRP-2) (Galactoprotein B3) (GAPB3) (VLA-3 subunit alpha) (CD antigen CD49c) [Cleaved into: Integrin alpha-3 heavy chain; Integrin alpha-3 light chain] | ITGA3 MSK18 |
| P20702 | ITAX_HUMAN | Integrin alpha-X (CD11 antigen-like family member C) (Leu M5) (Leukocyte adhesion glycoprotein p150, 95 alpha chain) (Leukocyte adhesion receptor p150, 95) (CD antigen CD11c) | ITGAX CD11C |
| P18084 | ITB5_HUMAN | Integrin beta-5 | ITGB5 |
| Q9UJ96 | KCNG2_HUMAN | Potassium voltage-gated channel subfamily G member 2 (Cardiac potassium channel subunit) (Voltage-gated potassium channel subunit Kv6.2) | KCNG2 KCNF2 |
| O95069 | KCNK2_HUMAN | Potassium channel subfamily K member 2 (Outward rectifying potassium channel protein TREK-1) (TREK-1 K(+) channel subunit) (Two pore domain potassium channel TREK-1) (Two pore potassium channel TPKC1) | KCNK2 TREK TREK1 |
| Q9H427 | KCNKF_HUMAN | Potassium channel subfamily K member 15 (Acid-sensitive potassium channel protein TASK-5) (TWIK-related acid-sensitive K(+) channel 5) (Two pore potassium channel KT3.3) (Two pore K(+) channel KT3.3) | KCNK15 TASK5 |
| O75578 | ITA10_HUMAN | Integrin alpha-10 | ITGA10 UNQ468/ PRO827 |
| P08514 | ITA2B_HUMAN | Integrin alpha-IIb (GPalpha IIb) (GPIIb) (Platelet membrane glycoprotein IIb) (CD antigen CD41) [Cleaved into: Integrin alpha-IIb heavy chain; Integrin alpha-IIb light chain, form 1; Integrin alpha-IIb light chain, form 2] | ITGA2B GP2B ITGAB |
| P23229 | ITA6_HUMAN | Integrin alpha-6 (CD49 antigen-like family member F) (VLA-6) (CD antigen CD49f) [Cleaved into: Integrin alpha-6 heavy chain; Integrin alpha-6 light chain; Processed integrin alpha-6 (Alpha6p)] | ITGA6 |

TABLE 1-continued

Illustrative proteins which may be incorporated into the present compositions and methods include the following (as used herein, "Entry" refers to the protein entry in the Uniprot database and "Entry name" refers to the protein entry in the Uniprot database):

| Entry | Entry name | Protein names | Gene names |
|---|---|---|---|
| P08648 | ITA5_HUMAN | Integrin alpha-5 (CD49 antigen-like family member E) (Fibronectin receptor subunit alpha) (Integrin alpha-F) (VLA-5) (CD antigen CD49e) [Cleaved into: Integrin alpha-5 heavy chain; Integrin alpha-5 light chain] | ITGA5 FNRA |
| Q13797 | ITA9_HUMAN | Integrin alpha-9 (Integrin alpha-RLC) | ITGA9 |
| P20701 | ITAL_HUMAN | Integrin alpha-L (CD11 antigen-like family member A) (Leukocyte adhesion glycoprotein LFA-1 alpha chain) (LFA-1A) (Leukocyte function-associated molecule 1 alpha chain) (CD antigen CD11a) | ITGAL CD11A |
| P26010 | ITB7_HUMAN | Integrin beta-7 (Gut homing receptor beta subunit) | ITGB7 |
| P48551 | INAR2_HUMAN | Interferon alpha/beta receptor 2 (IFN-R-2) (IFN-alpha binding protein) (IFN-alpha/beta receptor 2) (Interferon alpha binding protein) (Type I interferon receptor 2) | IFNAR2 IFNABR IFNARB |
| P15260 | INGR1_HUMAN | Interferon gamma receptor 1 (IFN-gamma receptor 1) (IFN-gamma-R1) (CDw119) (Interferon gamma receptor alpha-chain) (IFN-gamma-R-alpha) (CD antigen CD119) | IFNGR1 |
| Q01650 | LAT1_HUMAN | Large neutral amino acids transporter small subunit 1 (4F2 light chain) (4F2 LC) (4F2LC) (CD98 light chain) (Integral membrane protein E16) (L-type amino acid transporter 1) (hLAT1) (Solute carrier family 7 member 5) (y + system cationic amino acid transporter) | SLC7A5 CD98LC LAT1 MPE16 |
| Q9UHI5 | LAT2_HUMAN | Large neutral amino acids transporter small subunit 2 (L-type amino acid transporter 2) (hLAT2) (Solute carrier family 7 member 8) | SLC7A8 LAT2 |
| P42702 | LIFR_HUMAN | Leukemia inhibitory factor receptor (LIF receptor) (LIF-R) (CD antigen CD118) | LIFR |
| O75096 | LRP4_HUMAN | Low-density lipoprotein receptor-related protein 4 (LRP-4) (Multiple epidermal growth factor-like domains 7) | LRP4 KIAA0816 LRP10 MEGF7 |
| Q07820 | MCL1_HUMAN | Induced myeloid leukemia cell differentiation protein Mcl-1 (Bcl-2-like protein 3) (Bcl2-L-3) (Bcl-2-related protein EAT/mcl1) (mcl1/EAT) | MCL1 BCL2L3 |
| Q29980 | MICB_HUMAN | MHC class I polypeptide-related sequence B (MIC-B) | MICB PERB11.2 |
| Q99650 | OSMR_HUMAN | Oncostatin-M-specific receptor subunit beta (Interleukin-31 receptor subunit beta) (IL-31 receptor subunit beta) (IL-31R subunit beta) (IL-31R-beta) (IL-31RB) | OSMR OSMRB |
| Q86UW1 | OSTA_HUMAN | Organic solute transporter subunit alpha (OST-alpha) (Solute carrier family 51 subunit alpha) | SLC51A OSTA |
| P41143 | OPRD_HUMAN | Delta-type opioid receptor (D-OR-1) (DOR-1) | OPRD1 OPRD |
| Q96QU1 | PCD15_HUMAN | Protocadherin-15 | PCDH15 USH1F |
| P07202 | PERT_HUMAN | Thyroid peroxidase (TPO) (EC 1.11.1.8) | TPO |
| Q29983 | MICA_HUMAN | MHC class I polypeptide-related sequence A (MIC-A) | MICA PERB11.1 |
| Q7L4E1 | MIGA2_HUMAN | Mitoguardin 2 (Protein FAM73B) | MIGA2 C9orf54 FAM73B PSEC0112 |
| Q9BPX6 | MICU1_HUMAN | Calcium uptake protein 1, mitochondrial (Atopy-related autoantigen CALC) (ara CALC) (Calcium-binding atopy-related autoantigen 1) (allergen Hom s 4) | MICU1 CALC CBARA1 |
| Q8TCY5 | MRAP_HUMAN | Melanocortin-2 receptor accessory protein (B27) (Fat cell-specific low molecular weight protein) (Fat tissue-specific low MW protein) | MRAP C21orf61 FALP |
| Q8NAN2 | MIGA1_HUMAN | Mitoguardin 1 (Protein FAM73A) | MIGA1 FAM73A |
| Q13585 | MTR1L_HUMAN | Melatonin-related receptor (G protein-coupled receptor 50) (H9) | GPR50 |
| O15146 | MUSK_HUMAN | Muscle, skeletal receptor tyrosine-protein kinase (EC 2.7.10.1) (Muscle-specific tyrosine-protein kinase receptor) (MuSK) (Muscle-specific kinase receptor) | MUSK |
| Q96G30 | MRAP2_HUMAN | Melanocortin-2 receptor accessory protein 2 (MC2R accessory protein 2) | MRAP2 C6orf117 |
| O43908 | NKG2F_HUMAN | NKG2-F type II integral membrane protein (NK cell receptor F) (NKG2-F-activating NK receptor) | KLRC4 NKG2F |
| Q9Y2A7 | NCKP1_HUMAN | Nck-associated protein 1 (NAP 1) (Membrane-associated protein HEM-2) (p125Nap1) | NCKAP1 HEM2 KIAA0587 NAP1 |
| O00533 | NCHL1_HUMAN | Neural cell adhesion molecule L1-like protein (Close homolog of L1) [Cleaved into: Processed neural cell adhesion molecule L1-like protein] | CHL1 CALL |
| P26715 | NKG2A_HUMAN | NKG2-A/NKG2-B type II integral membrane protein (CD159 antigen-like family member A) (NK cell receptor A) (NKG2-A/B-activating NK receptor) (CD antigen CD159a) | KLRC1 NKG2A |
| Q9NZ94 | NLGN3_HUMAN | Neuroligin-3 (Gliotactin homolog) | NLGN3 KIAA1480 NL3 |
| P26717 | NKG2C_HUMAN | NKG2-C type II integral membrane protein (CD159 antigen-like family member C) (NK cell receptor C) (NKG2-C-activating NK receptor) (CD antigen CD159c) | KLRC2 NKG2C |
| Q07444 | NKG2E_HUMAN | NKG2-E type II integral membrane protein (NK cell receptor E) (NKG2-E-activating NK receptor) | KLRC3 NKG2E |

TABLE 1-continued

Illustrative proteins which may be incorporated into the present compositions and methods include the following (as used herein, "Entry" refers to the protein entry in the Uniprot database and "Entry name" refers to the protein entry in the Uniprot database):

| Entry | Entry name | Protein names | Gene names |
|---|---|---|---|
| Q99466 | NOTC4_HUMAN | Neurogenic locus notch homolog protein 4 (Notch 4) (hNotch4) [Cleaved into: Notch 4 extracellular truncation; Notch 4 intracellular domain] | NOTCH4 INT3 |
| O14786 | NRP1_HUMAN | Neuropilin-1 (Vascular endothelial cell growth factor 165 receptor) (CD antigen CD304) | NRP1 NRP VEGF165R |
| Q04721 | NOTC2_HUMAN | Neurogenic locus notch homolog protein 2 (Notch 2) (hN2) [Cleaved into: Notch 2 extracellular truncation (N2ECD); Notch 2 intracellular domain (N2ICD)] | NOTCH2 |
| O60462 | NRP2_HUMAN | Neuropilin-2 (Vascular endothelial cell growth factor 165 receptor 2) | NRP2 VEGF165R2 |
| Q86UW2 | OSTB_HUMAN | Organic solute transporter subunit beta (OST-beta) (Solute carrier family 51 subunit beta) | SLC51B OSTB |
| Q9P0L9 | PK2L1_HUMAN | Polycystic kidney disease 2-like 1 protein (Polycystin-2 homolog) (Polycystin-2L1) (Polycystin-L) (Polycystin-L1) | PKD2L1 PKD2L PKDL TRPP3 |
| Q8TDX9 | PK1L1_HUMAN | Polycystic kidney disease protein 1-like 1 (PC1-like 1 protein) (Polycystin-1L1) | PKD1L1 UNQ5785/ PRO19563 |
| Q16651 | PRSS8_HUMAN | Prostasin (EC 3.4.21.-) (Channel-activating protease 1) (CAP1) (Serine protease 8) [Cleaved into: Prostasin light chain; Prostasin heavy chain] | PRSS8 |
| Q96HA9 | PX11C_HUMAN | Peroxisomal membrane protein 11C (Peroxin-11C) (Peroxisomal biogenesis factor 11C) (Protein PEX11 homolog gamma) (PEX11-gamma) | PEX11G PEX11C |
| O60896 | RAMP3_HUMAN | Receptor activity-modifying protein 3 (Calcitonin-receptor-like receptor activity-modifying protein 3) (CRLR activity-modifying protein 3) | RAMP3 |
| O60895 | RAMP2_HUMAN | Receptor activity-modifying protein 2 (Calcitonin-receptor-like receptor activity-modifying protein 2) (CRLR activity-modifying protein 2) | RAMP2 |
| O60894 | RAMP1_HUMAN | Receptor activity-modifying protein 1 (Calcitonin-receptor-like receptor activity-modifying protein 1) (CRLR activity-modifying protein 1) | RAMP1 |
| O43157 | PLXB1_HUMAN | Plexin-B1 (Semaphorin receptor SEP) | PLXNB1 KIAA0407 PLXN5 SEP |
| O15031 | PLXB2_HUMAN | Plexin-B2 (MM1) | PLXNB2 KIAA0315 |
| Q9UG56 | PISD_HUMAN | Phosphatidylserine decarboxylase proenzyme, mitochondrial (EC 4.1.1.65) [Cleaved into: Phosphatidylserine decarboxylase beta chain; Phosphatidylserine decarboxylase alpha chain] | PISD |
| O75915 | PRAF3_HUMAN | PRA1 family protein 3 (ADP-ribosylation factor-like protein 6-interacting protein 5) (ARL-6-interacting protein 5) (Aip-5) (Cytoskeleton-related vitamin A-responsive protein) (Dermal papilla-derived protein 11) (GTRAP3-18) (Glutamate transporter EAAC1-interacting protein) (JM5) (Prenylated Rab acceptor protein 2) (Protein JWa) (Putative MAPK-activating protein PM27) | ARL6IP5 DERP11 JWA PRA2 PRAF3 HSPC127 |
| O96011 | PX11B_HUMAN | Peroxisomal membrane protein 11B (Peroxin-11B) (Peroxisomal biogenesis factor 11B) (Protein PEX11 homolog beta) (PEX11-beta) | PEX11B |
| O75192 | PX11A_HUMAN | Peroxisomal membrane protein 11A (HsPEX11p) (28 kDa peroxisomal integral membrane protein) (PMP28) (Peroxin-11A) (Peroxisomal biogenesis factor 11A) (Protein PEX11 homolog alpha) (PEX11-alpha) | PEX11A PEX11 |
| Q6ISU1 | PTCRA_HUMAN | Pre T-cell antigen receptor alpha (pT-alpha) (pTa) (pT-alpha-TCR) | PTCRA |
| Q68DV7 | RNF43_HUMAN | E3 ubiquitin-protein ligase RNF43 (EC 2.3.2.27) (RING finger protein 43) (RING-type E3 ubiquitin transferase RNF43) | RNF43 |
| P51811 | XK_HUMAN | Membrane transport protein XK (Kell complex 37 kDa component) (Kx antigen) (XK-related protein 1) | XK XKR1 XRG1 |
| Q04912 | RON_HUMAN | Macrophage-stimulating protein receptor (MSP receptor) (EC 2.7.10.1) (CDw136) (Protein-tyrosine kinase 8) (p185-Ron) (CD antigen CD136) [Cleaved into: Macrophage-stimulating protein receptor alpha chain; Macrophage-stimulating protein receptor beta chain] | MST1R PTK8 RON |
| Q96DX8 | RTP4_HUMAN | Receptor-transporting protein 4 (28 kDa interferon-responsive protein) (3CxxC-type zinc finger protein 4) | RTP4 IFRG28 Z3CXXC4 |
| Q8WTV0 | SCRB1_HUMAN | Scavenger receptor class B member 1 (SRB1) (CD36 and LIMPII analogous 1) (CLA-1) (CD36 antigen-like 1) (Collagen type I receptor, thrombospondin receptor-like 1) (SR-BI) (CD antigen CD36) | SCARB1 CD36L1 CLA1 |
| Q12884 | SEPR_HUMAN | Prolyl endopeptidase FAP (EC 3.4.21.26) (170 kDa melanoma membrane-bound gelatinase) (Dipeptidyl peptidase FAP) (EC 3.4.14.5) (Fibroblast activation protein alpha) (FAPalpha) (Gelatine degradation protease FAP) (EC 3.4.21.-) (Integral membrane serine protease) (Post-proline cleaving enzyme) (Serine integral membrane protease) (SIMP) (Surface-expressed protease) (Seprase) [Cleaved into: Antiplasmin-cleaving enzyme FAP, soluble form (APCE) (EC 3.4.14.5) (EC 3.4.21.-) (EC 3.4.21.26)] | FAP |
| Q9Y5M8 | SRPRB_HUMAN | Signal recognition particle receptor subunit beta (SR-beta) (Protein APMCF1) | SRPRB PSEC0230 |
| O15270 | SPTC2_HUMAN | Serine palmitoyltransferase 2 (EC 2.3.1.50) (Long chain base biosynthesis protein 2) (LCB 2) (Long chain base biosynthesis protein 2a) (LCB2a) (Serine-palmitoyl-CoA transferase 2) (SPT 2) | SPTLC2 KIAA0526 LCB2 |

TABLE 1-continued

Illustrative proteins which may be incorporated into the present compositions and methods include the following (as used herein, "Entry" refers to the protein entry in the Uniprot database and "Entry name" refers to the protein entry in the Uniprot database):

| Entry | Entry name | Protein names | Gene names |
|---|---|---|---|
| Q07837 | SLC31_HUMAN | Neutral and basic amino acid transport protein rBAT (NBAT) (D2h) (Solute carrier family 3 member 1) (b(0, +)-type amino acid transport protein) | SLC3A1<br>RBAT |
| O15269 | SPTC1_HUMAN | Serine palmitoyltransferase 1 (EC 2.3.1.50) (Long chain base biosynthesis protein 1) (LCB 1) (Serine-palmitoyl-CoA transferase 1) (SPT 1) (SPT1) | SPTLC1<br>LCB1 |
| P30874 | SSR2_HUMAN | Somatostatin receptor type 2 (SS-2-R) (SS2-R) (SS2R) (SRIF-1) | SSTR2 |
| Q9NUV7 | SPTC3_HUMAN | Serine palmitoyltransferase 3 (EC 2.3.1.50) (Long chain base biosynthesis protein 2b) (LCB2b) (Long chain base biosynthesis protein 3) (LCB 3) (Serine-palmitoyl-CoA transferase 3) (SPT 3) | SPTLC3<br>C20orf38<br>SPTLC2L |
| P32745 | SSR3_HUMAN | Somatostatin receptor type 3 (SS-3-R) (SS3-R) (SS3R) (SSR-28) | SSTR3 |
| P35346 | SSR5_HUMAN | Somatostatin receptor type 5 (SS-5-R) (SS5-R) (SS5R) | SSTR5 |
| P60508 | SYCY2_HUMAN | Syncytin-2 (Endogenous retrovirus group FRD member 1) (Envelope polyprotein) (HERV-FRD) (HERV-FRD_6p24.1 provirus ancestral Env polyprotein) [Cleaved into: Surface protein (SU); Transmembrane protein (TM)] | ERVFRD-1<br>ERVFRDE1<br>UNQ6191/<br>PRO20218 |
| Q86SS6 | SYT9_HUMAN | Synaptotagmin-9 (Synaptotagmin IX) (SytIX) | SYT9 |
| Q9BQG1 | SYT3_HUMAN | Synaptotagmin-3 (Synaptotagmin III) (SytIII) | SYT3 |
| Q5T7P8 | SYT6_HUMAN | Synaptotagmin-6 (Synaptotagmin VI) (SytVI) | SYT6 |
| Q6XYQ8 | SYT10_HUMAN | Synaptotagmin-10 (Synaptotagmin X) (SytX) | SYT10 |
| Q03518 | TAP1_HUMAN | Antigen peptide transporter 1 (APT1) (ATP-binding cassette sub-family B member 2) (Peptide supply factor 1) (Peptide transporter PSF1) (PSF-1) (Peptide transporter TAP1) (Peptide transporter involved in antigen processing 1) (Really interesting new gene 4 protein) | TAP1<br>ABCB2<br>PSF1<br>RING4<br>Y3 |
| Q03519 | TAP2_HUMAN | Antigen peptide transporter 2 (APT2) (ATP-binding cassette sub-family B member 3) (Peptide supply factor 2) (Peptide transporter PSF2) (PSF-2) (Peptide transporter TAP2) (Peptide transporter involved in antigen processing 2) (Really interesting new gene 11 protein) | TAP2<br>ABCB3<br>PSF2<br>RING11<br>Y1 |
| P01848 | TCA_HUMAN | T-cell receptor alpha chain C region | TRAC<br>TCRA |
| Q9UKZ4 | TEN1_HUMAN | Teneurin-1 (Ten-1) (Protein Odd Oz/ten-m homolog 1) (Tenascin-M1) (Ten-m1) (Teneurin transmembrane protein 1) [Cleaved into: Ten-1 intracellular domain (IDten-1) (Ten-1 ICD); Teneurin C-terminal-associated peptide (TCPA-1) (Ten-1 extracellular domain) (Ten-1 ECD)] | TENM1<br>ODZ1<br>TNM1 |
| Q9UL52 | TM11E_HUMAN | Transmembrane protease serine 11E (EC 3.4.21.-) (Serine protease DESC1) (Transmembrane protease serine 11E2) [Cleaved into: Transmembrane protease serine 11E non-catalytic chain; Transmembrane protease serine 11E catalytic chain] | TMPRSS11E<br>DESC1<br>TMPRSS11E2<br>UNQ742/<br>PRO1461 |
| P35590 | TIE1_HUMAN | Tyrosine-protein kinase receptor Tie-1 (EC 2.7.10.1) | TIE1<br>TIE |
| Q9Y2C9 | TLR6_HUMAN | Toll-like receptor 6 (CD antigen CD286) | TLR6 |
| Q9NT68 | TEN2_HUMAN | Teneurin-2 (Ten-2) (Protein Odd Oz/ten-m homolog 2) (Tenascin-M2) (Ten-m2) (Teneurin transmembrane protein 2) [Cleaved into: Ten-2, soluble form; Ten-2 intracellular domain (Ten-2 ICD)] | TENM2<br>KIAA1127<br>ODZ2<br>TNM2 |
| Q6N022 | TEN4_HUMAN | Teneurin-4 (Ten-4) (Protein Odd Oz/ten-m homolog 4) (Tenascin-M4) (Ten-m4) (Teneurin transmembrane protein 4) | TENM4<br>KIAA1302<br>ODZ4<br>TNM4 |
| Q15399 | TLR1_HUMAN | Toll-like receptor 1 (Toll/interleukin-1 receptor-like protein) (TIL) (CD antigen CD281) | TLR1<br>KIAA0012 |
| Q7RTY8 | TMPS7_HUMAN | Transmembrane protease serine 7 (EC 3.4.21.-) (Matriptase-3) | TMPRSS7 |
| P01850 | TRBC1_HUMAN | T-cell receptor beta-1 chain C region | TRBC1 |
| O15533 | TPSN_HUMAN | Tapasin (TPN) (TPSN) (NGS-17) (TAP-associated protein) (TAP-binding protein) | TAPBP<br>NGS17<br>TAPA |
| Q9BX84 | TRPM6_HUMAN | Transient receptor potential cation channel subfamily M member 6 (EC 2.7.11.1) (Channel kinase 2) (Melastatin-related TRP cation channel 6) | TRPM6<br>CHAK2 |
| P30530 | UFO_HUMAN | Tyrosine-protein kinase receptor UFO (EC 2.7.10.1) (AXL oncogene) | AXL<br>UFO |
| O00526 | UPK2_HUMAN | Uroplakin-2 (UP2) (Uroplakin II) (UPII) | UPK2 |
| Q92536 | YLAT2_HUMAN | Y + L amino acid transporter 2 (Cationic amino acid transporter, y + system) (Solute carrier family 7 member 6) (y(+)L-type amino acid transporter 2) (Y + LAT2) (y + LAT-2) | SLC7A6<br>KIAA0245 |
| Q9UM01 | YLAT1_HUMAN | Y + L amino acid transporter 1 (Monocyte amino acid permease 2) (MOP-2) (Solute carrier family 7 member 7) (y(+)L-type amino acid transporter 1) (Y + LAT1) (y + LAT-1) | SLC7A7 |
| O75631 | UPK3A_HUMAN | Uroplakin-3a (UP3a) (Uroplakin III) (UPIII) | UPK3A<br>UPK3 |
| Q9BT76 | UPK3B_HUMAN | Uroplakin-3b (UP3b) (Uroplakin IIIb) (UPIIIb) (p35) | UPK3B |
| P35916 | VGFR3_HUMAN | Vascular endothelial growth factor receptor 3 (VEGFR-3) (EC 2.7.10.1) (Fms-like tyrosine kinase 4) (FLT-4) (Tyrosine-protein kinase receptor FLT4) | FLT4<br>VEGFR3 |
| O75841 | UPK1B_HUMAN | Uroplakin-1b (UP1b) (Tetraspanin-20) (Tspan-20) (Uroplakin Ib) (UPIb) | UPK1B<br>TSPAN20 |

TABLE 1-continued

Illustrative proteins which may be incorporated into the present compositions and methods include the following (as used herein, "Entry" refers to the protein entry in the Uniprot database and "Entry name" refers to the protein entry in the Uniprot database):

| Entry | Entry name | Protein names | Gene names |
|---|---|---|---|
| Q9P0L0 | VAPA_HUMAN | Vesicle-associated membrane protein-associated protein A (VAMP-A) (VAMP-associated protein A) (VAP-A) (33 kDa VAMP-associated protein) (VAP-33) | VAPA VAP33 |
| Q9ULK5 | VANG2_HUMAN | Vang-like protein 2 (Loop-tail protein 1 homolog) (Strabismus 1) (Van Gogh-like protein 2) | VANGL2 KIAA1215 STB1 |
| Q8TAA9 | VANG1_HUMAN | Vang-like protein 1 (Loop-tail protein 2 homolog) (LPP2) (Strabismus 2) (Van Gogh-like protein 1) | VANGL1 STB2 |
| O95292 | VAPB_HUMAN | Vesicle-associated membrane protein-associated protein B/C (VAMP-B/VAMP-C) (VAMP-associated protein B/C) (VAP-B/VAP-C) | VAPB UNQ484/ PRO983 |
| Q9UPY5 | XCT_HUMAN | Cystine/glutamate transporter (Amino acid transport system xc-) (Calcium channel blocker resistance protein CCBR1) (Solute carrier family 7 member 11) (xCT) | SLC7A11 |
| Q6XR72 | ZNT10_HUMAN | Zinc transporter 10 (ZnT-10) (Manganese transporter SLC30A10) (Solute carrier family 30 member 10) | SLC30A10 ZNT10 ZNT8 |
| A0A024R0A1 | A0A024R0A1_HUMAN | Macrophage colony-stimulating factor 1 (CSF-1) (MCSF) | CSF1 hCG_40247 |
| P31785 | IL2RG_HUMAN | Cytokine receptor common subunit gamma (Interleukin-2 receptor subunit gamma) (IL-2 receptor subunit gamma) (IL-2R subunit gamma) (IL-2RG) (gammaC) (p64) (CD antigen CD132) | IL2RG |
| P32927 | IL3RB_HUMAN | Cytokine receptor common subunit beta (CDw131) (GM-CSF/IL-3/IL-5 receptor common beta subunit) (CD antigen CD131) | CSF2RB IL3RB IL5RB |
| P26951 | IL3RA_HUMAN | Interleukin-3 receptor subunit alpha (IL-3 receptor subunit alpha) (IL-3R subunit alpha) (IL-3R-alpha) (IL-3RA) (CD antigen CD123) | IL3RA IL3R |
| P15509 | CSF2R_HUMAN | Granulocyte-macrophage colony-stimulating factor receptor subunit alpha (GM-CSF-R-alpha) (GMCSFR-alpha) (GMR-alpha) (CDw116) (CD antigen CD116) | CSF2RA CSF2R CSF2RY |
| Q01344 | IL5RA_HUMAN | Interleukin-5 receptor subunit alpha (IL-5 receptor subunit alpha) (IL-5R subunit alpha) (IL-5R-alpha) (IL-5RA) (CDw125) (CD antigen CD125) | IL5RA IL5R |
| P08887 | IL6RA_HUMAN | Interleukin-6 receptor subunit alpha (IL-6 receptor subunit alpha) (IL-6R subunit alpha) (IL-6R-alpha) (IL-6RA) (IL-6R 1) (Membrane glycoprotein 80) (gp80) (CD antigen CD126) | IL6R |
| P40189 | IL6RB_HUMAN | Interleukin-6 receptor subunit beta (IL-6 receptor subunit beta) (IL-6R subunit beta) (IL-6R-beta) (IL-6RB) (CDw130) (Interleukin-6 signal transducer) (Membrane glycoprotein 130) (gp130) (Oncostatin-M receptor subunit alpha) (CD antigen CD130) | IL6ST |
| Q14626 | I11RA_HUMAN | Interleukin-11 receptor subunit alpha (IL-11 receptor subunit alpha) (IL-11R subunit alpha) (IL-11R-alpha) (IL-11RA) | IL11RA |
| P42702 | LIFR_HUMAN | Leukemia inhibitory factor receptor (LIF receptor) (LIF-R) (CD antigen CD118) | LIFR |
| Q99650 | OSMR_HUMAN | Oncostatin-M-specific receptor subunit beta (Interleukin-31 receptor subunit beta) (IL-31 receptor subunit beta) (IL-31R subunit beta) (IL-31R-beta) (IL-31RB) | OSMR OSMRB |
| P31785 | IL2RG_HUMAN | Cytokine receptor common subunit gamma (Interleukin-2 receptor subunit gamma) (IL-2 receptor subunit gamma) (IL-2R subunit gamma) (IL-2RG) (gammaC) (p64) (CD antigen CD132) | IL2RG |
| P01589 | IL2RA_HUMAN | Interleukin-2 receptor subunit alpha (IL-2 receptor subunit alpha) (IL-2-RA) (IL-2R subunit alpha) (IL2-RA) (TAC antigen) (p55) (CD antigen CD25) | IL2RA |
| P14784 | IL2RB_HUMAN | Interleukin-2 receptor subunit beta (IL-2 receptor subunit beta) (IL-2R subunit beta) (IL-2RB) (High affinity IL-2 receptor subunit beta) (Interleukin-15 receptor subunit beta) (p70-75) (p75) (CD antigen CD122) | IL2RB IL15RB |
| P24394 | IL4RA_HUMAN | Interleukin-4 receptor subunit alpha (IL-4 receptor subunit alpha) (IL-4R subunit alpha) (IL-4R-alpha) (IL-4RA) (CD antigen CD124) [Cleaved into: Soluble interleukin-4 receptor subunit alpha (Soluble IL-4 receptor subunit alpha) (Soluble IL-4R-alpha) (sIL4Ralpha/prot) (IL-4-binding protein) (IL4-BP)] | IL4R IL4RA 582J2.1 |
| P16871 | IL7RA_HUMAN | Interleukin-7 receptor subunit alpha (IL-7 receptor subunit alpha) (IL-7R subunit alpha) (IL-7R-alpha) (IL-7RA) (CDw127) (CD antigen CD127) | IL7R |
| Q01113 | IL9R_HUMAN | Interleukin-9 receptor (IL-9 receptor) (IL-9R) (CD antigen CD129) | IL9R |
| P78552 | I13R1_HUMAN | Interleukin-13 receptor subunit alpha-1 (IL-13 receptor subunit alpha-1) (IL-13R subunit alpha-1) (IL-13 R-alpha-1) (IL-13RA1) (Cancer/testis antigen 19) (CT19) (CD antigen CD213a1) | IL13RA1 IL13R IL13RA |
| Q14627 | I13R2_HUMAN | Interleukin-13 receptor subunit alpha-2 (IL-13 receptor subunit alpha-2) (IL-13R subunit alpha-2) (IL-13R-alpha-2) (IL-13RA2) (Interleukin-13-binding protein) (CD antigen CD213a2) | IL13RA2 IL13R |
| Q13651 | I10R1_HUMAN | Interleukin-10 receptor subunit alpha (IL-10 receptor subunit alpha) (IL-10R subunit alpha) (IL-10RA) (CDw210a) (Interleukin-10 receptor subunit 1) (IL-10R subunit 1) (IL-10R1) (CD antigen CD210) | IL10RA IL10R |
| P26992 | CNTFR_HUMAN | Ciliary neurotrophic factor receptor subunit alpha (CNTF receptor subunit alpha) (CNTFR-alpha) | CNTFR |
| Q9NPF7 | IL23A_HUMAN | Interleukin-23 subunit alpha (IL-23 subunit alpha) (IL-23-A) (Interleukin-23 subunit p19) (IL-23p19) | IL23A SGRF UNQ2498/ PRO5798 |

TABLE 1-continued

Illustrative proteins which may be incorporated into the present compositions and methods include the following (as used herein, "Entry" refers to the protein entry in the Uniprot database and "Entry name" refers to the protein entry in the Uniprot database):

| Entry | Entry name | Protein names | Gene names |
| --- | --- | --- | --- |
| P29459 | IL12A_HUMAN | Interleukin-12 subunit alpha (IL-12A) (Cytotoxic lymphocyte maturation factor 35 kDa subunit) (CLMF p35) (IL-12 subunit p35) (NK cell stimulatory factor chain 1) (NKSF1) | IL12A NKSF1 |
| Q8NEV9 | IL27A_HUMAN | Interleukin-27 subunit alpha (IL-27 subunit alpha) (IL-27-A) (IL27-A) (Interleukin-30) (p28) | IL27 IL27A IL30 |
| Q14213 | IL27B_HUMAN | Interleukin-27 subunit beta (IL-27 subunit beta) (IL-27B) (Epstein-Barr virus-induced gene 3 protein) (EBV-induced gene 3 protein) | EBI3 IL27B |

In various embodiments, the present heterodimeric proteins may be engineered to target one or more molecules that reside on human leukocytes including, without limitation, the extracellular domains (where applicable) of SLAMF4, IL-2Rα, IL-2 R β, ALCAM, B7-1, IL-4 R, B7-H3, BLAME/SLAMFS, CEACAM1, IL-6 R, IL-7 Rα, IL-10R α, IL-I0 R β, IL-12 R β 1, IL-12 R β 2, CD2, IL-13 R α 1, IL-13, CD3, CD4, ILT2/CDS5j, ILT3/CDS5k, ILT4/CDS5d, ILT5/CDS5a, lutegrin α 4/CD49d, CDS, Integrin α E/CD103, CD6, Integrin α M/CD 11 b, CDS, Integrin α X/CD11c, Integrin β 2/CDIS, KIR/CD15S, KIR2DL1, CD2S, KIR2DL3, KIR2DL4/CD15Sd, CD31/PECAM-1, KIR2DS4, LAG-3, CD43, LAIR1, CD45, LAIR2, CDS3, Leukotriene B4-R1, CDS4/SLAMF5, NCAM-L1, CD94, NKG2A, CD97, NKG2C, CD229/SLAMF3, NKG2D, CD2F-10/SLAMF9, NT-4, CD69, NTB-A/SLAMF6, Common γ Chain/IL-2 R γ, Osteopontin, CRACC/SLAMF7, PD-1, CRTAM, PSGL-1, CTLA-4, CX3CR1, CX3CL1, L-Selectin, SIRP β 1, SLAM, TCCR/WSX-1, DNAM-1, Thymopoietin, EMMPRIN/CD147, TIM-1, EphB6, TIM-2, TIM-3, TIM-4, Fcγ RIII/CD16, TIM-6, Granulysin, ICAM-1/CD54, ICAM-2/CD102, IFN-γR1, IFN-γ R2, TSLP, IL-1 R1 and TSLP R.

In some embodiments, the present heterodimeric proteins may be engineered to target one or more molecules involved in immune inhibition, including for example: CTLA-4, PD-L1, PD-L2, PD-1, BTLA, HVEM, TIM3, GAL9, LAG3, VISTANSIG8, KIR, 2B4, TIGIT, CD160 (also referred to as BY55), CHK 1 and CHK2 kinases, A2aR, CEACAM (e.g., CEACAM-1, CEACAM-3 and/or CEACAM-5), and various B-7 family ligands (including, but are not limited to, B7-1, B7-2, B7-DC, B7-H1, B7-H2, B7-H3, B7-H4, B7-H5, B7-H6 and B7-H7).

In some embodiments, the present heterodimeric proteins comprise an extracellular domain of an immune inhibitory agent.

In some embodiments, the present heterodimeric proteins comprise an extracellular domain of a soluble or membrane protein which has immune inhibitory properties.

In some embodiments, the present heterodimeric proteins simulate binding of an inhibitory signal ligand to its cognate receptor but inhibit the inhibitory signal transmission to an immune cell (e.g., a T cell, macrophage or other leukocyte).

In various embodiments, the heterodimeric protein comprises an immune inhibitory receptor extracellular domain and an immune stimulatory ligand extracellular domain which can, without limitation, deliver an immune stimulation to a T cell while masking a tumor cell's immune inhibitory signals. In various embodiments, the heterodimeric protein delivers a signal that has the net result of T cell activation.

In some embodiments, the present heterodimeric proteins comprise an extracellular domain of a soluble or membrane protein which has immune stimulatory properties.

In embodiments, a heterodimeric protein useful in the present invention comprises the extracellular domain of Gp130. Gp130 (also known as Interleukin-6 receptor subunit beta, IL-6R-beta, IL-6RB, and IL-6ST) is a signal-transducing molecule. The receptor systems for IL6, LIF, OSM, CNTF, IL11, CTF1 and BSF3 can utilize Gp130 for initiating signal transmission. Binding of IL6 to IL6R induces IL6ST homodimerization and formation of a high-affinity receptor complex, which activates Janus kinases. That causes phosphorylation of Gp130 tyrosine residues which in turn activates STAT3. Gp130 mediates signals which regulate immune response, hematopoiesis, pain control and bone metabolism (By similarity).

In embodiments, a heterodimeric protein useful in the present invention comprises a variant of the extracellular domain of Gp130. As examples, the variant may have at least about 60%, or at least about 61%, or at least about 62%, or at least about 63%, or at least about 64%, or at least about 65%, or at least about 66%, or at least about 67%, or at least about 68%, or at least about 69%, or at least about 70%, or at least about 71%, or at least about 72%, or at least about 73%, or at least about 74%, or at least about 75%, or at least about 76%, or at least about 77%, or at least about 78%, or at least about 79%, or at least about 80%, or at least about 81%, or at least about 82%, or at least about 83%, or at least about 84%, or at least about 85%, or at least about 86%, or at least about 87%, or at least about 88%, or at least about 89%, or at least about 90%, or at least about 91%, or at least about 92%, or at least about 93%, or at least about 94%, or at least about 95%, or at least about 96%, or at least about 97%, or at least about 98%, or at least about 99% sequence identity with the known amino acid sequence of Gp130, e.g., human Gp130.

In embodiments, the extracellular domain of Gp130 has the following amino acid sequence:

(SEQ ID NO: 18)
ELLDPCGYISPESPVVQLHSNFTAVCVLKEKCMDYFHVNANYIVWKTNHF

TIPKEQYTIINRTASSVTFTDIASLNIQLTCNILTFGQLEQNVYGITIIS

GLPPEKPKNLSCIVNEGKKMRCEWDGGRETHLETNFTLKSEWATHKFADC

KAKRDTPTSCTVDYSTVYFVNIEVWVEAENALGKVTSDHINFDPVYKVKP

NPPHNLSVINSEELSSILKLTWTNPSIKSVIILKYNIQYRTKDASTWSQI

PPEDTASTRSSFTVQDLKPFTEYVFRIRCMKEDGKGYWSDWSEEASGITY

EDRPSKAPSFWYKIDPSHTQGYRTVQLVWKTLPPFEANGKILDYEVTLTR

-continued

```
WKSHLQNYTVNATKLTVNLTNDRYLATLTVRNLVGKSDAAVLTIPACDFQ

ATHPVMDLKAFPKDNMLWVEWTTPRESVKKYILEWCVLSDKAPCITDWQQ

EDGTVHRTYLRGNLAESKCYLITVTPVYADGPGSPESIKAYLKQAPPSKG

PTVRTKKVGKNEAVLEWDQLPVDVQNGFIRNYTIFYRTIIGNETAVNVDS

SHTEYTLSSLTSDTLYMVRMAAYTDEGGKDGPEFTFTTPKFAQGEIE
```

In embodiments, a heterodimeric protein comprises a variant of the extracellular domain of Gp130. As examples, the variant may have at least about 60%, or at least about 61%, or at least about 62%, or at least about 63%, or at least about 64%, or at least about 65%, or at least about 66%, or at least about 67%, or at least about 68%, or at least about 69%, or at least about 70%, or at least about 71%, or at least about 72%, or at least about 73%, or at least about 74%, or at least about 75%, or at least about 76%, or at least about 77%, or at least about 78%, or at least about 79%, or at least about 80%, or at least about 81%, or at least about 82%, or at least about 83%, or at least about 84%, or at least about 85%, or at least about 86%, or at least about 87%, or at least about 88%, or at least about 89%, or at least about 90%, or at least about 91%, or at least about 92%, or at least about 93%, or at least about 94%, or at least about 95%, or at least about 96%, or at least about 97%, or at least about 98%, or at least about 99% sequence identity with SEQ ID NO: 18.

In embodiments, one chain of the heterodimeric protein comprises an amino acid sequence that is at least 95% identical to the amino acid sequence of SEQ ID NO: 18.

One of ordinary skill may select variants of the known amino acid sequence of Gp130 by consulting the literature, e.g., Hibi et al, "Molecular cloning and expression of an IL-6 signal transducer, gp130" Cell 63 (6), 1149-1157 (1990); Waetzig et al., "N-linked glycosylation is essential for the stability but not the signaling function of the interleukin-6 signal transducer glycoprotein 130", J. Biol. Chem. 285 (3), 1781-1789 (2010); Schutt et al., "gp130 activation is regulated by D2-D3 interdomain connectivity", Biochem. J. 450 (3), 487-496 (2013); Bravo et al., "Crystal structure of a cytokine-binding region of gp130", EMBO J. 17 (6), 1665-1674 (1998); Chow et al., "Structure of an extracellular gp130 cytokine receptor signaling complex", Science 291 (5511), 2150-2155 (2001); Boulanger et al., "Hexameric structure and assembly of the interleukin-6/IL-6 alpha-receptor/gp130 complex", Science 300 (5628), 2101-2104 (2003); Xu et al., "Crystal structure of the entire ectodomain of gp130: insights into the molecular assembly of the tall cytokine receptor complexes", J. Biol. Chem. 285 (28), 21214-21218 (2010), each of which is incorporated by reference in its entirety.

In embodiments, a heterodimeric protein useful in the present invention comprises the extracellular domain of IL-6RA. IL-6RA (also known as Interleukin-6 receptor subunit alpha, IL-6 receptor subunit alpha, IL-6R subunit alpha, and IL-6R-alpha) is part of the receptor for interleukin 6. Binds to IL6 with low affinity, but does not transduce a signal. Signal activation necessitate an association with gp130. Activation may lead to the regulation of the immune response, acute-phase reactions and hematopoiesis. Low concentration of a soluble form of IL6 receptor acts as an agonist of IL6 activity. Dysregulated production of IL6 and this receptor are implicated in the pathogenesis of many diseases, such as multiple myeloma, autoimmune diseases and prostate cancer.

In embodiments, a heterodimeric protein useful in the present invention comprises a variant of the extracellular domain of IL-6RA. As examples, the variant may have at least about 60%, or at least about 61%, or at least about 62%, or at least about 63%, or at least about 64%, or at least about 65%, or at least about 66%, or at least about 67%, or at least about 68%, or at least about 69%, or at least about 70%, or at least about 71%, or at least about 72%, or at least about 73%, or at least about 74%, or at least about 75%, or at least about 76%, or at least about 77%, or at least about 78%, or at least about 79%, or at least about 80%, or at least about 81%, or at least about 82%, or at least about 83%, or at least about 84%, or at least about 85%, or at least about 86%, or at least about 87%, or at least about 88%, or at least about 89%, or at least about 90%, or at least about 91%, or at least about 92%, or at least about 93%, or at least about 94%, or at least about 95%, or at least about 96%, or at least about 97%, or at least about 98%, or at least about 99% sequence identity with the known amino acid sequence of IL-6RA, e.g., human IL-6RA.

In embodiments, the extracellular domain of IL-6RA has the following amino acid sequence:

```
                                       (SEQ ID NO: 19)
LAPRRCPAQEVARGVLTSLPGDSVTLTCPGVEPEDNATVHWVLRKPAAGS

HPSRWAGMGRRLLLRSVQLHDSGNYSCYRAGRPAGTVHLLVDVPPEEPQL

SCFRKSPLSNVVCEWGPRSTPSLTTKAVLLVRKFQNSPAEDFQEPCQYSQ

ESQKFSCQLAVPEGDSSFYIVSMCVASSVGSKFSKTQTFQGCGILQPDPP

ANITVTAVARNPRWLSVTWQDPHSWNSSFYRLRFELRYRAERSKTFTTWM

VKDLQHHCVIHDAWSGLRHWQLRAQEEFGQGEWSEWSPEAMGTPWTESRS

PPAENEVSTPMQALTTNKDDDNILFRDSANATSLPVQDSSSVPLP
```

In embodiments, a heterodimeric protein comprises a variant of the extracellular domain of IL-6RA. As examples, the variant may have at least about 60%, or at least about 61%, or at least about 62%, or at least about 63%, or at least about 64%, or at least about 65%, or at least about 66%, or at least about 67%, or at least about 68%, or at least about 69%, or at least about 70%, or at least about 71%, or at least about 72%, or at least about 73%, or at least about 74%, or at least about 75%, or at least about 76%, or at least about 77%, or at least about 78%, or at least about 79%, or at least about 80%, or at least about 81%, or at least about 82%, or at least about 83%, or at least about 84%, or at least about 85%, or at least about 86%, or at least about 87%, or at least about 88%, or at least about 89%, or at least about 90%, or at least about 91%, or at least about 92%, or at least about 93%, or at least about 94%, or at least about 95%, or at least about 96%, or at least about 97%, or at least about 98%, or at least about 99% sequence identity with SEQ ID NO: 19.

In embodiments, one chain of the heterodimeric protein comprises an amino acid sequence that is at least 95% identical to the amino acid sequence of SEQ ID NO: 19.

One of ordinary skill may select variants of the known amino acid sequence of IL-6RA by consulting the literature, e.g., Yamasaki et al., "Cloning and expression of the human interleukin-6 (BSF-2/IFN beta 2) receptor" Science 241 (4867), 825-828 (1988); Buk et al., "Increased association with detergent-resistant membranes/lipid rafts of apically targeted mutants of the interleukin-6 receptor gp80" Eur. J. Cell Biol. 84 (10), 819-831 (2005); Yawata et al., Structure-function analysis of human IL-6 receptor: dissociation of amino acid residues required for IL-6-binding and for IL-6 signal transduction through gp130" EMBO J. 12 (4), 1705-1712 (1993); Horiuchi et al., "Soluble interleukin-6 receptors released from T cell or granulocyte/macrophage cell lines and human peripheral blood mononuclear cells are generated through an alternative splicing mechanism" Eur. J. Immunol. 24 (8), 1945-1948 (1994); Boulanger et al., "Hexameric structure and assembly of the interleukin-6/IL-6 alpha-receptor/gp130 complex", Science 300 (5628), 2101-2104 (2003), each of which is incorporated by reference in its entirety.

In embodiments, a heterodimeric protein useful in the present invention comprises the extracellular domain of IL-12A. IL-12A (also known as Interleukin-12 subunit alpha and IL-12 subunit p35) is a cytokine that can act as a growth factor for activated T and NK cells, enhance the lytic activity of NK/lymphokine-activated killer cells, and stimulate the production of IFN-gamma by resting PBMC. The cytokine is a disulfide-linked heterodimer composed of the 35-kD subunit encoded by this gene, and a 40-kD subunit that is a member of the cytokine receptor family. This cytokine is required for the T-cell-dependent induction of interferon gamma (INF-γ), and is important for the differentiation of both Th1 and Th2 cells. The responses of lymphocytes to this cytokine are mediated by the activator of transcription protein STAT4.

In embodiments, a heterodimeric protein useful in the present invention comprises a variant of the extracellular domain of IL-12A. As examples, the variant may have at least about 60%, or at least about 61%, or at least about 62%, or at least about 63%, or at least about 64%, or at least about 65%, or at least about 66%, or at least about 67%, or at least about 68%, or at least about 69%, or at least about 70%, or at least about 71%, or at least about 72%, or at least about 73%, or at least about 74%, or at least about 75%, or at least about 76%, or at least about 77%, or at least about 78%, or at least about 79%, or at least about 80%, or at least about 81%, or at least about 82%, or at least about 83%, or at least about 84%, or at least about 85%, or at least about 86%, or at least about 87%, or at least about 88%, or at least about 89%, or at least about 90%, or at least about 91%, or at least about 92%, or at least about 93%, or at least about 94%, or at least about 95%, or at least about 96%, or at least about 97%, or at least about 98%, or at least about 99% sequence identity with the known amino acid sequence of IL-12A, e.g., human IL-12A.

In embodiments, the extracellular domain of IL-12A has the following amino acid sequence:

```
                                        (SEQ ID NO: 20)
RNLPVATPDPGMFPCLHHSQNLLRAVSNMLQKARQTLEFYPCTSEEIDHE

DITKDKTSTVEACLPLELTKNESCLNSRETSFITNGSCLASRKTSFMMAL

CLSSIYEDLKMYQVEFKTMNAKLLMDPKRQIFLDQNMLAVIDELMQALNF

NSETVPQKSSLEEPDFYKTKIKLCILLHAFRIRAVTIDRVMSYLNAS
```

In embodiments, a heterodimeric protein comprises a variant of the extracellular domain of IL-12A. As examples, the variant may have at least about 60%, or at least about 61%, or at least about 62%, or at least about 63%, or at least about 64%, or at least about 65%, or at least about 66%, or at least about 67%, or at least about 68%, or at least about 69%, or at least about 70%, or at least about 71%, or at least about 72%, or at least about 73%, or at least about 74%, or at least about 75%, or at least about 76%, or at least about 77%, or at least about 78%, or at least about 79%, or at least about 80%, or at least about 81%, or at least about 82%, or at least about 83%, or at least about 84%, or at least about 85%, or at least about 86%, or at least about 87%, or at least about 88%, or at least about 89%, or at least about 90%, or at least about 91%, or at least about 92%, or at least about 93%, or at least about 94%, or at least about 95%, or at least about 96%, or at least about 97%, or at least about 98%, or at least about 99% sequence identity with SEQ ID NO: 20.

In embodiments, one chain of the heterodimeric protein comprises an amino acid sequence that is at least 95% identical to the amino acid sequence of SEQ ID NO: 20.

One of ordinary skill may select variants of the known amino acid sequence of IL-12A by consulting the literature, e.g., Wolf et al., "Cloning of cDNA for natural killer cell stimulatory factor, a heterodimeric cytokine with multiple biologic effects on T and natural killer cells", J. Immunol. 146 (9), 3074-3081 (1991); Devergne et al., "Epstein-Barr virus-induced gene 3 and the p35 subunit of interleukin 12 form a novel heterodimeric hematopoietin", Proc. Natl. Acad. Sci. U.S.A. 94 (22), 12041-12046 (1997); Yoon et al., "Charged residues dominate a unique interlocking topography in the heterodimeric cytokine interleukin-12", EMBO J. 19 (14), 3530-3541 (2000), each of which is incorporated by reference in its entirety.

In embodiments, a heterodimeric protein useful in the present invention comprises the extracellular domain of IL-27B. IL-27b (also known as Interleukin-27 subunit beta, IL-27 subunit beta, and IL-27B), together with IL-12a forms Interleukin 35 (IL-35). IL-35 is a dimeric protein composed of IL-12a and IL-273 chains, which are encoded by two separate genes called IL12A and EBI3, respectively. IL-27 has pro- and anti-inflammatory properties, that can regulate T-helper cell development, suppress T-cell proliferation, stimulate cytotoxic T-cell activity, induce isotype switching in B-cells, and that has diverse effects on innate immune cells. Its gene was identified by its induced expression in B lymphocytes in response Epstein-Barr virus infection. IL-27 regulates T cell and inflammatory responses, in part by activating the Jak/STAT pathway of CD4+ T cells.

In embodiments, a heterodimeric protein useful in the present invention comprises a variant of the extracellular domain of IL-27B. As examples, the variant may have at least about 60%, or at least about 61%, or at least about 62%, or at least about 63%, or at least about 64%, or at least about 65%, or at least about 66%, or at least about 67%, or at least about 68%, or at least about 69%, or at least about 70%, or at least about 71%, or at least about 72%, or at least about 73%, or at least about 74%, or at least about 75%, or at least about 76%, or at least about 77%, or at least about 78%, or at least about 79%, or at least about 80%, or at least about 81%, or at least about 82%, or at least about 83%, or at least about 84%, or at least about 85%, or at least about 86%, or at least about 87%, or at least about 88%, or at least about 89%, or at least about 90%, or at least about 91%, or at least about 92%, or at least about 93%, or at least about 94%, or at least about 95%, or at least about 96%, or at least about 97%, or at least about 98%, or at least about 99% sequence identity with the known amino acid sequence of IL-27B, e.g., human IL-27B.

In embodiments, the extracellular domain of IL-27B has the following amino acid sequence:

```
                                        (SEQ ID NO: 21)
RKGPPAALTLPRVQCRASRYPIAVDCSWTLPPAPNSTSPVSFIATYRLGM

AARGHSWPCLQQTPTSTSCTITDVQLFSMAPYVLNVTAVHPWGSSSSFVP
```

FITEHIIKPDPPEGVRLSPLAERQLQVQWEPPGSWPFPEIFSLKYWIRYK

RQGAARFHRVGPIEATSFILRAVRPRARYYVQVAAQDLTDYGELSDWSLP

ATATMSLGK

In embodiments, a heterodimeric protein comprises a variant of the extracellular domain of IL-27B. As examples, the variant may have at least about 60%, or at least about 61%, or at least about 62%, or at least about 63%, or at least about 64%, or at least about 65%, or at least about 66%, or at least about 67%, or at least about 68%, or at least about 69%, or at least about 70%, or at least about 71%, or at least about 72%, or at least about 73%, or at least about 74%, or at least about 75%, or at least about 76%, or at least about 77%, or at least about 78%, or at least about 79%, or at least about 80%, or at least about 81%, or at least about 82%, or at least about 83%, or at least about 84%, or at least about 85%, or at least about 86%, or at least about 87%, or at least about 88%, or at least about 89%, or at least about 90%, or at least about 91%, or at least about 92%, or at least about 93%, or at least about 94%, or at least about 95%, or at least about 96%, or at least about 97%, or at least about 98%, or at least about 99% sequence identity with SEQ ID NO: 21.

In embodiments, one chain of the heterodimeric protein comprises an amino acid sequence that is at least 95% identical to the amino acid sequence of SEQ ID NO: 21.

One of ordinary skill may select variants of the known amino acid sequence of IL-27B by consulting the literature, e.g., Devergne "Epstein-Barr virus-induced gene 3 and the p35 subunit of interleukin 12 form a novel heterodimeric hematopoietin", Proc. Natl. Acad. Sci. U.S.A. 94 (22), 12041-12046 (1997); Pflanz et al., "IL-27, a heterodimeric cytokine composed of EBI3 and p28 protein, induces proliferation of naive CD4+ T cells", Immunity 16 (6), 779-790 (2002); Batten and Ghilardi "The biology and therapeutic potential of interleukin 27", J. Mol. Med. 85 (7), 661-672 (2007), each of which is incorporated by reference in its entirety.

In embodiments, an alpha chain useful in a heterodimeric chimeric protein of the present invention comprises: (1) a first domain comprising the amino acid sequence of SEQ ID NO: 18, or a variant thereof, (b) a second domain comprises the amino acid sequence of SEQ ID NO: 20, or a variant thereof, and (c) an alpha core domain, or variant thereof, which comprises an amino acid sequence that is at least 95% identical to SEQ ID NO: 16 or SEQ ID NO: 24. Such an alpha chain may be referred to as "Gp130-Alpha-IL12A".

In embodiments, a Gp130-Alpha-IL12A chain used in the present invention and has the following amino acid sequence:

(SEQ ID NO: 22)
ELLDPCGYISPESPVVQLHSNFTAVCVLKEKCMDYFHVNANYIVWKTNHF

TIPKEQYTIINRTASSVTFTDIASLNIQLTCNILTFGQLEQNVYGITIIS

GLPPEKPKNLSCIVNEGKKMRCEWDGGRETHLETNFTLKSEWATHKFADC

KAKRDTPTSCTVDYSTVYFVNIEVWVEAENALGKVTSDHINFDPVYKVKP

NPPHNLSVINSEELSSILKLTWTNPSIKSVIILKYNIQYRTKDASTWSQI

PPEDTASTRSSFTVQDLKPFTEYVFRIRCMKEDGKGYWSDWSEEASGITY

EDRPSKAPSFWYKIDPSHTQGYRTVQLVWKTLPPFEANGKILDYEVTLTR

WKSHLQNYTVNATKLTVNLTNDRYLATLTVRNLVGKSDAAVLTIPACDFQ

ATHPVMDLKAFPKDNMLWVEWTTPRESVKKYILEWCVLSDKAPCITDWQQ

EDGTVHRTYLRGNLAESKCYLITVTPVYADGPGSPESIKAYLKQAPPSKG

PTVRTKKVGKNEAVLEWDQLPVDVQNGFIRNYTIFYRTIIGNETAVNVDS

SHTEYTLSSLTSDTLYMVRMAAYTDEGGKDGPEFTFTTPKFAQGEIEGSG

SRKGGKRGSKYGPPCPPCPAPEFLGGPSVFLFPPKPKDQLMISRTPEVTC

VVVDVSQEDPEVQFNWYVDGVEVHNAKTKPREEQFNSTYRVVSVLTVLHQ

DWLSGKEYKCKVSSKGLPSSIEKTISNATGQPREPQVYTLPPSQEEMTKN

QVSLTCLVKGFYPSDIAVEWESNGQPENNYKTTPPVLDSDGSFFLYSRLT

VDKSRWQEGNVFSCSVLHEALHNHYTQKSLSLSLGKDEGGEDGSGSRNLP

VATPDPGMFPCLHHSQNLLRAVSNMLQKARQTLEFYPCTSEEIDHEDITK

DKTSTVEACLPLELTKNESCLNSRETSFITNGSCLASRKTSFMMALCLSS

IYEDLKMYQVEFKTMNAKLLMDPKRQIFLDQNMLAVIDELMQALNFNSET

VPQKSSLEEPDFYKTKIKLCILLHAFRIRAVTIDRVMSYLNAS*

In embodiments, an beta chain useful in a heterodimeric chimeric protein of the present invention comprises: (1) a first domain comprising the amino acid sequence of SEQ ID NO: 19, or a variant thereof, (b) a second domain comprises the amino acid sequence of SEQ ID NO: 21, or a variant thereof, and (c) an alpha core domain, or variant thereof, which comprises an amino acid sequence that is at least 95% identical to SEQ ID NO: 17 or SEQ ID NO: 25. Such an alpha chain may be referred to as "IL6RA-Beta-IL27B". In embodiments, an IL6RA-Beta-IL27B chain used in the present invention and has the following amino acid sequence:

(SEQ ID NO: 23)
LAPRRCPAQEVARGVLTSLPGDSVTLTCPGVEPEDNATVHWVLRKPAAGS

HPSRWAGMGRRLLLRSVQLHDSGNYSCYRAGRPAGTVHLLVDVPPEEPQL

SCFRKSPLSNVVCEWGPRSTPSLTTKAVLLVRKFQNSPAEDFQEPCQYSQ

ESQKFSCQLAVPEGDSSFYIVSMCVASSVGSKFSKTQTFQGCGILQPDPP

ANITVTAVARNPRWLSVTWQDPHSWNSSFYRLRFELRYRAERSKTFTTWM

VKDLQHHCVIHDAWSGLRHVVQLRAQEEFGQGEWSEWSPEAMGTPWTESR

SPPAENEVSTPMQALTTNKDDDNILFRDSANATSLPVQDSSSVPLPGSGS

DEGGEDGSKYGPPCPPCPAPEFLGGPSVFLFPPKPKDQLMISRTPEVTCV

VVDVSQEDPEVQFNWYVDGVEVHNAKTKPREEQFNSTYRVVSVLTVLHQD

WLSGKEYKCKVSSKGLPSSIEKTISNATGQPREPQVYTLPPSQEEMTKNQ

VSLTCLVKGFYPSDIAVEWESNGQPENNYKTTPPVLDSDGSFFLYSRLTV

DKSRWQEGNVFSCSVLHEALHNHYTQKSLSLSLGKRKGGKRGSGSRKGPP

AALTLPRVQCRASRYPIAVDCSWTLPPAPNSTSPVSFIATYRLGMAARGH

SWPCLQQTPTSTSCTITDVQLFSMAPYVLNVTAVHPWGSSSSFVPFITEH

IIKPDPPEGVRLSPLAERQLQVQWEPPGSWPFPEIFSLKYWIRYKRQGAA

RFHRVGPIEATSFILRAVRPRARYYVQVAAQDLTDYGELSDWSLPATATM

SLGK*

When a Gp130-Alpha-IL12A chain and an IL6RA-Beta-IL27B chain are combined (within a cell or in vitro), they form a heterodimeric protein referred to herein as IL-6R-Fc-IL-35.

In embodiments, a heterodimeric protein useful in the present invention comprises the extracellular domain of IL-21r. Interleukin-21 receptor (also known as IL-21 receptor and IL-21R) is a receptor for interleukin-21 belongs to the type I cytokine receptors, and has been shown to form a heterodimeric receptor complex with the common gamma-chain, a receptor subunit also shared by the receptors for interleukin 2, 4, 7, 9, and 15. This receptor transduces the growth-promoting signal of IL21, and is important for the proliferation and differentiation of T cells, B cells, and natural killer (NK) cells. The ligand binding of this receptor leads to the activation of multiple downstream signaling molecules, including JAK1, JAK3, STAT1, and STAT3. Knockout studies of a similar gene in mouse suggest a role for this gene in regulating immunoglobulin production.

In embodiments, a heterodimeric protein useful in the present invention comprises a variant of the extracellular domain of IL-21r. As examples, the variant may have at least about 60%, or at least about 61%, or at least about 62%, or at least about 63%, or at least about 64%, or at least about 65%, or at least about 66%, or at least about 67%, or at least about 68%, or at least about 69%, or at least about 70%, or at least about 71%, or at least about 72%, or at least about 73%, or at least about 74%, or at least about 75%, or at least about 76%, or at least about 77%, or at least about 78%, or at least about 79%, or at least about 80%, or at least about 81%, or at least about 82%, or at least about 83%, or at least about 84%, or at least about 85%, or at least about 86%, or at least about 87%, or at least about 88%, or at least about 89%, or at least about 90%, or at least about 91%, or at least about 92%, or at least about 93%, or at least about 94%, or at least about 95%, or at least about 96%, or at least about 97%, or at least about 98%, or at least about 99% sequence identity with the known amino acid sequence of IL-21r, e.g., human IL-21r.

In embodiments, the extracellular domain of IL-21r has the following amino acid sequence:

```
                                        (SEQ ID NO: 26)
CPDLVCYTDYLQTVICILEMWNLHPSTLTLTWQDQYEELKDEATSCSLHR

SAHNATHATYTCHMDVFHFMADDIFSVNITDQSGNYSQECGSFLLAESIK

PAPPFNVTVTFSGQYNISWRSDYEDPAFYMLKGKLQYELQYRNRGDPWAV

SPRRKLISVDSRSVSLLPLEFRKDSSYELQVRAGPMPGSSYQGTWSEWSD

PVIFQTQSEELKE
```

In embodiments, a heterodimeric protein comprises a variant of the extracellular domain of IL-21r. As examples, the variant may have at least about 60%, or at least about 61%, or at least about 62%, or at least about 63%, or at least about 64%, or at least about 65%, or at least about 66%, or at least about 67%, or at least about 68%, or at least about 69%, or at least about 70%, or at least about 71%, or at least about 72%, or at least about 73%, or at least about 74%, or at least about 75%, or at least about 76%, or at least about 77%, or at least about 78%, or at least about 79%, or at least about 80%, or at least about 81%, or at least about 82%, or at least about 83%, or at least about 84%, or at least about 85%, or at least about 86%, or at least about 87%, or at least about 88%, or at least about 89%, or at least about 90%, or at least about 91%, or at least about 92%, or at least about 93%, or at least about 94%, or at least about 95%, or at least about 96%, or at least about 97%, or at least about 98%, or at least about 99% sequence identity with SEQ ID NO: 26.

In embodiments, one chain of the heterodimeric protein comprises an amino acid sequence that is at least 95% identical to the amino acid sequence of SEQ ID NO: 26.

One of ordinary skill may select variants of the known amino acid sequence of IL-21r by consulting the literature, e.g., Ozaki et al., "Cloning of a type I cytokine receptor most related to the IL-2 receptor beta chain", Proc. Natl. Acad. Sci. U.S.A. 97 (21), 11439-11444 (2000); Kotlarz et al., "Loss-of-function mutations in the IL-21 receptor gene cause a primary immunodeficiency syndrome" J. Exp. Med. 210 (3), 433-443 (2013); Hamming et al., "Crystal structure of interleukin-21 receptor (IL-21R) bound to IL-21 reveals that sugar chain interacting with WSXWS motif is integral part of IL-21R" J. Biol. Chem. 287 (12), 9454-9460 (2012), each of which is incorporated by reference in its entirety.

In embodiments, a heterodimeric protein useful in the present invention comprises the extracellular domain of IL2RG. Interleukin-2 receptor subunit gamma (also known as Cytokine receptor common subunit gamma, IL-2 receptor subunit gamma, IL-2R subunit gamma, and IL-2RG) is a common subunit for the receptors for a variety of interleukins, including those of interleukin-2, -4, -7 and -21, and is thus referred to as the common gamma chain. Mutations in this gene cause X-linked severe combined immunodeficiency (XSCID), as well as X-linked combined immunodeficiency (XCID), a less severe immunodeficiency disorder.

In embodiments, a heterodimeric protein useful in the present invention comprises a variant of the extracellular domain of IL2RG. As examples, the variant may have at least about 60%, or at least about 61%, or at least about 62%, or at least about 63%, or at least about 64%, or at least about 65%, or at least about 66%, or at least about 67%, or at least about 68%, or at least about 69%, or at least about 70%, or at least about 71%, or at least about 72%, or at least about 73%, or at least about 74%, or at least about 75%, or at least about 76%, or at least about 77%, or at least about 78%, or at least about 79%, or at least about 80%, or at least about 81%, or at least about 82%, or at least about 83%, or at least about 84%, or at least about 85%, or at least about 86%, or at least about 87%, or at least about 88%, or at least about 89%, or at least about 90%, or at least about 91%, or at least about 92%, or at least about 93%, or at least about 94%, or at least about 95%, or at least about 96%, or at least about 97%, or at least about 98%, or at least about 99% sequence identity with the known amino acid sequence of IL2RG, e.g., human IL2RG.

In embodiments, the extracellular domain of IL2RG has the following amino acid sequence:

```
                                        (SEQ ID NO: 27)
LNTTILTPNGNEDTTADFFLTTMPTDSLSVSTLPLPEVQCFVFNVEYMNC

TWNSSSEPQPTNLTLHYWYKNSDNDKVQKCSHYLFSEEITSGCQLQKKEI

HLYQTFVVQLQDPREPRRQATQMLKLQNLVIPWAPENLTLHKLSESQLEL

NWNNRFLNHCLEHLVQYRTDWDHSWTEQSVDYRHKFSLPSVDGQKRYTFR

VRSRFNPLCGSAQHWSEWSHPIHWGSNTSKENPFLFALEA
```

In embodiments, a heterodimeric protein comprises a variant of the extracellular domain of IL2RG. As examples, the variant may have at least about 60%, or at least about 61%, or at least about 62%, or at least about 63%, or at least about 64%, or at least about 65%, or at least about 66%, or at least about 67%, or at least about 68%, or at least about 69%, or at least about 70%, or at least about 71%, or at least about 72%, or at least about 73%, or at least about 74%, or at least about 75%, or at least about 76%, or at least about 77%, or at least about 78%, or at least about 79%, or at least about 80%, or at least about 81%, or at least about 82%, or at least about 83%, or at least about 84%, or at least about 85%, or at least about 86%, or at least about 87%, or at least about 88%, or at least about 89%, or at least about 90%, or at least about 91%, or at least about 92%, or at least about 93%, or at least about 94%, or at least about 95%, or at least about 96%, or at least about 97%, or at least about 98%, or at least about 99% sequence identity with SEQ ID NO: 27.

In embodiments, one chain of the heterodimeric protein comprises an amino acid sequence that is at least 95% identical to the amino acid sequence of SEQ ID NO: 27.

One of ordinary skill may select variants of the known amino acid sequence of IL2RG by consulting the literature, e.g., Takeshita et al., "Cloning of the gamma chain of the human IL-2 receptor", Science 257 (5068), 379-382 (1992); Ratthe et al., "Interleukin-15 enhances human neutrophil phagocytosis by a Syk-dependent mechanism: importance of the IL-15Ralpha chain", J. Leukoc. Biol. 76 (1), 162-168 (2004); Bamborough et al., "The interleukin-2 and interleukin-4 receptors studied by molecular modelling", Structure 2 (9), 839-851 (1994); Wang et al., "Structure of the quaternary complex of interleukin-2 with its alpha, beta, and gammac receptors" Science 310 (5751), 1159-1163 (2005); Stauber et al., "Crystal structure of the IL-2 signaling complex: paradigm for a heterotrimeric cytokine receptor", Proc. Natl. Acad. Sci. U.S.A. 103 (8), 2788-2793 (2006), each of which is incorporated by reference in its entirety.

In embodiments, an alpha chain useful in a heterodimeric chimeric protein of the present invention comprises: (1) a first domain comprising the amino acid sequence of SEQ ID NO: 26, or a variant thereof, (b) a second domain comprises the amino acid sequence of SEQ ID NO: 20, or a variant thereof, and (c) an alpha core domain, or variant thereof, which comprises an amino acid sequence that is at least 95% identical to SEQ ID NO: 16 or SEQ ID NO: 24. Such an alpha chain may be referred to as "IL21r-Alpha-IL12a".

In embodiments, an IL21r-Alpha-IL12α chain used in the present invention and has the following amino acid sequence:

(SEQ ID NO: 28)
CPDLVCYTDYLQTVICILEMWNLHPSTLTLTWQDQYEELKDEATSCSLHR

SAHNATHATYTCHMDVFHFMADDIFSVNITDQSGNYSQECGSFLLAESIK

PAPPFNVTVTFSGQYNISWRSDYEDPAFYMLKGKLQYELQYRNRGDPWAV

SPRRKLISVDSRSVSLLPLEFRKDSSYELQVRAGPMPGSSYQGTWSEWSD

PVIFQTQSEELKEGSGSRKGGKRGSKYGPPCPPCPAPEFLGGPSVFLFPP

KPKDQLMISRTPEVTCVVVDVSQEDPEVQFNWYVDGVEVHNAKTKPREEQ

FNSTYRVVSVLTVLHQDWLSGKEYKCKVSSKGLPSSIEKTISNATGQPRE

PQVYTLPPSQEEMTKNQVSLTCLVKGFYPSDIAVEWESNGQPENNYKTTP

PVLDSDGSFFLYSRLTVDKSRWQEGNVFSCSVLHEALHNHYTQKSLSLSL

GKDEGGEDGSGSRNLPVATPDPGMFPCLHHSQNLLRAVSNMLQKARQTLE

FYPCTSEEIDHEDITKDKTSTVEACLPLELTKNESCLNSRETSFITNGSC

LASRKTSFMMALCLSSIYEDLKMYQVEFKTMNAKLLMDPKRQIFLDQNML

AVIDELMQALNFNSETVPQKSSLEEPDFYKTKIKLCILLHAFRIRAVTID

RVMSYLNAS

In embodiments, an beta chain useful in a heterodimeric chimeric protein of the present invention comprises: (1) a first domain comprising the amino acid sequence of SEQ ID NO: 27, or a variant thereof, (b) a second domain comprises the amino acid sequence of SEQ ID NO: 21, or a variant thereof, and (c) an alpha core domain, or variant thereof, which comprises an amino acid sequence that is at least 95% identical to SEQ ID NO: 17 or SEQ ID NO: 25. Such a beta chain may be referred to as "IL2rg-Beta-IL27B".

In embodiments, an IL2rg-Beta-IL27B chain used in the present invention and has the following amino acid sequence:

(SEQ ID NO: 29)
LNTTILTPNGNEDTTADFFLTTMPTDSLSVSTLPLPEVQCFVFNVEYMNC

TWNSSSEPQPTNLTLHYWYKNSDNDKVQKCSHYLFSEEITSGCQLQKKEI

HLYQTFVVQLQDPREPRRQATQMLKLQNLVIPWAPENLTLHKLSESQLEL

NWNNRFLNHCLEHLVQYRTDWDHSWTEQSVDYRHKFSLPSVDGQKRYTFR

VRSRFNPLCGSAQHWSEWSHPIHWGSNTSKENPFLFALEAGSGSDEGGED

GSKYGPPCPPCPAPEFLGGPSVFLFPPKPKDQLMISRTPEVTCVVVDVSQ

EDPEVQFNWYVDGVEVHNAKTKPREEQFNSTYRVVSVLTVLHQDWLSGKE

YKCKVSSKGLPSSIEKTISNATGQPREPQVYTLPPSQEEMTKNQVSLTCL

VKGFYPSDIAVEWESNGQPENNYKTTPPVLDSDGSFFLYSRLTVDKSRWQ

EGNVFSCSVLHEALHNHYTQKSLSLSLGKRKGGKRGSGSRKGPPAALTLP

RVQCRASRYPIAVDCSWTLPPAPNSTSPVSFIATYRLGMAARGHSWPCLQ

QTPTSTSCTITDVQLFSMAPYVLNVTAVHPWGSSSSFVPFITEHIIKPDP

PEGVRLSPLAERQLQVQWEPPGSWPFPEIFSLKYWIRYKRQGAARFHRVG

PIEATSFILRAVRPRARYYVQVAAQDLTDYGELSDWSLPATATMSLGK

When an IL21r-Alpha-IL12α chain and an IL2rg-Beta-IL27B chain are combined (within a cell or in vitro), they form a heterodimeric protein referred to herein as IL-21R-Fc-IL-35.

In embodiments, an alpha chain useful in a heterodimeric chimeric protein of the present invention comprises: (1) a first domain comprising the amino acid sequence of SEQ ID NO: 26, or a variant thereof, (b) a second domain comprises the amino acid sequence of SEQ ID NO: 20, or a variant thereof, and (c) an alpha core domain, or variant thereof, which comprises an amino acid sequence that is at least 95% identical to SEQ ID NO: 17 or SEQ ID NO: 25. Such an alpha chain may be referred to as "IL21r-Beta-IL12a".

In embodiments, an IL21r-Beta-IL12a chain used in the present invention and has the following amino acid sequence:

(SEQ ID NO: 37)
CPDLVCYTDYLQTVICILEMWNLHPSTLTLTWQDQYEELKDEATSCSLHR

SAHNATHATYTCHMDVFHFMADDIFSVNITDQSGNYSQECGSFLLAESIK

PAPPFNVTVTFSGQYNISWRSDYEDPAFYMLKGKLQYELQYRNRGDPWAV

SPRRKLISVDSRSVSLLPLEFRKDSSYELQVRAGPMPGSSYQGTWSEWSD

-continued

```
PVIFQTQSEELKEGSGSDEGGEDGSKYGPPCPPCPAPEFLGGPSVFLFPP

KPKDQLMISRTPEVTCVVVDVSQEDPEVQFNWYVDGVEVHNAKTKPREEQ

FNSTYRVVSVLTVLHQDWLSGKEYKCKVSSKGLPSSIEKTISNATGQPRE

PQVYTLPPSQEEMTKNQVSLTCLVKGFYPSDIAVEWESNGQPENNYKTTP

PVLDSDGSFFLYSRLTVDKSRWQEGNVFSCSVLHEALHNHYTQKSLSLSL

GKRKGGKRGSGSRNLPVATPDPGMFPCLHHSQNLLRAVSNMLQKARQTLE

FYPCTSEEIDHEDITKDKTSTVEACLPLELTKNESCLNSRETSFITNGSC

LASRKTSFMMALCLSSIYEDLKMYQVEFKTMNAKLLMDPKRQIFLDQNML

AVIDELMQALNFNSETVPQKSSLEEPDFYKTKIKLCILLHAFRIRAVTID

RVMSYLNAS
```

In embodiments, an beta chain useful in a heterodimeric chimeric protein of the present invention comprises: (1) a first domain comprising the amino acid sequence of SEQ ID NO: 27, or a variant thereof, (b) a second domain comprises the amino acid sequence of SEQ ID NO: 21, or a variant thereof, and (c) an alpha core domain, or variant thereof, which comprises an amino acid sequence that is at least 95% identical to SEQ ID NO: 16 or SEQ ID NO: 24. Such a beta chain may be referred to as "IL2rg-Alpha-IL27B".

In embodiments, an IL2rg-Alpha-IL27B chain used in the present invention and has the following amino acid sequence:

```
                                          (SEQ ID NO: 36)
LNTTILTPNGNEDTTADFFLTTMPTDSLSVSTLPLPEVQCFVFNVEYMNC

TWNSSSEPQPTNLTLHYWYKNSDNDKVQKCSHYLFSEEITSGCQLQKKEI

HLYQTFVVQLQDPREPRRQATQMLKLQNLVIPWAPENLTLHKLSESQLEL

NWNNRFLNHCLEHLVQYRTDWDHSWTEQSVDYRHKFSLPSVDGQKRYTFR

VRSRFNPLCGSAQHWSEWSHPIHWGSNTSKENPFLFALEAGSGSRKGGKR

GSKYGPPCPPCPAPEFLGGPSVFLFPPKPKDQLMISRTPEVTCVVVDVSQ

EDPEVQFNWYVDGVEVHNAKTKPREEQFNSTYRVVSVLTVLHQDWLSGKE

YKCKVSSKGLPSSIEKTISNATGQPREPQVYTLPPSQEEMTKNQVSLTCL

VKGFYPSDIAVEWESNGQPENNYKTTPPVLDSDGSFFLYSRLTVDKSRWQ

EGNVFSCSVLHEALHNHYTQKSLSLSLGKDEGGEDGSGSRKGPPAALTLP

RVQCRASRYPIAVDCSWTLPPAPNSTSPVSFIATYRLGMAARGHSWPCLQ

QTPTSTSCTITDVQLFSMAPYVLNVTAVHPWGSSSSFVPFITEHIIKPDP

PEGVRLSPLAERQLQVQWEPPGSWPFPEIFSLKYWIRYKRQGAARFHRVG

PIEATSFILRAVRPRARYYVQVAAQDLTDYGELSDWSLPATATMSLGK
```

When an IL21r-Beta-IL12α chain and an IL2rg-Alpha-IL27B chain are combined (within a cell or in vitro), they form a heterodimeric protein may also be referred to herein as IL-21R-Fc-IL-35.

In embodiments, a heterodimeric protein useful in the present invention comprises the extracellular domain of IFNgR. IFNgR (also known as Interferon gamma receptor 1, IFN-gamma receptor 1, IFN-gamma-R1, IFN-gamma-R-alpha, IFNgR, and IFNGR1) associates with IFNGR2 to form a receptor for the cytokine interferon gamma (IFNG). Ligand binding stimulates activation of the JAK/STAT signaling pathway. It plays an essential role in the IFN-gamma pathway that is required for the cellular response to infectious agents. A genetic variation in IFNGR1 is associated with susceptibility to *Helicobacter pylori* infection. In addition, defects in IFNGR1 are a cause of Mendelian susceptibility to mycobacterial disease, also known as familial disseminated atypical mycobacterial infection.

In embodiments, a heterodimeric protein useful in the present invention comprises a variant of the extracellular domain of IFNgR. As examples, the variant may have at least about 60%, or at least about 61%, or at least about 62%, or at least about 63%, or at least about 64%, or at least about 65%, or at least about 66%, or at least about 67%, or at least about 68%, or at least about 69%, or at least about 70%, or at least about 71%, or at least about 72%, or at least about 73%, or at least about 74%, or at least about 75%, or at least about 76%, or at least about 77%, or at least about 78%, or at least about 79%, or at least about 80%, or at least about 81%, or at least about 82%, or at least about 83%, or at least about 84%, or at least about 85%, or at least about 86%, or at least about 87%, or at least about 88%, or at least about 89%, or at least about 90%, or at least about 91%, or at least about 92%, or at least about 93%, or at least about 94%, or at least about 95%, or at least about 96%, or at least about 97%, or at least about 98%, or at least about 99% sequence identity with the known amino acid sequence of IFNgR, e.g., human IFNgR.

In embodiments, the extracellular domain of IFNgR has the following amino acid sequence:

```
                                          (SEQ ID NO: 30)
EMGTADLGPSSVPTPTNVTIESYNMNPIVYWEYQIMPQVPVFTVEVKNYG

VKNSEWIDACINISHHYCNISDHVGDPSNSLWVRVKARVGQKESAYAKSE

EFAVCRDGKIGPPKLDIRKEEKQIMIDIFHPSVFVNGDEQEVDYDPETTC

YIRVYNVYVRMNGSEIQYKILTQKEDDCDEIQCQLAIPVSSLNSQYCVSA

EGVLHVWGVTTEKSKEVCITIFNSSIKG
```

In embodiments, a heterodimeric protein comprises a variant of the extracellular domain of IFNgR. As examples, the variant may have at least about 60%, or at least about 61%, or at least about 62%, or at least about 63%, or at least about 64%, or at least about 65%, or at least about 66%, or at least about 67%, or at least about 68%, or at least about 69%, or at least about 70%, or at least about 71%, or at least about 72%, or at least about 73%, or at least about 74%, or at least about 75%, or at least about 76%, or at least about 77%, or at least about 78%, or at least about 79%, or at least about 80%, or at least about 81%, or at least about 82%, or at least about 83%, or at least about 84%, or at least about 85%, or at least about 86%, or at least about 87%, or at least about 88%, or at least about 89%, or at least about 90%, or at least about 91%, or at least about 92%, or at least about 93%, or at least about 94%, or at least about 95%, or at least about 96%, or at least about 97%, or at least about 98%, or at least about 99% sequence identity with SEQ ID NO: 30.

In embodiments, one chain of the heterodimeric protein comprises an amino acid sequence that is at least 95% identical to the amino acid sequence of SEQ ID NO: 30.

One of ordinary skill may select variants of the known amino acid sequence of IFNgR by consulting the literature, e.g., Aguet et al., "Molecular cloning and expression of the human interferon-gamma receptor" Cell 55 (2), 273-280 (1988); Stuber et al., "Alignment of disulfide bonds of the extracellular domain of the interferon gamma receptor and investigation of their role in biological activity", Biochemistry 32 (9), 2423-2430 (1993); Sakatsume et al., "The Jak kinases differentially associate with the alpha and beta (accessory factor) chains of the interferon gamma receptor to form a functional receptor unit capable of activating STAT transcription factors", J. Biol. Chem. 270 (29), 17528-17534 (1995); Walter et al., "Crystal structure of a complex between interferon-gamma and its soluble high-affinity receptor", Nature 376 (6537), 230-235 (1995); Sogabe et al., "Neutralizing epitopes on the extracellular interferon gamma receptor (IFNgammaR) alpha-chain characterized by homolog scanning mutagenesis and X-ray crystal structure of the A6 fab-IFNgammaR1-108 complex", J. Mol. Biol. 273 (4), 882-897 (1997); Thiel et al., "Observation of an unexpected third receptor molecule in the crystal structure of human interferon-gamma receptor complex", Structure 8 (9), 927-936 (2000); van de Wetering et al., "Functional analysis of naturally occurring amino acid substitutions in human IFN-gammaR1." Mol. Immunol. 47:1023-1030(2010), each of which is incorporated by reference in its entirety.

In embodiments, a heterodimeric protein useful in the present invention comprises the extracellular domain of IFNGR2. IFNGR2 (also known as Interferon gamma receptor 2, also known as IFN-gamma receptor 2, and IFN-gamma-R2) is the non-ligand-binding beta chain of the gamma interferon receptor. Human interferon-gamma receptor is a heterodimer of IFNGR1 and IFNGR2. Ligand binding stimulates activation of the JAK/STAT signaling pathway. IFNGR2 is required for signal transduction in contrast to other receptor subunit responsible for ligand binding. Defects in IFNGR2 are a cause of Mendelian susceptibility to mycobacterial disease (MSMD), also known as familial disseminated atypical mycobacterial infection. MSMD is a genetically heterogeneous disease with autosomal recessive, autosomal dominant or X-linked inheritance.

In embodiments, a heterodimeric protein useful in the present invention comprises a variant of the extracellular domain of IFNGR2. As examples, the variant may have at least about 60%, or at least about 61%, or at least about 62%, or at least about 63%, or at least about 64%, or at least about 65%, or at least about 66%, or at least about 67%, or at least about 68%, or at least about 69%, or at least about 70%, or at least about 71%, or at least about 72%, or at least about 73%, or at least about 74%, or at least about 75%, or at least about 76%, or at least about 77%, or at least about 78%, or at least about 79%, or at least about 80%, or at least about 81%, or at least about 82%, or at least about 83%, or at least about 84%, or at least about 85%, or at least about 86%, or at least about 87%, or at least about 88%, or at least about 89%, or at least about 90%, or at least about 91%, or at least about 92%, or at least about 93%, or at least about 94%, or at least about 95%, or at least about 96%, or at least about 97%, or at least about 98%, or at least about 99% sequence identity with the known amino acid sequence of IFNGR2, e.g., human IFNGR2.

In embodiments, the extracellular domain of IFNGR2 has the following amino acid sequence:

```
                                    (SEQ ID NO: 31)
SQLPAPQHPKIRLYNAEQVLSWEPVALSNSTRPVVYQVQFKYTDSKWFTA

DIMSIGVNCTQITATECDFTAASPSAGFPMDFNVTLRLRAELGALHSAWV

TMPWFQHYRNVTVGPPENIEVTPGEGSLIIRFSSPFDIADTSTAFFCYYV
```

-continued
```
HYWEKGGIQQVKGPFRSNSISLDNLKPSRVYCLQVQAQLLWNKSNIFRVG

HLSNISCYETMADASTELQQ
```

In embodiments, a heterodimeric protein comprises a variant of the extracellular domain of IFNGR2. As examples, the variant may have at least about 60%, or at least about 61%, or at least about 62%, or at least about 63%, or at least about 64%, or at least about 65%, or at least about 66%, or at least about 67%, or at least about 68%, or at least about 69%, or at least about 70%, or at least about 71%, or at least about 72%, or at least about 73%, or at least about 74%, or at least about 75%, or at least about 76%, or at least about 77%, or at least about 78%, or at least about 79%, or at least about 80%, or at least about 81%, or at least about 82%, or at least about 83%, or at least about 84%, or at least about 85%, or at least about 86%, or at least about 87%, or at least about 88%, or at least about 89%, or at least about 90%, or at least about 91%, or at least about 92%, or at least about 93%, or at least about 94%, or at least about 95%, or at least about 96%, or at least about 97%, or at least about 98%, or at least about 99% sequence identity with SEQ ID NO: 31.

In embodiments, one chain of the heterodimeric protein comprises an amino acid sequence that is at least 95% identical to the amino acid sequence of SEQ ID NO: 31.

One of ordinary skill may select variants of the known amino acid sequence of IFNGR2 by consulting the literature, e.g., Soh et al., "Identification and sequence of an accessory factor required for activation of the human interferon gamma receptor", Cell 76 (5), 793-802 (1994); Sakatsume et al., "The Jak kinases differentially associate with the alpha and beta (accessory factor) chains of the interferon gamma receptor to form a functional receptor unit capable of activating STAT transcription factors", J. Biol. Chem. 270 (29), 17528-17534 (1995); Rosenzweig et al., "Characterization of a dipeptide motif regulating IFN-gamma receptor 2 plasma membrane accumulation and IFN-gamma responsiveness", J. Immunol. 173 (6), 3991-3999 (2004); Mikulecky et al., "Crystal structure of human interferon-gamma receptor 2 reveals the structural basis for receptor specificity", Acta Crystallogr. D 75, 1017-1024 (2016); Kotenko et al., "Interaction between the components of the interferon gamma receptor complex." J. Biol. Chem. 270: 20915-20921(1995), each of which is incorporated by reference in its entirety.

In embodiments, an alpha chain useful in a heterodimeric chimeric protein of the present invention comprises: (1) a first domain comprising the amino acid sequence of SEQ ID NO: 30, or a variant thereof, (b) a second domain comprises the amino acid sequence of SEQ ID NO: 20, or a variant thereof, and (c) an alpha core domain, or variant thereof, which comprises an amino acid sequence that is at least 95% identical to SEQ ID NO: 16 or SEQ ID NO: 24. Such an alpha chain may be referred to as "IFNgR-Alpha-IL12a".

In embodiments, an IFNgR-Alpha-IL12α chain used in the present invention and has the following amino acid sequence:

```
                                    (SEQ ID NO: 32)
EMGTADLGPSSVPTPTNVTIESYNMNPIVYWEYQIMPQVPVFTVEVKNYG

VKNSEWIDACINISHHYCNISDHVGDPSNSLWVRVKARVGQKESAYAKSE

EFAVCRDGKIGPPKLDIRKEEKQIMIDIFHPSVFVNGDEQEVDYDPETTC
```

-continued

```
YIRVYNVYVRMNGSEIQYKILTQKEDDCDEIQCQLAIPVSSLNSQYCVSA

EGVLHVWGVTTEKSKEVCITIFNSSIKGGSGSRKGGKRGSKYGPPCPPCP

APEFLGGPSVFLFPPKPKDQLMISRTPEVTCVVVDVSQEDPEVQFNWYVD

GVEVHNAKTKPREEQFNSTYRVVSVLTVLHQDWLSGKEYKCKVSSKGLPS

SIEKTISNATGQPREPQVYTLPPSQEEMTKNQVSLTCLVKGFYPSDIAVE

WESNGQPENNYKTTPPVLDSDGSFFLYSRLTVDKSRWQEGNVFSCSVLHE

ALHNHYTQKSLSLSLGKDEGGEDGSGSRNLPVATPDPGMFPCLHHSQNLL

RAVSNMLQKARQTLEFYPCTSEEIDHEDITKDKTSTVEACLPLELTKNES

CLNSRETSFITNGSCLASRKTSFMMALCLSSIYEDLKMYQVEFKTMNAKL

LMDPKRQIFLDQNMLAVIDELMQALNFNSETVPQKSSLEEPDFYKTKIKL

CILLHAFRIRAVTIDRVMSYLNAS
```

In embodiments, an beta chain useful in a heterodimeric chimeric protein of the present invention comprises: (1) a first domain comprising the amino acid sequence of SEQ ID NO: 31, or a variant thereof, (b) a second domain comprises the amino acid sequence of SEQ ID NO: 21, or a variant thereof, and (c) an alpha core domain, or variant thereof, which comprises an amino acid sequence that is at least 95% identical to SEQ ID NO: 17 or SEQ ID NO: 25. Such a beta chain may be referred to as "IFNGR2-Beta-IL27B".

In embodiments, an IFNGR2-Beta-IL27B chain used in the present invention and has the following amino acid sequence:

```
                                        (SEQ ID NO: 33)
SQLPAPQHPKIRLYNAEQVLSWEPVALSNSTRPVVYQVQFKYTDSKWFTA

DIMSIGVNCTQITATECDFTAASPSAGFPMDFNVTLRLRAELGALHSAWV

TMPWFQHYRNVTVGPPENIEVTPGEGSLIIRFSSPFDIADTSTAFFCYYV

HYWEKGGIQQVKGPFRSNSISLDNLKPSRVYCLQVQAQLLWNKSNIFRVG

HLSNISCYETMADASTELQQGSGSDEGGEDGSKYGPPCPPCPAPEFLGGP

SVFLFPPKPKDQLMISRTPEVTCVVVDVSQEDPEVQFNWYVDGVEVHNAK

TKPREEQFNSTYRVVSVLTVLHQDWLSGKEYKCKVSSKGLPSSIEKTISN

ATGQPREPQVYTLPPSQEEMTKNQVSLTCLVKGFYPSDIAVEWESNGQPE

NNYKTTPPVLDSDGSFFLYSRLTVDKSRWQEGNVFSCSVLHEALHNHYTQ

KSLSLSLGKRKGGKRGSGSRKGPPAALTLPRVQCRASRYPIAVDCSWTLP

PAPNSTSPVSFIATYRLGMAARGHSWPCLQQTPTSTSCTITDVQLFSMAP

YVLNVTAVHPWGSSSSFVPFITEHIIKPDPPEGVRLSPLAERQLQVQWEP

PGSWPFPEIFSLKYWIRYKRQGAARFHRVGPIEATSFILRAVRPRARYYV

QVAAQDLTDYGELSDWSLPATATMSLGK
```

When an IFNgR-Alpha-IL12α chain and an IFNGR2-Beta-IL27B chain are combined (within a cell or in vitro), they form a heterodimeric protein referred to herein as IFNγR-Fc-IL-35.

In embodiments, an alpha chain useful in a heterodimeric chimeric protein of the present invention comprises: (1) a first domain comprising the amino acid sequence of SEQ ID NO: 30, or a variant thereof, (b) a second domain comprises the amino acid sequence of SEQ ID NO: 20, or a variant thereof, and (c) an alpha core domain, or variant thereof, which comprises an amino acid sequence that is at least 95% identical to SEQ ID NO: 17 or SEQ ID NO: 25. Such an alpha chain may be referred to as "IFNgR-Beta-IL12α".

In embodiments, an IFNgR-Beta-IL12α chain used in the present invention and has the following amino acid sequence:

```
                                        (SEQ ID NO: 38)
EMGTADLGPSSVPTPTNVTIESYNMNPIVYWEYQIMPQVPVFTVEVKNYG

VKNSEWIDACINISHHYCNISDHVGDPSNSLWVRVKARVGQKESAYAKSE

EFAVCRDGKIGPPKLDIRKEEKQIMIDIFHPSVFVNGDEQEVDYDPETTC

YIRVYNVYVRMNGSEIQYKILTQKEDDCDEIQCQLAIPVSSLNSQYCVSA

EGVLHVWGVTTEKSKEVCITIFNSSIKGGSGSDEGGEDGSKYGPPCPPCP

APEFLGGPSVFLFPPKPKDQLMISRTPEVTCVVVDVSQEDPEVQFNWYVD

GVEVHNAKTKPREEQFNSTYRVVSVLTVLHQDWLSGKEYKCKVSSKGLPS

SIEKTISNATGQPREPQVYTLPPSQEEMTKNQVSLTCLVKGFYPSDIAVE

WESNGQPENNYKTTPPVLDSDGSFFLYSRLTVDKSRWQEGNVFSCSVLHE

ALHNHYTQKSLSLSLGKRKGGKRGSGSRNLPVATPDPGMFPCLHHSQNLL

RAVSNMLQKARQTLEFYPCTSEEIDHEDITKDKTSTVEACLPLELTKNES

CLNSRETSFITNGSCLASRKTSFMMALCLSSIYEDLKMYQVEFKTMNAKL

LMDPKRQIFLDQNMLAVIDELMQALNFNSETVPQKSSLEEPDFYKTKIKL

CILLHAFRIRAVTIDRVMSYLNAS
```

In embodiments, an beta chain useful in a heterodimeric chimeric protein of the present invention comprises: (1) a first domain comprising the amino acid sequence of SEQ ID NO: 31, or a variant thereof, (b) a second domain comprises the amino acid sequence of SEQ ID NO: 21, or a variant thereof, and (c) an alpha core domain, or variant thereof, which comprises an amino acid sequence that is at least 95% identical to SEQ ID NO: 16 or SEQ ID NO: 24. Such a beta chain may be referred to as "IFNGR2-Alpha-IL27B".

In embodiments, an IFNGR2-Alpha-IL27B chain used in the present invention and has the following amino acid sequence:

```
                                        (SEQ ID NO: 39)
SQLPAPQHPKIRLYNAEQVLSWEPVALSNSTRPVVYQVQFKYTDSKWFTA

DIMSIGVNCTQITATECDFTAASPSAGFPMDFNVTLRLRAELGALHSAWV

TMPWFQHYRNVTVGPPENIEVTPGEGSLIIRFSSPFDIADTSTAFFCYYV

HYWEKGGIQQVKGPFRSNSISLDNLKPSRVYCLQVQAQLLWNKSNIFRVG

HLSNISCYETMADASTELQQGSGSRKGGKRGSKYGPPCPPCPAPEFLGGP

SVFLFPPKPKDQLMISRTPEVTCVVVDVSQEDPEVQFNWYVDGVEVHNAK

TKPREEQFNSTYRVVSVLTVLHQDWLSGKEYKCKVSSKGLPSSIEKTISN

ATGQPREPQVYTLPPSQEEMTKNQVSLTCLVKGFYPSDIAVEWESNGQPE

NNYKTTPPVLDSDGSFFLYSRLTVDKSRWQEGNVFSCSVLHEALHNHYTQ

KSLSLSLGKDEGGEDGSGSRKGPPAALTLPRVQCRASRYPIAVDCSWTLP

PAPNSTSPVSFIATYRLGMAARGHSWPCLQQTPTSTSCTITDVQLFSMAP

YVLNVTAVHPWGSSSSFVPFITEHIIKPDPPEGVRLSPLAERQLQVQWEP
```

-continued

PGSWPFPEIFSLKYWIRYKRQGAARFHRVGPIEATSFILRAVRPRARYYV

QVAAQDLTDYGELSDWSLPATATMSLGK

When an IFNgR-Beta-IL12α chain and an IFNGR2-Alpha-IL27B chain are combined (within a cell or in vitro), they form a heterodimeric protein may also be referred to herein as IFNγR-Fc-IL-35.

One embodiment of the IL-6R-Fc-IL-35 heterodimeric protein is disclosed above, i.e., comprising a Gp130-Alpha-IL12A chain and an IL6RA-Beta-IL27B chain. In alternate embodiment, an IL-6R-Fc-IL-35 heterodimeric protein can comprise an IL6RA-Alpha-IL12a chain and a Gp130-Beta-IL27b.

In embodiments, an alpha chain useful in a heterodimeric chimeric protein of the present invention comprises: (1) a first domain comprising the amino acid sequence of SEQ ID NO: 19, or a variant thereof, (b) a second domain comprises the amino acid sequence of SEQ ID NO: 20, or a variant thereof, and (c) an alpha core domain, or variant thereof, which comprises an amino acid sequence that is at least 95% identical to SEQ ID NO: 16 or SEQ ID NO: 24. Such an alpha chain may be referred to as "IL6RA-Alpha-IL12a".

In embodiments, an IL6RA-Alpha-IL12α chain used in the present invention and has the following amino acid sequence:

(SEQ ID NO: 34)
LAPRRCPAQEVARGVLTSLPGDSVTLTCPGVEPEDNATVHWVLRKPAAGS

HPSRWAGMGRRLLLRSVQLHDSGNYSCYRAGRPAGTVHLLVDVPPEEPQL

CFRKSPLSNVVCEWGPRSTPSLTTKAVLLVRKFQNSPAEDFQEPCQYSQE

SQKFSCQLAVPEGDSSFYIVSMCVASSVGSKFSKTQTFQGCGILQPDPPA

NITVTAVARNPRWLSVTWQDPHSWNSSFYRLRFELRYRAERSKTFTTWMV

KDLQHHCVIHDAWSGLRHVVQLRAQEEFGQGEWSEWSPEAMGTPWTESRS

PPAENEVSTPMQALTTNKDDDNILFRDSANATSLPVQDSSSVPLPGSGSR

KGGKRGSKYGPPCPPCPAPEFLGGPSVFLFPPKPKDQLMISRTPEVTCVV

VDVSQEDPEVQFNWYVDGVEVHNAKTKPREEQFNSTYRVVSVLTVLHQDW

LSGKEYKCKVSSKGLPSSIEKTISNATGQPREPQVYTLPPSQEEMTKNQV

SLTCLVKGFYPSDIAVEWESNGQPENNYKTTPPVLDSDGSFFLYSRLTVD

KSRWQEGNVFSCSVLHEALHNHYTQKSLSLSLGKDEGGEDGSGSRNLPVA

TPDPGMFPCLHHSQNLLRAVSNMLQKARQTLEFYPCTSEEIDHEDITKDK

TSTVEACLPLELTKNESCLNSRETSFITNGSCLASRKTSFMMALCLSSIY

EDLKMYQVEFKTMNAKLLMDPKRQIFLDQNMLAVIDELMQALNFNSETVP

QKSSLEEPDFYKTKIKLCILLHAFRIRAVTIDRVMSYLNAS

In embodiments, an beta chain useful in a heterodimeric chimeric protein of the present invention comprises: (1) a first domain comprising the amino acid sequence of SEQ ID NO: 18, or a variant thereof, (b) a second domain comprises the amino acid sequence of SEQ ID NO: 21, or a variant thereof, and (c) an alpha core domain, or variant thereof, which comprises an amino acid sequence that is at least 95% identical to SEQ ID NO: 17 or SEQ ID NO: 25. Such a beta chain may be referred to as "Gp130-Beta-IL27b".

In embodiments, a Gp130-Beta-IL27b chain used in the present invention and has the following amino acid sequence:

(SEQ ID NO: 35)
ELLDPCGYISPESPVVQLHSNFTAVCVLKEKCMDYFHVNANYIVWKTNHF

TIPKEQYTIINRTASSVTFTDIASLNIQLTCNILTFGQLEQNVYGITIIS

GLPPEKPKNLSCIVNEGKKMRCEWDGGRETHLETNFTLKSEWATHKFADC

KAKRDTPTSCTVDYSTVYFVNIEVWVEAENALGKVTSDHINFDPVYKVKP

NPPHNLSVINSEELSSILKLTWTNPSIKSVIILKYNIQYRTKDASTWSQI

PPEDTASTRSSFTVQDLKPFTEYVFRIRCMKEDGKGYWSDWSEEASGITY

EDRPSKAPSFWYKIDPSHTQGYRTVQLVWKTLPPFEANGKILDYEVTLTR

WKSHLQNYTVNATKLTVNLTNDRYLATLTVRNLVGKSDAAVLTIPACDFQ

ATHPVMDLKAFPKDNMLWVEWTTPRESVKKYILEWCVLSDKAPCITDWQQ

EDGTVHRTYLRGNLAESKCYLITVTPVYADGPGSPESIKAYLKQAPPSKG

PTVRTKKVGKNEAVLEWDQLPVDVQNGFIRNYTIFYRTIIGNETAVNVDS

SHTEYTLSSLTSDTLYMVRMAAYTDEGGKDGPEFTFTTPKFAQGEIE

When an IL6RA-Alpha-IL12a chain and a Gp130-Beta-IL27b chain are combined (within a cell or in vitro), they form a heterodimeric protein may also be referred to herein as IL-6R-Fc-IL-35.

In various embodiments, the present heterodimeric protein may comprise variants of any of the known cytokines, growth factors, and/or hormones. In various embodiments, the present heterodimeric proteins may comprise variants of any of the known receptors for cytokines, growth factors, and/or hormones. In various embodiments, the present heterodimeric proteins may comprises variants of any of the known extracellular domains, for instance, a sequence having at least about 60%, or at least about 61%, or at least about 62%, or at least about 63%, or at least about 64%, or at least about 65%, or at least about 66%, or at least about 67%, or at least about 68%, or at least about 69%, or at least about 70%, or at least about 71%, or at least about 72%, or at least about 73%, or at least about 74%, or at least about 75%, or at least about 76%, or at least about 77%, or at least about 78%, or at least about 79%, or at least about 80%, or at least about 81%, or at least about 82%, or at least about 83%, or at least about 84%, or at least about 85%, or at least about 86%, or at least about 87%, or at least about 88%, or at least about 89%, or at least about 90%, or at least about 91%, or at least about 92%, or at least about 93%, or at least about 94%, or at least about 95%, or at least about 96%, or at least about 97%, or at least about 98%, or at least about 99%) sequence identity with the known amino acid or nucleic acid sequences.

In various embodiments, the present heterodimeric protein may comprise an amino acid sequence having one or more amino acid mutations relative to any of the known protein sequences. In some embodiments, the one or more amino acid mutations may be independently selected from substitutions, insertions, deletions, and truncations.

In some embodiments, the amino acid mutations are amino acid substitutions, and may include conservative and/or non-conservative substitutions.

"Conservative substitutions" may be made, for instance, on the basis of similarity in polarity, charge, size, solubility, hydrophobicity, hydrophilicity, and/or the amphipathic nature of the amino acid residues involved. The 20 naturally occurring amino acids can be grouped into the following six standard amino acid groups: (1) hydrophobic: Met, Ala, Val, Leu, Ile; (2) neutral hydrophilic: Cys, Ser, Thr; Asn, Gln; (3)

acidic: Asp, Glu; (4) basic: His, Lys, Arg; (5) residues that influence chain orientation: Gly, Pro; and (6) aromatic: Trp, Tyr, Phe.

As used herein, "conservative substitutions" are defined as exchanges of an amino acid by another amino acid listed within the same group of the six standard amino acid groups shown above. For example, the exchange of Asp by Glu retains one negative charge in the so modified polypeptide. In addition, glycine and proline may be substituted for one another based on their ability to disrupt α-helices.

As used herein, "non-conservative substitutions" are defined as exchanges of an amino acid by another amino acid listed in a different group of the six standard amino acid groups (1) to (6) shown above.

In various embodiments, the substitutions may also include non-classical amino acids (e.g., selenocysteine, pyrrolysine, N-formylmethionine β-alanine, GABA and 6-Aminolevulinic acid, 4-aminobenzoic acid (PABA), D-isomers of the common amino acids, 2,4-diaminobutyric acid, α-amino isobutyric acid, 4-aminobutyric acid, Abu, 2-amino butyric acid, γ-Abu, ε-Ahx, 6-amino hexanoic acid, Aib, 2-amino isobutyric acid, 3-amino propionic acid, ornithine, norleucine, norvaline, hydroxyproline, sarcosme, citrulline, homocitrulline, cysteic acid, t-butylglycine, t-butylalanine, phenylglycine, cyclohexylalanine, β-alanine, fluoro-amino acids, designer amino acids such as β methyl amino acids, C α-methyl amino acids, N α-methyl amino acids, and amino acid analogs in general).

Mutations may also be made to the nucleotide sequences of the heterodimeric proteins by reference to the genetic code, including taking into account codon degeneracy.

In various embodiments, the present heterodimeric proteins are capable of, and can be used in methods comprising, promoting immune activation (e.g., against tumors). In various embodiments, the present heterodimeric proteins are capable of, and can be used in methods comprising, suppressing immune inhibition (e.g., that allows tumors to survive). In various embodiments, the present heterodimeric protein provides improved immune activation and/or improved suppression of immune inhibition.

In various embodiments, the present heterodimeric proteins are capable of, or can be used in methods comprising, modulating the amplitude of an immune response, e.g., modulating the level of effector output. In some embodiments, e.g., when used for the treatment of cancer, the present heterodimeric protein alters the extent of immune stimulation as compared to immune inhibition to increase the amplitude of a T cell response, including, without limitation, stimulating increased levels of cytokine production, proliferation or target killing potential.

In various embodiments, the present heterodimeric proteins, in some embodiments are capable of, or find use in methods involving, masking an inhibitory ligand on the surface of a tumor cell and replacing that immune inhibitory ligand with an immune stimulatory ligand. Accordingly, the present heterodimeric proteins, in some embodiments are capable of, or find use in methods involving, reducing or eliminating an inhibitory immune signal and/or increasing or activating an immune stimulatory signal. For example, a tumor cell bearing an inhibitory signal (and thus evading an immune response) may be substituted for a positive signal binding on a T cell that can then attack a tumor cell. Accordingly, in some embodiments, an inhibitory immune signal is masked by the present heterodimeric proteins and a stimulatory immune signal is activated. Such beneficial properties are enhanced by the single construct approach of the present heterodimeric proteins. For instance, the signal replacement can be effected nearly simultaneously and the signal replacement is tailored to be local at a site of clinical importance (e.g., the tumor microenvironment).

In various embodiments, the present heterodimeric proteins are capable of, or find use in methods comprising, stimulating or enhancing the binding of immune stimulatory receptor/ligand pairs.

In other embodiments, the present heterodimeric proteins are capable of, or find use in methods involving, enhancing, restoring, promoting and/or stimulating immune modulation. In some embodiments, the present heterodimeric proteins described herein, restore, promote and/or stimulate the activity or activation of one or more immune cells against tumor cells including, but not limited to: T cells, cytotoxic T lymphocytes, T helper cells, natural killer (NK) cells, natural killer T (NKT) cells, anti-tumor macrophages (e.g., M1 macrophages), B cells, and dendritic cells. In some embodiments, the present heterodimeric proteins enhance, restore, promote and/or stimulate the activity and/or activation of T cells, including, by way of a non-limiting example, activating and/or stimulating one or more T-cell intrinsic signals, including a pro-survival signal; an autocrine or paracrine growth signal; a p38 MAPK-, ERK-, STAT-, JAK-, AKT- or PI3K-mediated signal; an anti-apoptotic signal; and/or a signal promoting and/or necessary for one or more of: proinflammatory cytokine production or T cell migration or T cell tumor infiltration.

In some embodiments, the present heterodimeric proteins are capable of, or find use in methods involving, causing an increase of one or more of T cells (including without limitation cytotoxic T lymphocytes, T helper cells, natural killer T (NKT) cells), B cells, natural killer (NK) cells, natural killer T (NKT) cells, dendritic cells, monocytes, and macrophages (e.g., one or more of M1 and M2) into a tumor or the tumor microenvironment. In some embodiments, the present heterodimeric proteins are capable of, or find use in methods involving, inhibiting and/or causing a decrease in recruitment of immunosuppressive cells (e.g., myeloid-derived suppressor cells (MDSCs), regulatory T cells (Tregs), tumor associated neutrophils (TANs), M2 macrophages, and tumor associated macrophages (TAMs)) to the tumor and/or tumor microenvironment (TME). In some embodiments, the present therapies may alter the ratio of M1 versus M2 macrophages in the tumor site and/or TME to favor M1 macrophages.

In various embodiments, the present heterodimeric proteins are capable of, and can be used in methods comprising, inhibiting and/or reducing T cell inactivation and/or immune tolerance to a tumor, comprising administering an effective amount of a heterodimeric protein described herein to a subject. In some embodiments, the present heterodimeric proteins are able to increase the serum levels of various cytokines including, but not limited to, one or more of IFNγ, IL-2, IL-4, IL-5, IL-6, IL-9, IL-10, IL-13, IL-17A, IL-17F, and IL-22. In some embodiments, the present heterodimeric proteins are capable of enhancing IL-2, IL-4, IL-5, IL-10, IL-13, IL-17A, IL-22, or IFNγ in the serum of a treated subject.

In various embodiments, the present heterodimeric proteins inhibit, block and/or reduce cell death of an anti-tumor CD8+ and/or CD4+ T cell; or stimulate, induce, and/or increase cell death of a pro-tumor T cell. T cell exhaustion is a state of T cell dysfunction characterized by progressive loss of proliferative and effector functions, culminating in clonal deletion. Accordingly, a pro-tumor T cell refers to a state of T cell dysfunction that arises during many chronic infections and cancer. This dysfunction is defined by poor proliferative and/or effector functions, sustained expression of inhibitory receptors and a transcriptional state distinct from that of functional effector or memory T cells. Exhaustion prevents optimal control of infection and tumors. In addition, an anti-tumor CD8+ and/or CD4+ T cell refers to T cells that can mount an immune response to a tumor. Illustrative pro-tumor T cells include, but are not limited to, Tregs, CD4+ and/or CD8+ T cells expressing one or more checkpoint inhibitory receptors, Th2 cells and Th17 cells. Checkpoint inhibitory receptors refers to receptors (e.g., CTLA-4, B7-H3, B7-H4, TIM-3) expressed on immune cells that prevent or inhibit uncontrolled immune responses.

In various embodiments, the present heterodimeric proteins are capable of, and can be used in methods comprising, increasing a ratio of effector T cells to regulatory T cells. Illustrative effector T cells include ICOS$^+$ effector T cells; cytotoxic T cells (e.g., $\alpha\beta$ TCR, CD3$^+$, CD8$^+$, CD45RO$^+$); CD4$^+$ effector T cells (e.g., $\alpha\beta$ TCR, CD3$^+$, CD4$^+$, CCR7$^+$, CD62Lhi, IL$^-$7R/CD127$^+$); CD8$^+$ effector T cells (e.g., $\alpha\beta$ TCR, CD3$^+$, CD8$^+$, CCR7$^+$, CD62Lhi, IL$^-$7 R/CD127$^+$); effector memory T cells (e.g., CD62Llow, CD44$^+$, TCR, CD3$^+$, IL7R/CD127$^+$, IL-15R$^+$, CCR7low); central memory T cells (e.g., CCR7$^+$, CD62L$^+$, CD27$^+$; or CCR7hi, CD44$^+$, CD62Lhi, TCR, CD3$^+$, IL-7R/CD127$^+$, IL-15 R$^+$); CD62L$^+$ effector T cells; CD8$^+$ effector memory T cells (TEM) including early effector memory T cells (CD27$^+$CD62L$^-$) and late effector memory T cells (CD27$^-$ CD62L$^-$) (TemE and TemL, respectively); CD127($^+$)CD25(low/–) effector T cells; CD127($^-$)CD250 effector T cells; CD8$^+$ stem cell memory effector cells (TSCM) (e.g., CD44(low)CD62L (high)CD122(high)sca($^+$)); TH1 effector T-cells (e.g., CXCR3$^+$, CXCR6$^+$ and CCR5$^+$; or $\alpha\beta$ TCR, CD3$^+$, CD4$^+$, IL-12R$^+$, IFN$\gamma$R$^+$, CXCR3$^+$), TH2 effector T cells (e.g., CCR3$^+$, CCR4$^+$ and CCR8$^+$; or $\alpha\beta$ TCR, CD3$^+$, CD4$^+$, IL-4R$^+$, IL-33R$^+$, CCR4$^+$, IL-17RB$^+$, CRTH2$^+$); TH9 effector T cells (e.g., $\alpha\beta$ TCR, CD3$^+$, CD4$^+$); TH17 effector T cells (e.g., $\alpha\beta$ TCR, CD3$^+$, CD4$^+$, IL-23R$^+$, CCR6$^+$, IL-1R$^+$); CD4$^+$CD45RO$^+$CCR7$^+$ effector T cells, CD4$^+$ CD45RO$^+$CCR7($^-$) effector T cells; and effector T cells secreting IL-2, IL-4 and/or IFN-$\gamma$. Illustrative regulatory T cells include ICOS$^+$ regulatory T cells, CD4$^+$CD25$^+$ FOXP3$^+$ regulatory T cells, CD4$^+$CD25$^+$ regulatory T cells, CD4$^+$CD25$^-$ regulatory T cells, CD4$^+$CD25high regulatory T cells, TIM-3+PD-1$^+$ regulatory T cells, lymphocyte activation gene-3 (LAG-3)$^+$ regulatory T cells, CTLA-4/CD152$^+$ regulatory T cells, neuropilin-1 (Nrp-1)$^+$ regulatory T cells, CCR4+CCR8$^+$ regulatory T cells, CD62L (L-selectin)$^+$ regulatory T cells, CD45RBlow regulatory T cells, CD127low regulatory T cells, LRRC32/GARP$^+$ regulatory T cells, CD39$^+$ regulatory T cells, GITR$^+$ regulatory T cells, LAP$^+$ regulatory T cells, 1B11$^+$ regulatory T cells, BTLA$^+$ regulatory T cells, type 1 regulatory T cells (Tr1 cells), T helper type 3 (Th3) cells, regulatory cell of natural killer T cell phenotype (NKTregs), CD8$^+$ regulatory T cells, CD8$^+$ CD28$^-$ regulatory T cells and/or regulatory T-cells secreting IL-10, IL-35, TGF-$\beta$, TNF-$\alpha$, Galectin-1, IFN-$\gamma$ and/or MCP1.

In various embodiments, the present heterodimeric proteins are capable of, and can be used in methods comprising, transiently stimulating effector T cells for no longer than about 12 hours, about 24 hours, about 48 hours, about 72 hours or about 96 hours or about 1 week or about 2 weeks. In various embodiments, the present heterodimeric proteins are capable of, and can be used in methods comprising, transiently depleting or inhibiting regulatory T cells for no longer than about 12 hours, about 24 hours, about 48 hours, about 72 hours or about 96 hours or about 1 week or about 2 weeks. In various embodiments, the transient stimulation of effector T cells and/or transient depletion or inhibition of regulatory T cells occurs substantially in a patient's bloodstream or in a particular tissue/location including lymphoid tissues such as for example, the bone marrow, lymph-node, spleen, thymus, mucosa-associated lymphoid tissue (MALT), non-lymphoid tissues, or in the tumor microenvironment.

In various embodiments, the present heterodimeric proteins provide advantages including, without limitation, ease of use and ease of production. This is because two distinct immunotherapy agents are combined into a single product which allows for a single manufacturing process instead of two independent manufacturing processes. In addition, administration of a single agent instead of two separate agents allows for easier administration and greater patient compliance. Further, in contrast to, for example, monoclonal antibodies, which are large multimeric proteins containing numerous disulfide bonds and post-translational modifications such as glycosylation, the present heterodimeric proteins are easier and more cost effective to manufacture.

In various embodiments, the present heterodimeric proteins provide synergistic therapeutic effects as it allows for improved site-specific interplay of two immunotherapy agents. In some embodiments, the present heterodimeric proteins provide the potential for reducing off-site and/or systemic toxicity.

Diseases; Methods of Treatment, and Patient Selections

In various embodiments, the present invention pertains to the use of the heterodimeric proteins for the treatment of one or more autoimmune diseases or disorders. In various embodiments, the treatment of an autoimmune disease or disorder may involve modulating the immune system with the present heterodimeric proteins to favor immune inhibition over immune stimulation. Illustrative autoimmune diseases or disorders treatable with the present heterodimeric proteins include those in which the body's own antigens become targets for an immune response, such as, for example, rheumatoid arthritis, systemic lupus erythematosus, diabetes mellitus, ankylosing spondylitis, Sjögren's syndrome, inflammatory bowel diseases (e.g., colitis ulcerosa, Crohn's disease), multiple sclerosis, sarcoidosis, psoriasis, Grave's disease, Hashimoto's thyroiditis, psoriasis, hypersensitivity reactions (e.g., allergies, hay fever, asthma, and acute edema cause type I hypersensitivity reactions), and vasculitis.

Exemplary autoimmune diseases or conditions that may be treated or prevented using the heterodimeric protein of the invention include, but are not limited to, multiple sclerosis, diabetes mellitus, lupus, celiac disease, Crohn's disease, ulcerative colitis, Guillain-Barre syndrome, scleroderms, Goodpasture's syndrome, Wegener's granulomatosis, autoimmune epilepsy, Rasmussen's encephalitis, Primary biliary sclerosis, Sclerosing cholangitis, Autoimmune hepatitis, Addison's disease, Hashimoto's thyroiditis, Fibromyalgia, Menier's syndrome; transplantation rejection (e.g., prevention of allograft rejection), pernicious anemia, rheumatoid arthritis, systemic lupus erythematosus, dermatomyositis, Sjögren's syndrome, lupus erythematosus, multiple sclerosis, myasthenia gravis, Reiter's syndrome, Grave's disease, and other autoimmune diseases.

In various embodiments, the present invention pertains to cancers and/or tumors; for example, the treatment or prevention of cancers and/or tumors. As described elsewhere herein, the treatment of cancer may involve in various embodiments, modulating the immune system with the present heterodimeric proteins to favor immune stimulation over immune inhibition.

Cancers or tumors refer to an uncontrolled growth of cells and/or abnormal increased cell survival and/or inhibition of apoptosis which interferes with the normal functioning of the bodily organs and systems. Included are benign and malignant cancers, polyps, hyperplasia, as well as dormant tumors or micrometastases. Also, included are cells having abnormal proliferation that is not impeded by the immune system (e.g., virus infected cells). The cancer may be a primary cancer or a metastatic cancer. The primary cancer may be an area of cancer cells at an originating site that becomes clinically detectable, and may be a primary tumor. In contrast, the metastatic cancer may be the spread of a disease from one organ or part to another non-adjacent organ or part. The metastatic cancer may be caused by a cancer cell that acquires the ability to penetrate and infiltrate surrounding normal tissues in a local area, forming a new tumor, which may be a local metastasis. The cancer may also be caused by a cancer cell that acquires the ability to penetrate the walls of lymphatic and/or blood vessels, after which the cancer cell is able to circulate through the bloodstream (thereby being a circulating tumor cell) to other sites and tissues in the body. The cancer may be due to a process such as lymphatic or hematogeneous spread. The cancer may also be caused by a tumor cell that comes to rest at another site, re-penetrates through the vessel or walls, continues to multiply, and eventually forms another clinically detectable tumor. The cancer may be this new tumor, which may be a metastatic (or secondary) tumor.

The cancer may be caused by tumor cells that have metastasized, which may be a secondary or metastatic tumor. The cells of the tumor may be like those in the original tumor. As an example, if a breast cancer or colon cancer metastasizes to the liver, the secondary tumor, while present in the liver, is made up of abnormal breast or colon cells, not of abnormal liver cells. The tumor in the liver may thus be a metastatic breast cancer or a metastatic colon cancer, not liver cancer.

The cancer may have an origin from any tissue. The cancer may originate from melanoma, colon, breast, or prostate, and thus may be made up of cells that were originally skin, colon, breast, or prostate, respectively. The cancer may also be a hematological malignancy, which may be leukemia or lymphoma. The cancer may invade a tissue such as liver, lung, bladder, or intestinal.

Representative cancers and/or tumors of the present invention include, but are not limited to, a basal cell carcinoma, biliary tract cancer; bladder cancer; bone cancer; brain and central nervous system cancer; breast cancer; cancer of the peritoneum; cervical cancer; choriocarcinoma; colon and rectum cancer; connective tissue cancer; cancer of the digestive system; endometrial cancer; esophageal cancer; eye cancer; cancer of the head and neck; gastric cancer (including gastrointestinal cancer); glioblastoma; hepatic carcinoma; hepatoma; intra-epithelial neoplasm; kidney or renal cancer; larynx cancer; leukemia; liver cancer; lung cancer (e.g., small-cell lung cancer, non-small cell lung cancer, adenocarcinoma of the lung, and squamous carcinoma of the lung); melanoma; myeloma; neuroblastoma; oral cavity cancer (lip, tongue, mouth, and pharynx); ovarian cancer; pancreatic cancer; prostate cancer; retinoblastoma; rhabdomyosarcoma; rectal cancer; cancer of the respiratory system; salivary gland carcinoma; sarcoma; skin cancer; squamous cell cancer; stomach cancer; testicular cancer; thyroid cancer; uterine or endometrial cancer; cancer of the urinary system; vulval cancer; lymphoma including Hodgkin's and non-Hodgkin's lymphoma, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia; chronic lymphocytic leukemia (CLL); acute lymphoblastic leukemia (ALL); Hairy cell leukemia; chronic myeloblastic leukemia; as well as other carcinomas and sarcomas; and post-transplant lymphoproliferative disorder (PTLD), as well as abnormal vascular proliferation associated with phakomatoses, edema (such as that associated with brain tumors), and Meigs' syndrome.

In some embodiments, the heterodimeric protein is used to treat a subject that has a treatment-refractory cancer. In some embodiments, the heterodimeric protein is used to treat a subject that is refractory to one or more immune-modulating agents. For example, in some embodiments, the heterodimeric protein is used to treat a subject that presents no response to treatment, or even progress, after 12 weeks or so of treatment. For instance, in some embodiments, the subject is refractory to a PD-1 and/or PD-L1 and/or PD-L2 agent, including, for example, nivolumab (ONO-4538/BMS-936558, MDX1106, OPDIVO, BRISTOL MYERS SQUIBB), pembrolizumab (KEYTRUDA, MERCK), pidilizumab (CT-011, CURE TECH), MK-3475 (MERCK), BMS 936559 (BRISTOL MYERS SQUIBB), Ibrutinib (PHARMACYCLICS/ABBVIE), atezolizumab (TECENTRIQ, GENENTECH), and/or MPDL328OA (ROCHE)-refractory patients. For instance, in some embodiments, the subject is refractory to an anti-CTLA-4 agent, e.g., ipilimumab (YERVOY)-refractory patients (e.g., melanoma patients). Accordingly, in various embodiments, the present invention provides methods of cancer treatment that rescue patients that are non-responsive to various therapies, including monotherapy of one or more immune-modulating agents.

In various embodiments, the present invention provides heterodimeric proteins which target a cell or tissue within the tumor microenviroment. In some embodiments, the cell or tissue within the tumor microenvironment expresses one or more targets or binding partners of the heterodimeric protein. The tumor microenvironment refers to the cellular milieu, including cells, secreted proteins, physiological small molecules, and blood vessels in which the tumor exists. In some embodiments, the cells or tissue within the tumor microenvironment are one or more of: tumor vasculature; tumor-infiltrating lymphocytes; fibroblast reticular cells; endothelial progenitor cells (EPC); cancer-associated fibroblasts; pericytes; other stromal cells; components of the extracellular matrix (ECM); dendritic cells; antigen presenting cells; T-cells; regulatory T cells; macrophages; neutrophils; and other immune cells located proximal to a tumor. In various embodiments, the present heterodimeric protein targets a cancer cell. In some embodiments, the cancer cell expresses one or more of targets or binding partners of the heterodimeric protein.

In various embodiments, the heterodimeric protein of the invention may target a cell (e.g., cancer cell or immune cell) that expresses any of the receptors as described herein. For example, the heterodimeric protein of the invention may target a cell that expresses any of the receptors for a cytokine, growth factor, and/or hormone as described herein.

In some embodiments, the present methods provide treatment with the heterodimeric protein in a patient who is refractory to an additional agent, such "additional agents" being described elsewhere herein, inclusive, without limitation, of the various chemotherapeutic agents described herein.

In some aspects, the present chimeric agents are used to eliminate intracellular pathogens. In some aspects, the present chimeric agents are used to treat one or more infections. In some embodiments, the present heterodimeric proteins are used in methods of treating viral infections (including, for example, HIV and HCV), parasitic infections (including, for example, malaria), and bacterial infections. In various embodiments, the infections induce immunosuppression. For example, HIV infections often result in immunosuppression in the infected subjects. Accordingly, as described elsewhere herein, the treatment of such infections may involve, in various embodiments, modulating the immune system with the present heterodimeric proteins to favor immune stimulation over immune inhibition. Alternatively, the present invention provides methods for treating infections that induce immunoactivation. For example, intestinal helminth infections have been associated with chronic immune activation. In these embodiments, the treatment of such infections may involve modulating the immune system with the present heterodimeric proteins to favor immune inhibition over immune stimulation.

In various embodiments, the present invention provides methods of treating viral infections including, without limitation, acute or chronic viral infections, for example, of the respiratory tract, of papilloma virus infections, of herpes simplex virus (HSV) infection, of human immunodeficiency virus (HIV) infection, and of viral infection of internal organs such as infection with hepatitis viruses. In some embodiments, the viral infection is caused by a virus of family Flaviviridae. In some embodiments, the virus of family Flaviviridae is selected from Yellow Fever Virus, West Nile virus, Dengue virus, Japanese Encephalitis Virus, St. Louis Encephalitis Virus, and Hepatitis C Virus. In other embodiments, the viral infection is caused by a virus of family Picornaviridae, e.g., poliovirus, rhinovirus, coxsackievirus. In other embodiments, the viral infection is caused by a member of Orthomyxoviridae, e.g., an influenza virus. In other embodiments, the viral infection is caused by a member of Retroviridae, e.g., a lentivirus. In other embodiments, the viral infection is caused by a member of Paramyxoviridae, e.g., respiratory syncytial virus, a human parainfluenza virus, rubulavirus (e.g., mumps virus), measles virus, and human metapneumovirus. In other embodiments, the viral infection is caused by a member of Bunyaviridae, e.g., hantavirus. In other embodiments, the viral infection is caused by a member of Reoviridae, e.g., a rotavirus.

In various embodiments, the present invention provides methods of treating parasitic infections such as protozoan or helminths infections. In some embodiments, the parasitic infection is by a protozoan parasite. In some embodiments, the oritiziab parasite is selected from intestinal protozoa, tissue protozoa, or blood protozoa. Illustrative protozoan parasites include, but are not limited to, *Entamoeba hystolytica, Giardia lamblia, Cryptosporidium muris, Trypanosomatida gambiense, Trypanosomatida rhodesiense, Trypanosomatida crusi, Leishmania mexicana, Leishmania braziliensis, Leishmania tropica, Leishmania donovani, Toxoplasma Plasmodium vivax, Plasmodium ovale, Plasmodium malariae, Plasmodium falciparum, Trichomonas vaginalis,* and *Histomonas meleagridis*. In some embodiments, the parasitic infection is by a helminthic parasite such as nematodes (e.g., Adenophorea). In some embodiments, the parasite is selected from Secementea (e.g., *Trichuris trichiura, Ascaris lumbricoides, Enterobius vermicularis, Ancylostoma duodenale, Necator americanus, Strongyloides stercoralis, Wuchereria bancrofti, Dracunculus medinensis*). In some embodiments, the parasite is selected from trematodes (e.g., blood flukes, liver flukes, intestinal flukes, and lung flukes). In some embodiments, the parasite is selected from: *Schistosoma mansoni, Schistosoma haematobium, Schistosoma japonicum, Fasciola hepatica, Fasciola gigantica, Heterophyes heterophyes, Paragonimus westermani*. In some embodiments, the parasite is selected from cestodes (e.g., *Taenia solium, Taenia saginata, Hymenolepis nana, Echinococcus granulosus*).

In various embodiments, the present invention provides methods of treating bacterial infections. In various embodiments, the bacterial infection is by gram-positive bacteria, gram-negative bacteria, aerobic and/or anaerobic bacteria. In various embodiments, the bacteria are selected from, but not limited to, *Staphylococcus, Lactobacillus, Streptococcus, Sarcina, Escherichia, Enterobacter, Klebsiella, Pseudomonas, Acinetobacter, Mycobacterium, Proteus, Campylobacter, Citrobacter, Neisseria, Bacillus, Bacteroides, Peptococcus, Clostridium, Salmonella, Shigella, Serratia, Haemophilus, Brucella* and other organisms. In some embodiments, the bacteria is selected from, but not limited to, *Pseudomonas aeruginosa, Pseudomonas fluorescens, Pseudomonas acidovorans, Pseudomonas alcaligenes, Pseudomonas putida, Stenotrophomonas maltophilia, Burkholderia cepacia, Aeromonas hydrophilia, Escherichia coli, Citrobacter freundii, Salmonella typhimurium, Salmonella typhi, Salmonella paratyphi, Salmonella enteritidis, Shigella dysenteriae, Shigella flexneri, Shigella sonnei, Enterobacter cloacae, Enterobacter aerogenes, Klebsiella pneumoniae, Klebsiella oxytoca, Serratia marcescens, Francisella tularensis, Morganella morganii, Proteus mirabilis, Proteus vulgaris, Providencia alcalifaciens, Providencia rettgeri, Providencia stuartii, Acinetobacter baumannii, Acinetobacter calcoaceticus, Acinetobacter haemolyticus, Yersinia enterocolitica, Yersinia pestis, Yersinia pseudotuberculosis, Yersinia intermedia, Bordetella pertussis, Bordetella parapertussis, Bordetella bronchiseptica, Haemophilus influenzae, Haemophilus parainfluenzae, Haemophilus haemolyticus, Haemophilus parahaemolyticus, Haemophilus ducreyi, Pasteurella multocida, Pasteurella haemolytica, Branhamella catarrhalis, Helicobacter pylori, Campylobacter fetus, Campylobacter jejuni, Campylobacter coli, Borrelia burgdorferi, Vibrio cholerae, Vibrio parahaemolyticus, Legionella pneumophila, Listeria monocytogenes, Neisseria gonorrhoeae, Neisseria meningitidis, Kingella, Moraxella, Gardnerella vaginalis, Bacteroides fragilis, Bacteroides distasonis, Bacteroides* 3452A homology group, *Bacteroides vulgatus, Bacteroides ovalus, Bacteroides thetaiotaomicron, Bacteroides uniformis, Bacteroides eggerthii, Bacteroides splanchnicus, Clostridium difficile, Mycobacterium tuberculosis, Mycobacterium avium, Mycobacterium intracellulare, Mycobacterium leprae, Corynebacterium diphtheriae, Corynebacterium ulcerans, Streptococcus pneumoniae, Streptococcus agalactiae, Streptococcus pyogenes, Enterococcus faecalis, Enterococcus faecium, Staphylococcus aureus, Staphylococcus epidermidis, Staphylococcus saprophyticus, Staphylococcus intermedius, Staphylococcus hyicus* subsp. *hyicus, Staphylococcus haemolyticus, Staphylococcus hominis,* or *Staphylococcus saccharolyticus*.

In still another other aspect, the present invention is directed toward methods of treating and preventing T cell-mediated diseases and disorders, such as, but not limited to diseases or disorders described elsewhere herein and inflammatory disease or disorder, graft-versus-host disease (GVHD), transplant rejection, and T cell proliferative disorder.

In some aspects, the present chimeric agents are used in methods of activating a T cell, e.g., via the extracellular domain having an immune stimulatory signal.

In some aspects, the present chimeric agents are used in methods of preventing the cellular transmission of an immunosuppressive signal.

Combination Therapies and Conjugation

In some embodiments, the invention provides for heterodimeric proteins and methods that further comprise administering an additional agent to a subject. In some embodiments, the invention pertains to co-administration and/or co-formulation. Any of the compositions described herein may be co-formulated and/or co-administered.

In some embodiments, any heterodimeric protein described herein acts synergistically when co-administered with another agent and is administered at doses that are lower than the doses commonly employed when such agents are used as monotherapy. In various embodiments, any agent referenced herein may be used in combination with any of the heterodimeric proteins described herein.

In various embodiments, any of the heterodimeric proteins disclosed herein may be co-administered with another heterodimeric protein disclosed herein. Without wishing to be bound by theory, it is believed that a combined regimen involving the administration of one or more heterodimeric proteins which induce an innate immune response and one or more heterodimeric proteins which induce an adaptive immune response may provide synergistic effects (e.g., synergistic anti-tumor effects).

In various embodiments, any heterodimeric protein which induces an innate immune response may be utilized in the present invention. In various embodiments, any heterodimeric protein which induces an adaptive immune response may be utilized in the present invention.

In some embodiments, inclusive of, without limitation, cancer applications, the present invention pertains to chemotherapeutic agents as additional agents. Examples of chemotherapeutic agents include, but are not limited to, alkylating agents such as thiotepa and CYTOXAN cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (e.g., bullatacin and bullatacinone); a camptothecin (including the synthetic analogue topotecan); bryostatin; cally statin; CC-1065 (including its adozelesin, carzelesin and bizelesin synthetic analogues); cryptophycins (e.g., cryptophycin 1 and cryptophycin 8); dolastatin; duocarmycin (including the synthetic analogues, KW-2189 and CB 1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammall and calicheamicin omegall (see, e.g., Agnew, Chem. Intl. Ed. Engl., 33: 183-186 (1994)); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycins, dactinomycin, daunorubicin, detorubicin, 6-diazo-5-oxo-L-norleucine, ADRIAMYCIN doxorubicin (including morpholino-doxorubicin, cyanomorpholino-doxorubicin, 2-pyrrolino-doxorubicin and deoxy doxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as minoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (e.g., T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL paclitaxel (Bristol-Myers Squibb Oncology, Princeton, N.J.), ABRAXANE Cremophor-free, albumin-engineered nanoparticle formulation of paclitaxel (American Pharmaceutical Partners, Schaumberg, 111), and TAXOTERE doxetaxel (Rhone-Poulenc Rorer, Antony, France); chloranbucil; GEMZAR gemcitabine; 6-thioguanine; mercaptopurine; methotrexate; platinum analogs such as cisplatin, oxaliplatin and carboplatin; vinblastine; platinum; etoposide (VP-16); ifosfamide; mitoxantrone; vincristine; NAVELBINE. vinorelbine; novantrone; teniposide; edatrexate; daunomycin; aminopterin; xeloda; ibandronate; irinotecan (Camptosar, CPT-11) (including the treatment regimen of irinotecan with κ-FU and leucovorin); topoisomerase inhibitor RFS 2000; difluoromethylornithine (DMFO); retinoids such as retinoic acid; capecitabine; combretastatin; leucovorin (LV); oxaliplatin, including the oxaliplatin treatment regimen (FOLFOX); lapatinib (TYKERB); inhibitors of PKC-α, Raf, H-Ras, EGFR (e.g., erlotinib (Tarceva)) and VEGF-A that reduce cell proliferation and pharmaceutically acceptable salts, acids or derivatives of any of the above. In addition, the methods of treatment can further include the use of radiation. In addition, the methods of treatment can further include the use of photodynamic therapy.

In various embodiments, inclusive of, without limitation, cancer applications, the present additional agent is one or more immune-modulating agents selected from an agent that blocks, reduces and/or inhibits PD-1 and PD-L1 or PD-L2 and/or the binding of PD-1 with PD-L1 or PD-L2 (by way of non-limiting example, one or more of nivolumab (ONO- 4538/BMS-936558, MDX1106, OPDIVO, BRISTOL MYERS SQUIBB), pembrolizumab (KEYTRUDA, Merck), MK-3475 (MERCK), BMS 936559 (BRISTOL MYERS SQUIBB), atezolizumab (TECENTRIQ, GENENTECH), MPDL328OA (ROCHE)), an agent that increases and/or stimulates CD137 (4-1BB) and/or the binding of CD137 (4-1BB) with one or more of 4-1BB ligand (by way of non-limiting example, urelumab (BMS-663513 and anti-4-1BB antibody), and an agent that blocks, reduces and/or inhibits the activity of CTLA-4 and/or the binding of CTLA-4 with one or more of AP2M1, CD80, CD86, SHP-2, and PPP2R5A and/or the binding of OX40 with OX40L (by way of non-limiting example GBR 830 (GLENMARK), MED16469 (MEDIMMUNE).

In some embodiments, inclusive of, without limitation, infectious disease applications, the present invention pertains to anti-infectives as additional agents. In some embodiments, the anti-infective is an anti-viral agent including, but not limited to, Abacavir, Acyclovir, Adefovir, Amprenavir, Atazanavir, Cidofovir, Darunavir, Delavirdine, Didanosine, Docosanol, Efavirenz, Elvitegravir, Emtricitabine, Enfuvirtide, Etravirine, Famciclovir, and Foscarnet. In some embodiments, the anti-infective is an anti-bacterial agent including, but not limited to, cephalosporin antibiotics (cephalexin, cefuroxime, cefadroxil, cefazolin, cephalothin, cefaclor, cefamandole, cefoxitin, cefprozil, and ceftobiprole); fluoroquinolone antibiotics (cipro, Levaquin, floxin, tequin, avelox, and norflox); tetracycline antibiotics (tetracycline, minocycline, oxytetracycline, and doxycycline); penicillin antibiotics (amoxicillin, ampicillin, penicillin V, dicloxacillin, carbenicillin, vancomycin, and methicillin); monobactam antibiotics (aztreonam); and carbapenem antibiotics (ertapenem, doripenem, imipenem/cilastatin, and meropenem). In some embodiments, the anti-infectives include anti-malarial agents (e.g., chloroquine, quinine, mefloquine, primaquine, doxycycline, artemether/lumefantrine, atovaquone/proguanil and sulfadoxine/pyrimethamine), metronidazole, tinidazole, ivermectin, pyrantel pamoate, and albendazole.

In some embodiments, inclusive, without limitation, of autoimmune applications, the additional agent is an immunosuppressive agent. In some embodiments, the immunosuppressive agent is an anti-inflammatory agent such as a steroidal anti-inflammatory agent or a non-steroidal anti-inflammatory agent (NSAID). Steroids, particularly the adrenal corticosteroids and their synthetic analogues, are well known in the art. Examples of corticosteroids useful in the present invention include, without limitation, hydroxyltriamcinolone, alpha-methyl dexamethasone, beta-methyl betamethasone, beclomethasone dipropionate, betamethasone benzoate, betamethasone dipropionate, betamethasone valerate, clobetasol valerate, desonide, desoxymethasone, dexamethasone, diflorasone diacetate, diflucortolone valerate, fluadrenolone, fluclorolone acetonide, flumethasone pivalate, fluosinolone acetonide, fluocinonide, flucortine butylester, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone acetonide, medrysone, amcinafel, amcinafide, betamethasone and the balance of its esters, chloroprednisone, clocortelone, clescinolone, dichlorisone, difluprednate, flucloronide, flunisolide, fluoromethalone, fluperolone, fluprednisolone, hydrocortisone, meprednisone, paramethasone, prednisolone, prednisone, beclomethasone dipropionate. (NSAIDS) that may be used in the present invention, include but are not limited to, salicylic acid, acetyl salicylic acid, methyl salicylate, glycol salicylate, salicylmides, benzyl-2,5-diacetoxybenzoic acid, ibuprofen, fulindac, naproxen, ketoprofen, etofenamate, phenylbutazone, and indomethacin. In some embodiments, the immunosupressive agent may be cytostatics such as alkylating agents, antimetabolites (e.g., azathioprine, methotrexate), cytotoxic antibiotics, antibodies (e.g., basiliximab, dacliziumab, and muromonab), anti-immunophilins (e.g., cyclosporine, tacrolimus, sirolimus), inteferons, opioids, TNF binding proteins, mycophenolates, and small biological agents (e.g., fingolimod, myriocin).

In some embodiments, the heterodimeric proteins (and/or additional agents) described herein, include derivatives that are modified, i.e., by the covalent attachment of any type of molecule to the composition such that covalent attachment does not prevent the activity of the composition. For example, but not by way of limitation, derivatives include composition that have been modified by, inter alia, glycosylation, lipidation, acetylation, pegylation, phosphorylation, amidation, derivatization by known protecting/blocking groups, proteolytic cleavage, linkage to a cellular ligand or other protein, etc. Any of numerous chemical modifications can be carried out by known techniques, including, but not limited to specific chemical cleavage, acetylation, formylation, metabolic synthesis of turicamycin, etc. Additionally, the derivative can contain one or more non-classical amino acids. In still other embodiments, the heterodimeric proteins (and/or additional agents) described herein further comprise a cytotoxic agent, comprising, in illustrative embodiments, a toxin, a chemotherapeutic agent, a radioisotope, and an agent that causes apoptosis or cell death. Such agents may be conjugated to a composition described herein.

The heterodimeric proteins (and/or additional agents) described herein may thus be modified post-translationally to add effector moieties such as chemical linkers, detectable moieties such as for example fluorescent dyes, enzymes, substrates, bioluminescent materials, radioactive materials, and chemiluminescent moieties, or functional moieties such as for example streptavidin, avidin, biotin, a cytotoxin, a cytotoxic agent, and radioactive materials.

Formulations

The heterodimeric proteins (and/or additional agents) described herein can possess a sufficiently basic functional group, which can react with an inorganic or organic acid, or a carboxyl group, which can react with an inorganic or organic base, to form a pharmaceutically acceptable salt. A pharmaceutically acceptable acid addition salt is formed from a pharmaceutically acceptable acid, as is well known in the art. Such salts include the pharmaceutically acceptable salts listed in, for example, *Journal of Pharmaceutical Science*, 66, 2-19 (1977) and *The Handbook of Pharmaceutical Salts; Properties, Selection, and Use*. P. H. Stahl and C. G. Wermuth (eds.), Verlag, Zurich (Switzerland) 2002, which are hereby incorporated by reference in their entirety.

In some embodiments, the compositions described herein are in the form of a pharmaceutically acceptable salt.

Further, any heterodimeric protein (and/or additional agents) described herein can be administered to a subject as a component of a composition that comprises a pharmaceutically acceptable carrier or vehicle. Such compositions can optionally comprise a suitable amount of a pharmaceutically acceptable excipient so as to provide the form for proper administration. Pharmaceutical excipients can be liquids, such as water and oils, including those of petroleum, animal, vegetable, or synthetic origin, such as peanut oil, soybean oil, mineral oil, sesame oil and the like. The pharmaceutical excipients can be, for example, saline, gum acacia, gelatin, starch paste, talc, keratin, colloidal silica, urea and the like. In addition, auxiliary, stabilizing, thickening, lubricating, and coloring agents can be used. In one embodiment, the pharmaceutically acceptable excipients are sterile when administered to a subject. Water is a useful excipient when any agent described herein is administered intravenously. Saline solutions and aqueous dextrose and glycerol solutions can also be employed as liquid excipients, specifically for injectable solutions. Suitable pharmaceutical excipients also include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Any agent described herein, if desired, can also comprise minor amounts of wetting or emulsifying agents, or pH buffering agents.

In some embodiments, the compositions described herein are resuspended in a saline buffer (including, without limitation TBS, PBS, and the like).

In various embodiments, the heterodimeric proteins may by conjugated and/or fused with another agent to extend half-life or otherwise improve pharmacodynamic and pharmacokinetic properties. In some embodiments, the heterodimeric proteins may be fused or conjugated with one or more of PEG, XTEN (e.g., as rPEG), polysialic acid (POLYXEN), albumin (e.g., human serum albumin or HAS), elastin-like protein (ELP), PAS, HAP, GLK, CTP, transferrin, and the like. In various embodiments, each of the individual heterodimeric proteins is fused to one or more of the agents described in BioDrugs (2015) 29:215-239, the entire contents of which are hereby incorporated by reference.

Administration, Dosing, and Treatment Regimens

The present invention includes the described heterodimeric protein (and/or additional agents) in various formulations. Any heterodimeric protein (and/or additional agents) described herein can take the form of solutions, suspensions, emulsion, drops, tablets, pills, pellets, capsules, capsules containing liquids, powders, sustained-release formulations, suppositories, emulsions, aerosols, sprays, suspensions, or any other form suitable for use. DNA or RNA constructs encoding the protein sequences may also be used. In one embodiment, the composition is in the form of a capsule (see, e.g., U.S. Pat. No. 5,698,155). Other examples of suitable pharmaceutical excipients are described in Remington's Pharmaceutical Sciences 1447-1676 (Alfonso R. Gennaro eds., 19th ed. 1995), incorporated herein by reference.

Where necessary, the formulations comprising the heterodimeric protein (and/or additional agents) can also include a solubilizing agent. Also, the agents can be delivered with a suitable vehicle or delivery device as known in the art. Combination therapies outlined herein can be co-delivered in a single delivery vehicle or delivery device. Compositions for administration can optionally include a local anesthetic such as, for example, lignocaine to lessen pain at the site of the injection.

The formulations comprising the heterodimeric protein (and/or additional agents) of the present invention may conveniently be presented in unit dosage forms and may be prepared by any of the methods well known in the art of pharmacy. Such methods generally include the step of bringing the therapeutic agents into association with a carrier, which constitutes one or more accessory ingredients. Typically, the formulations are prepared by uniformly and intimately bringing the therapeutic agent into association with a liquid carrier, a finely divided solid carrier, or both, and then, if necessary, shaping the product into dosage forms of the desired formulation (e.g., wet or dry granulation, powder blends, etc., followed by tableting using conventional methods known in the art).

In one embodiment, any heterodimeric protein (and/or additional agents) described herein is formulated in accordance with routine procedures as a composition adapted for a mode of administration described herein.

Routes of administration include, for example: intradermal, intramuscular, intraperitoneal, intravenous, subcutaneous, intranasal, epidural, oral, sublingual, intranasal, intracerebral, intravaginal, transdermal, rectally, by inhalation, or topically, particularly to the ears, nose, eyes, or skin. In some embodiments, the administering is effected orally or by parenteral injection. In most instances, administration results in the release of any agent described herein into the bloodstream.

Any heterodimeric protein (and/or additional agents) described herein can be administered orally. Such heterodimeric proteins (and/or additional agents) can also be administered by any other convenient route, for example, by intravenous infusion or bolus injection, by absorption through epithelial or mucocutaneous linings (e.g., oral mucosa, rectal and intestinal mucosa, etc.) and can be administered together with another biologically active agent. Administration can be systemic or local. Various delivery systems are known, e.g., encapsulation in liposomes, microparticles, microcapsules, capsules, etc., and can be used to administer.

In specific embodiments, it may be desirable to administer locally to the area in need of treatment. In one embodiment, for instance in the treatment of cancer, the heterodimeric protein (and/or additional agents) are administered in the tumor microenvironment (e.g., cells, molecules, extracellular matrix and/or blood vessels that surround and/or feed a tumor cell, inclusive of, for example, tumor vasculature; tumor-infiltrating lymphocytes; fibroblast reticular cells; endothelial progenitor cells (EPC); cancer-associated fibroblasts; pericytes; other stromal cells; components of the extracellular matrix (ECM); dendritic cells; antigen presenting cells; T-cells; regulatory T cells; macrophages; neutrophils; and other immune cells located proximal to a tumor) or lymph node and/or targeted to the tumor microenvironment or lymph node. In various embodiments, for instance in the treatment of cancer, the heterodimeric protein (and/or additional agents) are administered intratumorally.

In the various embodiments, the present heterodimeric protein allows for a dual effect that provides less side effects than are seen in conventional immunotherapy (e.g., treatments with one or more of OPDIVO, KEYTRUDA, YERVOY, and TECENTRIQ). For example, the present heterodimeric proteins reduce or prevent commonly observed immune-related adverse events that affect various tissues and organs including the skin, the gastrointestinal tract, the kidneys, peripheral and central nervous system, liver, lymph nodes, eyes, pancreas, and the endocrine system; such as hypophysitis, colitis, hepatitis, pneumonitis, rash, and rheumatic disease. Further, the present local administration, e.g., intratumorally, obviate adverse event seen with standard systemic administration, e.g., IV infusions, as are used with conventional immunotherapy (e.g., treatments with one or more of OPDIVO, KEYTRUDA, YERVOY, and TECENTRIQ).

Dosage forms suitable for parenteral administration (e.g., intravenous, intramuscular, intraperitoneal, subcutaneous and intra-articular injection and infusion) include, for example, solutions, suspensions, dispersions, emulsions, and the like. They may also be manufactured in the form of sterile solid compositions (e.g., lyophilized composition), which can be dissolved or suspended in sterile injectable medium immediately before use. They may contain, for example, suspending or dispersing agents known in the art.

The dosage of any heterodimeric protein (and/or additional agents) described herein as well as the dosing schedule can depend on various parameters, including, but not limited to, the disease being treated, the subject's general health, and the administering physician's discretion. Any heterodimeric protein described herein, can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concurrently with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of an additional agent, to a subject in need thereof. In various embodiments any heterodimeric protein and additional agent described herein are administered 1 minute apart, 10 minutes apart, 30 minutes apart, less than 1 hour apart, 1 hour apart, 1 hour to 2 hours apart, 2 hours to 3 hours apart, 3 hours to 4 hours apart, 4 hours to 5 hours apart, 5 hours to 6 hours apart, 6 hours to 7 hours apart, 7 hours to 8 hours apart, 8 hours to 9 hours apart, 9 hours to 10 hours apart, 10 hours to 11 hours apart, 11 hours to 12 hours apart, 1 day apart, 2 days apart, 3 days apart, 4 days apart, 5 days apart, 6 days apart, 1 week apart, 2 weeks apart, 3 weeks apart, or 4 weeks apart.

In various embodiments, the present invention relates to the co-administration of a heterodimeric protein which induces an innate immune response and another heterodimeric protein which induces an adaptive immune response. In such embodiments, the heterodimeric protein which induces an innate immune response may be administered before, concurrently with, or subsequent to administration of the heterodimeric protein which induces an adaptive immune response. For example, the heterodimeric proteins may be administered 1 minute apart, 10 minutes apart, 30 minutes apart, less than 1 hour apart, 1 hour apart, 1 hour to 2 hours apart, 2 hours to 3 hours apart, 3 hours to 4 hours apart, 4 hours to 5 hours apart, 5 hours to 6 hours apart, 6 hours to 7 hours apart, 7 hours to 8 hours apart, 8 hours to 9 hours apart, 9 hours to 10 hours apart, 10 hours to 11 hours apart, 11 hours to 12 hours apart, 1 day apart, 2 days apart, 3 days apart, 4 days apart, 5 days apart, 6 days apart, 1 week apart, 2 weeks apart, 3 weeks apart, or 4 weeks apart. In an exemplary embodiment, the heterodimeric protein which induces an innate immune response and the heterodimeric protein which induces an adaptive response are administered 1 week apart, or administered on alternate weeks (i.e., administration of the heterodimeric protein inducing an innate immune response is followed 1 week later with administration of the heterodimeric protein which induces an adaptive immune response and so forth).

The dosage of any heterodimeric protein (and/or additional agents) described herein can depend on several factors including the severity of the condition, whether the condition is to be treated or prevented, and the age, weight, and health of the subject to be treated. Additionally, pharmacogenomic (the effect of genotype on the pharmacokinetic, pharmacodynamic or efficacy profile of a therapeutic) information about a particular subject may affect dosage used. Furthermore, the exact individual dosages can be adjusted somewhat depending on a variety of factors, including the specific combination of the agents being administered, the time of administration, the route of administration, the nature of the formulation, the rate of excretion, the particular disease being treated, the severity of the disorder, and the anatomical location of the disorder. Some variations in the dosage can be expected.

For administration of any heterodimeric protein (and/or additional agents) described herein by parenteral injection, the dosage may be about 0.1 mg to about 250 mg per day, about 1 mg to about 20 mg per day, or about 3 mg to about 5 mg per day. Generally, when orally or parenterally administered, the dosage of any agent described herein may be about 0.1 mg to about 1500 mg per day, or about 0.5 mg to about 10 mg per day, or about 0.5 mg to about 5 mg per day, or about 200 to about 1,200 mg per day (e.g., about 200 mg, about 300 mg, about 400 mg, about 500 mg, about 600 mg, about 700 mg, about 800 mg, about 900 mg, about 1,000 mg, about 1,100 mg, about 1,200 mg per day).

In some embodiments, administration of the heterodimeric protein (and/or additional agents) described herein is by parenteral injection at a dosage of about 0.1 mg to about 1500 mg per treatment, or about 0.5 mg to about 10 mg per treatment, or about 0.5 mg to about 5 mg per treatment, or about 200 to about 1,200 mg per treatment (e.g., about 200 mg, about 300 mg, about 400 mg, about 500 mg, about 600 mg, about 700 mg, about 800 mg, about 900 mg, about 1,000 mg, about 1,100 mg, about 1,200 mg per treatment).

In some embodiments, a suitable dosage of the heterodimeric protein (and/or additional agents) is in a range of about 0.01 mg/kg to about 100 mg/kg of body weight, or about 0.01 mg/kg to about 10 mg/kg of body weight of the subject, for example, about 0.01 mg/kg, about 0.02 mg/kg, about 0.03 mg/kg, about 0.04 mg/kg, about 0.05 mg/kg, about 0.06 mg/kg, about 0.07 mg/kg, about 0.08 mg/kg, about 0.09 mg/kg, about 0.1 mg/kg, about 0.2 mg/kg, about 0.3 mg/kg, about 0.4 mg/kg, about 0.5 mg/kg, about 0.6 mg/kg, about 0.7 mg/kg, about 0.8 mg/kg, about 0.9 mg/kg, about 1 mg/kg, about 1.1 mg/kg, about 1.2 mg/kg, about 1.3 mg/kg, about 1.4 mg/kg, about 1.5 mg/kg, about 1.6 mg/kg, about 1.7 mg/kg, about 1.8 mg/kg, 1.9 mg/kg, about 2 mg/kg, about 3 mg/kg, about 4 mg/kg, about 5 mg/kg, about 6 mg/kg, about 7 mg/kg, about 8 mg/kg, about 9 mg/kg, about 10 mg/kg body weight, inclusive of all values and ranges therebetween.

In another embodiment, delivery can be in a vesicle, in particular a liposome (see Langer, 1990, Science 249:1527-1533; Treat et al., in *Liposomes in the Therapy of Infectious Disease and Cancer*, Lopez-Berestein and Fidler (eds.), Liss, New York, pp. 353-365 (1989).

Any heterodimeric protein (and/or additional agents) described herein can be administered by controlled-release or sustained-release means or by delivery devices that are well known to those of ordinary skill in the art. Examples include, but are not limited to, those described in U.S. Pat. Nos. 3,845,770; 3,916,899; 3,536,809; 3,598,123; 4,008, 719; 5,674,533; 5,059,595; 5,591,767; 5,120,548; 5,073, 543; 5,639,476; 5,354,556; and 5,733,556, each of which is incorporated herein by reference in its entirety. Such dosage forms can be useful for providing controlled- or sustained-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Controlled- or sustained-release of an active ingredient can be stimulated by various conditions, including but not limited to, changes in pH, changes in temperature, stimulation by an appropriate wavelength of light, concentration or availability of enzymes, concentration or availability of water, or other physiological conditions or compounds.

In another embodiment, polymeric materials can be used (see *Medical Applications of Controlled Release*, Langer and Wise (eds.), CRC Pres., Boca Raton, Fla. (1974); *Controlled Drug Bioavailability, Drug Product Design and Performance*, Smolen and Ball (eds.), Wiley, New York (1984); Ranger and Peppas, 1983, *J. Macromol. Sci. Rev. Macromol. Chem.* 23:61; see also Levy et al., 1985, *Science* 228:190; During et al., 1989, *Ann. Neurol.* 25:351; Howard et al., 1989, *J. Neurosurg.* 71:105).

In another embodiment, a controlled-release system can be placed in proximity of the target area to be treated, thus requiring only a fraction of the systemic dose (see, e.g., Goodson, in *Medical Applications of Controlled Release*, supra, vol. 2, pp. 115-138 (1984)). Other controlled-release systems discussed in the review by Langer, 1990, *Science* 249:1527-1533) may be used.

Administration of any heterodimeric protein (and/or additional agents) described herein can, independently, be one to four times daily or one to four times per month or one to six times per year or once every two, three, four or five years. Administration can be for the duration of one day or one month, two months, three months, six months, one year, two years, three years, and may even be for the life of the subject.

The dosage regimen utilizing any heterodimeric protein (and/or additional agents) described herein can be selected in accordance with a variety of factors including type, species, age, weight, sex and medical condition of the subject; the severity of the condition to be treated; the route of administration; the renal or hepatic function of the subject; the pharmacogenomic makeup of the individual; and the specific compound of the invention employed. Any heterodimeric protein (and/or additional agents) described herein can be administered in a single daily dose, or the total daily dosage can be administered in divided doses of two, three or four times daily. Furthermore, any heterodimeric protein (and/or additional agents) described herein can be administered continuously rather than intermittently throughout the dosage regimen.

Cells and Nucleic Acids

In various embodiments, the present invention provides an expression vector, comprising a nucleic acid encoding the heterodimeric protein (e.g., a heterodimeric protein comprising a first and second polypeptide chains) described herein. In various embodiments, the expression vector comprises DNA or RNA. In various embodiments, the expression vector is a mammalian expression vector.

Both prokaryotic and eukaryotic vectors can be used for expression of the heterodimeric protein. Prokaryotic vectors include constructs based on *E. coli* sequences (see, e.g., Makrides, *Microbiol Rev* 1996, 60:512-538). Non-limiting examples of regulatory regions that can be used for expression in *E. coli* include lac, trp, lpp, phoA, recA, tac, T3, T7 and $\lambda P_L$. Non-limiting examples of prokaryotic expression vectors may include the λgt vector series such as λgt11 (Huynh et al., in "DNA Cloning Techniques, Vol. I: A Practical Approach," 1984, (D. Glover, ed.), pp. 49-78, IRL Press, Oxford), and the pET vector series (Studier et al., *Methods Enzymol* 1990, 185:60-89). Prokaryotic host-vector systems cannot perform much of the post-translational processing of mammalian cells, however. Thus, eukaryotic host-vector systems may be particularly useful. A variety of regulatory regions can be used for expression of the heterodimeric proteins in mammalian host cells. For example, the SV40 early and late promoters, the cytomegalovirus (CMV) immediate early promoter, and the Rous sarcoma virus long terminal repeat (RSV-LTR) promoter can be used. Inducible promoters that may be useful in mammalian cells include, without limitation, promoters associated with the metallothionein II gene, mouse mammary tumor virus glucocorticoid responsive long terminal repeats (MMTV-LTR), the β-interferon gene, and the hsp70 gene (see, Williams et al., *Cancer Res* 1989, 49:2735-42; and Taylor et al., *Mol Cell Biol* 1990, 10:165-75). Heat shock promoters or stress promoters also may be advantageous for driving expression of the fusion proteins in recombinant host cells.

In some embodiments, expression vectors of the invention comprise a nucleic acid encoding at least the first and/or second polypeptide chains of the heterodimeric proteins (and/or additional agents), or a complement thereof, operably linked to an expression control region, or complement thereof, that is functional in a mammalian cell. The expression control region is capable of driving expression of the operably linked blocking and/or stimulating agent encoding nucleic acid such that the blocking and/or stimulating agent is produced in a human cell transformed with the expression vector.

Expression control regions are regulatory polynucleotides (sometimes referred to herein as elements), such as promoters and enhancers, that influence expression of an operably linked nucleic acid. An expression control region of an expression vector of the invention is capable of expressing operably linked encoding nucleic acid in a human cell. In an embodiment, the cell is a tumor cell. In another embodiment, the cell is a non-tumor cell. In an embodiment, the expression control region confers regulatable expression to an operably linked nucleic acid. A signal (sometimes referred to as a stimulus) can increase or decrease expression of a nucleic acid operably linked to such an expression control region. Such expression control regions that increase expression in response to a signal are often referred to as inducible. Such expression control regions that decrease expression in response to a signal are often referred to as repressible. Typically, the amount of increase or decrease conferred by such elements is proportional to the amount of signal present; the greater the amount of signal, the greater the increase or decrease in expression.

In an embodiment, the present invention contemplates the use of inducible promoters capable of effecting high level of expression transiently in response to a cue. For example, when in the proximity of a tumor cell, a cell transformed with an expression vector for the heterodimeric protein (and/or additional agents) comprising such an expression control sequence is induced to transiently produce a high level of the agent by exposing the transformed cell to an appropriate cue. Illustrative inducible expression control regions include those comprising an inducible promoter that is stimulated with a cue such as a small molecule chemical compound. Particular examples can be found, for example, in U.S. Pat. Nos. 5,989,910, 5,935,934, 6,015,709, and 6,004,941, each of which is incorporated herein by reference in its entirety.

Expression control regions and locus control regions include full-length promoter sequences, such as native promoter and enhancer elements, as well as subsequences or polynucleotide variants which retain all or part of full-length or non-variant function. As used herein, the term "functional" and grammatical variants thereof, when used in reference to a nucleic acid sequence, subsequence or fragment, means that the sequence has one or more functions of native nucleic acid sequence (e.g., non-variant or unmodified sequence).

As used herein, "operable linkage" refers to a physical juxtaposition of the components so described as to permit them to function in their intended manner. In the example of an expression control element in operable linkage with a nucleic acid, the relationship is such that the control element modulates expression of the nucleic acid. Typically, an expression control region that modulates transcription is juxtaposed near the 5' end of the transcribed nucleic acid (i.e., "upstream"). Expression control regions can also be located at the 3' end of the transcribed sequence (i.e., "downstream") or within the transcript (e.g., in an intron). Expression control elements can be located at a distance away from the transcribed sequence (e.g., 100 to 500, 500 to 1000, 2000 to 5000, or more nucleotides from the nucleic acid). A specific example of an expression control element is a promoter, which is usually located 5' of the transcribed sequence. Another example of an expression control element is an enhancer, which can be located 5' or 3' of the transcribed sequence, or within the transcribed sequence.

Expression systems functional in human cells are well known in the art, and include viral systems. Generally, a promoter functional in a human cell is any DNA sequence capable of binding mammalian RNA polymerase and initiating the downstream (3') transcription of a coding sequence into mRNA. A promoter will have a transcription initiating region, which is usually placed proximal to the 5' end of the coding sequence, and typically a TATA box located 25-30 base pairs upstream of the transcription initiation site. The TATA box is thought to direct RNA polymerase II to begin RNA synthesis at the correct site. A promoter will also typically contain an upstream promoter element (enhancer element), typically located within 100 to 200 base pairs upstream of the TATA box. An upstream promoter element determines the rate at which transcription is initiated and can act in either orientation. Of particular use as promoters are the promoters from mammalian viral genes, since the viral genes are often highly expressed and have a broad host range. Examples include the SV40 early promoter, mouse mammary tumor virus LTR promoter, adenovirus major late promoter, herpes simplex virus promoter, and the CMV promoter.

Typically, transcription termination and polyadenylation sequences recognized by mammalian cells are regulatory regions located 3' to the translation stop codon and thus, together with the promoter elements, flank the coding sequence. The 3' terminus of the mature mRNA is formed by site-specific post-translational cleavage and polyadenylation. Examples of transcription terminator and polyadenylation signals include those derived from SV40. Introns may also be included in expression constructs.

There are a variety of techniques available for introducing nucleic acids into viable cells. Techniques suitable for the transfer of nucleic acid into mammalian cells in vitro include the use of liposomes, electroporation, microinjection, cell fusion, polymer-based systems, DEAE-dextran, viral transduction, the calcium phosphate precipitation method, etc. For in vivo gene transfer, a number of techniques and reagents may also be used, including liposomes; natural polymer-based delivery vehicles, such as chitosan and gelatin; viral vectors are also suitable for in vivo transduction. In some situations, it is desirable to provide a targeting agent, such as an antibody or ligand specific for a tumor cell surface membrane protein. Where liposomes are employed, proteins which bind to a cell surface membrane protein associated with endocytosis may be used for targeting and/or to facilitate uptake, e.g., capsid proteins or fragments thereof tropic for a particular cell type, antibodies for proteins which undergo internalization in cycling, proteins that target intracellular localization and enhance intracellular half-life. The technique of receptor-mediated endocytosis is described, for example, by Wu et al., J. Biol. Chem. 262, 4429-4432 (1987); and Wagner et al., Proc. Natl. Acad. Sci. USA 87, 3410-3414 (1990).

Where appropriate, gene delivery agents such as, e.g., integration sequences can also be employed. Numerous integration sequences are known in the art (see, e.g., Nunes-Duby et al., Nucleic Acids Res. 26:391-406, 1998; Sadwoski, J. Bacteriol., 165:341-357, 1986; Bestor, Cell, 122 (3):322-325, 2005; Plasterk et al., TIG 15:326-332, 1999; Kootstra et al., Ann. Rev. Pharm. Toxicol., 43:413-439, 2003). These include recombinases and transposases. Examples include Cre (Sternberg and Hamilton, J. Mol. Biol., 150:467-486, 1981), lambda (Nash, Nature, 247, 543-545, 1974), Flp (Broach, et al., Cell, 29:227-234, 1982), R (Matsuzaki, et al., J. Bacteriology, 172:610-618, 1990), cpC31 (see, e.g., Groth et al., J. Mol. Biol. 335:667-678, 2004), sleeping beauty, transposases of the mariner family (Plasterk et al., supra), and components for integrating viruses such as AAV, retroviruses, and antiviruses having components that provide for virus integration such as the LTR sequences of retroviruses or lentivirus and the ITR sequences of AAV (Kootstra et al., Ann. Rev. Pharm. Toxicol., 43:413-439, 2003). In addition, direct and targeted genetic integration strategies may be used to insert nucleic acid sequences encoding the chimeric fusion proteins including CRISPR/CAS9, zinc finger, TALEN, and meganuclease gene-editing technologies.

In one aspect, the invention provides expression vectors for the expression of the heterodimeric proteins (and/or additional agents) that are viral vectors. Many viral vectors useful for gene therapy are known (see, e.g., Lundstrom, Trends Biotechnol., 21: 1 17, 122, 2003. Illustrative viral vectors include those selected from Antiviruses (LV), retroviruses (RV), adenoviruses (AV), adeno-associated viruses (MV), and a viruses, though other viral vectors may also be used. For in vivo uses, viral vectors that do not integrate into the host genome are suitable for use, such as a viruses and adenoviruses. Illustrative types of a viruses include Sindbis virus, Venezuelan equine encephalitis (VEE) virus, and Semliki Forest virus (SFV). For in vitro uses, viral vectors that integrate into the host genome are suitable, such as retroviruses, AAV, and Antiviruses. In one embodiment, the invention provides methods of transducing a human cell in vivo, comprising contacting a solid tumor in vivo with a viral vector of the invention.

In various embodiments, the present invention provides a host cell, comprising the expression vector comprising the heterodimeric protein described herein.

Expression vectors can be introduced into host cells for producing the present heterodimeric proteins. Cells may be cultured in vitro or genetically engineered, for example. Useful mammalian host cells include, without limitation, cells derived from humans, monkeys, and rodents (see, for example, Kriegler in "Gene Transfer and Expression: A Laboratory Manual," 1990, New York, Freeman & Co.). These include monkey kidney cell lines transformed by SV40 (e.g., COS-7, ATCC CRL 1651); human embryonic kidney lines (e.g., 293, 293-EBNA, or 293 cells subcloned for growth in suspension culture, Graham et al., *J Gen Virol* 1977, 36:59); baby hamster kidney cells (e.g., BHK, ATCC CCL 10); Chinese hamster ovary-cells-DHFR (e.g., CHO, Urlaub and Chasin, *Proc Natl Acad Sci USA* 1980, 77:4216); DG44 CHO cells, CHO-K1 cells, mouse sertoli cells (Mather, *Biol Reprod* 1980, 23:243-251); mouse fibroblast cells (e.g., NIH-3T3), monkey kidney cells (e.g., CV1 ATCC CCL 70); African green monkey kidney cells. (e.g., VERO-76, ATCC CRL-1587); human cervical carcinoma cells (e.g., HELA, ATCC CCL 2); canine kidney cells (e.g., MDCK, ATCC CCL 34); buffalo rat liver cells (e.g., BRL 3A, ATCC CRL 1442); human lung cells (e.g., W138, ATCC CCL 75); human liver cells (e.g., Hep G2, HB 8065); and mouse mammary tumor cells (e.g., MMT 060562, ATCC CCL51). Illustrative cancer cell types for expressing the fusion proteins described herein include mouse fibroblast cell line, NIH3T3, mouse Lewis lung carcinoma cell line, LLC, mouse mastocytoma cell line, P815, mouse lymphoma cell line, EL4 and its ovalbumin transfectant, E.G7, mouse melanoma cell line, B16F10, mouse fibrosarcoma cell line, MC57, and human small cell lung carcinoma cell lines, SCLC #2 and SCLC #7.

Host cells can be obtained from normal or affected subjects, including healthy humans, cancer patients, and patients with an infectious disease, private laboratory deposits, public culture collections such as the American Type Culture Collection, or from commercial suppliers.

Cells that can be used for production of the present heterodimeric proteins in vitro, ex vivo, and/or in vivo include, without limitation, epithelial cells, endothelial cells, keratinocytes, fibroblasts, muscle cells, hepatocytes; blood cells such as T lymphocytes, B lymphocytes, monocytes, macrophages, neutrophils, eosinophils, megakaryocytes, granulocytes; various stem or progenitor cells, in particular hematopoietic stem or progenitor cells (e.g., as obtained from bone marrow), umbilical cord blood, peripheral blood, fetal liver, etc. The choice of cell type depends on the type of tumor or infectious disease being treated or prevented, and can be determined by one of skill in the art.

Production and purification of Fc-containing macromolecules (such as Fc fusion proteins) has become a standardized process, with minor modifications between products. For example, many Fc containing macromolecules are produced by human embryonic kidney (HEK) cells (or variants thereof) or Chinese Hamster Ovary (CHO) cells (or variants thereof) or in some cases by bacterial or synthetic methods. Following production, the Fc containing macromolecules that are secreted by HEK or CHO cells are purified through binding to Protein A columns and subsequently 'polished' using various methods. Generally speaking, purified Fc containing macromolecules are stored in liquid form for some period of time, frozen for extended periods of time or in some cases lyophilized. In various embodiments, production of the heterodimeric proteins contemplated herein may have unique characteristics as compared to traditional Fc containing macromolecules. In certain examples, the heterodimeric proteins may be purified using specific chromatography resins, or using chromatography methods that do not depend upon Protein A capture. In other embodiments, the heterodimeric proteins may be purified in an oligomeric state, or in multiple oligomeric states, and enriched for a specific oligomeric state using specific methods. Without being bound by theory, these methods could include treatment with specific buffers including specified salt concentrations, pH and additive compositions. In other examples, such methods could include treatments that favor one oligomeric state over another. The heterodimeric proteins obtained herein may be additionally 'polished' using methods that are specified in the art. In some embodiments, the heterodimeric proteins are highly stable and able to tolerate a wide range of pH exposure (between pH 3-12), are able to tolerate a large number of freeze/thaw stresses (greater than 3 freeze/thaw cycles) and are able to tolerate extended incubation at high temperatures (longer than 2 weeks at 40 degrees C.). In other embodiments, the heterodimeric proteins are shown to remain intact, without evidence of degradation, deamidation, etc. under such stress conditions.

Subjects and/or Animals

In some embodiments, the subject and/or animal is a mammal, e.g., a human, mouse, rat, guinea pig, dog, cat, horse, cow, pig, rabbit, sheep, or non-human primate, such as a monkey, chimpanzee, or baboon. In other embodiments, the subject and/or animal is a non-mammal, such, for example, a zebrafish. In some embodiments, the subject and/or animal may comprise fluorescently-tagged cells (with e.g., GFP). In some embodiments, the subject and/or animal is a transgenic animal comprising a fluorescent cell.

In some embodiments, the subject and/or animal is a human. In some embodiments, the human is a pediatric human. In other embodiments, the human is an adult human. In other embodiments, the human is a geriatric human. In other embodiments, the human may be referred to as a patient.

In certain embodiments, the human has an age in a range of from about 0 months to about 6 months old, from about 6 to about 12 months old, from about 6 to about 18 months old, from about 18 to about 36 months old, from about 1 to about 5 years old, from about 5 to about 10 years old, from about 10 to about 15 years old, from about 15 to about 20 years old, from about 20 to about 25 years old, from about 25 to about 30 years old, from about 30 to about 35 years old, from about 35 to about 40 years old, from about 40 to about 45 years old, from about 45 to about 50 years old, from about 50 to about 55 years old, from about 55 to about 60 years old, from about 60 to about 65 years old, from about 65 to about 70 years old, from about 70 to about 75 years old, from about 75 to about 80 years old, from about 80 to about 85 years old, from about 85 to about 90 years old, from about 90 to about 95 years old or from about 95 to about 100 years old.

In other embodiments, the subject is a non-human animal, and therefore the invention pertains to veterinary use. In a specific embodiment, the non-human animal is a household pet. In another specific embodiment, the non-human animal is a livestock animal.

Kits

The invention provides kits that can simplify the administration of any agent described herein. An illustrative kit of the invention comprises any composition described herein in unit dosage form. In one embodiment, the unit dosage form is a container, such as a pre-filled syringe, which can be sterile, containing any agent described herein and a pharmaceutically acceptable carrier, diluent, excipient, or vehicle. The kit can further comprise a label or printed instructions instructing the use of any agent described herein. The kit may also include a lid speculum, topical anesthetic, and a cleaning agent for the administration location. The kit can also further comprise one or more additional agent described herein. In one embodiment, the kit comprises a container containing an effective amount of a composition of the invention and an effective amount of another composition, such those described herein.

Definitions

As used in this Specification and the appended claims, the singular forms "a," "an" and "the" include plural referents unless the context clearly dictates otherwise.

Unless specifically stated or obvious from context, as used herein, the term "or" is understood to be inclusive and covers both "or" and "and".

Unless specifically stated or obvious from context, as used herein, the term "about" is understood as within a range of normal tolerance in the art, for example within 2 standard deviations of the mean. About is understood to be within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

A stated range is understood to be any value between and at the limits of the stated range. As examples, a range between 1 and 5 includes 1, 2, 3, 4, and 5; a range between 1 and 10 includes 1, 2, 3, 4, 5, 6, 7, 8, 9, and 10; and a range between 1 and 100 includes 1, 2, 3, 4, 5, 6, 7, 8, 9, 10, 11, 12, 13, 14, 15, 16, 17, 18, 19 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100.

Unless defined otherwise, all technical and scientific terms used herein have the same meaning as commonly understood by one of ordinary skill in the art to which the invention pertains. Although other probes, compositions, methods, and kits similar, or equivalent, to those described herein can be used in the practice of the present invention, the preferred materials and methods are described herein. It is to be understood that the terminology used herein is for the purpose of describing particular embodiments only, and is not intended to be limiting.

Any aspect or embodiment described herein can be combined with any other aspect or embodiment as disclosed herein.

The invention will be further described in the following example, which does not limit the scope of the invention described in the claims.

EXAMPLES

Figure 2:
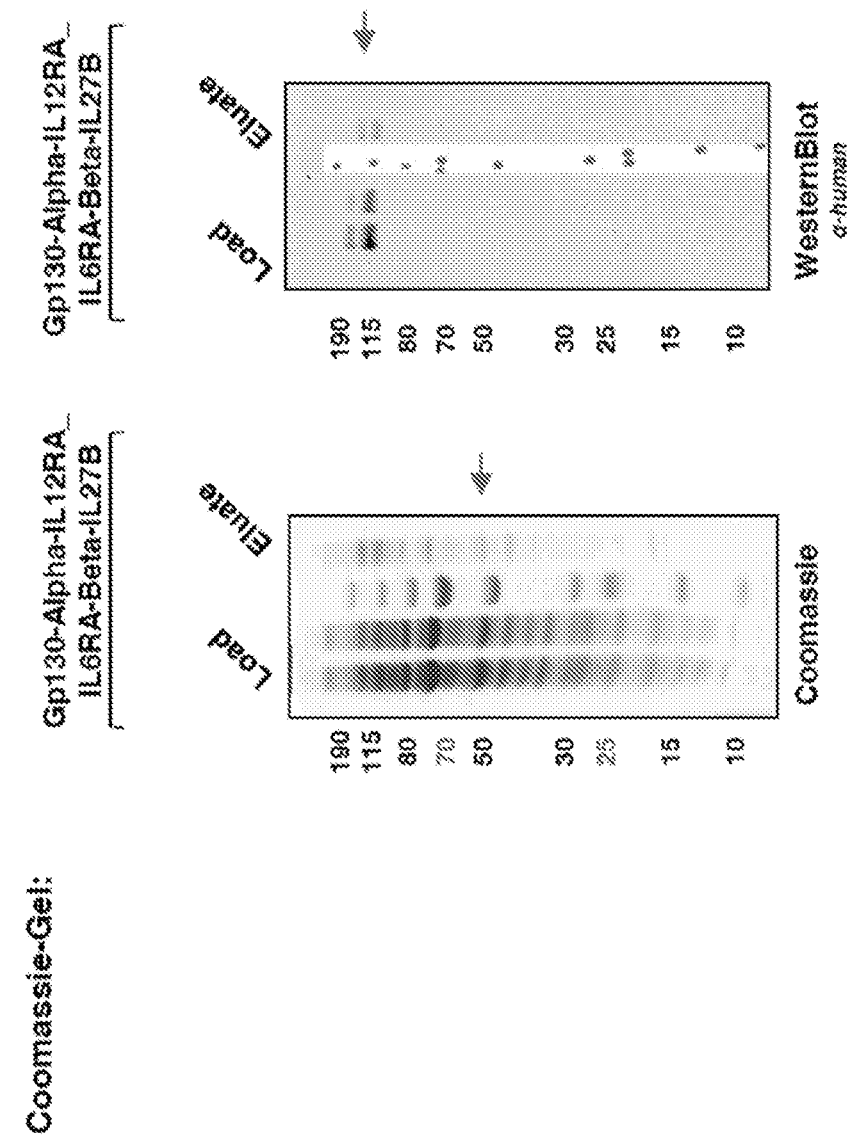
FIG. 2 provides Western blot analysis of a production run of gp130-Fc-IL12a and IL6RA-Fc-IL27β from a transient transfection culture. The secreted protein was captured using affinity chromatography and eluted from the column to obtain a protein which contains a domain recognized by a human Fc specific antibody. Because the protein was run under denaturing conditions, individual bands are visualized for the alpha and beta strands.

Example 1: Construction and Characterization of the IL-6R-Fc-IL-35 Heterodimeric Protein A heterodimeric protein comprising the IL6 receptor (IL6R) linked by a charge polarized core domain to IL-35 was constructed (see, e.g., FIG. 1). Specifically, the heterodimeric protein comprises two polypeptide chains. The first polypeptide chain comprises the IL6R subunit Gp130 linked by a charge polarized core domain to the IL-35 subunit IL12α. The second polypeptide chain comprises the IL6R subunit IL6Rα linked by a charge polarized core domain to the IL-35 subunit IL276. The IL-6R-Fc-IL-35 heterodimeric protein was expressed in mammalian cells by a dual transient transfection with both the IL6RA-Beta-IL27β and gp130-Alpha-IL12α constructs. Coomassie staining indicated the presence of expressed proteins, which were confirmed using an anti-human IgG Western blot to include proteins corresponding to the approximate molecular weights of the Alpha and Beta constructs (see, e.g., FIG. 2).

Additional analysis of the purified protein under non-reduced, reduced and reduced and deglycosylated conditions provided further evidence for assembly of the heterodimeric construct. Specifically, anti-human Fc and anti-human IL-6R staining by Western blot demonstrated the presence of a single high-molecular weight band corresponding to the approximate molecular weight of the alpha/beta heterodimer comprising IL-6R-Fc-IL-35. This heterodimer could be disassembled into the constituent alpha and beta strands under reducing conditions, which showed an apparent molecular weight higher than the predicted molecular weight based on amino acid content alone. This was expected due to the known presence of glycosylation sites, and deglycosylation of the alpha and beta strands led to those individual proteins appearing at their predicted molecular weights by Western analysis (see, e.g., FIG. 3).

Figure 3:
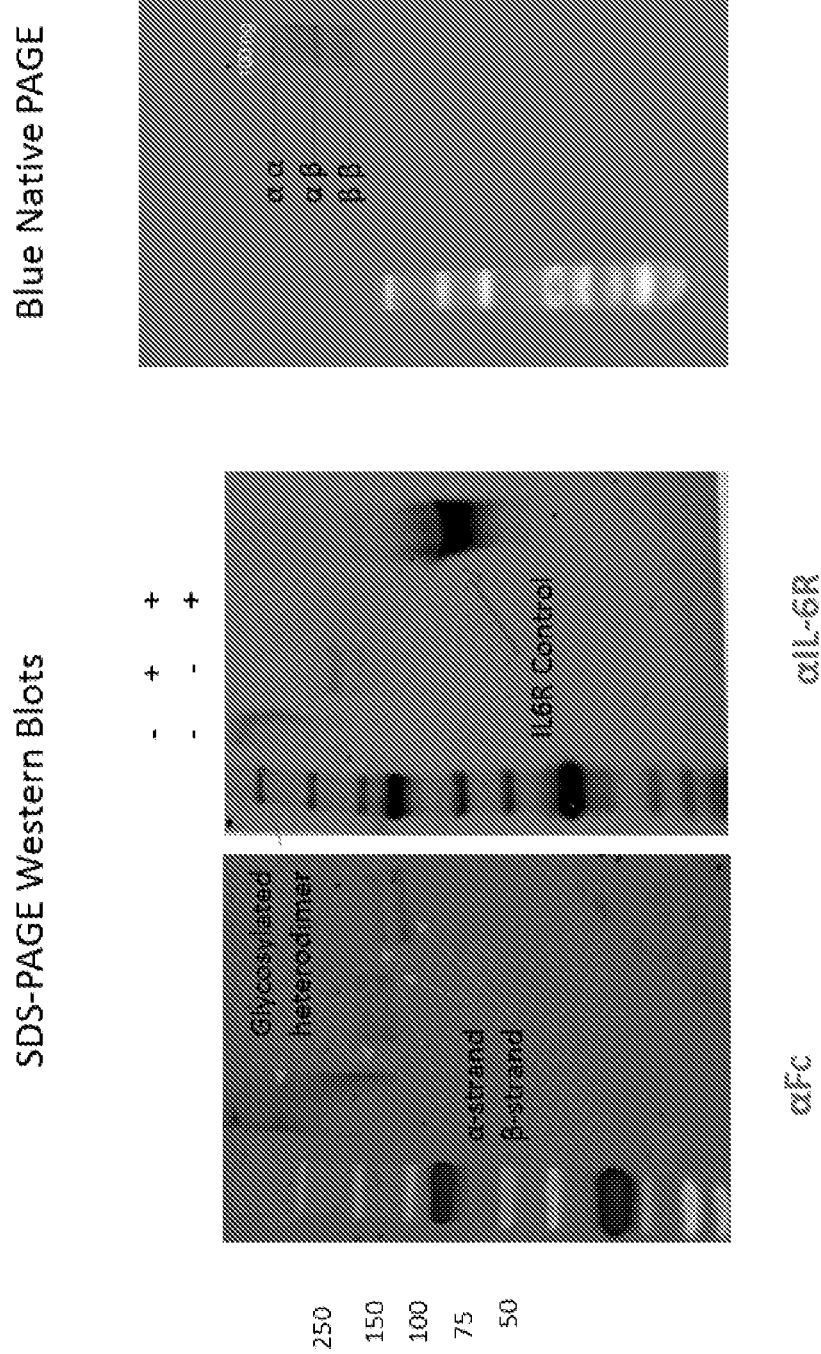
FIG. 3 provides Western blot analysis of the purified gp130-Fc-IL12α and IL6RA-Fc-IL27β heterodimeric protein. The SDS-PAGE gels (left two gels) indicated the presence of a single band at approximately 300 kDa under non-denaturing conditions (left lane beside the molecular weight ladder in each blot). This band could be separated to the constituent alpha and beta strands following incubation with beta-mercaptoethanol (middle lane in each gel), which ran at an apparent molecular weight which was higher than predicted, and potentially indicative of post-translational modifications including glycosylation. This was confirmed in the right-most lane in each gel, which indicated that the molecular weight of the alpha and beta strands decreased to the predicted molecular weight following removal of N- and O-linked glycosylations. For the gel on the right, the native PAGE gel was used to further investigate the proportion of the purified protein which existed in the alpha/beta heterodimer form as compared to the alpha/alpha or beta/beta homodimer form. The gel indicated an enrichment of the alpha/beta heterodimer to approximately 60% of the total protein in the preparation as compared to approximately 30% of the alpha/alpha homodimer and 10% of the beta/beta homodimer.
Figure 4:
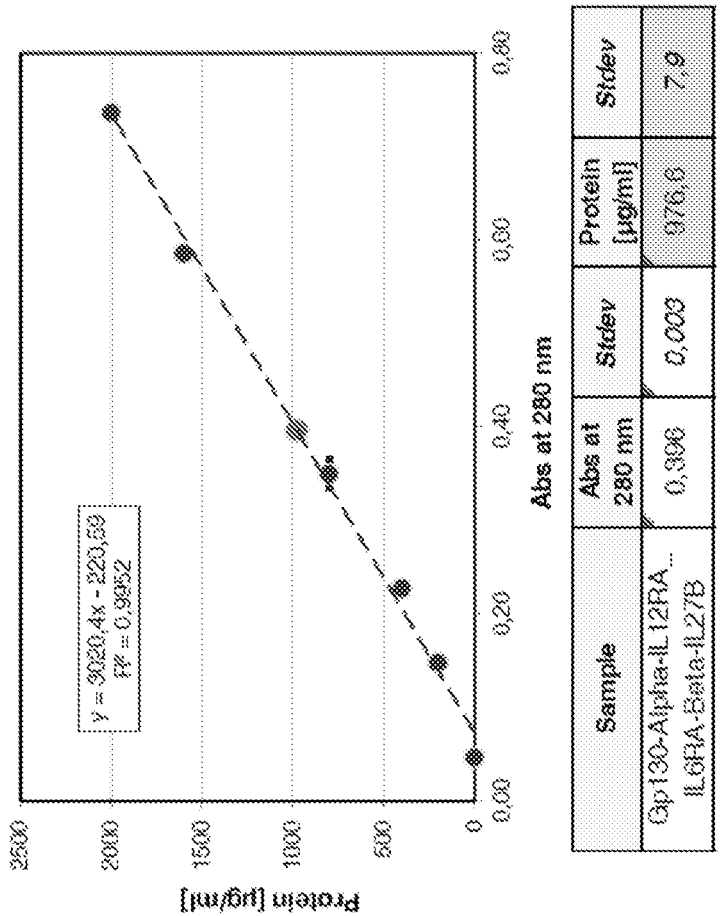
FIG. 4 depicts quantification of captured heterodimeric IL-6R-Fc-IL-35 protein using spectrophotometry.

Additionally, because the presence of SDS may disrupt any charge interactions which contribute to protein multimerization, the IL-6R-Fc-IL-35 construct was further analyzed by Blue Native PAGE. These data indicate that a majority of the secreted protein (estimated at 60%) represents the alpha/beta heterodimer (FIG. 3). The concentration of the purified IL-6R-Fc-IL-35 protein was confirmed by spectrophotometric analysis (see, e.g., FIG. 4).

Figure 5:
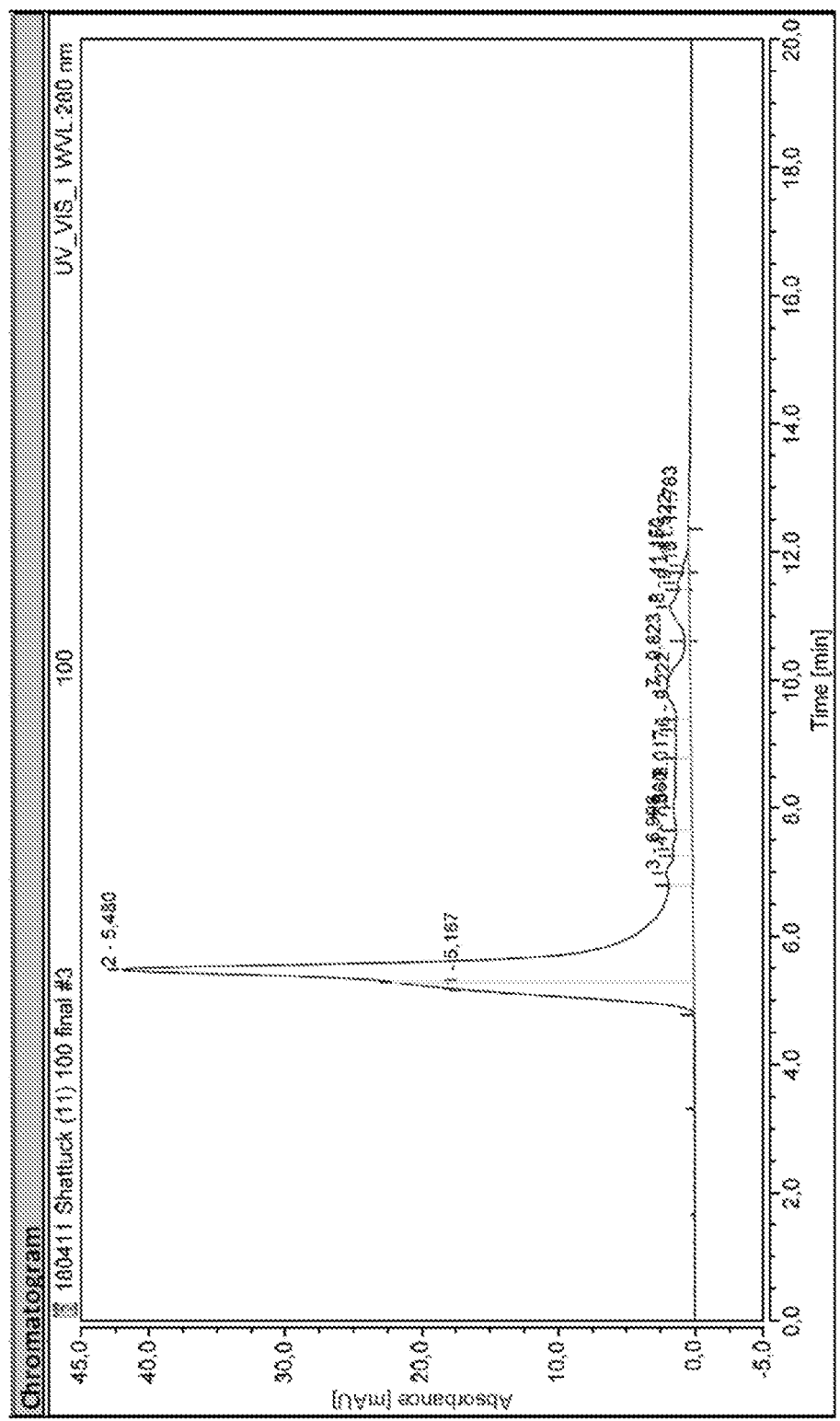
FIG. 5 provides a size-exclusion chromatography (SEC) chromatogram of the IL-6R-Fc-IL-35 construct following dual transfection of the gp130-alpha-IL12A and IL6RA-beta-IL27B constructs in CHO cells followed by purification of the secreted protein using protein A.
Figure 6:
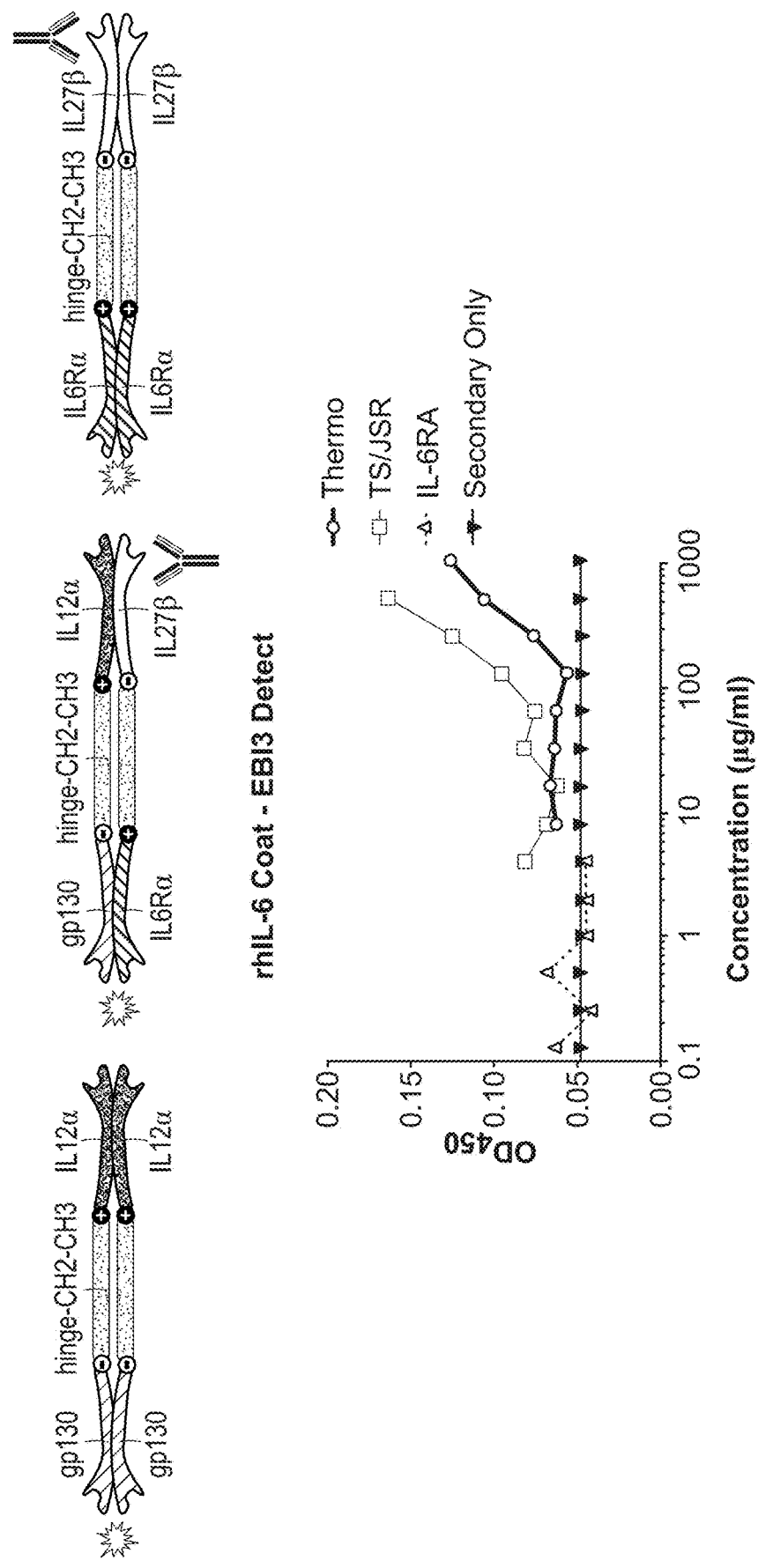
FIG. 6 provides a schematic of an ELISA assay that was developed to demonstrate that the IL-6R-Fc-IL-35 protein was capable of binding to immobilized human IL-6. Only the intended species (shown in the upper middle diagram) was expected to bind IL-6 in this assay, which could be specifically detected with an antibody against the IL-27a (EBI3) domain of the heterodimer.
Figure 7:
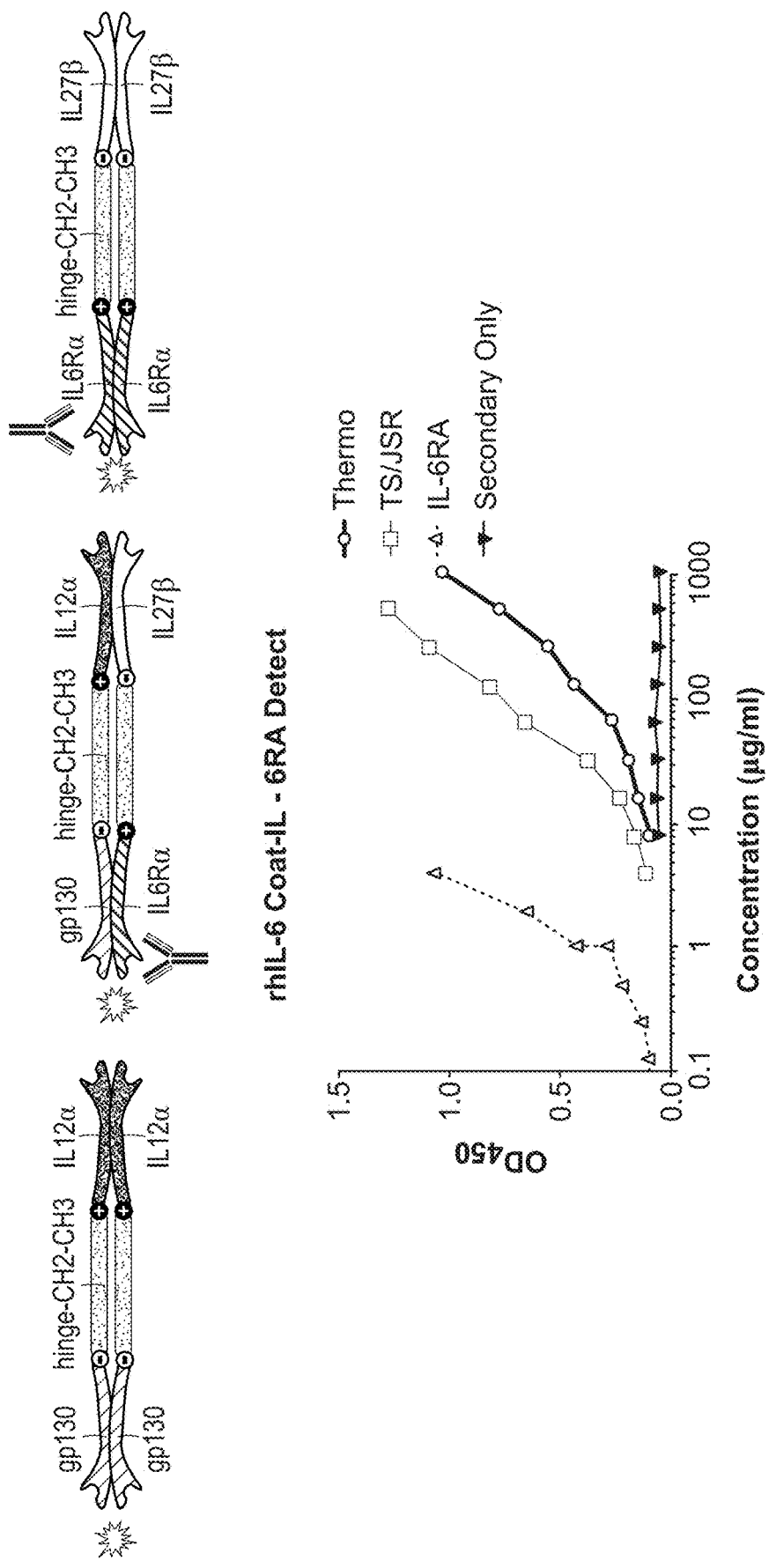
FIG. 7 provides another schematic of an ELISA assay that was developed to demonstrate that the IL-6R-Fc-IL-35 protein was capable of binding to immobilized human IL-6. The bound protein was detected using the IL-6RA domain.
Figure 8:
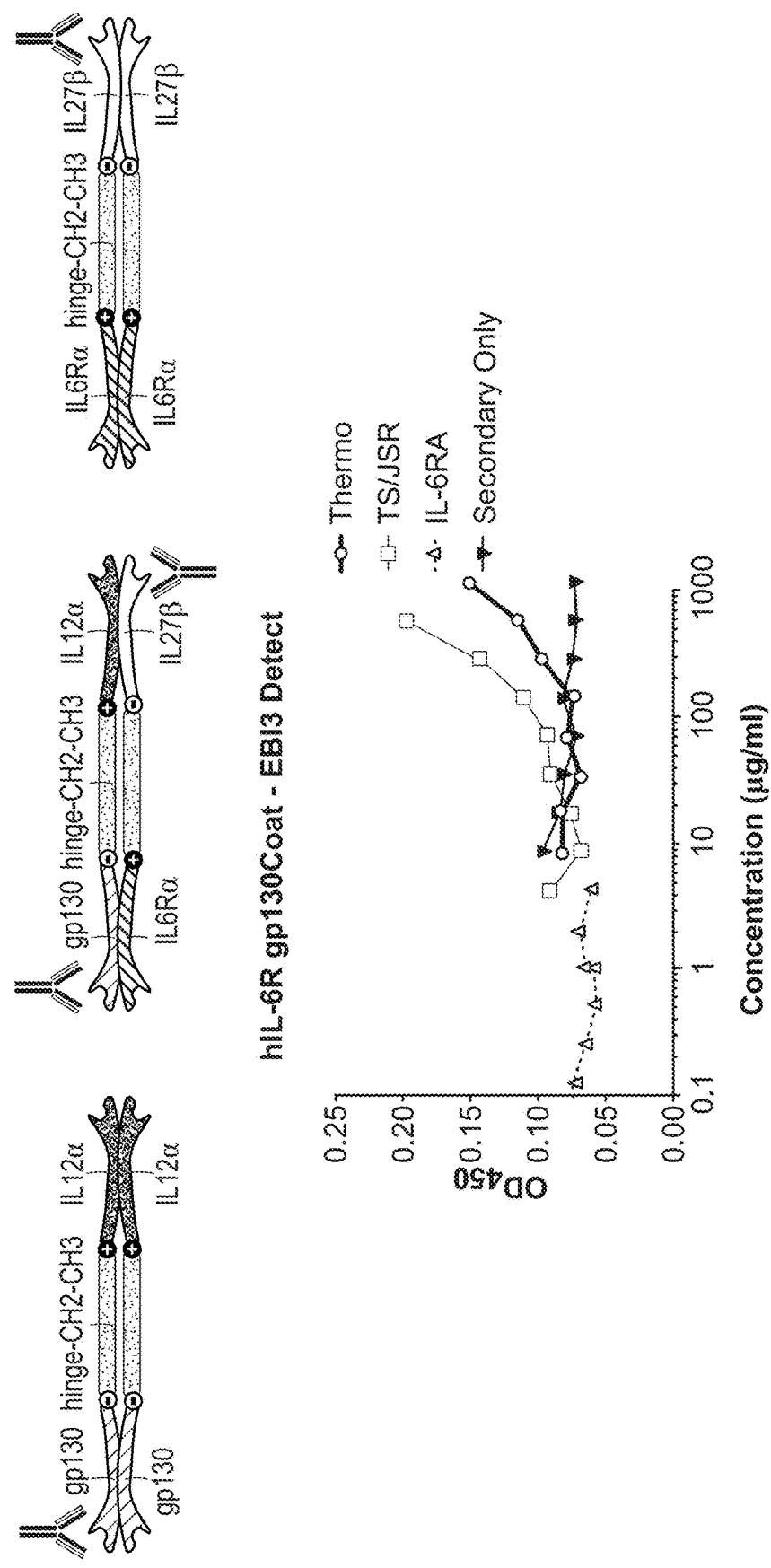
FIG. 8 provides a schematic of an ELISA assay that was developed which specifically captured an exemplary heterodimeric protein of the invention using an anti-human gp130 antibody and detected the bound protein with an anti-human IL-27a (EBI3) antibody.
Figure 9:
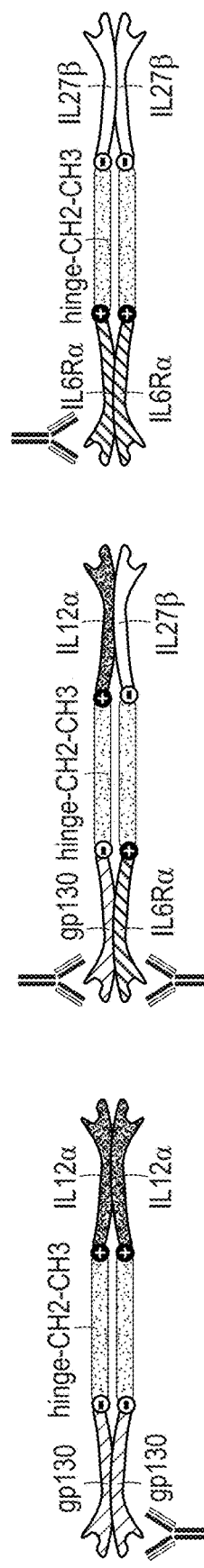
FIG. 9 provides a schematic of an ELISA assay that was developed which specifically captured an exemplary heterodimeric protein of the invention using an anti-human gp130 antibody and detected the bound protein using the IL-6RA domain.
Figure 9:
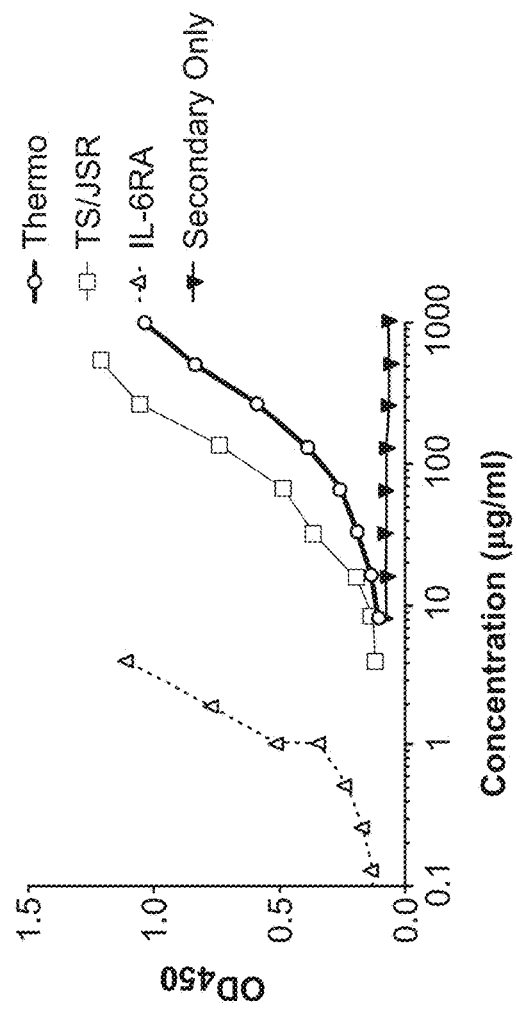
Figure 10:
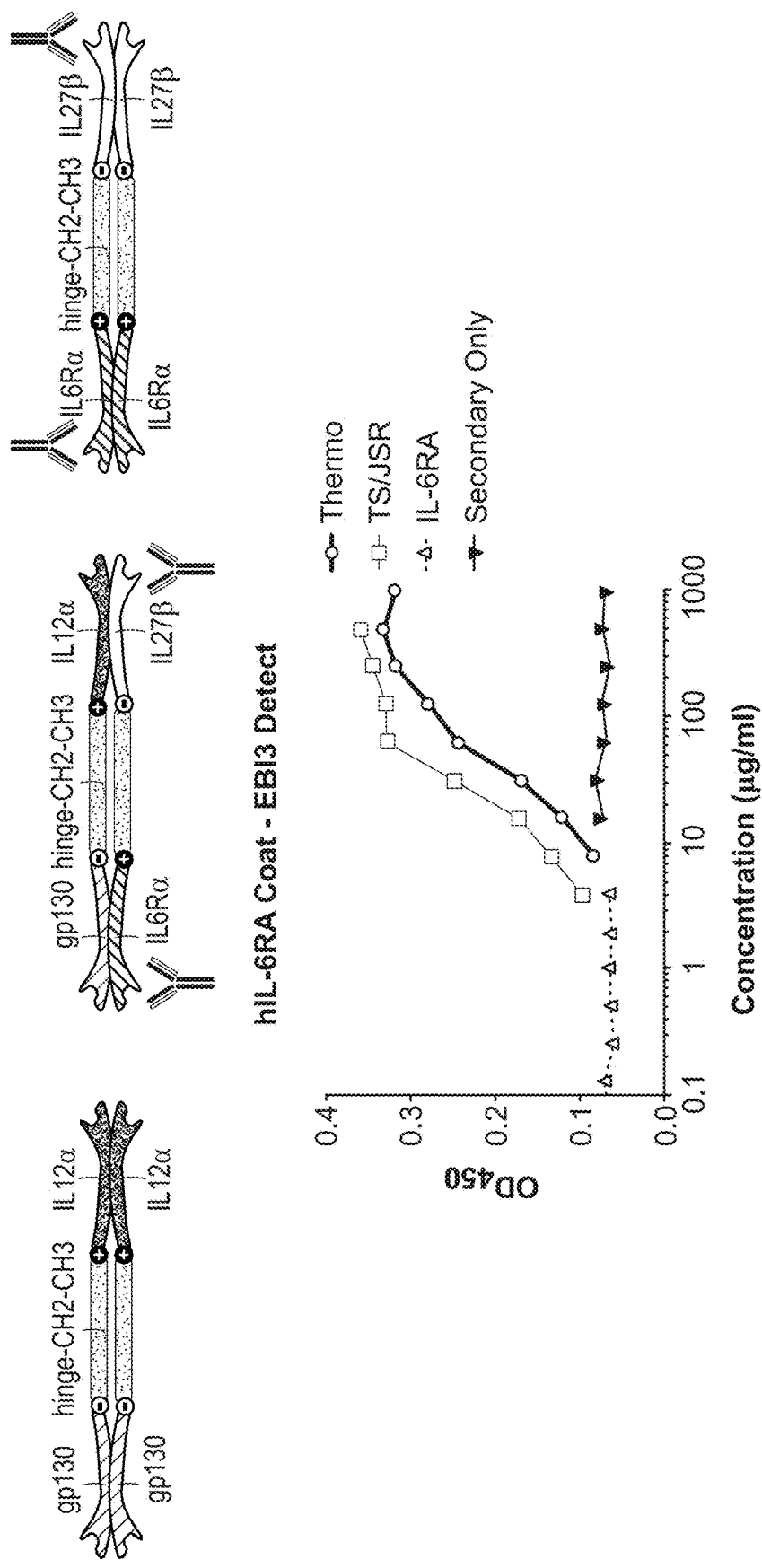
FIG. 10 provides a schematic of an ELISA assay that was developed which specifically captured an exemplary heterodimeric protein of the invention using the IL-6RA domain and detected the bound protein with an anti-human IL-27a (EBI3) antibody.
Figure 11:
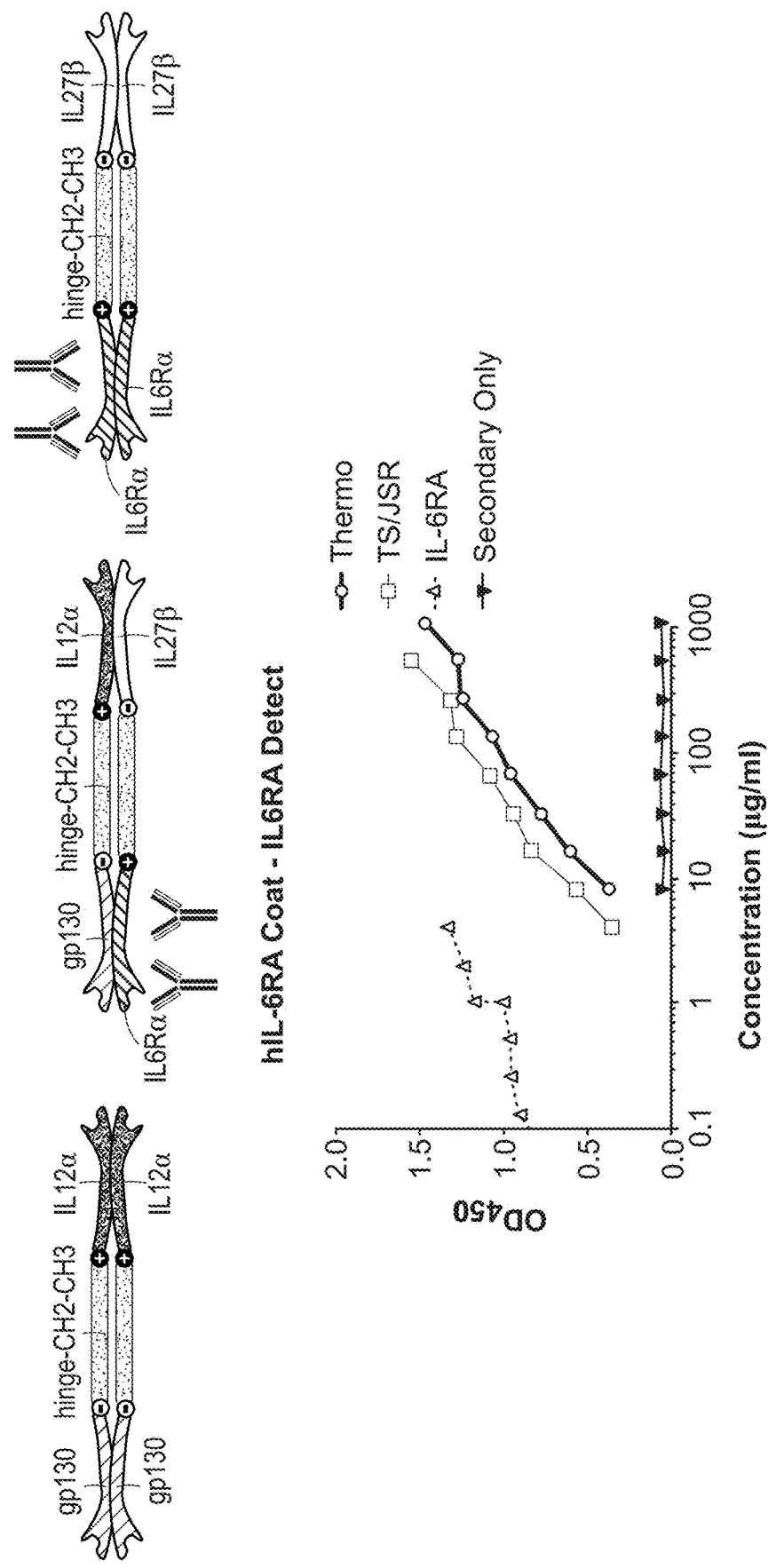
FIG. 11 provides a schematic of an ELISA assay that was developed which specifically captured an exemplary heterodimeric protein of the invention using the IL-6RA domain and detected the bound protein using the IL-6RA domain.
Figure 12:
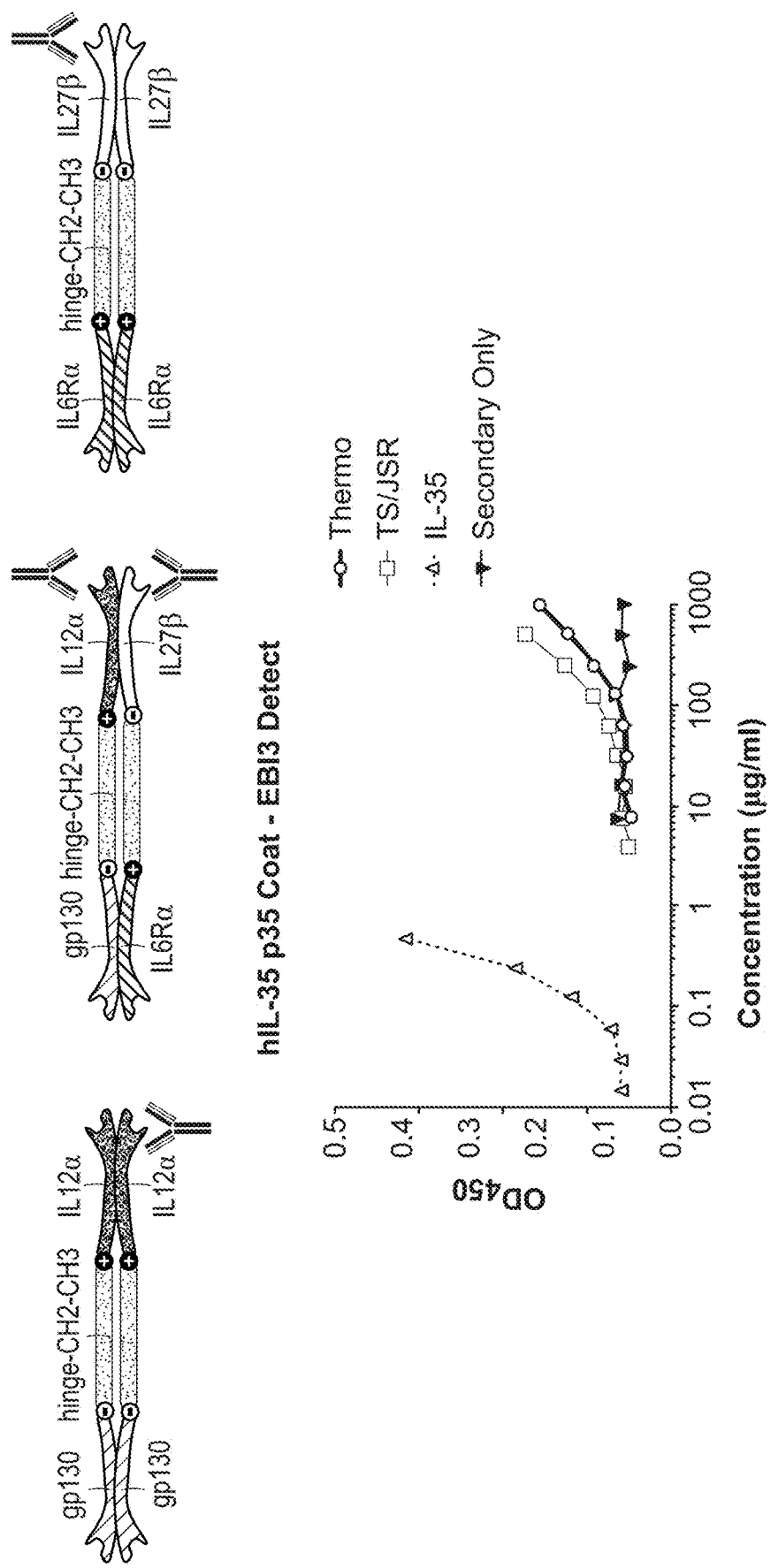
FIG. 12 provides a schematic of an ELISA assay that was developed which specifically captured an exemplary heterodimeric protein of the invention using the IL-12a p35 and detected the bound protein with an anti-human IL-27a (EBI3) antibody.
Figure 13:
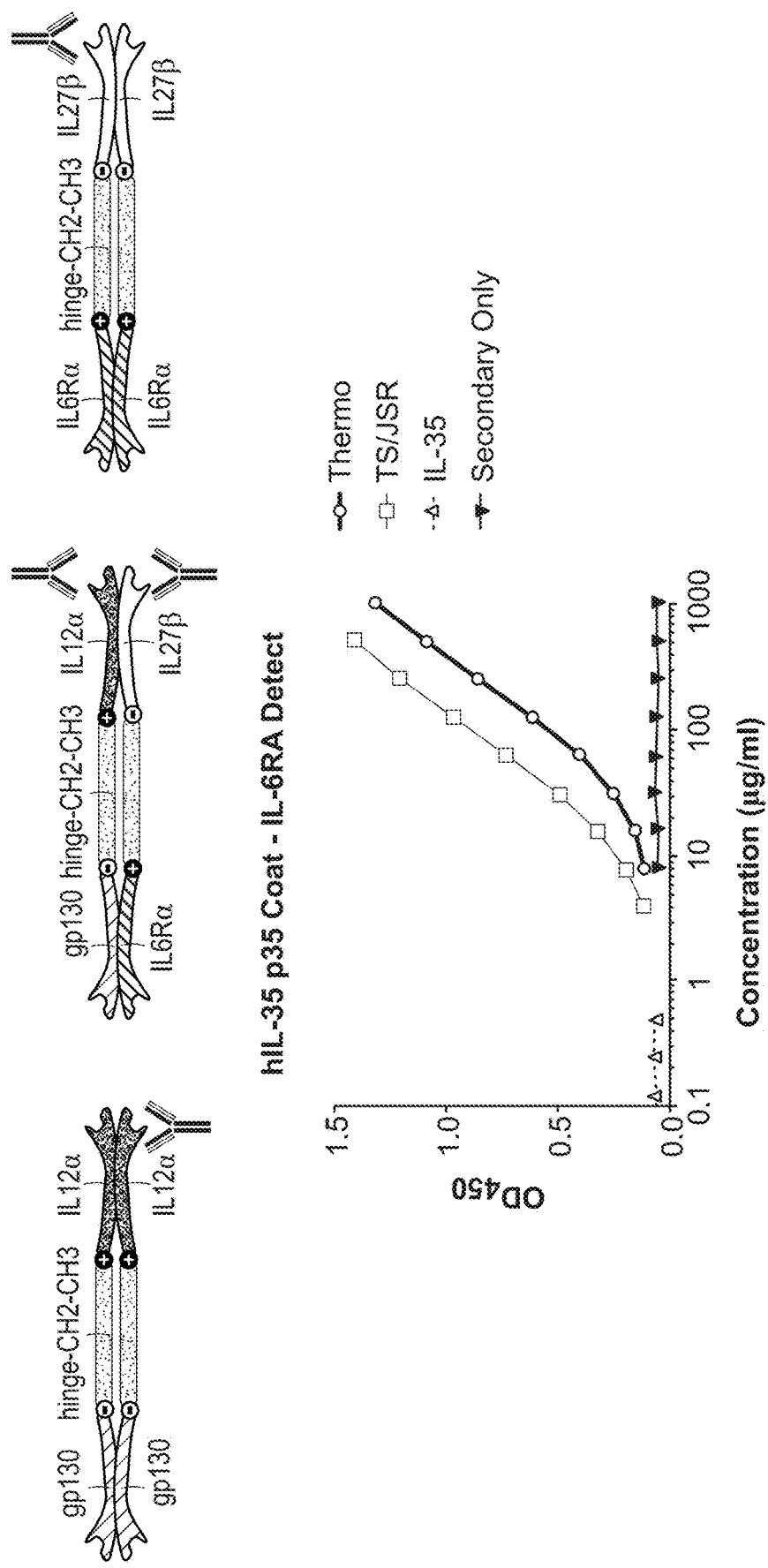
FIG. 13 provides a schematic of an ELISA assay that was developed which specifically captured an exemplary heterodimeric protein of the invention using the IL-12a p35 domain and detected the bound protein with the IL-6RA domain.
Figure 14:
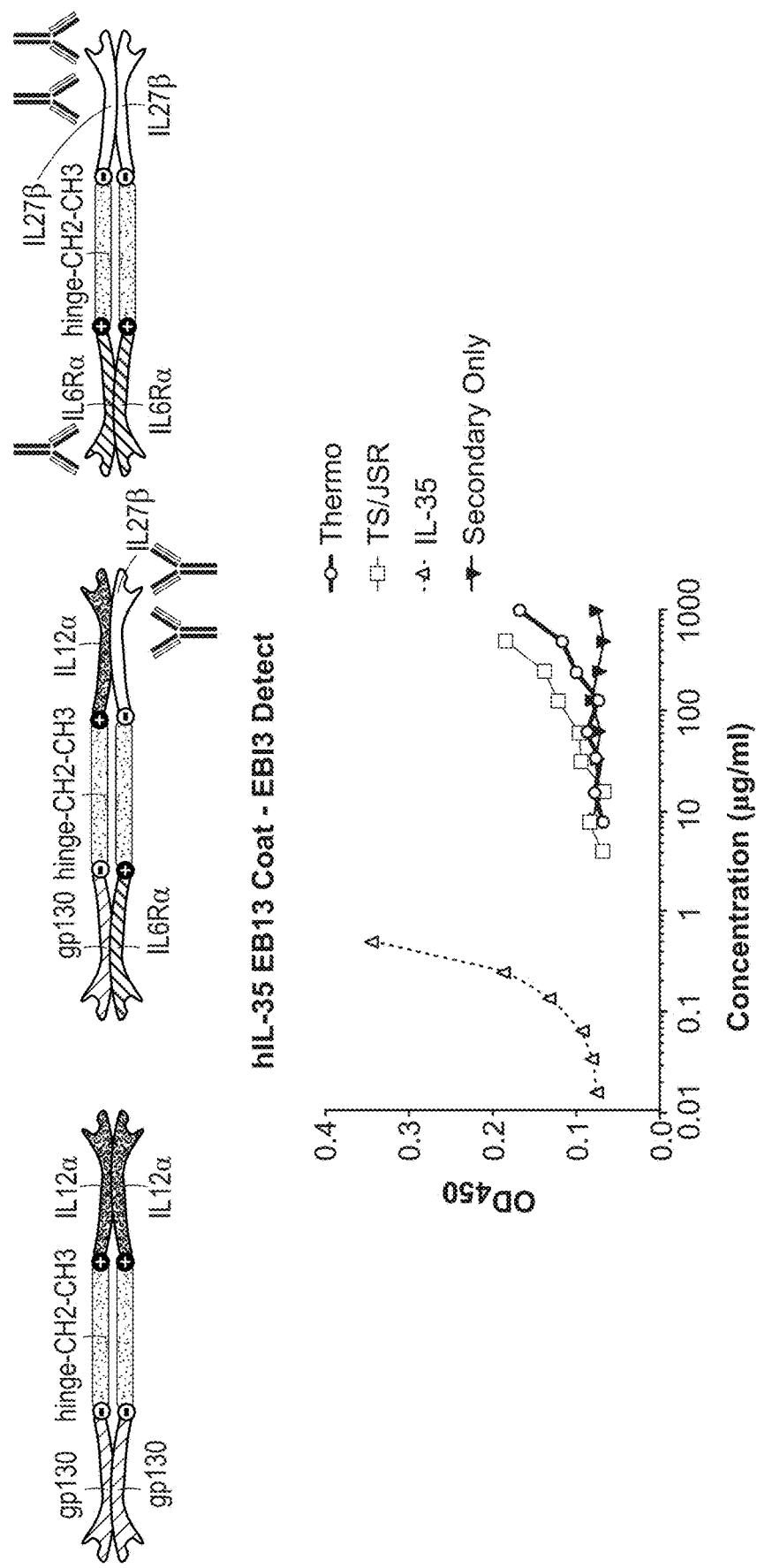
FIG. 14 provides a schematic of an ELISA assay that was developed which specifically captured an exemplary heterodimeric protein of the invention using an anti-human IL-27a (EBI3) antibody and detected the bound protein with the anti-human IL-27a (EBI3) antibody.

Size-exclusion chromatography (SEC) was performed of the IL-6R-Fc-IL-35 heterodimeric protein following dual transfection of the gp130-Fc(alpha)-IL12A and IL6RA-Fc (beta)-IL27B constructs in CHO cells followed by purification of the secreted protein using protein A. The appearance of a single peak by SEC indicated that there is likely only a single species of heterodimeric protein present, which was intended from using charge polarized linker domains (Fc-alpha and Fc-beta) in the two constructs (FIG. 5).

Figure 15:
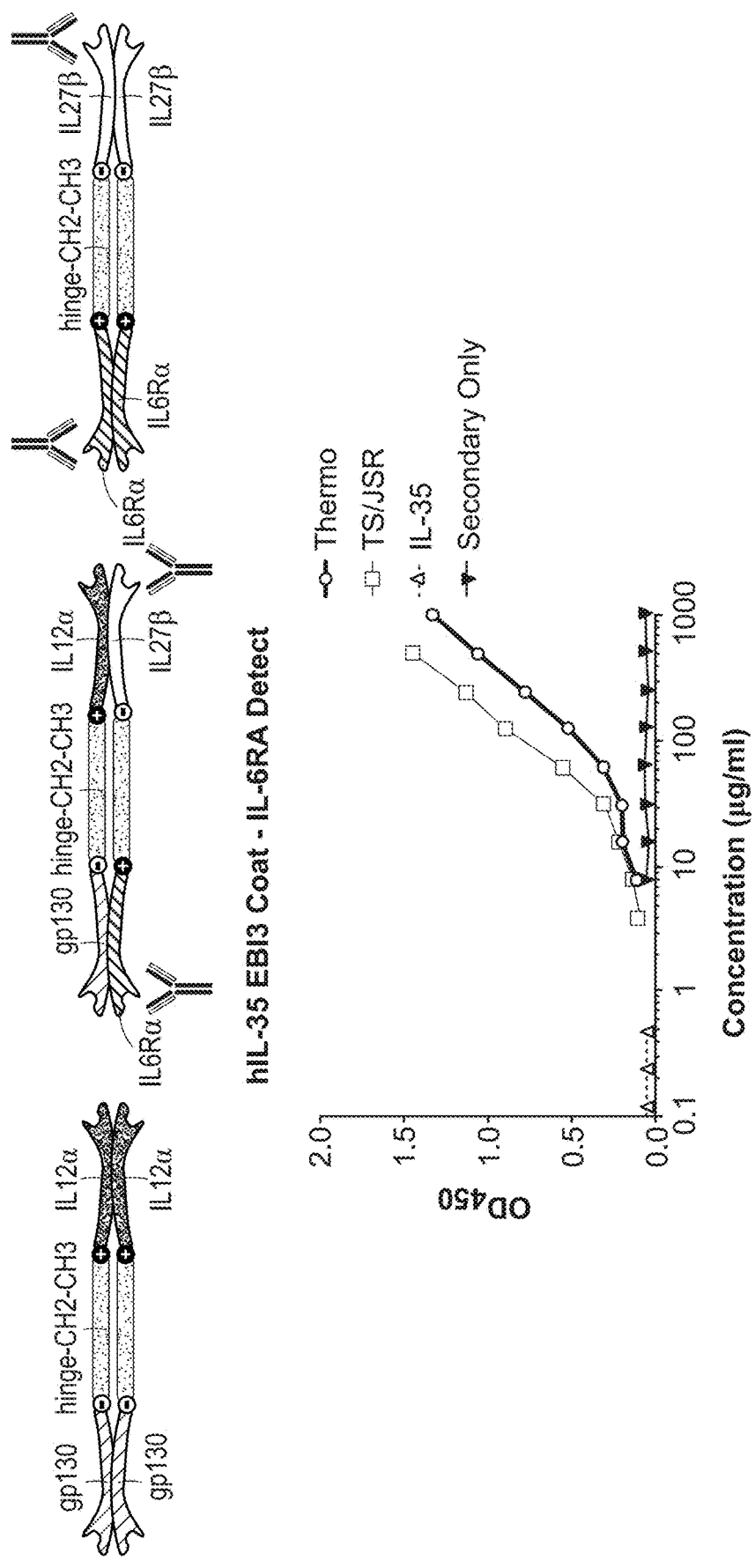
FIG. 15 provides a schematic of an ELISA assay that was developed which specifically captured an exemplary heterodimeric protein of the invention using an anti-human IL-27a (EBI3) antibody and detected the bound protein with the IL-6RA domain.

To confirm that the assembled IL-6R-Fc-IL-35 heterodimer retained the ability to engage with the cognate ligand (e.g., IL-6) and be recognized by specific antibodies against each constituent protein of the assembled heterodimer (i.e., IL-6RA, gp130, IL27(3/EBI3 and IL12α), a series of ELISA assays were performed to demonstrate the specific presence of the IL-6R-Fc-IL-35 heterodimer. In FIG. 6 to FIG. 15, the schematic of the ELISA assays is illustrated in the top portion of each figure. In the schematic, the capture and detection strategy is illustrated. In each case, the presence of the IL-6R-Fc-IL-35 heterodimer was observed through capture with recombinant IL-6 and detection with anti-IL-27B/EBI3 (FIG. 6), capture with recombinant IL-6 and detection with anti-human IL-6RA (FIG. 7), capture with anti-human gp130 and detection with anti-IL27B/EBI3 (FIG. 8), capture with anti-human gp130 and detection with anti-human IL-6RA (FIG. 9), capture with anti-IL-6RA and detection with anti-IL27B/EBI3 (FIG. 10), capture with anti-IL-6RA detection and with anti-IL-6RA (FIG. 11), capture with anti-human p35 and detection with anti-IL-27B/EBI3 (FIG. 12), capture with anti-human p35 and detection with anti-human IL-6RA (FIG. 13), capture with anti-human p35 and detection with anti-IL27B/EBI3 (FIG. 14), and capture with anti-IL27B/EBI3 and detection with anti-human IL-6RA (FIG. 15).

The sequence of an illustrative charge polarized core domain (negative-positive, i.e., "alpha core domain") is provided by SEQ ID NO: 16 and an illustrative alpha core domain comprising knob in hole mutations is provided in SEQ ID NO: 24.

The sequence of an illustrative charge polarized core domain (positive-negative, i.e., "beta core domain") is provided by SEQ ID NO: 17 and an illustrative beta core domain comprising knob in hole mutations is provided in SEQ ID NO: 25.

The sequences of the components of illustrative polypeptide chains are set forth in SEQ ID NO: 18 for the Gp130 ECD (Type 1), in SEQ ID NO: 19 for the IL-6RA ECD (Type 1), in SEQ ID NO: 20 for the IL-12a (Type 2, first part of IL-35), and in SEQ ID NO: 21 for the IL-27b (Type 2, second part of IL-35).

An illustrative Gp130-Alpha-IL12A chain had the sequence set forth in SEQ ID NO: 22, and an illustrative IL6RA-Beta-IL27B chain had the sequence set forth in SEQ ID NO: 23.

In alternate embodiment, an IL-6R-Fc-IL-35 heterodimeric protein can comprise an IL6RA-Alpha-IL12α chain (SEQ ID NO: 34) and a Gp130-Beta-IL27b chain (SEQ ID NO: 35).

Example 2: Further Characterization of the IL-6R-Fc-IL-35 Heterodimeric Protein

Figure 16B:
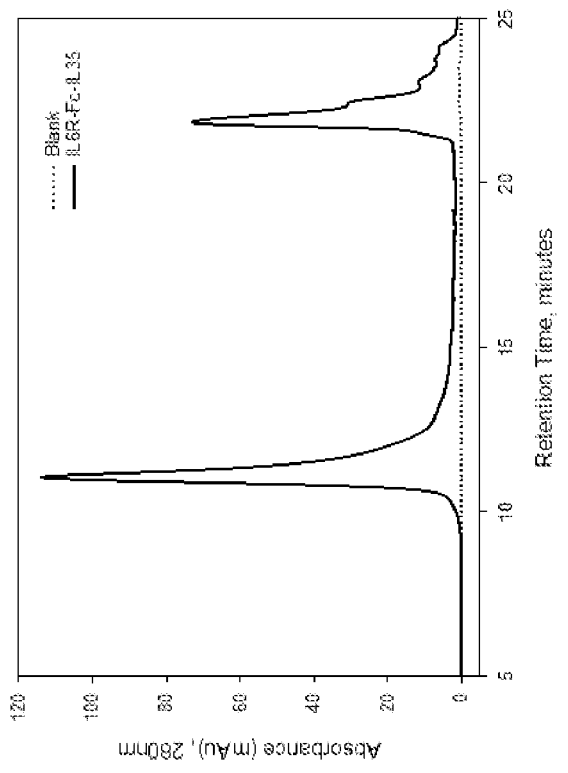
FIG. 16A and FIG. 16B provide size-exclusion chromatography (SEC) chromatogram of the IL-6R-Fc-IL-35 heterodimeric protein IL-6R-Fc-IL-35.
Figure 16A:
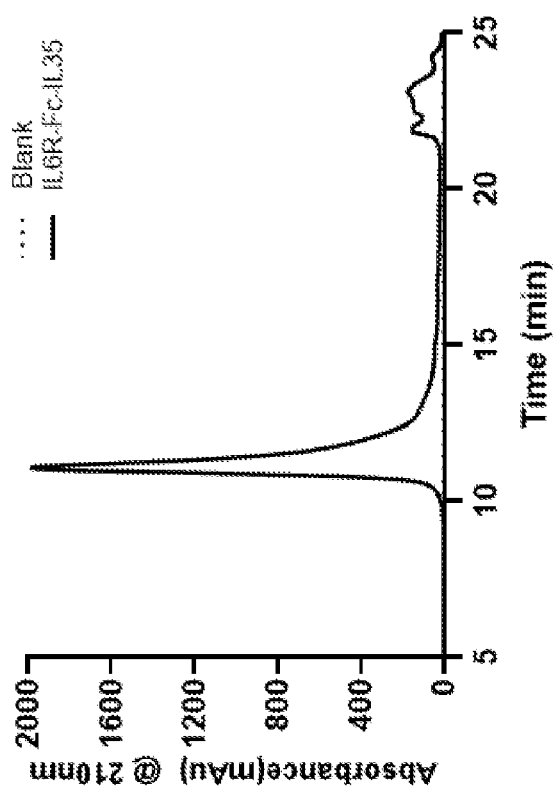

Size-exclusion chromatography (SEC) was performed with the IL-6R-Fc-IL-35 heterodimeric protein. The appearance of a single peak by SEC, with an absorbance wavelength of 210 nm, indicated that there is likely only a single species of protein present, which was intended from using charge polarized linker domains (Fc-alpha and Fc-beta) in the two constructs (FIG. 16A). Interestingly, SEC with an absorbance wavelength of 280 nm showed a second, lower molecular weight band (FIG. 16B).

IL-6R-Fc-IL-35 heterodimeric protein was then used in an IL-6 SINK Assay. Here, the ability of the IL-6R-Fc-IL-35 heterodimeric protein to sequester IL6 was tested. Cultures of DS-1 cells, a B cell line that is dependent on exogenous IL6 for survival, was incubated with the IL-6R-Fc-IL-35 heterodimeric protein and in the presence of exogenous IL6. When the DS-1 cells are not exposed to IL6, cell death results. Thus, these experiments were conducted to determine if the IL-6R-Fc-IL-35 heterodimeric protein can sequester IL6 and lead to DS-1 cell death.

DS-1 cells were cultured in the presence of IL-6R-Fc-IL-35 at increasing molar ratios to IL-6 for 24 hours. Cell death was measured by caspase 3/7 activity (with a luciferase readout).

Figure 17:
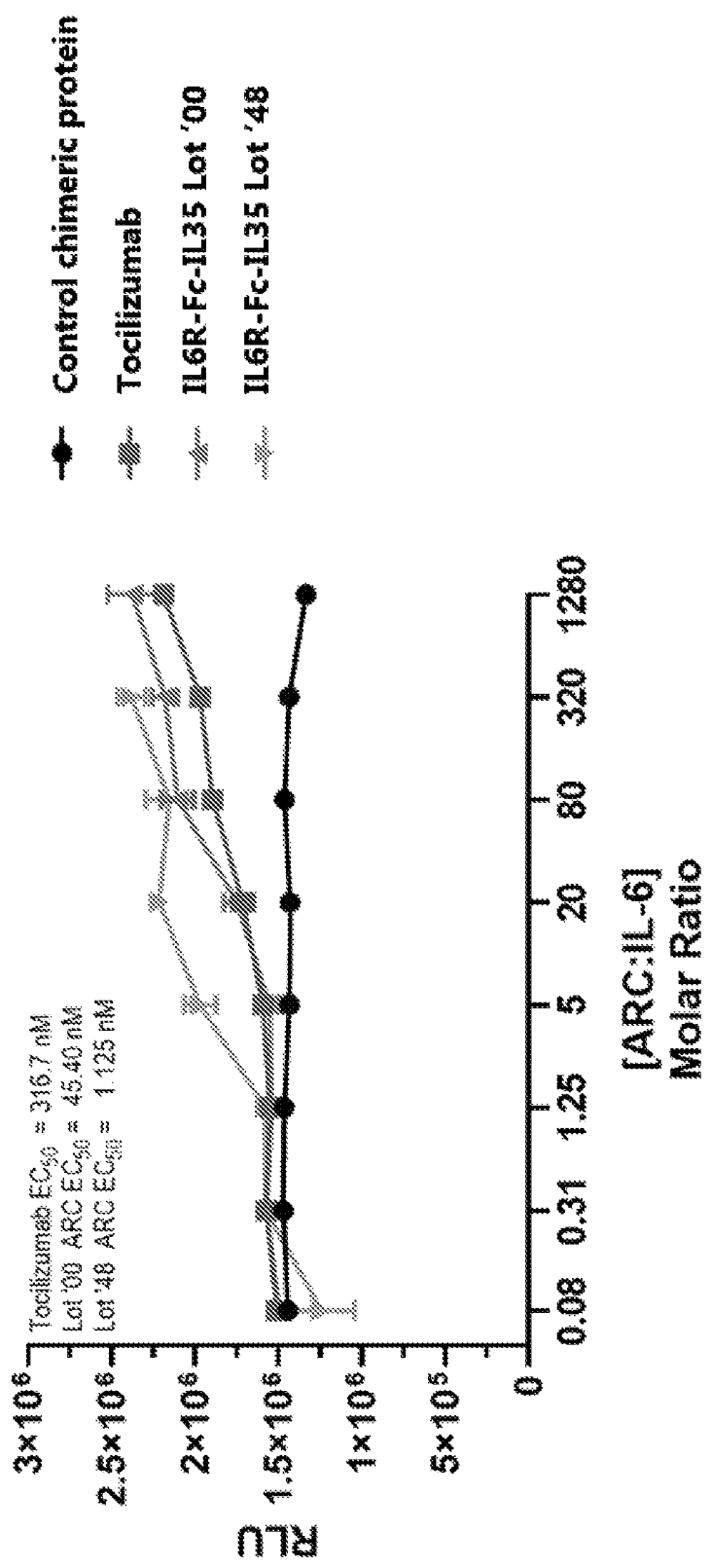
FIG. 17 is a graph showing the results of an IL-6 SINK Assay using the IL-6R-Fc-IL-35 heterodimeric protein.

FIG. 17 shows that IL-6R-Fc-IL-35 heterodimeric protein (identified as Lot '00 and Lot '48) are able to induce cell death in DS-1 cells. Indeed, depending on the lot used, the heterodimeric protein showed between 7 and 281 times greater sequestering of IL-6 than Tocilizumab (an anti-human IL-6 receptor monoclonal antibody which blocks DS-1's binding to IL6) depending on the lot used.

The functionality of IL-6R-Fc-IL-35 heterodimeric protein was then tested. IL-35 has been reported to induce an atypical regulatory phenotype in CD4 T Cells, which is characterized by little or no FoxP3 production coupled with production of IL-35. Additionally, IL-35 is known to turn off TGF-β and IL-10 production.

Figure 18:
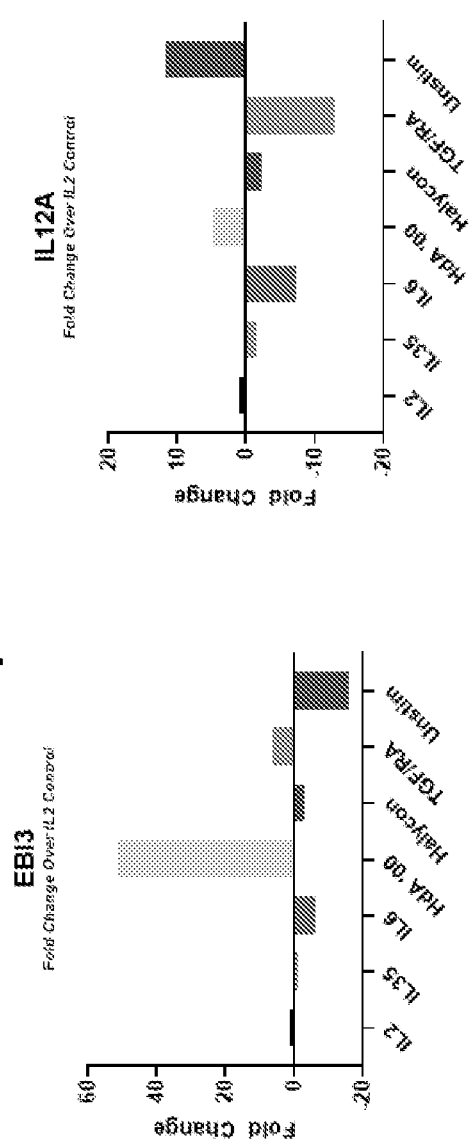
FIG. 18 includes graph showing the ability of the IL-6R-Fc-IL-35 heterodimeric protein (identified as HdA '00) to induce at least IL-35. The condition "Halycon" refers to treatments with a control chimeric protein.
Figure 18:
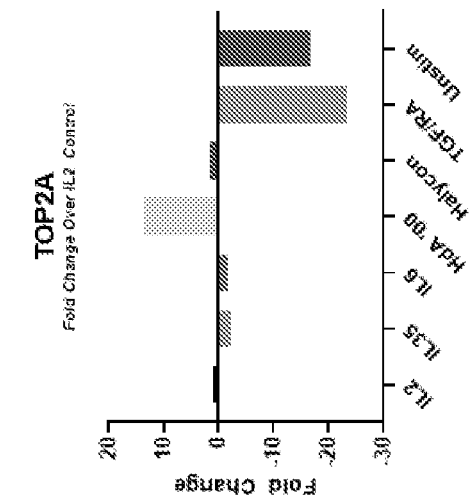
Figure 18:
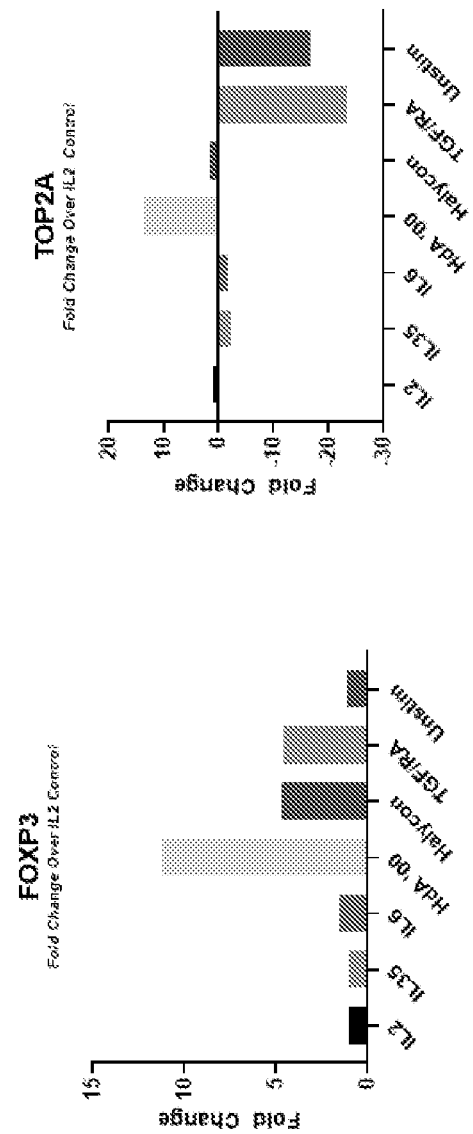
Figure 18:
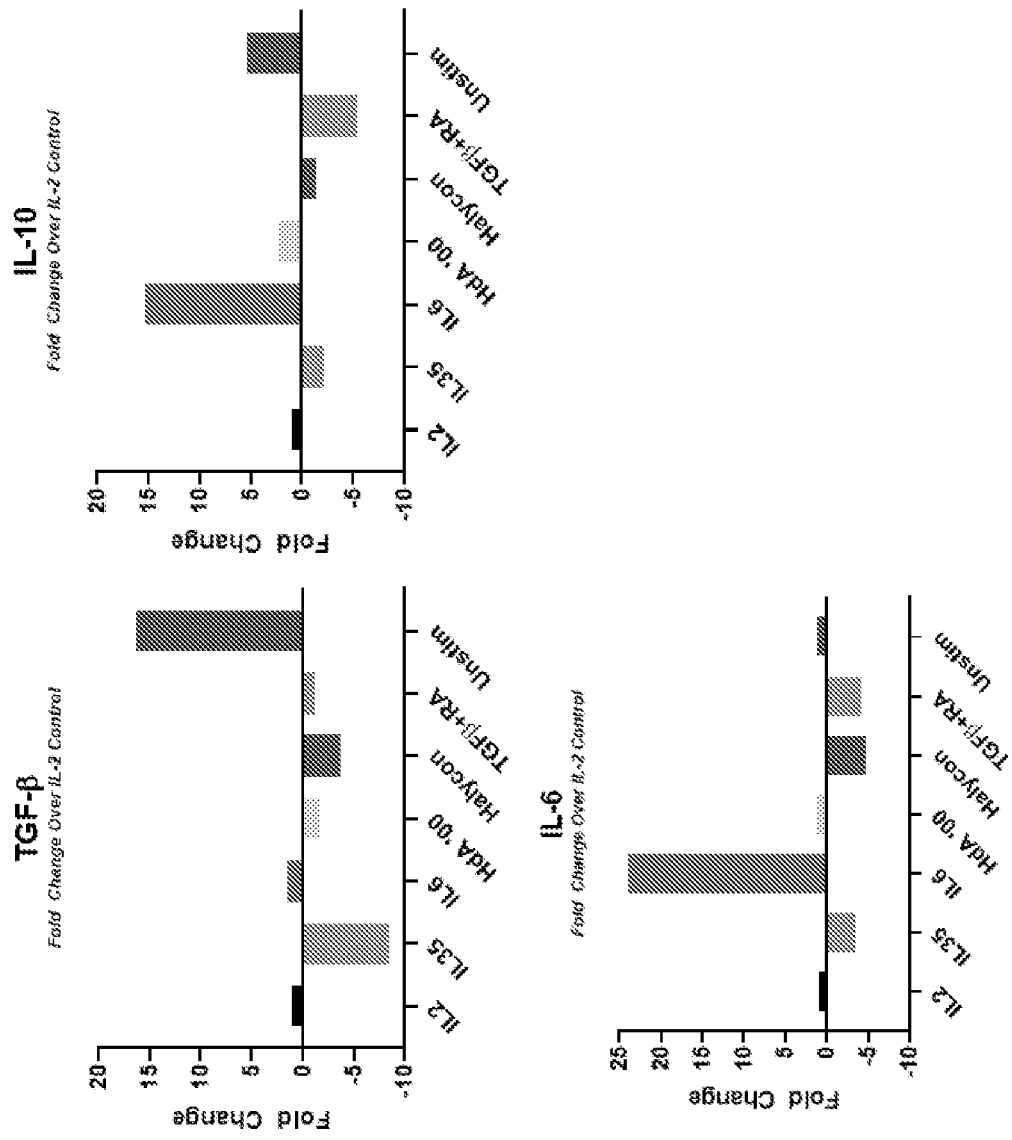

Here, magnetically enriched human naïve CD4 T cells were isolated from a single donor and activated with αCD3/αCD28 beads and cultured for 5 days in the presence of the indicated agent (shown in FIG. 18). Total mRNA was isolated and RT-qPCR performed.

FIG. 18 shows that the IL-6R-Fc-IL-35 heterodimeric protein (identified as HdA '00) induces IL-35 (which is a dimer of EBI3 and IL12A) production. Surprisingly, the heterodimeric protein also increases production of FoxP3. Moreover, the IL-6R-Fc-IL-35 heterodimeric protein was permissive for cell proliferation, unlike the other treated agents. Although, IL-35 is known to turn off TGF-β and IL-10 production, the IL-6R-Fc-IL-35 heterodimeric protein resulted in detectable levels of IL-10 production (2× over control). Finally, the heterodimeric protein has no notable impact on IL-6 production.

Figure 19A:
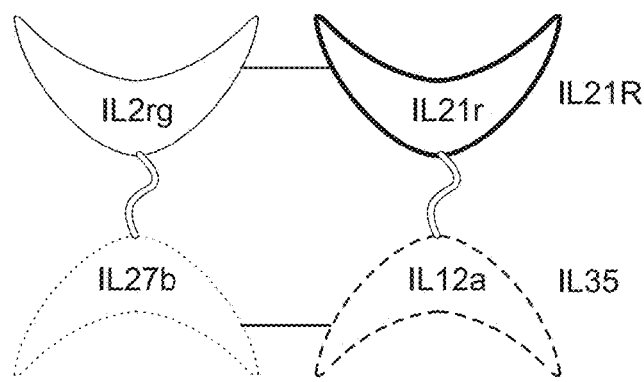
FIG. 19A shows a schematic of the IL-21R-Fc-IL-35 heterodimeric protein comprising a IL-21r-Fc(alpha)-IL12a chain and a IL2rg-Fc(beta)-IL27B chain.

Example 3: Construction and Characterization of the IL-21R-Fc-IL-35 Heterodimeric Protein Constructs encoding an IL21r-Alpha-IL12a chain and an IL2rg-Beta-IL27B chain were dual transfected into CHO cells, followed by purification of the secreted protein using protein A. When an IL21r-Alpha-IL12a chain and an IL2rg-Beta-IL27B chain are combined (within a cell or in vitro), they form a heterodimeric protein referred to herein as IL-21R-Fc-IL-35. (FIG. 19A).

Figure 19B:
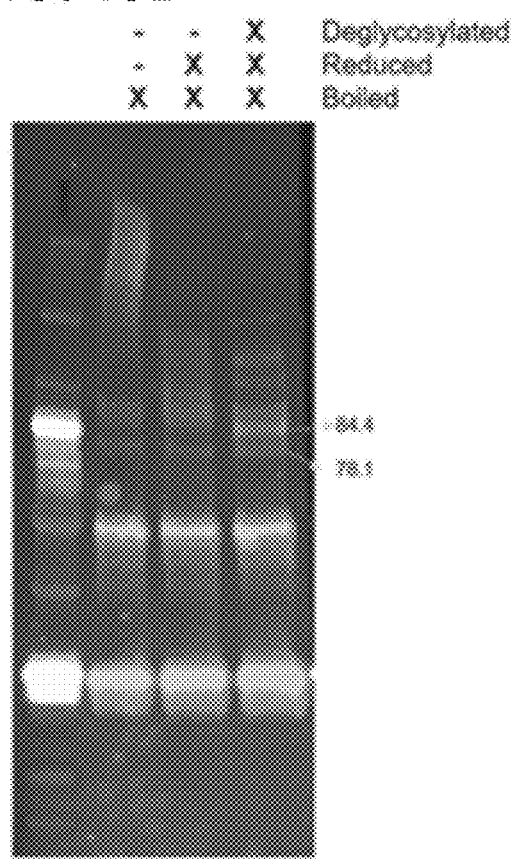
FIG. 19B shows an SDS-PAGE gel indicating the presence of two single bands at approximately 84.4 kDa and 78.1 kDa under reduced deglycosylated conditions (right-most lane).

Western blots were performed on expressed heterodimeric proteins. These revealed, under denaturing and deglycosylated conditions, bands corresponding to the predicted molecular weights of the IL21r-Alpha-IL12α chain and the IL2rg-Beta-IL27B chain (FIG. 19B).

Figure 20:
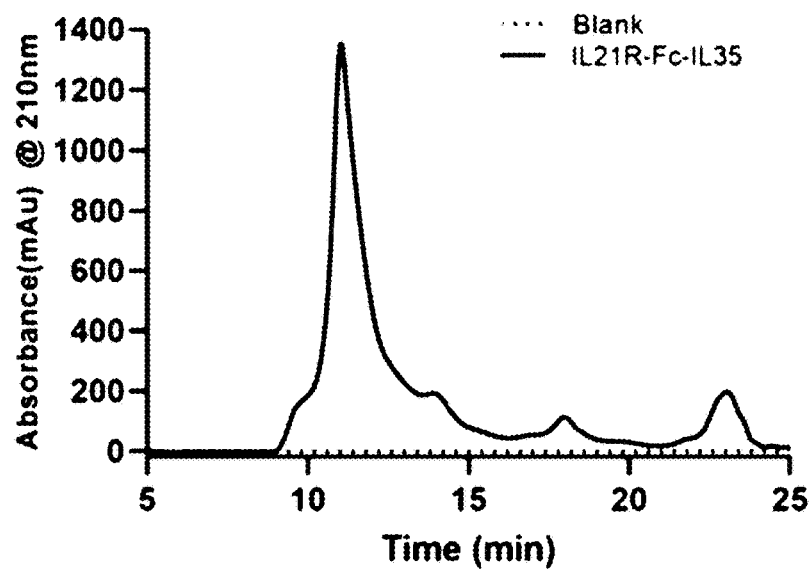
FIG. 20 provides a size-exclusion chromatography (SEC) chromatogram of the IL-21R-Fc-IL-35 IFNγR-Fc-IL-35 heterodimeric protein following dual transfection of the IL-21r-Fc(alpha)-IL12a and IL2rg-Fc(beta)-IL27B constructs in CHO cells followed by purification of the secreted protein using protein A.

Size-exclusion chromatography (SEC) was performed with the IL-21R-Fc-IL-35 heterodimeric protein. The appearance of a single peak by SEC indicated that there is likely only a single species of protein present, which was intended from using charge polarized linker domains (Fc-alpha and Fc-beta) in the two constructs (FIG. 20).

In these experiments, an illustrative charge polarized core domain (negative-positive, i.e., "alpha core domain") sequence is provided by SEQ ID NO: 16 and an illustrative alpha core domain comprising knob in hole mutations is provided in SEQ ID NO: 24. An illustrative charge polarized core domain (positive-negative, i.e., "beta core domain") sequence is provided by SEQ ID NO: 17 and an illustrative beta core domain comprising knob in hole mutations is provided in SEQ ID NO: 25.

The sequences of the components of illustrative polypeptide chains used in this example are set forth in SEQ ID NO: 26 for the extracellular domain of IL-21r, in SEQ ID NO: 27 for the extracellular domain of IL2RG, in SEQ ID NO: 20 for the IL-12a, and in SEQ ID NO: 21 for the IL-27b. An illustrative IL21r-Alpha-IL12a chain had the sequence set forth in SEQ ID NO: 28, and an illustrative IL2rg-Beta-IL27B chain had the sequence set forth in SEQ ID NO: 29.

In alternate embodiment, an IL-21R-Fc-IL-35 heterodimeric protein can comprise an IL2rg-Alpha-IL27B chain (SEQ ID NO: 36) and an IL21r-Beta-IL12a chain (SEQ ID NO: 37).

Example 4: Construction and Characterization of the IFNγR-Fc-IL-35 Heterodimeric Protein Constructs encoding an IFNgR-Alpha-IL12a chain and an IFNGR2-Beta-IL27B chain were dual transfected into CHO cells, followed by purification of the secreted protein using protein A. When an IFNgR-Alpha-IL12α chain and an IFNGR2-Beta-IL27B chain are combined (within a cell or in vitro), they form a heterodimeric protein referred to herein as IFNγR-Fc-IL-35.

Figure 21:
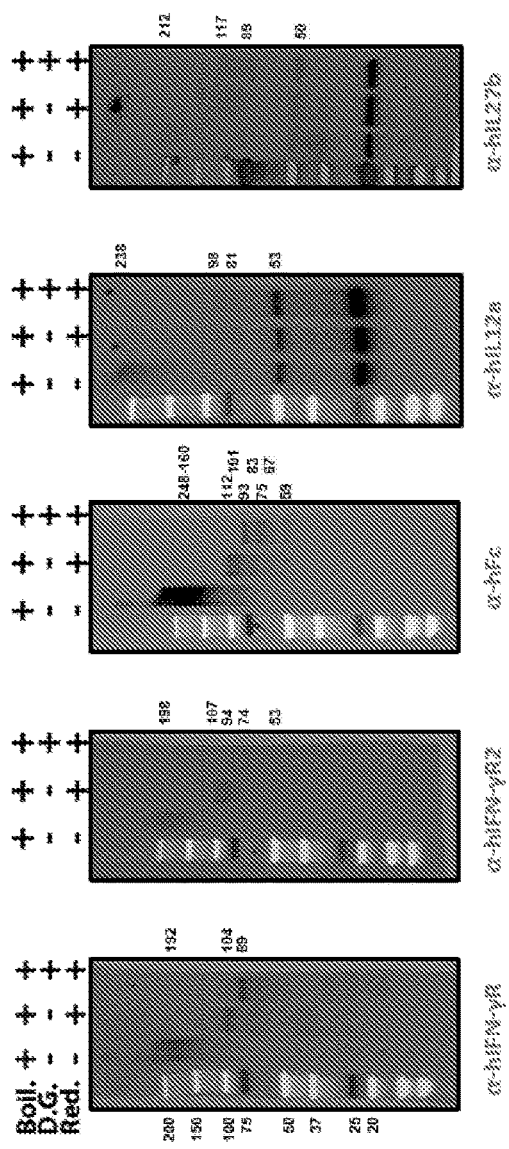
FIG. 21 are western blot analyses of the IFNγR-Fc-IL-35 heterodimeric protein comprising the IFNgR-Alpha-IL12a chain and the IFNGR2-Beta-IL27B chain probed with an antibody indicated below each blot. The proteins were run under non-denaturing conditions (left lane beside the molecular weight ladder in each blot), denaturing conditions with beta-mercaptoethanol treatment (middle lane in each gel), and both denaturing and deglycosylation treatments.

Western blots were performed on the IFNγR-Fc-IL-35 heterodimeric protein comprising the IFNgR-Alpha-IL12α chains and the hIFNGR2-Beta-IL27B chain probed with an antibody indicated below each blot. These revealed, under denaturing and deglycosylated conditions, bands corresponding to the predicted molecular weights of the IFNgR-Alpha-IL12α and the hIFNGR2-Beta-IL27B (FIG. 21). Bands noted in yellow highlighting are non-specific bands.

Figure 22:
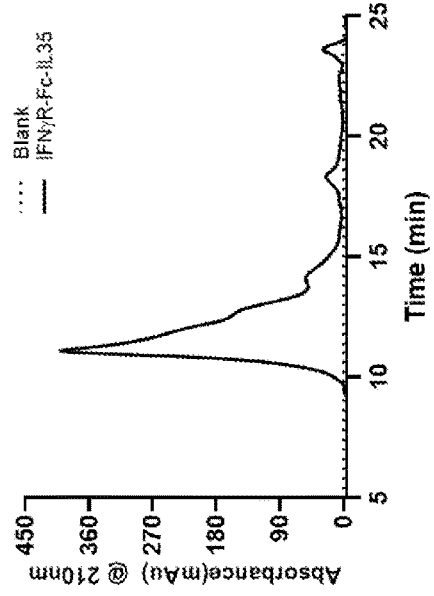
FIG. 22 provides a size-exclusion chromatography (SEC) chromatogram of the IFNγR-Fc-IL-35 heterodimeric protein following dual transfection of the IFNgR-Alpha-IL12a and IFNGR2-Beta-IL27B chain constructs in CHO cells followed by purification of the secreted protein using protein A.

Size-exclusion chromatography (SEC) was performed with the IFNγR-Fc-IL-35 heterodimeric protein. The appearance of a single peak by SEC indicated that there is likely only a single species of protein present, which was intended from using charge polarized linker domains (Fc-alpha and Fc-beta) in the two constructs (FIG. 22).

In these experiments, an illustrative charge polarized core domain (negative-positive, i.e., "alpha core domain") sequence is provided by SEQ ID NO: 16 and an illustrative alpha core domain comprising knob in hole mutations is provided in SEQ ID NO: 24. An illustrative charge polarized core domain (positive-negative, i.e., "beta core domain") sequence is provided by SEQ ID NO: 17 and an illustrative beta core domain comprising knob in hole mutations is provided in SEQ ID NO: 25.

The sequences of the components of illustrative polypeptide chains used in this example are set forth in SEQ ID NO: 30 for the extracellular domain of IFNgR, in SEQ ID NO: 31 for the extracellular domain of IFNGR2, in SEQ ID NO: 20 for the IL-12a, and in SEQ ID NO: 21 for the IL-27b. An illustrative IFNgR-Alpha-IL12α chain had the sequence set forth in SEQ ID NO: 32, and an illustrative IFNGR2-Beta-IL27B chain had the sequence set forth in SEQ ID NO: 33.

In alternate embodiment, an IFNγR-Fc-IL-35 heterodimeric protein can comprise an IFNGR2-Alpha-IL27B chain (SEQ ID NO: 39) and an IFNgR-Beta-IL12α chain (SEQ ID NO: 38).

EQUIVALENTS

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

Those skilled in the art will recognize, or be able to ascertain, using no more than routine experimentation, numerous equivalents to the specific embodiments described specifically herein. Such equivalents are intended to be encompassed in the scope of the following claims.

INCORPORATION BY REFERENCE

All patents and publications referenced herein are hereby incorporated by reference in their entireties.

The publications discussed herein are provided solely for their disclosure prior to the filing date of the present application. Nothing herein is to be construed as an admission that the present invention is not entitled to antedate such publication by virtue of prior invention.

As used herein, all headings are simply for organization and are not intended to limit the disclosure in any manner. The content of any individual section may be equally applicable to all sections.

What is claimed is:

1. A heterodimeric protein comprising a first polypeptide chain and a second polypeptide chain, wherein:
   the first polypeptide chain comprises a first subunit of a first protein at the amino terminus linked by a first charge polarized core domain to a first subunit of a second protein at the carboxy terminus; and
   the second polypeptide chain comprises a second subunit of the first protein at the amino terminus linked by a second charge polarized core domain to a second subunit of the second protein at the carboxy terminus; and
   the first polypeptide chain and the second polypeptide chain form a heterodimer through electrostatic interactions between positively charged amino acid residues and negatively charged amino acid residues on the first and second charge polarized core domains,
   the first and second charge polarized core domains comprise a hinge-CH2-CH3 Fc domain,
   one of the first protein and the second protein is interleukin-35 (IL-35) and
   the other of the first protein and the second protein is selected from interleukin-2 receptor (IL-2R), interleukin-3 receptor (IL-3R), interleukin-4 receptor (IL-4R), interleukin-5 receptor (IL-5R), interleukin-6 receptor (IL-6R), interleukin-7 receptor (IL-7R), interleukin-9 receptor (IL-9R), interleukin-10 receptor (IL-10R), interleukin-11 receptor (IL-11R), interleukin-12 receptor (IL-12R), interleukin-13 receptor (IL-13R), interleukin-15 receptor (IL-15R), interleukin-17 receptor (IL-17R), interleukin-18 receptor (IL-18R), interleukin-20 receptor (IL-20R), interleukin-21 receptor (IL-21R), interleukin-22 receptor (IL-22R), interleukin-23 receptor (IL-23R), interleukin-27 receptor (IL-27R), interferon alpha receptor (IFN-αR), interferon beta receptor (IFN-βR), and interferon gamma receptor (IFN-γR).

2. The heterodimeric protein of claim 1, wherein the linker comprises:
   the hinge-CH2-CH3 Fc domain derived from IgG1; or
   the hinge-CH2-CH3 Fc domain derived from IgG4.

3. The heterodimeric protein of claim 1, wherein the first and/or second charge polarized core domain further comprise peptides having positively and/or negatively charged amino acid residues at the amino and carboxy terminus of the charge polarized core domain.

4. The heterodimeric protein of claim 3, wherein the peptide comprising positively charged amino acid residues include one or more of amino acids selected from histidine (His), lysine (Lys), and arginine (Arg).

5. The heterodimeric protein of claim 4, wherein the peptide comprising positively charged amino acid residues comprises the sequence RKGGKR (SEQ ID NO: 11) or GSGSRKGGKRGS (SEQ ID NO: 12).

6. The heterodimeric protein of claim 3, wherein the peptide comprising negatively charged amino acid residues include one or more amino acids selected from aspartic acid (Asp) and glutamic acid (Glu).

7. The heterodimeric protein of claim 6, wherein the peptide comprising positively charged amino acid residues comprises the sequence DEGGED (SEQ ID NO: 13) or GSGSDEGGEDGS (SEQ ID NO: 14).

8. The heterodimeric protein of claim 1, wherein the first and/or second charge polarized core domain comprises one or more amino acid changes for promoting heterodimerization via increased hydrogen bonding and/or van der Waals forces.

9. The heterodimeric protein of claim 8, wherein the one or more amino acid changes creates a knob in hole motif, wherein:
   the knob in hole motif is formed by one or more amino acid changes that replaces one or more tyrosine (Y) residues with one or more threonine (T) residues in the first charge polarized core domain and/or is formed by one or more amino acid changes that replaces one or more threonine (T) residues with one or more tyrosine (Y) residues in the second charge polarized core domain, and/or
   the knob in hole motif is formed by one or more amino acid changes that replaces one or more tyrosine (Y) residues with one or more threonine (T) residues in the second charge polarized core domain and/or is formed by one or more amino acid changes that replaces one or more threonine (T) residues with one or more tyrosine (Y) residues in the first charge polarized core domain.

10. The heterodimeric protein of claim 8, wherein one or both of the charge polarized core domains comprise:
    one or more effector and complement silencing substitutions selected from L234A, L235A (LALA), and P329G; and/or
    one or more half-life extension mutations selected from M252Y, S254T, and T256E.

11. The heterodimeric protein of claim 1, wherein the first protein is IL-35.

12. The heterodimeric protein of claim 1, wherein the second protein is IL-35.

13. The heterodimeric protein of claim 1, wherein the first protein and the second protein, or the second protein and the first protein are (i) IL-35 and IL-6R, (ii) IL-21R and IL-35, or (iii) and IL-35, respectively.

14. The heterodimeric protein of claim 1, wherein
    the first or second protein is IL-35 comprising the IL-12α and IL-27β subunits,
    the first or second protein is IL-6R comprising the IL-6Rα and gp130 subunits,
    the first or second protein is IL-21R comprising the IL-21r and IL-2rg subunits, or
    the first or second protein is IFN-γR comprising the IFN-gR and IFNGR2 subunits.

15. The heterodimeric protein of claim 1, wherein the first or second protein is IL-6R and comprises the IL-6RA and gp130 subunits, and the other protein is IL-35 and comprises the IL12α and IL-27β subunits.

16. The heterodimeric protein of claim 1, wherein:
    the heterodimeric protein is capable of both (i) delivering an immune inhibitory signal and (ii) masking immune stimulatory signal.

17. A nucleic acid encoding the first and/or second polypeptide chains of the heterodimeric protein of claim 1.

18. An expression vector comprising the nucleic acid of claim 17.

19. The heterodimeric protein of claim 14, wherein the first or second protein is IL-21R comprising the IL-21r and IL-2rg subunits.

20. The heterodimeric protein of claim 14, wherein the first or second protein is IFN-γR comprising the IFN-gR and IFNGR2 subunits.

* * * * *